(12) United States Patent
Aldrich et al.

(10) Patent No.: US 7,989,430 B2
(45) Date of Patent: Aug. 2, 2011

(54) ANTIBACTERIAL AGENTS

(75) Inventors: Courtney Aldrich, Minneapolis, MN (US); Ravindranadh Venkata Somu, Woburn, MA (US)

(73) Assignee: Regents of the University of Minnesota, St. Paul, MN (US)

( * ) Notice: Subject to any disclaimer, the term of this patent is extended or adjusted under 35 U.S.C. 154(b) by 433 days.

(21) Appl. No.: 12/096,463

(22) PCT Filed: Dec. 6, 2006

(86) PCT No.: PCT/US2006/046433
§ 371 (c)(1),
(2), (4) Date: Jun. 6, 2008

(87) PCT Pub. No.: WO2007/067559
PCT Pub. Date: Jun. 14, 2007

(65) Prior Publication Data
US 2008/0293666 A1 Nov. 27, 2008

Related U.S. Application Data

(60) Provisional application No. 60/742,729, filed on Dec. 6, 2005.

(51) Int. Cl.
*A01N 43/04* (2006.01)
*A61K 31/70* (2006.01)
(52) U.S. Cl. .......... 514/45; 514/43; 514/46; 514/47; 514/48; 536/23.1; 536/25.3; 536/26.1; 536/26.7; 536/27.1; 536/27.13
(58) Field of Classification Search .................. None
See application file for complete search history.

(56) References Cited

U.S. PATENT DOCUMENTS
5,824,657 A 10/1998 Hill et al.

FOREIGN PATENT DOCUMENTS
WO WO 2006/113615 A2 10/2006

OTHER PUBLICATIONS

Ferreras et al. Nature Chemical Biology (2005), vol. 1, pp. 29-32.*
Kristinsson et al. In Synthesis and Chemistry of Agrochemicals IV; ACS Symposium Series (1995), pp. 206-219.*
Crofton British Medical Journal (1960), pp. 370-373.*
International Search Report and Written Opinion of the International Searching Authority, PCT/US2006/46433, May 24, 2007, 8 pages.
Boshoff, "The Transcriptional Responses of Mycobacterium tuberculosis to Inhibitors of Metabolism" *J. Biol. Chem.*, 279, 40174-40184 (2004).
Burns, "Selective Reduction of Disulfides by Tris(2-carboxyethyl)phosphine", *J. Org. Chem.*, 56, 2648-2650 (1991).
De Voss, "The salicylate-derived mycobactin siderophores of Mycobacterium tuberculosis are essential for growth in macrophages", *Proc. Natl. Acad. Sci.*, 97, 1252-1257 (2000).
Domenech, "Contribution of the Mycobacterium tuberculosis MmpL Protein Family to Virulence and Drug Resistance", *Infection and Immunity*, 73, 3492-3501 (2005).
Ferreras, "Small-molecule inhibition of siderophore biosynthesis in *Mycobacterium tuberculosis* and *Yersinia pestis*", *Nature Chemical Biology*, Vo. 1 Num. 1, 29-32 (2005).
Linne, "Reactions Catalyzed by Mature and Recombinant Nonribosomal Peptide Synthetases", *Methods Enzymol.*, 388, 293-315 (2004).
Liu, "A General Synthesis of 5'-Azido-5'-deoxy-2',3'-O-isopropylidene Nucleosides", *J. Org. Chem.* 66, 8643-8645 (2001).
Somu, "Rationally Designed Nucleoside Antibiotics that Inhibit Siderophore Biosynthesis of *Mycobacterium tuberculosis*", *J. Med. Chem.*, 49(1), 31-34 (2006).
Tibshirani, "Diagnosis of multiple cancer types by shrunken centroids of gene expression", *Proc. Natl. Acad. Sci.*, 99, 6567-6572 (2002).
Vannada, "Design, Synthesis, and Biological Evaluation of β-Ketosulfonamide Adenylation Inhibitors as Potential Antitubercular Agents", *Org. Lett.*, 8(21), 4707-4710 (2006).
Vergne, "Iron Chelators from Mycobacteria (1954-1999) and Potential Therapeutic Applications", *Nat. Prod. Rep.*, 17(1), 99-116 (2000).
Wayne, "Nonreplicating Persistence of Mycobacterium Tuberculosis", *Ann. Rev. Microbiol.*, 55, 139-163 (2001).

* cited by examiner

*Primary Examiner* — Patrick Lewis
(74) *Attorney, Agent, or Firm* — Viksnins Harris & Padys PLLP

(57) ABSTRACT

The invention provides compounds of formula (I) and salts thereof: $R_1$-L-$R_2$—B wherein $R_1$, L, $R_2$, and B have any of the values defined herein, as well as compositions comprising such compounds, and therapeutic methods comprising the administration of such compounds or salts. The compounds block siderophore production in bacteria and are useful as antibacterial agents.

20 Claims, 4 Drawing Sheets

| Example | R | Example | R |
|---|---|---|---|
| 1 | 2-hydroxyphenyl | 22 | 2,3-dihydroxyphenyl |
| 3 | phenyl | 23 | 3,4-dihydroxyphenyl |
| 2 | 2-aminophenyl | 24 | 3-chloro-2-hydroxyphenyl |
| 17 | 2-fluorophenyl | 25 | 5-chloro-2-hydroxyphenyl |
| 18 | 2-chlorophenyl | 26 | 4-chloro-2-hydroxyphenyl |
| 19 | 2-nitrophenyl | 27 | 4-amino-2-hydroxyphenyl |
| 20 | 2-chloropyridin-3-yl | 28 | 3-fluoro-2-hydroxyphenyl |
| 21 | 2-fluoropyridin-3-yl | 29 | 2-oxo-1,2-dihydropyridin-3-yl |

| Example | R | Example | R |
|---|---|---|---|
| 1 | adenine | 36 | 2-iodoadenine |
| 30 | hypoxanthine | 37 | 2-phenyladenine |
| 31 | N6,N6-dimethyladenine | 38 | 2-(phenylamino)adenine |
| 32 | N6-cyclopropyladenine | 39 | 2-(phenylethynyl)adenine |
| 33 | 8-bromoadenine | 40 | 7-deazaadenine |
| 34 | 8-azidoadenine | 41 | 4-amino-1H-indole |
| 35 | 8-aminoadenine | | |

| Example | R |
|---------|---|
| 1 | ribose with OH, OH and Ad |
| 42 | deoxyribose with OH and Ad |
| 43 | deoxyribose with OH and Ad |
| 44 | dideoxy unsaturated with Ad |
| 44 | dideoxy with Ad |
| 46 | acyclic with O-Ad |

ANTIBACTERIAL AGENTS

CROSS-REFERENCE TO RELATED APPLICATION

This application is a National Stage application under 35 U.S.C. §371 and claims the benefit of International Application No. PCT/US2006/046433 having an International Filing Date of Dec. 6, 2006, which claims priority from U.S. Application No. 60/742,729, filed Dec. 6, 2005, which applications are herein incorporated by reference.

BACKGROUND OF THE INVENTION

Almost all bacteria require iron for their survival and have evolved sophisticated iron acquisition systems to obtain this vital element from their environment. During infection many pathogens synthesize and secrete small molecule iron chelators known as siderophores that sequester iron from the host then transport the siderophore-iron complex back into the bacterium. The crucial role of siderophores for virulence has been demonstrated for several noted bacterial pathogens including *Mycobacterium tuberculosis, Yersenia pestis, Vibrio cholera, Bacillus anthracis* and *Pseudomonas aeroginosa* the causative agents respectively of tuberculosis, plague, cholera, anthrax, and opportunistic infections in patients with cystic fibrosis. All of these pathogens produce mixed-ligand siderophores that are biosynthesized by multi-functional proteins known as non-ribosomal peptide synthetases (NRPS) often in combination with polyketide synthases (PKSs).

Tuberculosis (TB) is the leading bacterial cause of infectious disease mortality. The current WHO-approved treatment for TB, known as directly observed therapy short-course (DOTS), involves a three- or four-drug regimen comprising isoniazid, rifampin, pyrazinamide, and/or ethambutol for a minimum of 6 months. While these first-line agents remain useful in treating susceptible *Mycobacterium tuberculosis* strains, the emergence of multi-drug resistant tuberculosis demands the development of new drugs. Currently, there is a need for therapeutic agents and methods that are useful for treating bacterial infections, including bacterial infections caused by pathogens that synthesize and secrete small molecule iron chelators.

SUMMARY OF THE INVENTION

The present invention provides compounds, salts, compositions, and methods that are useful for inhibiting adenylating enzymes and/or thiolation domains and for treating bacterial infections. Accordingly, in one embodiment the invention provides a compound of the invention which is a compound of formula I:

$$R_1\text{-}L\text{-}R_2\text{---}B \quad (I)$$

wherein:

$R_1$ is a ring selected from phenyl, furyl, thienyl, pyridyl, pyrrolyl, cyclohexyl, cyclopentyl, pyranyl, 1,2-dihydro-2-oxo-1H-pyrid-3-yl, and 2-oxopyranyl; which ring is optionally substituted with one or more (e.g. 1, 2, 3, or 4) $R_a$; or $R_1$-L- together are a group of the following formula:

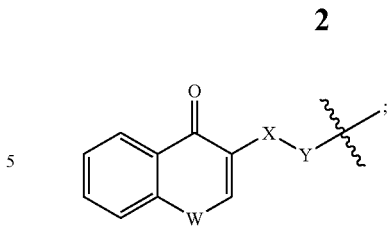

L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, —C(=O)—C(R$_b$)$_2$—C(=O)—NH—, —CH=CH—S(=O)$_2$—NH—, —C(=O)—C(=N$_2$)—S(=O)$_2$—NH—, —S(=O)$_2$—C(R$_b$)$_2$—S(=O)$_2$—NH—, —S(=O)—(=NH)—C(R$_b$)$_2$—S(=O)$_2$—NH—, —C(=O)—C(=O)—C(R$_b$)$_2$—NH—, —C(=O)—C(=O)—C(=O)—NH—, —C(=O)—C(R$_b$)$_2$—S(=O)$_2$—NH—, —CH(OH)—C(R$_b$)$_2$—P(=O)(OH)O—, —C(=O)—NH—C(=O)—NH—, —CH=CH—P(=O)(OH)O—, —CH=CH—C(=O)—NH—, —C(=O)—NH—, —C(=O)—NH—S(=O)$_2$—CH$_2$—, —S(=O)$_2$—NH—C(=O)—NH—, —C(=O)—NH—NH—C(=O)—CH$_2$—, —C(=O)—NH—O—C(=O)—CH$_2$—, —S(=O)$_2$—NH—S(=O)$_2$—NH—, —C(=O)—CH=CH—C(=O)—NH—,

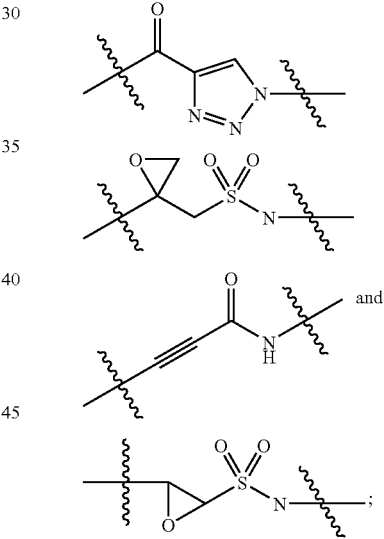

$R_2$ is —CH$_2$—CH$_2$—O—CH$_2$— or has the following formula:

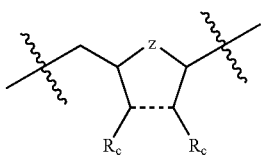

wherein the bond represented by  is a single bond and each $R_c$ is independently hydrogen, hydroxy, fluoro, azido, (C$_1$-C$_{12}$)alkoxy, (C$_1$-C$_{12}$)alkanoyloxy, or amino; or the bond represented by  is a double bond and each $R_c$ is absent;

B is:

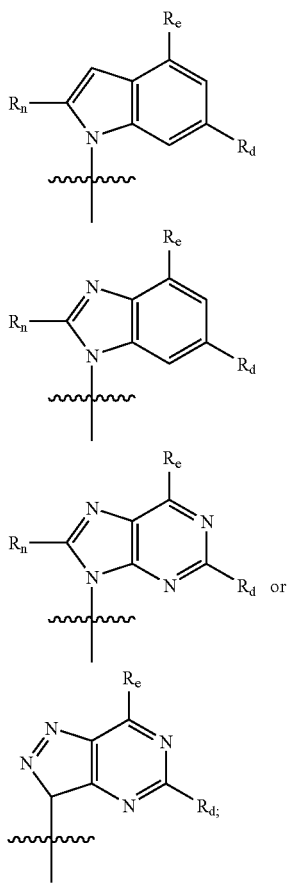

W is O or NH:
X is —C(=O)— or —S(=O)$_2$—;
Y is —NH— or —O—;
Z is O, —NH—, —CH$_2$—CH$_2$—, or CH$_2$;

each R$_a$ is independently hydroxy, amino, halo, (C$_1$-C$_6$)alkanoyloxy, nitro, (C$_1$-C$_6$)alkyl, (C$_2$-C$_6$)alkenyl, (C$_2$-C$_6$)alkynyl, or (C$_1$-C$_6$)alkanoylthio;

each R$_b$ is independently hydrogen, fluoro, or chloro;

each R$_d$ is independently azido, hydrogen, halo, (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkylthio, (C$_2$-C$_6$)alkenyloxy, (C$_1$-C$_6$)alkenylthio, (C$_2$-C$_6$)alkynyloxy, (C$_1$-C$_6$)alkynylthio, aryl, aryl(C$_1$-C$_6$)alkyl, aryl(C$_2$-C$_6$)alkenyl, aryl(C$_2$-C$_6$)alkynyl, carboxy(C$_1$-C$_6$)alkyl, carboxy(C$_1$-C$_6$)alkenyl, or NR$_f$R$_g$; wherein each R$_f$ and R$_g$ is independently hydrogen, aryl, aryloxy, or (C$_1$-C$_6$)alkyl;

each R$_e$ is independently hydrogen, hydroxy, (C$_1$-C$_6$)alkylthio, or NR$_k$R$_m$; wherein each R$_k$ and R$_m$ is independently hydrogen, (C$_3$-C$_6$)cycloalkyl aryl, or (C$_1$-C$_6$)alkyl; and each R$_n$ is independently hydrogen, halo, azido, or amino; or a pharmaceutically acceptable salt thereof;

excluding the compound 5'-O—(N-(2-Hydroxybenzoyl)sulfamoyl)-adenosine.

In another embodiment the invention provides a salt of a compound of formula I.

In another embodiment the invention provides a salt of a compound of formula I in solid form.

In another embodiment the invention also provides a pharmaceutical composition comprising a compound of formula I, or a pharmaceutically acceptable salt or prodrug thereof, in combination with a pharmaceutically acceptable diluent or carrier. The composition can optionally further comprise one or more additional therapeutic agents (e.g. antibiotic agents).

In another embodiment the invention also provides a pharmaceutical composition comprising: 1) a compound of formula I, or a pharmaceutically acceptable salt or prodrug thereof, 2) a pharmaceutically acceptable diluent or carrier, and 3) one or more additional agents selected from isoniazid, ethambutol, rifampin, pyrazinamide, streptomycin, capreomycin, kanamycin, amikacin, ethionamide, para-aminosalicylic acid, cycloserine, ciprofloxacin, and ofloxacin.

In another embodiment the invention provides a therapeutic method for treating a bacterial infection in an animal (e.g. a mammal) comprising administering an effective amount of a compound of formula I, or a pharmaceutically acceptable salt or prodrug thereof to the animal. In another embodiment the invention provides a therapeutic method for treating a bacterial infection in an animal comprising administering an effective amount of 1) a compound of formula I or a pharmaceutically acceptable salt or prodrug thereof and 2) one or more additional agents selected from isoniazid, ethambutol, rifampin, pyrazinamide, streptomycin, capreomycin, kanamycin, amikacin, ethionamide, para-aminosalicylic acid, cycloserine, ciprofloxacin, and ofloxacin to the animal.

In another embodiment the invention provides a method for inhibiting an adenylating enzyme (e.g. MbtA, DhbE, YbtE, VibE, EntE) comprising contacting the enzyme with an effective inhibitory amount of a compound of formula I, or a pharmaceutically acceptable salt thereof.

In another embodiment the invention provides a method for inhibiting an adenylating enzyme (e.g. MbtA, DhbE, YbtE, VibE, EntE) in an animal in need thereof comprising administering an effective inhibitory amount of a compound of formula I, or a pharmaceutically acceptable salt or prodrug thereof to the animal.

In another embodiment the invention provides a method for inhibiting an adenylating enzyme (e.g. MbtA, DhbE, YbtE, VibE, EntE) in vitro comprising contacting a sample comprising the enzyme with an effective inhibitory amount of a compound of formula I, or a pharmaceutically acceptable salt thereof.

In another embodiment the invention provides a method of treating a bacterial infection in a plant comprising contacting the plant with an effective amount of a compound of formula I, or a salt or prodrug thereof.

In another embodiment the invention provides a compound of formula I, or a pharmaceutically acceptable salt thereof, for use in medical therapy (e.g. for use in treating a bacterial infection), as well as the use of a compound of formula I, or a pharmaceutically acceptable salt thereof, for the manufacture of a medicament useful for the treatment of a bacterial infection in a mammal, such as a human.

The invention also provides processes and intermediated disclosed herein that are useful for preparing compounds of formula (I) or salts thereof.

DETAILED DESCRIPTION

Figure 1:
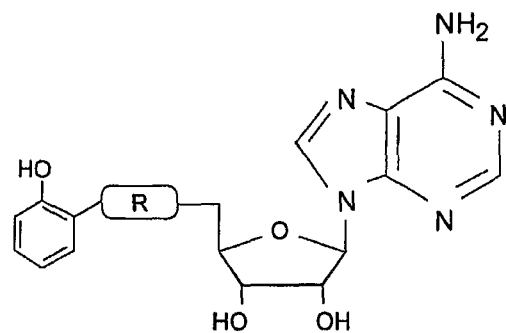
FIGS. 1-4 illustrate representative compounds of the invention.
Figure 2:
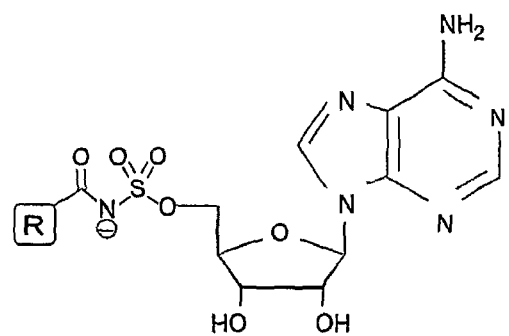
Figure 3:
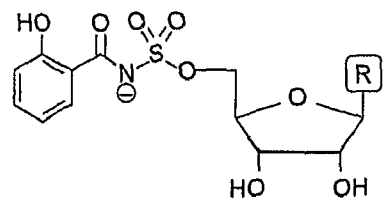
Figure 4:
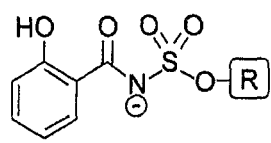

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

The term "treating" as used herein includes preventing the development of a bacterial infection in an animal or plant, as well as partially or completely eliminating an existing infection.

The term "prodrug" includes compounds that can be converted to a compound of formula I or a salt thereof in situ. Thus, prodrugs include compounds that can be prepared by modifying one or more functional groups in a compound of formula I to provide the prodrug. A variety of suitable modifications are known in the art. For example, the term includes compounds that can be converted (e.g. hydrolyzed or metabolized) to provide a compound of Formula I upon administration to an animal or upon contact with a plant. Suitable prodrugs for alcohols, acids, amines and phosphates are well known, for example see Wagner C. R., et al., *J Med. Res. Rev.*, 2000, 20, 417-451.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antibiotic activity using the standard tests described herein, or using other similar tests which are well known in the art. In one embodiment of the invention the $R_2$ groups have the absolute configuration of natural nucleoside sugars.

Specific and preferred values listed below for radicals, substituents, and ranges, are for illustration only; they do not exclude other defined values or other values within defined ranges for the radicals and substituents Specifically, $(C_1$-$C_6)$alkyl can be methyl, ethyl, propyl, isopropyl, butyl, iso-butyl, sec-butyl, pentyl, 3-pentyl, or hexyl; $(C_1$-$C_6)$alkoxy can be methoxy, ethoxy, propoxy, isopropoxy, butoxy, iso-butoxy, sec-butoxy, pentoxy, 3-pentoxy, or hexyloxy; $(C_2$-$C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2$-$C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1$-$C_6)$alkanoyloxy can be formyloxy, acetoxy, propanoyloxy, butanoyloxy, isobutanoyloxy, pentanoyloxy, or hexanoyloxy; $(C_1$-$C_{12})$alkanoyloxy can be formyloxy, acetoxy, propanoyloxy, butanoyloxy, isobutanoyloxy, pentanoyloxy, hexanoyloxy, heptanoyloxy, octanoyloxy, nonanoyloxy, decanoyloxy, undecanoyloxy, or dodecanoyloxy; $(C_1$-$C_{12})$ alkanoyl can be formyl, acetyl, propanoyl, butanoyl, isobutanoyl, pentanoyl, hexanoyl, heptanoyl, octanoyl, nonanoyl, decanoyl, undecanoyl, or dodecanoyl; $(C_2$-$C_6)$alkanoylthio can be acetylthio, propanoylthio, butanoylthio, isobutanoylthio, pentanoylthio, or hexanoylthio; and aryl can be phenyl, indenyl, or naphthyl.

A specific value for $R_1$ is a ring selected from phenyl, furyl, thienyl, pyridyl, and pyrrolyl, which ring is optionally substituted with one or more (e.g. 1, 2, 3, or 4) $R_a$.

A specific value for $R_1$ is a ring selected from cyclohexyl, cyclopentyl, pyranyl, and 2-oxopyranyl, which ring is optionally substituted with one or more (e.g. 1, 2, 3, or 4) $R_a$.

A specific value for $R_1$ is a ring that is substituted with a hydroxy group at the position ortho to the position where $R_1$ attaches to L, and wherein the ring is further optionally substituted with one or more $R_a$.

A specific value for $R_1$ is a ring of the following formula:

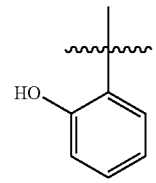

wherein the ring is optionally substituted with one or more $R_a$.

A specific value for $R_1$ is 2-hydroxyphenyl, phenyl, 2-aminophenyl, 2-fluorophenyl, 2-chlorophenyl, 2-nitrophenyl, 2-chloropyrid-3-yl, 2-fluoropyrid-3-yl, 2,3-dihydroxyphenyl, 3,4-dihydroxyphenyl, 2-hydroxy-3-chlorophenyl, 2-hydroxy-4-chlorophenyl, 2-hydroxy-5-chlorophenyl, 2-hydroxy-4-aminophenyl, 2-hydroxy-5-fluorophenyl, or 1,2-dihydro-2-oxo-1H-pyrid-3-yl.

A specific value for $R_1$ is 2-hydroxyphenyl, 2-aminophenyl, phenyl, 2,3-dihydroxyphenyl, 4-amino-2-hydroxyphenyl, 2-fluorophenyl, 2-chlorophenyl, 2-hydroxy-3-pyridyl, 2-hydroxy-4-pyridyl, 4-hydroxy-3-pyridyl, 3-hydroxy-2-pyridyl, 2-oxo-3-pyranyl, 2-acetoxyphenyl, 2-propanoyloxyphenyl, 2-acetylthiophenyl, 2-propanoylthiophenyl, cyclopentyl, cyclohexyl, 2-hydroxycyclopentyl, 2-hydroxycyclohexyl, or 2,6-dihydroxyphenyl.

A specific value for L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, —C(=O)—NH—S(=O)$_2$—CH$_2$—, —S(=O)$_2$—NH—C(=O)—N—, —C(=O)—NH—NH—C(=O)—CH$_2$—, —C(=O)—NH—O—C(=O)—CH$_2$—, —S(=O)$_2$—NH—S(=O)$_2$—NH—, —C(=O)—CH=CH—C(=O)—NH—, and —C(=O)—C(R$_b$)$_2$—C(=O)—NH—, and

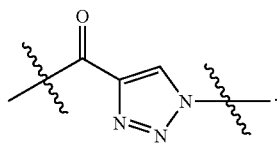

A specific value for L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, and —C(=O)—C(R$_b$)$_2$—C(=O)—NH—, and

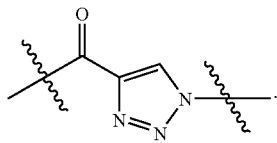

A specific value for L is selected from —CH=CH—S(=O)₂—NH—, —C(=O)—C(R$_b$)₂—S(=O)₂—NH—, —C(=O)—C(=N₂)—S(=O)₂—NH—, A specific value for L is selected from —S(=O)₂—C(R$_b$)₂—S(=O)₂—NH—, —S(=O)(=NH)—C(R$_b$)₂—S(=O)₂—NH—, —S(=O)₂—NH—C(=O)—NH—, —C(=O)—C(=O)—C(R$_b$)₂—NH—, —C(=O)—C(=O)—C(=O)—NH—.

A specific value for L is —C(=O)—NH—S(=O)₂—NH—.

A specific value for R₁-L- together is a group of the following formula:

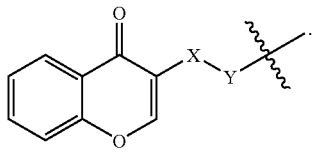

A specific value for R₂ is —CH₂—CH₂—O—CH₂—.
A specific value for R₂ is selected from

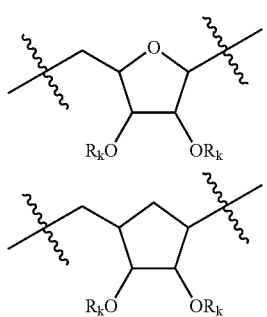

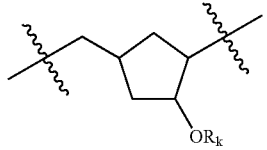

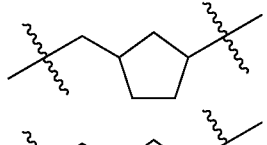

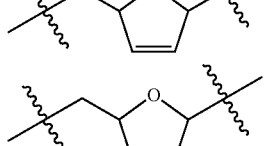

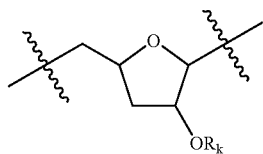

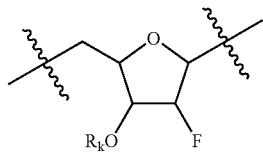

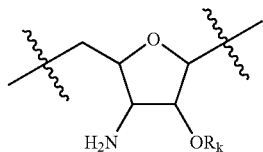

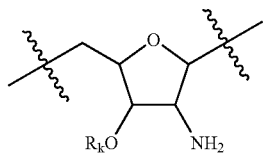

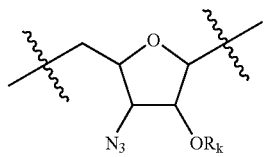

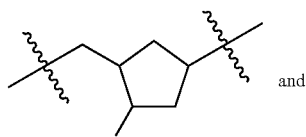

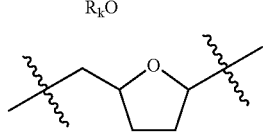

wherein each R$_k$ is independently hydrogen or (C₁-C₁₂)alkanoyl

A specific value for R₂ is selected from

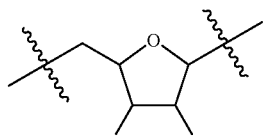

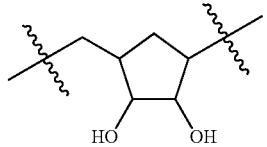

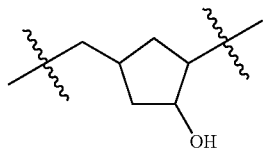

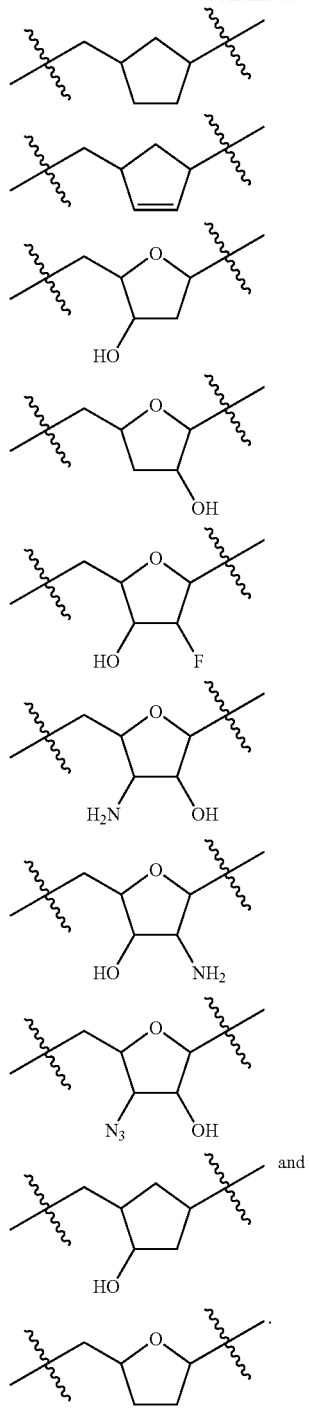
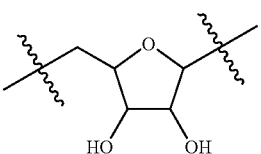
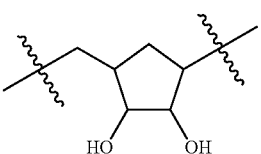
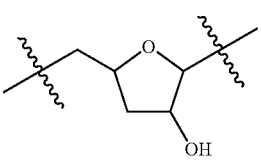
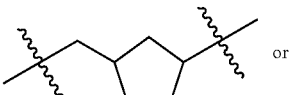
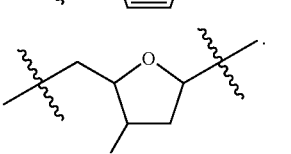
A specific value for B is:
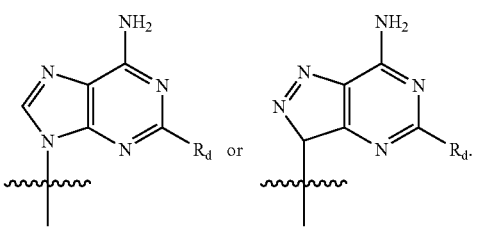
A specific value for B is
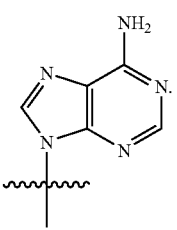
A specific value for $R_2$ is
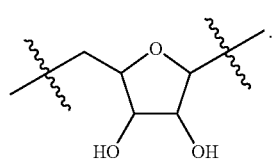
A specific value for $R_2$ is —$CH_2$—$CH_2$—O—$CH_2$—,
A specific compound of the invention is a compound of formula II
$$R_1-C(=O)-NH-S(=O)_2-NH-R_2-B \quad (II)$$
or a pharmaceutically acceptable salt thereof.

A specific compound of the invention is a compound of formula III

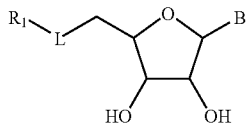

or a pharmaceutically acceptable salt thereof.

A specific compound of the invention is a compound of formula IV:

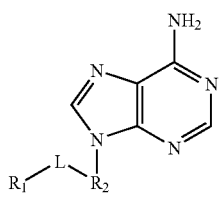

or a pharmaceutically acceptable salt thereof.

A specific compound of the invention is a compound of formula V:

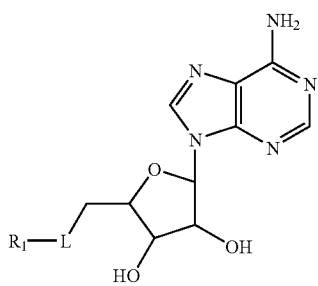

or a pharmaceutically acceptable salt thereof.

A specific compound of the invention is a salt of a compound of formula I:

$$R_1\text{-}L\text{-}R_2\text{—}B \quad (I)$$

wherein:

$R_1$ is a ring selected from phenyl, furyl, thienyl, pyridyl, pyrrolyl, cyclohexyl, cyclopentyl, pyranyl, 1,2-dihydro-2-oxo-1H-pyrid-3-yl, and 2-oxopyranyl; which ring is optionally substituted with one or more (e.g. 1, 2, 3, or 4) $R_a$; or $R_1$-L- together are a group of the following formula:

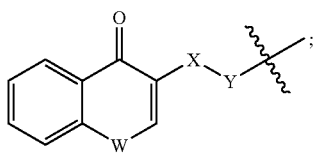

L is selected from —C(=O)—NH—S(=O)$_2$—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, —C(=O)—C(R$_b$)$_2$—C(=O)—NH—, —CH=CH—S(=O)$_2$—NH—, —C(=O)—C(=N$_2$)—S(=O)$_2$—NH—, —S(=O)$_2$—C(R$_b$)$_2$—S(=O)$_2$—NH—, —S(=O)(=NH)—C(R$_b$)$_2$—S(=O)$_2$—NH—, —C(=O)—C(=O)—C(R$_b$)$_2$—NH—, —C(=O)—C(=O)—C(=O)—NH—, —C(=O)—C(R$_b$)$_2$—S(=O)$_2$—NH—, —CH(OH)—C(R$_b$)$_2$—P(=O)(OH)O—, —C(=O)—NH—C(=O)—NH—, —CH=CH—P(=O)(OH)O—, —CH=CH—C(=O)—NH—, —C(=O)—NH—, —C(=O)—NH—S(=O)$_2$—CH$_2$—, —S(=O)$_2$—NH—C(=O)—NH—, —C(=O)—NH—NH—C(=O)—CH$_2$—, —C(=O)—NH—O—C(=O)—CH$_2$—, —S(=O)$_2$—NH—S(=O)$_2$—NH—, —C(=O)—CH=CH—C(=O)—NH—,

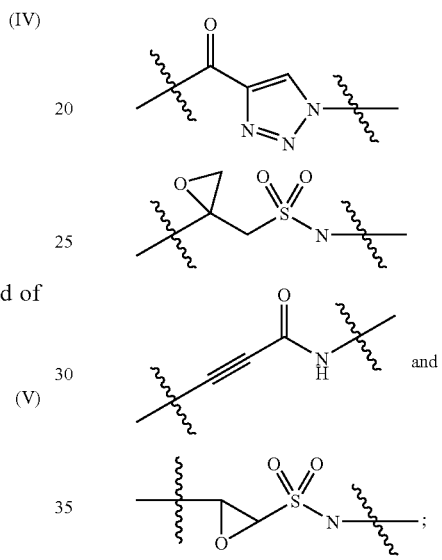

and

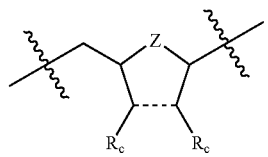

$R_2$ is —CH$_2$—CH$_2$—O—CH$_2$— or has the following formula:

wherein the bond represented by ------ is a single bond and each $R_c$ is independently hydrogen, hydroxy, fluoro, azido, (C$_1$-C$_{12}$)alkoxy, (C$_1$-C$_{12}$)alkanoyloxy, or amino; or the bond represented by ------ is a double bond and each $R_c$ is absent;

B is:

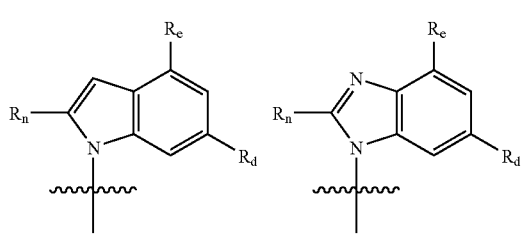

-continued

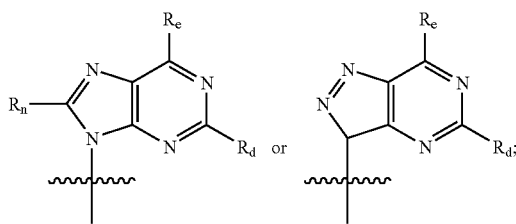

W is O or NH:

X is —C(=O)— or —S(=O)$_2$—;

Y is —NH— or —O—;

Z is O, —NH—, —CH$_2$—CH$_2$—, or CH$_2$;

each R$_a$ is independently hydroxy, amino, halo, (C$_1$-C$_6$)alkanoyloxy, nitro, (C$_1$-C$_6$)alkyl, (C$_2$-C$_6$)alkenyl, (C$_2$-C$_6$)alkynyl, or (C$_1$-C$_6$)alkanoylthio;

each R$_b$ is independently hydrogen, fluoro, or chloro;

each R$_d$ is independently azido, hydrogen, halo, (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkylthio, (C$_2$-C$_6$)alkenyloxy, (C$_1$-C$_6$)alkenylthio, (C$_2$-C$_6$)alkynyloxy, (C$_1$-C$_6$)alkynylthio, aryl, aryl(C$_1$-C$_6$)alkyl, aryl(C$_2$-C$_6$)alkenyl, aryl(C$_2$-C$_6$)alkynyl, carboxy(C$_1$-C$_6$)alkyl, carboxy(C$_1$-C$_6$)alkenyl, or NR$_f$R$_g$; wherein each R$_f$ and R$_g$ is independently hydrogen, aryl, aryloxy, or (C$_1$-C$_6$)alkyl;

each R$_e$ is independently hydrogen, hydroxy, (C$_1$-C$_6$)alkylthio, or NR$_k$R$_m$; wherein each R$_k$ and R$_m$ is independently hydrogen, (C$_3$-C$_6$)cycloalkyl aryl, or (C$_1$-C$_6$)alkyl; and each R$_n$ is independently hydrogen, halo, azido, or amino.

A specific compound of the invention is a salt of a compound of formula I:

R$_1$-L-R$_2$—B  (I)

wherein:

R$_1$ is a ring selected from phenyl, furyl, thienyl, pyridyl, pyrrolyl, cyclohexyl, cyclopentyl, pyranyl, and 2-oxopyranyl; which ring is optionally substituted with one or more (e.g. 1, 2, 3, or 4) R$_a$; or R$_1$-L- together are a group of the following formula:

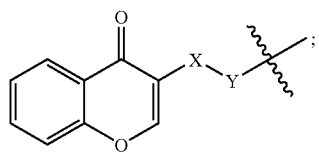

L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, —C(=O)—C(R$_b$)$_2$—C(=O)—NH—, —CH=CH—S(=O)$_2$—NH—, —C(=O)—C(=N$_2$)—S(=O)$_2$—NH—, —S(=O)$_2$—C(R$_b$)$_2$—S(=O)$_2$—NH—, —S(=O)(=NH)—C(R$_b$)$_2$—S(=O)$_2$—NH—, —C(=O)—C(=O)—C(R$_b$)$_2$—NH—, —C(=O)—C(=O)—C(=O)—NH—, —C(=O)—C(R$_b$)$_2$—S(=O)$_2$—NH—,

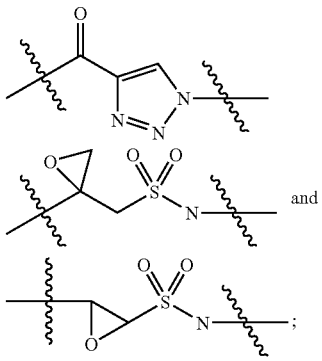

R$_2$ is —CH$_2$—CH$_2$—O—CH$_2$— or has the following formula:

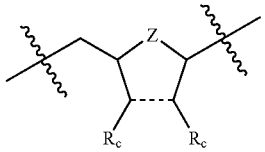

wherein the bond represented by ------ is a single bond and each R$_c$ is independently hydrogen, hydroxy, fluoro, azido, (C$_1$-C$_{12}$)alkanoyloxy, or amino; or the bond represented by ------ is a double bond and each R$_c$ is absent;

B is:

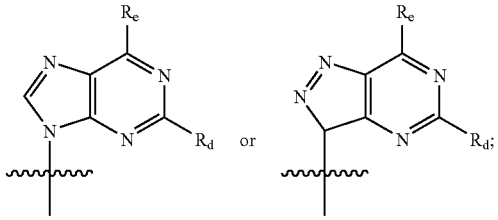

X is —C(=O)— or —S(=O)$_2$—;

Y is —NH— or —O—;

Z is O, or CH$_2$;

each R$_a$ is independently hydroxy, amino, halo, (C$_1$-C$_6$)alkanoyloxy or (C$_1$-C$_6$)alkanoylthio;

each R$_b$ is independently hydrogen, fluoro, or chloro;

each R$_d$ is independently hydrogen, halo, (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkylthio, (C$_2$-C$_6$)alkenyloxy, (C$_1$-C$_6$)alkenylthio, (C$_2$-C$_6$)alkynyloxy, (C$_1$-C$_6$)alkynylthio, or NR$_f$R$_g$; wherein each R$_f$ and R$_g$ is independently hydrogen or (C$_1$-C$_6$)alkyl; and each R$_e$ is independently hydroxy or amino. In one embodiment of the invention, the salt is in a solid form.

Another specific compound of the invention is a compound of formula I:

R$_1$-L-R$_2$—B  (I)

wherein:

R$_1$ is a ring selected from phenyl, furyl, thienyl, pyridyl, pyrrolyl, cyclohexyl, cyclopentyl, pyranyl, and 2-oxopyranyl; which ring is optionally substituted with one or more (e.g. 1, 2, 3, or 4) R$_a$; or R$_1$-L- together are a group of the following formula:

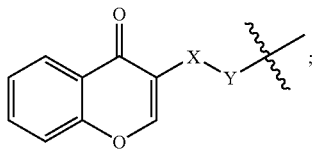

L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)—O—, —C(=O)—C(R$_b$)$_2$—C(=O)—NH—, —CH=CH—S(=O)$_2$—NH—, —C(=O)—C(=N$_2$)—S(=O)$_2$—NH—, —S(=O)$_2$—C(R$_b$)$_2$—S(=O)$_2$—NH—, —S(=O)(=NH)—C(R$_b$)$_2$—S(=O)$_2$—NH—, —C(=O)—C(=O)—C(R$_b$)$_2$—NH—, —C(=O)—C(=O)—C(=O)—NH—,

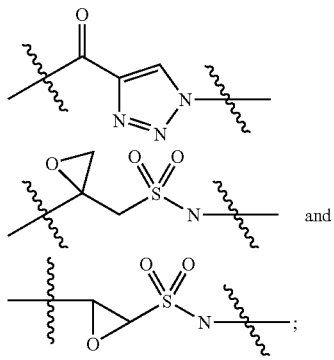

R$_2$ is —CH$_2$—CH$_2$—O—CH$_2$— or has the following formula:

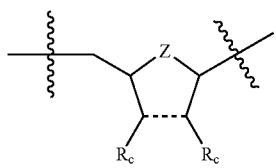

wherein the bond represented by ------ is a single bond and each R$_c$ is independently hydrogen, hydroxy, fluoro, azido, (C$_1$-C$_{12}$)alkanoyloxy, or amino; or the bond represented by ------ is a double bond and each R$_c$ is absent;

B is:

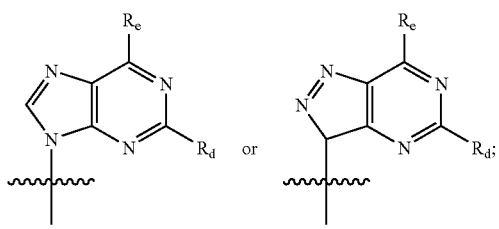

X is —C(=O)— or —S(=O)$_2$—;
Y is —NH— or —O—;
Z is O, or CH$_2$;
each R$_a$ is independently hydroxy, amino, halo, (C$_1$-C$_6$)alkanoyloxy or (C$_1$-C$_6$)alkanoylthio;

each R$_b$ is independently hydrogen, fluoro, or chloro;
each R$_d$ is independently hydrogen, halo, (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkylthio, (C$_2$-C$_6$)alkenyloxy, (C$_1$-C$_6$)alkenylthio, (C$_2$-C$_6$)alkynyloxy, (C$_1$-C$_6$)alkynylthio, or NR$_f$R$_g$; wherein each R$_f$ and R$_g$ is independently hydrogen or (C$_1$-C$_6$)alkyl; and each R$_e$ is independently hydroxy or amino;

or a pharmaceutically acceptable salt or prodrug thereof.

Another specific value for R$_1$ is a ring selected from phenyl, furyl, thienyl, pyridyl, pyrrolyl, cyclohexyl, cyclopentyl, pyranyl, and 2-oxopyranyl; which ring is optionally substituted with one or more (e.g. 1, 2, 3, or 4) R$_a$; or R$_1$-L- together are a group of the following formula:

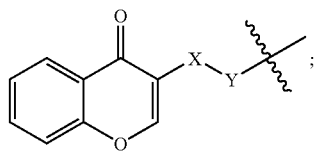

wherein R$_a$ is independently hydroxy, amino, halo, (C$_1$-C$_6$)alkanoyloxy or (C$_1$-C$_6$)alkanoylthio.

Another specific value for L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)—O—, —C(=O)—C(R$_b$)$_2$—C(=O)—NH—, —CH=CH—S(=O)$_2$—NH—, —C(=O)—C(=N$_2$)—S(=O)$_2$—NH—, —S(=O)$_2$—C(R$_b$)$_2$—S(=O)$_2$—NH—, —S(=O)(=NH)—C(R$_b$)$_2$—S(=O)$_2$—NH—, —C(=O)—C(=O)—C(R$_b$)$_2$—NH—, —C(=O)—C(=O)—C(=O)—NH—,

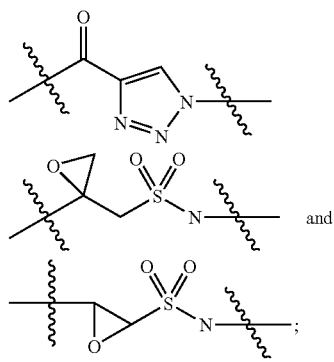

wherein each R$_b$ is independently hydrogen, fluoro, or chloro.

Another specific value for R$_2$ is —CH$_2$—CH$_2$—O—CH$_2$— or the following formula:

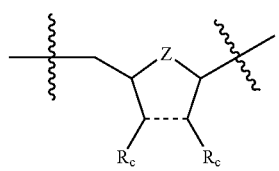

wherein the bond represented by ------ is a single bond and each R$_c$ is independently hydrogen, hydroxy, fluoro, azido, (C$_1$-C$_{12}$)alkanoyloxy, or amino; or the bond represented by ------ is a double bond and each R$_c$ is absent; and Z is O, or CH$_2$.

Another specific value for B is:

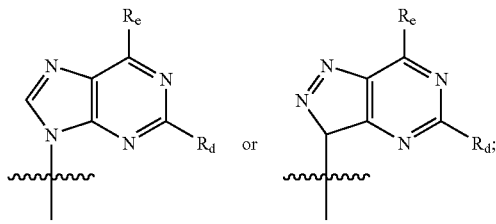

wherein each $R_d$ is independently hydrogen, halo, $(C_1\text{-}C_6)$ alkyl, $(C_2\text{-}C_6)$alkenyl, $(C_2\text{-}C_6)$alkynyl, $(C_1\text{-}C_6)$alkoxy, $(C_1\text{-}C_6)$alkylthio, $(C_2\text{-}C_6)$alkenyloxy, $(C_1\text{-}C_6)$alkenylthio, $(C_2\text{-}C_6)$alkynyloxy, $(C_1\text{-}C_6)$alkynylthio, or $NR_fR_g$; wherein each $R_f$ and $R_g$ is independently hydrogen or $(C_1\text{-}C_6)$alkyl; and each $R_e$ is independently hydroxy or amino.

Synthesis of Representative Compounds of the Invention

The synthesis of a representative compound of the invention (Compound 34) is illustrated below.

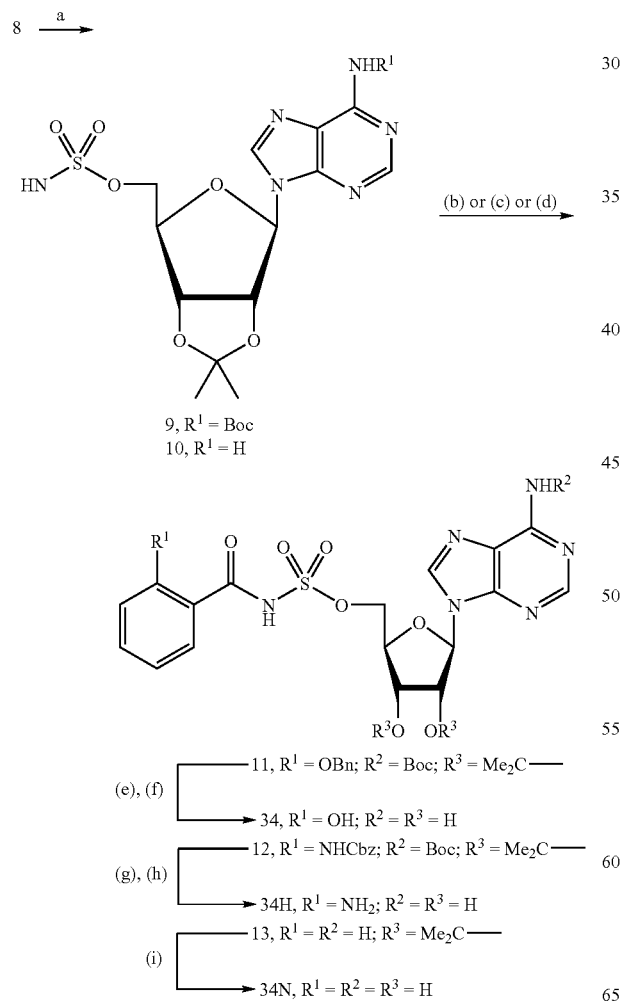

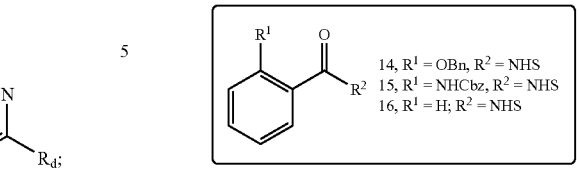

[a]Reaction conditions: (a) NH$_2$SO$_2$Cl, NaH, 89%; (b) 9, 14, Cs$_2$CO$_3$, 92%; (c) 9, 15, Cs$_2$CO$_3$, 85%; (d) 10, 16, Cs$_2$CO$_3$, 86%; (e) H$_2$, Pd/C, 79%; (f) 80% aq. TFA, 94%; (g) H$_2$, Pd/C, 84%; (h) 80% aq. TFA, 89%; (i) 80% aq. TFA, 74%.

Sulfamoylation of N$^6$-Boc-2',3'-isopropylidene adenosine 8 (prepared in 3 steps from 2',3'-isopropylidene adenosine) provided Compound 9. Coupling to the N-hydroxysuccinimide (NHS) ester of O-benzyl salicylic acid 14 mediated by Cs$_2$CO$_3$ afforded Compound 11. Sequential deprotection of the benzyl ether by catalytic hydrogenation followed by the isopropylidene acetal and Boc carbamate with aqueous trifluoroacetic acid provided salicyl-sulfamate 34 that was isolated as the triethylammonium salt. Both anthraniloyl-sulfamate 34N also isolated as the triethylammonium salt and benzoyl-sulfamate 34H isolated in the acid-form were prepared in an analogous fashion.

The synthesis of a representative compound of the invention Compound 35 is illustrated below.

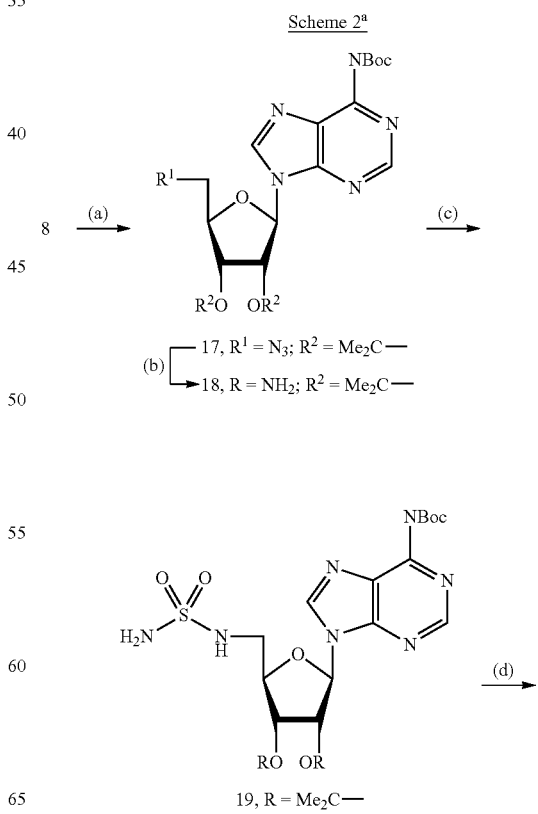

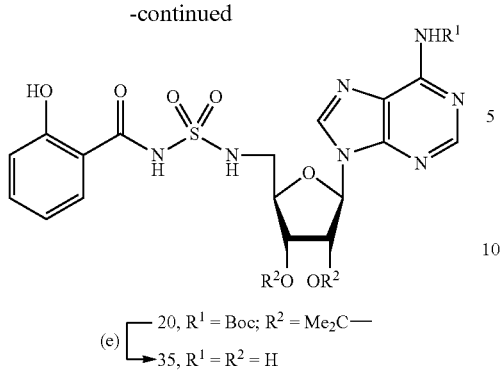

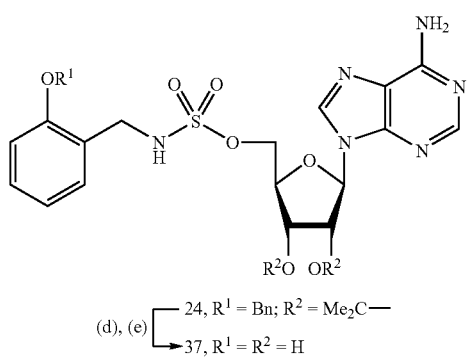

(e) ⎡ 20, R¹ = Boc; R² = Me₂C—
    ⎣→ 35, R¹ = R² = H

[a]Reaction conditions: (a) CBr₄, PPh₃, NaN₃, 50%; (b) H₂, Pd/C, 70%; (c) NH₂SO₂Cl, NaH, 39%; (d) salicylic acid, CDI, DBU, 40%; (e) 80% aq. TFA, 81%.

Treatment of 8 under Appel conditions (CBr₄, PPh₃) afforded the intermediate 5'-bromide that was converted in-situ to the corresponding azide 17. Catalytic hydrogenation afforded the 5'-amino derivative 18, which was sulfamoylated to provide sulfamide 19. Coupling to salicylic acid mediated by CDI and DBU yielded 20 that was treated with aqueous TFA to afford compound 35.

The synthesis of a representative compound of the invention (Compound 37) is illustrated below.

Scheme 3[a]

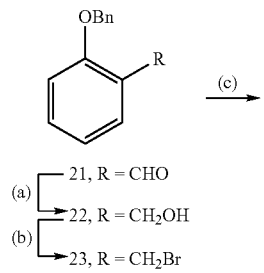

(d), (e) ⎡ 24, R¹ = Bn; R² = Me₂C—
         ⎣→ 37, R¹ = R² = H

[a]Reaction conditions: (a) NaBH₄, 99%; (b) CBr₄, PPh₃, 94%; (c) 10, Cs₂CO₃, 83%; (d) H₂, Pd/C, 76%; (d) 80% aq. TFA, 83%.

Reduction of 21 with NaBH₄ provided compound 22 that was converted to bromide 23. Alkylation of 5'-O-sulfamoyl adenosine 10 with Compound 23 employing Cs₂CO₃ yielded Compound 24, which was deprotected to furnish Compound 37.

The synthesis of representative compounds of the invention (Compounds 38 and 39) is illustrated below.

Scheme 4[a]

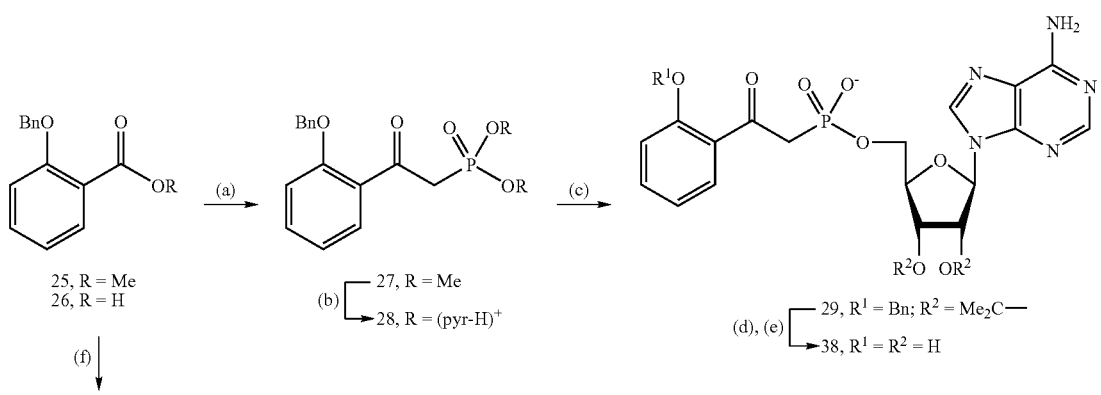

(d), (e) ⎡ 29, R¹ = Bn; R² = Me₂C—
         ⎣→ 38, R¹ = R² = H

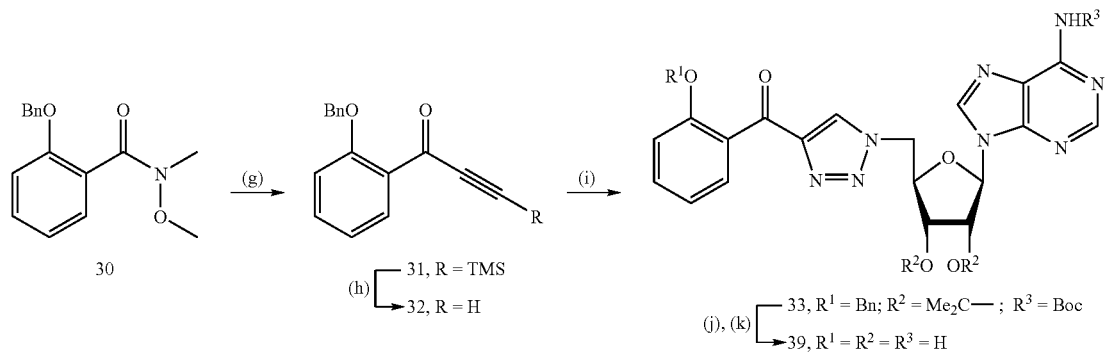

<sup>a</sup>Reaction conditions: (a) LiCH$_2$P(O)(OMe)$_2$, 76%; (b) i) TMSBr, ii) pyr., 100%; (c) TrisylSO$_2$Cl,2',3'-isopropylidene adenosine, 6%; (d) H$_2$, Pd/C, 40%; (e) aq. TFA, 90%; (f) i) (COCl)$_2$, ii) Me(OMe)NH·HCl, 80%; (g) TMS-acetylene, n-BuLi, 76%; (h) TBAF, 79%; (i) 17, CuI, ascorbic acid, 89%; (j) H$_2$, Pd/C, 100%; (k) aq. TFA, 90%.

β-Ketophosphonate inhibitor 38 was prepared by addition of the lithium anion of methyl dimethylphosphonate to methyl benzoate derivative 25 to provide Compound 27. Treatment with TMSBr afforded phosphonic acid 28 that was coupled with 2',3'-isopropylidene adenosine employing 2,4,6-triisopropylbenzenesulfonylchloride to yield Compound 29. Stepwise deprotection of the benzyl ether and isopropylidene acetal furnished target inhibitor 38.

The novel acyltriazole inhibitor 39 was prepared from O-benzylsalicylic acid 26 by conversion to Weinreb amide 30. Addition of the lithium anion of TMS-acetylene to Compound 30 afforded Compound 31 that was deprotected with TBAF to afford ynone 32. The copper catalyzed Hüisgen 1,3-dipolar cycloaddition between ynone 32 and azide 17 provided exclusively the regioisomeric 1,4-triazole 33 that was deprotected to afford Compound 39.

Linkers "L"

The design of the linker group "L" can provide intermediate mimics, irreversible inactivators, or transition-state inhibitors that can target either the adenylation and/or thiolation domain of MbtA and MbtB respectively.

1) Intermediate Mimics are reversible competitive inhibitors of the adenylation enzyme MbtA; 2) Irreversible Inactivators are designed to covalently modify the phosphopantetheinyl (ppan) cofactor of the thiolation domain of MbtB; and 3) Transition-State Inhibitors inhibit the second half-reaction catalyzed by MbtA. These inhibitors may function either as reversible tight binders of MbtA or if they possess an electrophilic group they may form a covalent adduct with the thiol terminus of the ppan cofactor of MbtB, thus acting as dual adenylation and thiolation inhibitors. Representative examples of each type of linker are shown below.

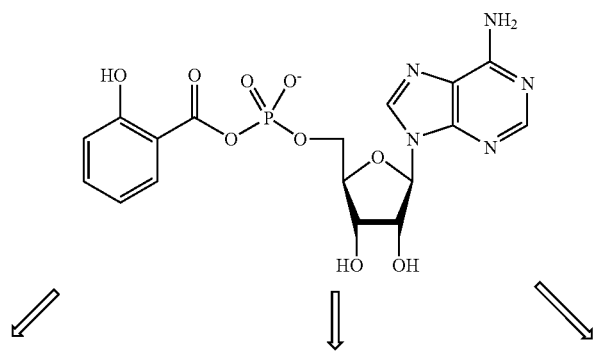

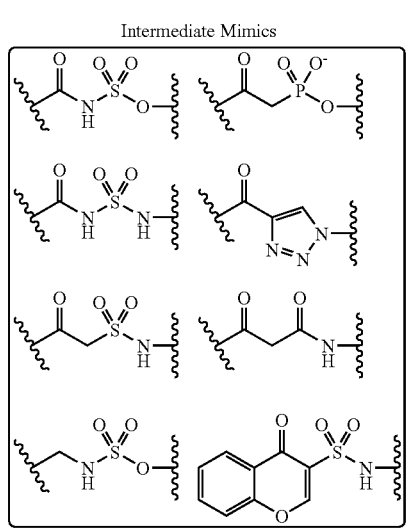

Intermediate Mimics

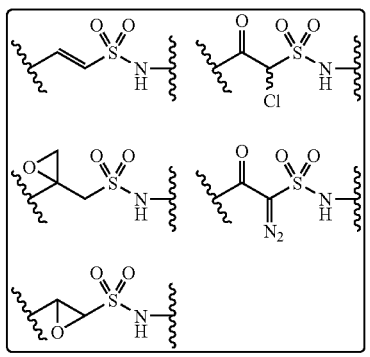

Irreversible Inactivators

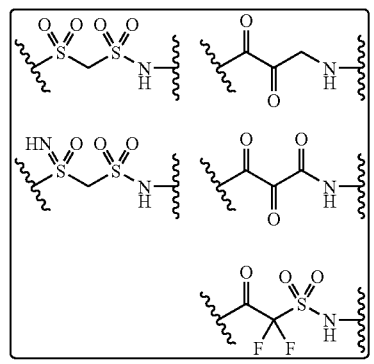

Transition State Inhibitors

Representative compounds of the invention that incorporate such linkers can be prepared as described below.

Scheme 5[a]

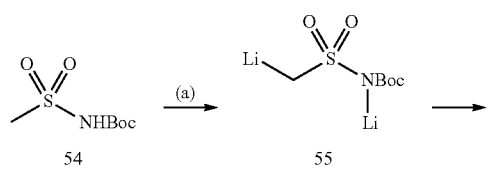

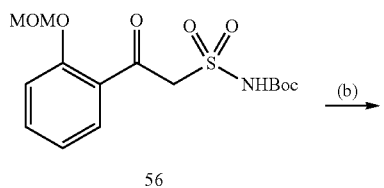

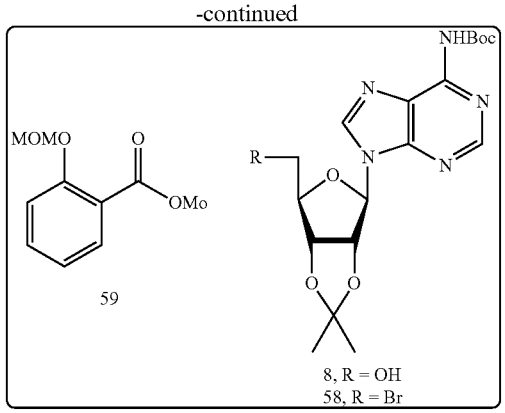

[a]Reaction conditions: (a) i) LDA (2.0 equiv.), THF, 59, 0° C.; (b) DIAD, PPh$_3$, THF, 8 or KOtBu, 58 (c) aq. TFA.

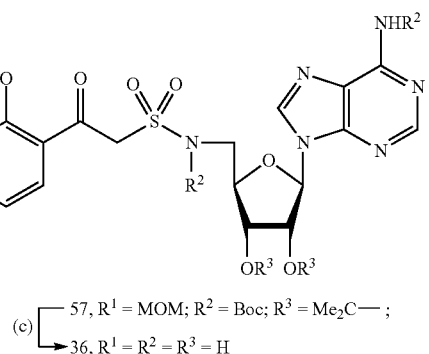

57, R$^1$ = MOM; R$^2$ = Boc; R$^3$ = Me$_2$C—;
36, R$^1$ = R$^2$ = R$^3$ = H

Compound 36 can be prepared by treatment of known Boc-sulfonamide 54 with LDA to afford dianion 55. Subsequent addition to methyl salicylate derivative 59 provides β-ketosulfonamide 56. Mitsunobu reaction of Compound 56 with N$^6$-Boc-2,3-isopropylidene adenosine 8 provides compound 57. Alternatively, displacement of the 5'-bromide of adenosine derivative 58 with the potassium salt of Boc-sulfonamide 56 provides Compound 57. Simultaneous deprotection of the MOM acetal, isopropylidene ketal and Boc carbamates furnishes Compound 36.

The β-ketosulfonamide intermediate 57 serves as a versatile scaffold for preparing other compounds of the invention. As illustrated below, the active methylene group can be chlorinated by N-chlorosuccinimide to afford Compound 46, converted to the α-diazo derivative using 4-acetamidobenzenesulfonyl azide to yield Compound 47, or fluorinated (e.g. with Selectfluor) to furnish Compound 53.

Sodium borohydride mediated reduction of 57 in turn provides 60 and subsequent treatment with LDA promotes elimination to Compound 43. Following TFA mediated deprotection, epoxidation of vinylsulfonamide with H$_2$O$_2$ provides Compound 45, while treatment of β-ketosulfonamide with Corey's dimethylsulfonium methylide provides Compound 44. Both epoxides 44 and 45 should be isolated as a mixture of diastereomeric epoxides.

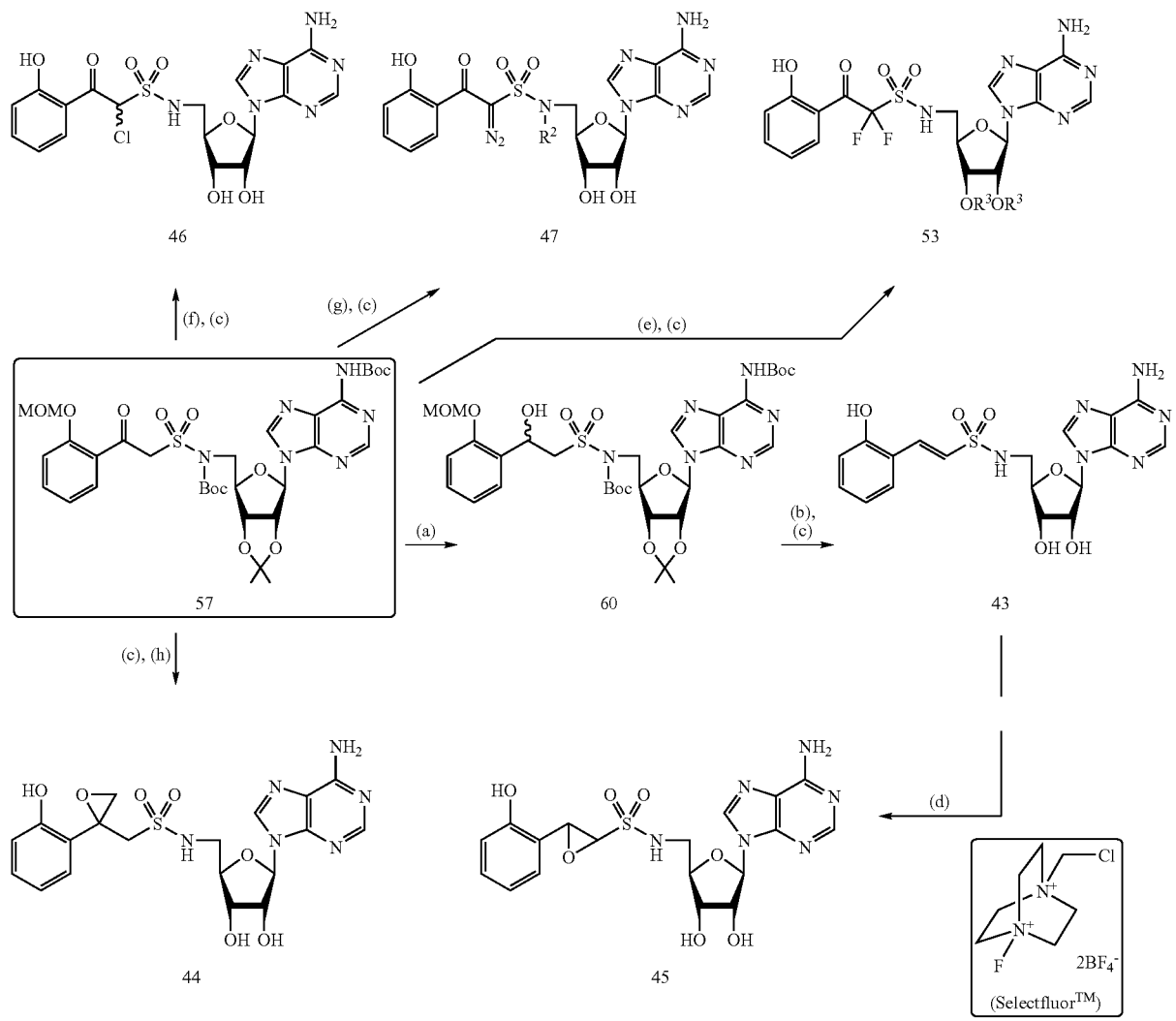
Scheme 6[a]
[a]Reaction conditions: (a) i) NaBH$_4$, MeOH; (b) LDA, THF; (c) 80% aq. TFA; (d) H$_2$O$_2$, THF:H$_2$O; (e) Selectfluor, DBU, THF; (f) NCS, DCM; (g) 4-acetamidobenzenesulfonyl azide, DBU; (h) Me$_3$S$^+$I$^-$
Alternatively, Compound 43 can be prepared as illustrated below.
Scheme 7[a]
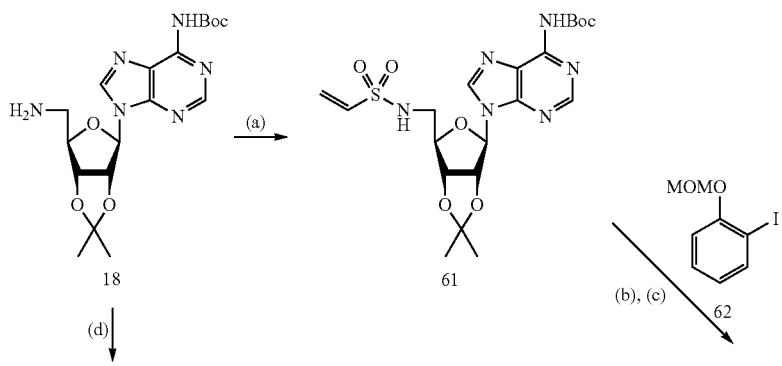

-continued

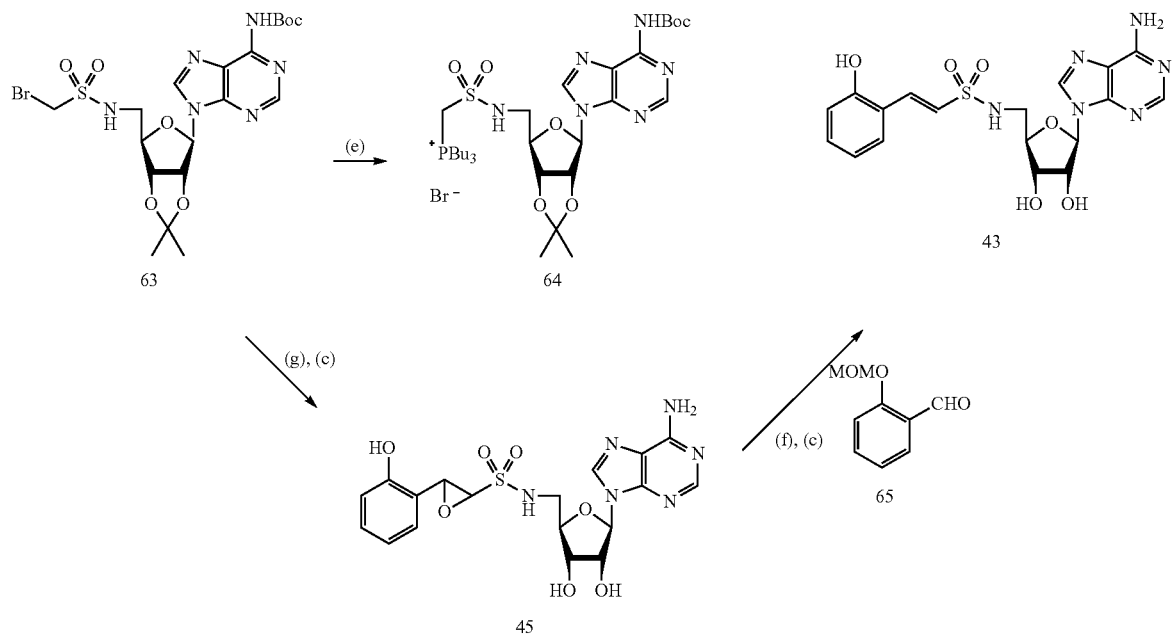

<sup>a</sup>Reaction conditions: (a) ClCH₂CH₂SO₂Cl, Et₃N (2.0 equiv.); (b) Pd(PPh₃)₂Cl₂, DMF, Et₃N, 62, 100° C.; (c) aq. TFA; (d) BrCH₂SO₂Cl, DMAP; (e) PBu₃, DCM; (f) Et₃N, THF; (g) 65, NaH.

Treatment of Compound 18 with 2-chloroethylsulfonyl chloride and one equivalent of Et₃N first provides a sulfonamide intermediate. Addition of a second equivalent of Et₃N then promotes β-elimination and provides Compound 61. Heck coupling with aryl iodide 62 mediated by Pd(PPh₃)Cl₂ yields Compound 43 after deprotection.

Yet another alternate route to Compound 43 involves treatment of 18 with bromomethylsulfonyl chloride to furnish Compound 63, which can be converted to the phosphonium salt and coupled to aldehyde 65 through a Horner-Wadsworth-Emmons olefination. Darzen's condensation of Compound 63 with aldehyde 65 provides a direct entry to epoxysulfonamide 45.

Representative compounds of the invention can also be illustrated as follows.

Scheme 8<sup>a</sup>

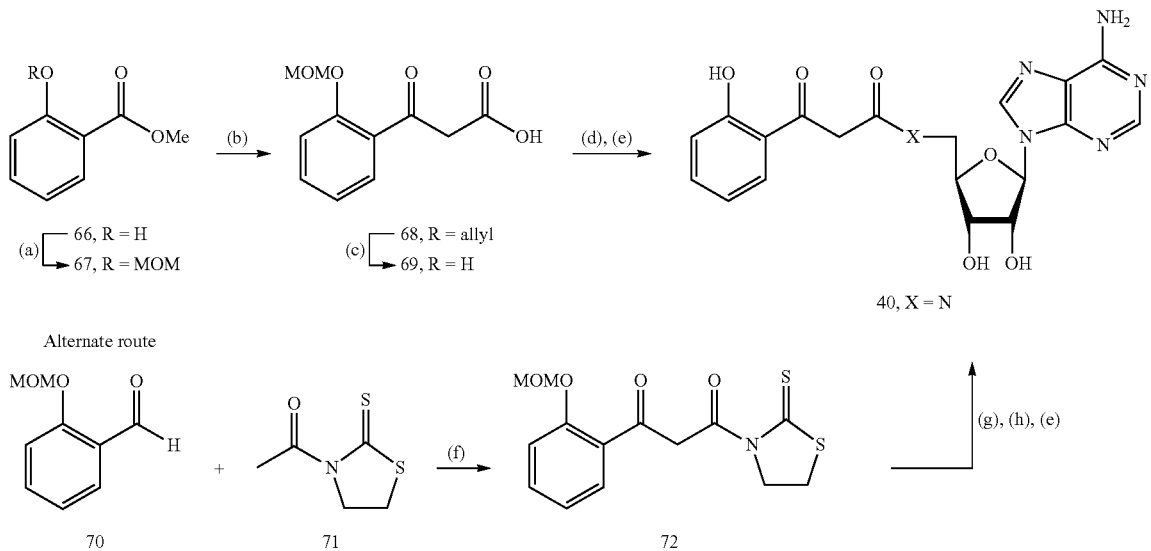

<sup>a</sup>Reaction conditions: (a) MOMCl, K₂CO₃, acetone; (b) allyl acetate, LDA, THF; (c) Pd(PPh₃)₄, PhSO₂Na, THF/MeOH; (d) EDC, HOBt, 18; (e) aq. TFA; (f) TiCl₄, DIPEA; (g) 18, DMAP, DCM; (h) SO₃•pyr, DMSO.

Synthesis of β-ketoamide 40 begins by MOM protection of methyl salicylate 66 to provide Compound 67. Subsequent crossed Claisen condensation with the lithium enolate of allyl acetate furnishes Compound 68. Palladium catalyzed deprotection utilizing phenylsulfinic acid as the allyl scavenger provides β-hydroxy acid 69 which is coupled to Compound 18 followed by TFA mediated deprotection to afford Compound 40. The proposed carbodiimide mediated activation of a β-ketoacid, while direct, is potentially plagued by aberrant decarboxylation. Alternatively, a crossed Aldol condensation between 70 and 71 provides Compound 72. DMAP catalyzed displacement of the thiazolidinethione with Compound 18 followed by Parikh-Doering oxidation of the β-hydroxy group and deprotection affords Compound 40.

As illustrated below, synthesis of sulfonylsulfonamide 48 and sulfoximinylsulfonamide 49 begins with MOM protection of known disulfide 73 to provide Compound 74 that is reduced with NaBH$_4$ to yield mercaptophenol 75. Alkylation of 75 with bromomethylsulfonamide 63 provides intermediate 76 that can be oxidized by NaIO$_4$ to provide a mixture of diastereomeric sulfoxides 77 or treated with mCPBA to furnish target sulfonylsulfonamide 48. Imination of sulfoxide 77 by O-mesitylenesulfonylhydroxylamine yields sulfoximinylsulfonamide 49.

The α-diketone 51 and the tricarbonyl 52, transition state inhibitors that contain an electrophilic carbonyl group, can be synthesized as illustrated below.

Scheme 10$^a$

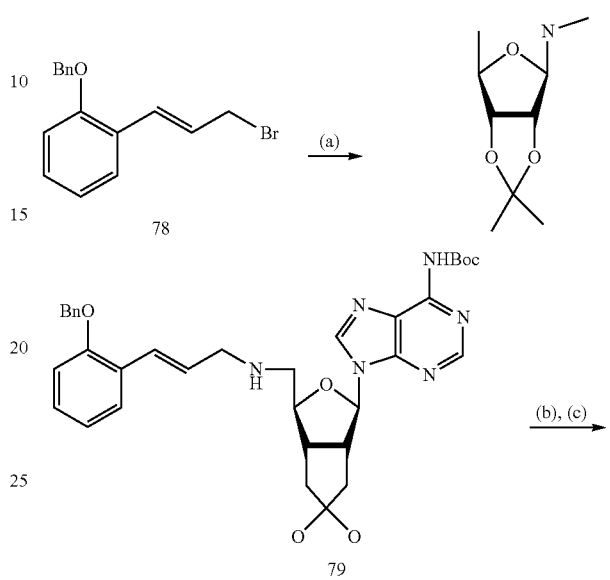

Scheme 9$^a$

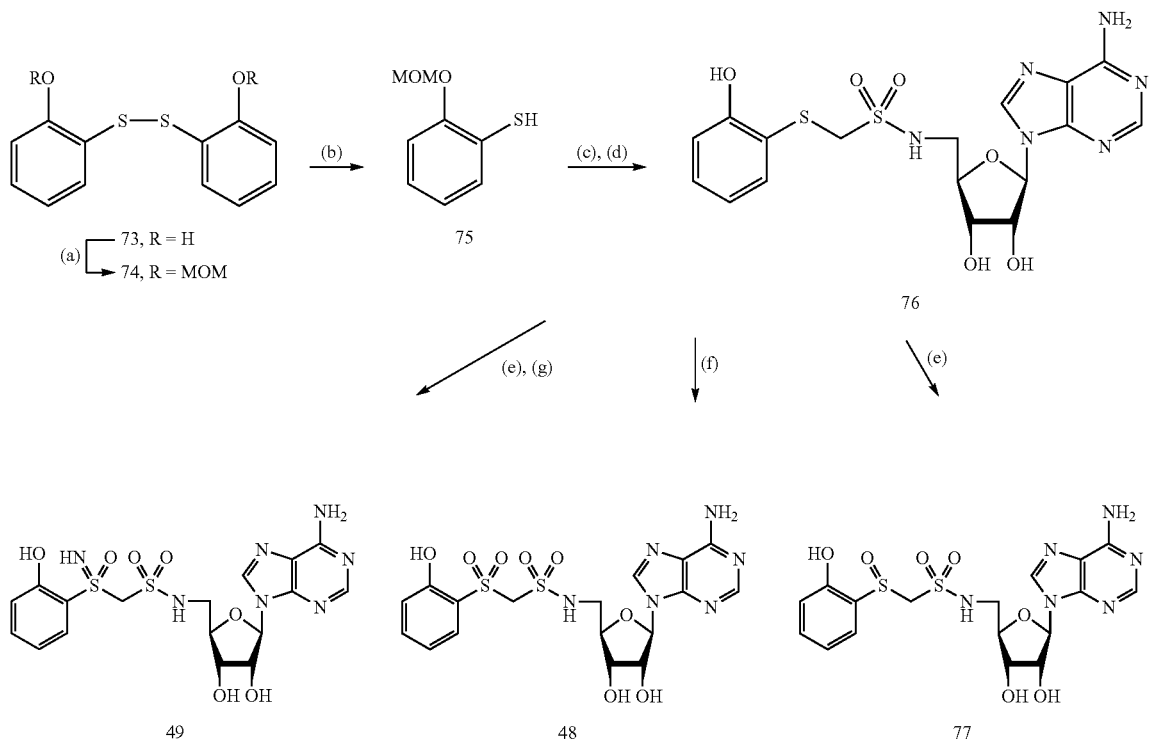

$^a$Reaction conditions: (a) MOMCl, K$_2$CO$_3$, acetone; (b) NaBH$_4$, MeOH; (c) Cs$_2$CO$_3$, DMF; (d) aq. TFA; (e) NaIO$_4$, THF/H$_2$O; (f) mCPBA, EtOAc; (g) O-mesitylenesulfonylhydroxylamine (MSH), MeCN.

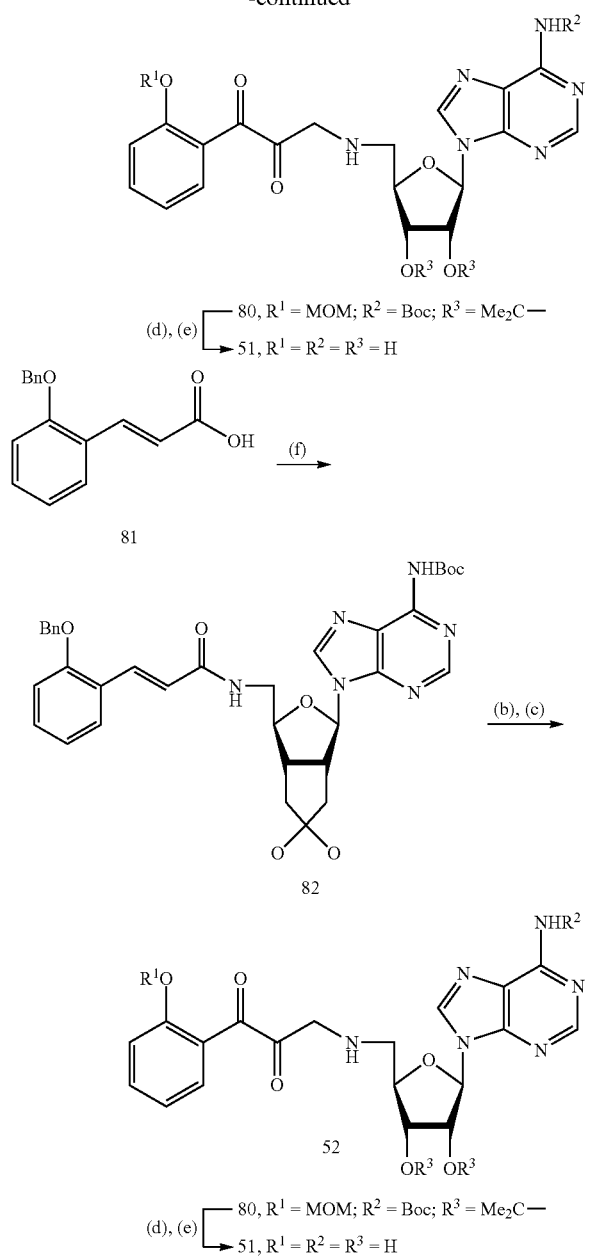

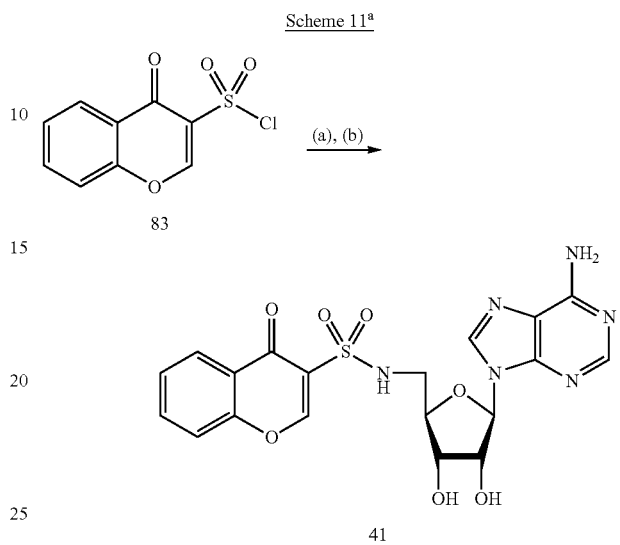

Chromone analogue 41 can be prepared by coupling known sulfonyl chloride 83 to Compound 18 followed by deprotection to furnish Compound 41.

Scheme 11[a]

[a]Reaction conditions: (a) 18, Et$_3$N; (b) aq. TFA.

$R_1$ Modifications

The following $R_1$ groups can be incorporated into the compounds of the invention using known synthetic methods or using methods similar to those described herein.

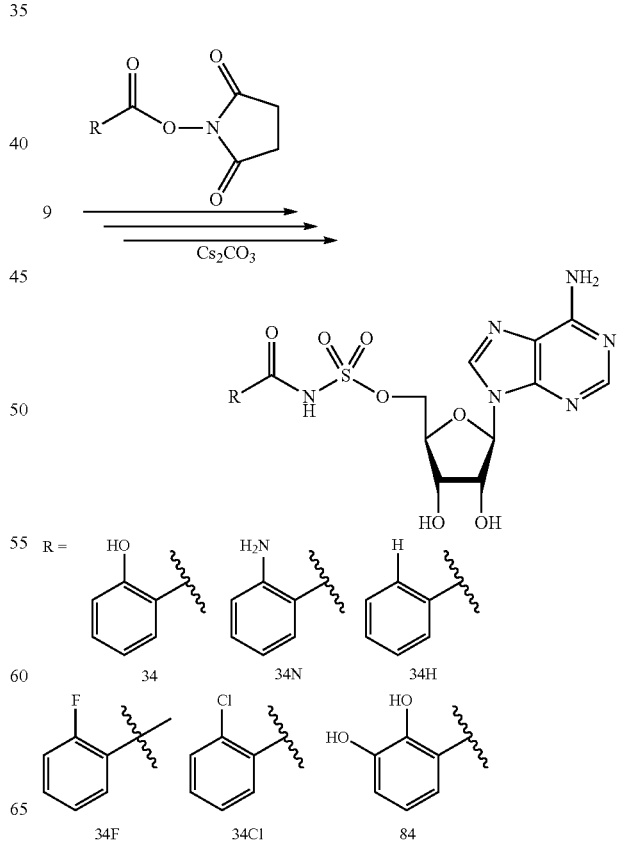

[a]Reaction conditions: (a) 18, Cs$_2$CO$_3$, DMF; (b) OsO$_4$ (1 mol %), NMO, THF; (c) TEMPO, DCM; (d) H$_2$, Pd/C; (e) aq. TFA; (f) 18, EDC, DCM.

Synthesis of α-diketone 51 commences with alkylation of Compound 18 with known allylic bromide 78 employing Cs$_2$CO$_3$ to furnish Compound 79. Standard OsO$_4$ catalyzed dihydroxylation followed by TEMPO mediated oxidation is expected to provide Compound 80 that can be sequentially deprotected to provide Compound 51. The unique vicinal tricarbonyl scaffold can be assembled using the elegant methodology developed by Wasserman; however, this requires the use of ozonolysis or dimethyldioxirane to liberate the tricarbonyl, which is expected to be incompatible with the adenine moiety. Instead a simple EDC mediated coupling of Compound 81 with Compound 18 to furnish vinylamide 82 that can be oxidized in a stepwise fashion to provide the tricarbonyl Compound 52 after deprotection.

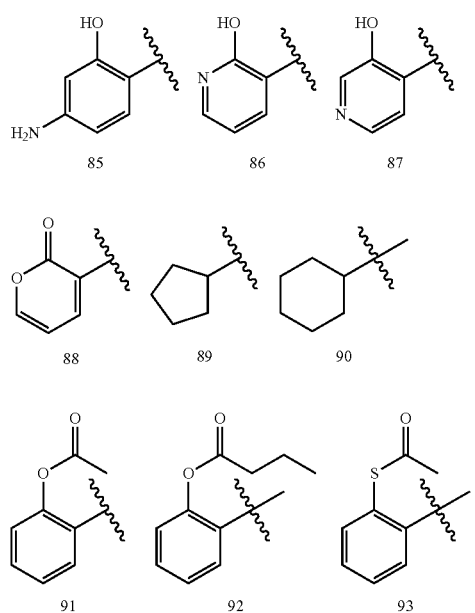

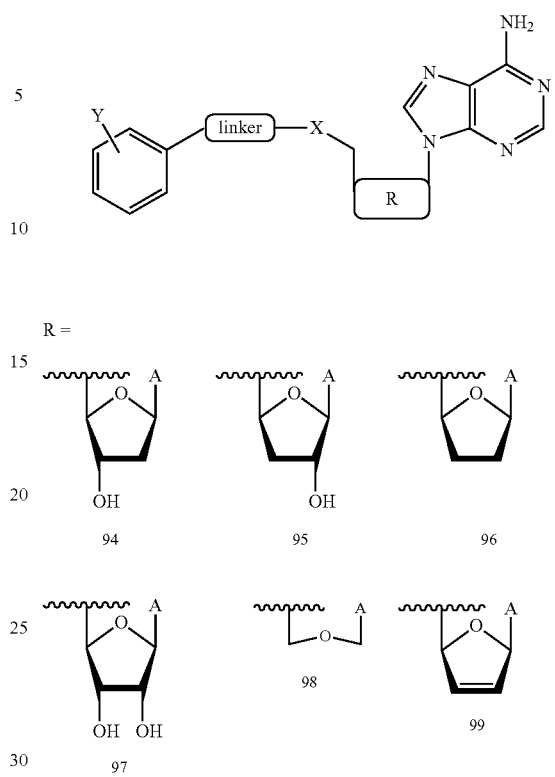

The phenol function of the salicyl moiety provides a handle to introduce various acyl groups that can potentially i) provide irreversible mechanism based inhibitors, ii) serve to enhance the lipophilicity, and iii) act as pro-drugs if the corresponding acyl groups can be hydrolyzed by one of the many lipases present in *M. tuberculosis*. Acetyl analog 91 is noteworthy since it can potentially acetylate the nucleophilic sulfhydryl group of the phosphopantetheinyl (ppan) arm of the downstream protein MbtB. The butyryl analog 92 serves to increase the lipophilicity and longer chain analogs can be evaluated if this is found to bind with reasonable affinity. The corresponding thioacetyl analog 93 is a more reactive thioester and transthioesterification to the ppan arm of MbtB should be enhanced. Since MbtA catalyzes the transfer of the acyl adenylate onto MbtB, it could itself hydrolyze the pro-drug obviating the need for an accessory lipase. Inhibitors 34F, 34Cl, 84-90 can be prepared by coupling the respective activated N-hydroxy succinimide (OSu) esters to sulfamate 9 and elaborated to the final targets in analogy to the preparation of 34. Derivatives 91-93 will require a slight modification to this procedure since the acyl groups of the respective aryl-OSu esters may not be stable to the basic conditions utilized to effect coupling to 9. Instead the free acids can be coupled to sulfamate 9 employing PyBOP and DIPEA in DMF. The corresponding carboxylic acids of 34F, 34Cl, 84-86, 89-91 are commercially available while the carboxylic acids employed for the synthesis of 87, 88 can be prepared from known procedures. Compounds 92-93 can be synthesized by acylation of commercially available salicylic acid and 2-mercaptobenzoic acid respectively.

$R_2$ Modifications

The $R_2$ groups described herein can be incorporated into the compounds of the invention using known synthetic methods or using methods similar to those described herein. For illustration, a specific set of $R_2$ groups is shown and discussed below.

Inhibitors 94-96 are prepared from the corresponding commercially available adenosine nucleosides while carbocyclic analog 97 is derived from the natural product aristeromycin (supplied by R. Vince, Center for Drug Design, University of Minnesota). Inhibitors 98 and 99 can be prepared from acycloadenosine and carbocyclic adenosine respectively, which are prepared according to the literature procedures. The $N^6$-Boc protected nucleosides can be used for the synthesis of 94-99 and the 2' and 3' alcohols of 94-95 are protected as TBS ethers while 97 is protected as the acetonide. The protected nucleosides can be coupled to the linker portion of formula I using known procedures.

B Modifications

The following B groups can be incorporated into the compounds of the invention using known synthetic methods or using methods similar to those described herein

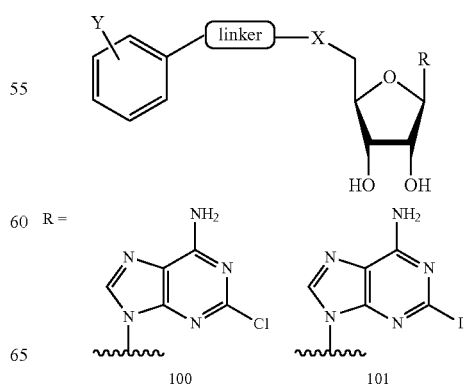

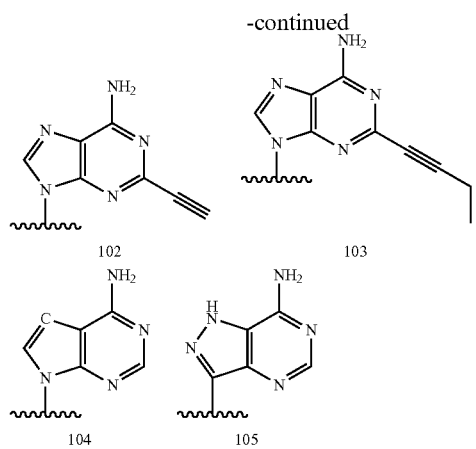

The 2-chloroadenosine analog 100 notable since the electron-withdrawing chlorine serves to decrease the basicity of the adenine $NH_2$ group and thus decreases the susceptibility of this function to deamination by purine deaminase—one of the major metabolizing enzymes of purine catabolism. In the present case, the chlorine is also expected to provide a slight increase in lipophilicity. The 2-iodoadenosine analog 101 follows this trend and has the additional benefit that the iodo group provides a handle for introduction of various functionality through either palladium or copper mediated reactions. Thus, analogs 102 and 103, which contain a 2- and 4-carbon alkynyl chain appended to the C-2 position, can be prepared from 101. Moreover, these analogs increase the lipophilicity. Finally, two analogs with modifications to the purine heterocycle can be synthesized. These are 7-deazadenosine analog 104 and the fluorescent C-nucleoside derivative 105 that provides metabolic stability of the labile glycosidic linkage and may allow for the development of a fluorescent displacement assay to measure binding affinities (in one embodiment the invention also provides such an assay). Nucleosides 100, 101, and 102-103 are prepared by established methods while 104 is a natural product known as Tubericidin (Dr. Herbert Nagasawa at the V. A. Hospital, Minneapolis, Minn. generously provided 2 g of this valuable natural product) and 105 is derived from Formycin A, which is commercially available from Sigma.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Ferreras, J. A., et al., *Nature Chem. Biol.* 2005, 1, 29-32 reported the activity of analogue 34 against *M. tuberculosis* H37Rv ($MIC_{50}$ 2.2 μM). These studies likely utilized the free acid form of Compound 34, since the isolation of the salt form was not reported, and since it was explicitly stated that the compound was "uncharged" (see page 29 therein). It has now been determined that the free acid is extremely acidic (calculated $pK_a=0.6$), and that it is chemically unstable; the free acid was found to decompose significantly during storage at 0° C. As a result, the free acid of Compound 34 is not an attractive drug candidate. The salt form of Compound 34 that was prepared in Example 1 below was found to be significantly more stable than the free acid discussed by Ferreras, J. A., et al. Additionally, the salt form was found to be about 28 times more potent against *M. tuberculosis* H37Rv than the free acid. Accordingly, in one embodiment of the invention, the compounds of the invention exclude the compound 5'-O—(N-(2-hydroxybenzoyl)sulfamoyl)adenosine. In another embodiment, the invention provides a salt of the compound 5'-O—(N-(2-hydroxybenzoyl)sulfamoyl)adenosine. Typically, the salt will be at least about 2 times more stable than the free acid. In another embodiment of the invention, the salt is at least about 5 times more stable than the free acid.

The compounds of formula I can be formulated as pharmaceutical compositions and administered to a host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to act as an inhibitor of one or more adenylating enzymes and/or to produce an antibiotic effect can be determined using pharmacological models which are well known to the art, or using the assays described below.

Adenylation Inhibition Assay. An ATP-[$^{32}$P]PP$_i$ exchange assay that can be used to measure the substrate specificity of adenylation domains has been described (see Linne, U.; Marahiel, M. A. *Methods Enzymol.* 2004, 388, 293-315). The assay exploits the equilibrium nature of the acylation reaction which can be summarized as follows: E+S+ATP↔[E-S-AMP]+PP$_i$. Since the product S-AMP remains tightly bound to the enzyme, a steady-state kinetic analysis in the forward direction cannot be performed due to product inhibition. However, measurement in the reverse direction allows one to examine substrate selectivity in a steady-state process. Thus, $^{32}$PP$_i$ is added and its incorporation to [$^{32}$P]ATP is measured. The $^{32}$P-ATP formed is isolated by adsorption onto charcoal and the charcoal is washed to remove [$^{32}$P]PP$_i$. The charcoal is transferred to a scintillation vial and counts are measured on a Beckman 6800 scintillation counter using liquid-scintillation-counting. Data Analysis. The counts obtained from above are used to determine the initial velocity of $^{32}$P-ATP formation ($v_0$). Measuring the initial velocity ($v_0$) at in the presence of various concentrations of inhibitor allows one to measure the $K_I$ values of the inhibitors. Potential irreversible inactivators are examined for any noncompetitive behavior by pre-incubating with MbtA for various times. A time dependent inhibition is evidence for irreversible inactivation.

Thiolation Domain Inhibition Assay. The thiolation domain of MbtB is hereafter simply referred to as ArCP or aryl carrier protein domain. The ability of the thiolation domain inhibitors to irreversibly modify the phosphopantetheinyl cofactor of ArCP can be evaluated using the representative enzymatic assay conditions described below. These conditions are based in part on the assay developed by Walsh and co-workers for the covalent incorporation of aryl and amino acids onto thiolation domains. These researchers utilized both mass spectrometry as well as a radiolabeled substrates to verify acylation of the thiolation domains. In order to directly confirm the covalent adduct LC-MS-MS analysis of a proteolysis digest of the inhibitor-modified ArCP can be used to confirm site-specific labeling of the phosphopantetheinyl moiety. MALDI-TOF is sufficient to confirm overall covalent labeling. Additionally, HPLC analysis can be utilized to determine the rate of irreversible modification. Thiolation domains do not possess innate specificity and rely on the cognate adenylation domains to channel the substrate onto the ppan cofactor, thus MbtA will be included in the enzymatic assay. The background non-specific rate due to diffusional collision of the inhibitor and ArCP is expected to be negligible. In fact, Cox and co-workers have succeeded in loading simple thioester substrates onto independent ACP domains of PKS modules and have indeed observed covalent modification; however, this required in some cases several hours to achieve complete modification demonstrating that the non-specific diffusional loading can take place albeit at an extraordinary low rate whereas Walsh and co-workers observed rates of 130 min$^{-1}$ for loading of a PCP domain by the cognate adenylating enzyme. In order to remove any ambiguity from the results the C7S ArCP mutant can also be employed. Assay to measure covalent modification. MbtA (1 μM) and C7S holo-ArCP (1 μM) in 100 mM Tris.HCl (pH 7.5), 1 mM Tris-(2-carboxyethyl)phosphine (TCEP), 10 mM MgCl$_2$, and 5% DMSO in a final volume of 200 μL is incubated at 37° C. with 25 μM inhibitor. TCEP introduced by Whitesides as an alternative and non-nucleophilic reducing agent is used in place of the common reducing agent DTT that possesses competitive thiol groups (Burns, J. A., et al., *J. Org. Chem.* 1991, 56, 2648-2650). After a specified time (~30 min) the entire reaction mixture is filtered using a 30 kD MWCO filter (Amicon, YM-30) to remove MbtA (MW 59.3 kDa). The filtrate is then diluted 10-fold with ddH$_2$O and concentrated to ⅒ volume using a 3 kD MWCO filter (Amicon, YM-3) to purify ArCP (9.1 kDa). This process is repeated twice more and the resulting purified inhibitor-bound-ArCP adduct is digested with trypsin and analyzed by LC-MS-MS using a Finnigan-MAT apparatus equipped with an ion-trap employing ESI ionization (Mass Spec Core Facility, University of Minnesota). Assay to measure pseudo-first order rate constant of inactivation. The assay can be repeated as above; however, it will likely be necessary to significantly dilute the enzyme concentrations in order to reduce the observed rate. Since the inhibitors are first bound by MbtA then channeled to ArCP, we will use a 10-fold excess of MbtA relative to ArCP. The inhibitor and MbtA are first incubated for 10 minutes to form a MbtA-inhibitor complex. Addition of ArCP initiates the reaction and the observed rate of modification of ArCP is a pseudo first-order process. The reaction will be quenched with TCA and the ArCP can be purified as described above; however, the purified mixture of ArCP and inhibitor-ArCP adduct can be directly analyzed by HPLC. Cox and co-workers have shown that acylated thiolation domains (e.g. holo-ACP-acyl adduct: calculated mass 9601 Da, $t_{ret}$[min]=14.8 min) can be resolved by HPLC from thiolation domains (holo-ACP: calculated mass 9441 Da, $t_{ret}$[min]=15.9 min) where the mass difference is less than 200. These researchers employed a Phenomenex "Jupiter" column (250×4.6 mm, C5, 300 Å) at a flow-rate of 1 mL/min. Buffer A=0.1% TFA in ddH$_2$O, buffer B=0.05% TFA in CH$_3$CN. These conditions can also be employed to determine the pseudo first-order rate constant for inactivation of ArCP, which provides a measure of inhibitor potency for irreversible inactivators.

Cytotoxicity Assay. This is a standard assay used to screen for toxicity of nucleoside analogues. P388 cells are plated in 12-well plates at 1.5×10$^5$ cells per well (2 mL). A two-fold serial dilution of the compound is prepared to provide a final concentration from 100 μg/mL down to 1.56 μg/mL and a final concentration of 1% DMSO. The cells are incubated at 37° C., 5% CO$_2$ for 3 days and the cells are counted using a hemocytometer and the data analyzed using Graphpad Prism Version 4.0 to provide IC$_{50}$ values. Puromycin is used as a positive control while DMSO is employed as the negative control. Representative compounds of the invention were tested in this assay and they did not display significant toxicity at the maximum concentration tested (100 μg/mL).

Siderophore Production Assays. This assay was developed in Dr. Clifton Barry's labs and uses a low iron GAST (glycerol-alanine-salts) medium except ferric ammonium citrate is omitted and Tween 80 is added to 0.05% (see De Voss, J. J., *Proc. Natl. Acad. Sci. USA* 2000, 97, 1252-1257). Low-iron GAST (50 mL) is inoculated with H37Rv to an OD$_{650}$ of 0.05 and incubated at 37° C. Cultures are grown in this medium to an OD650 of 0.20 after which cells are harvested and resuspended in an equivalent volume of Chelex-deferrated GAST medium. Cultures (1 mL) are treated with the inhibitors at 10 and 100× the MIC$_{99}$ values from drug stocks in DMSO whereas a control culture is treated with an equivalent amount of DMSO (0.5%). Siderophore inhibition is dependent on the initial cell density as larger cell densities require a higher drug concentration due to drug inactivation by the higher cell count as well as increased likelihood of resistant mutants. To monitor mycobactin biosynthesis, [7-$^{14}$C]salicylic acid is added to the cultures to a specific activity of 1.25 mCi/mL. After 3 days of incubation, the cultures are centrifuged. The carboxymycobactins in the supernatant are recovered as the iron complex by addition of ferric chloride (0.555 mM final concentration) and extraction with chloroform. The lipid soluble mycobactins in turn are isolated from the cell pellet, which is suspended in ethanol and agitated overnight. The supernatant is treated with ferric chloride (2 mM final concentration), incubated for one hour and partitioned between chloroform and water. The organic layer is concentrated to afford crude mycobactins. The crude mycobactins and carboxymycobactins are taken up in a minimum of chloroform and subjected to TLC analysis eluting with the ternary solvent system consisting of 2:3:3 petroleum ether:n-butanol:ethyl acetate. The plate is dried and analyzed by a PhosporImager.

Microarray Analysis. Dr. Barry's group has developed this assay to generate data sets of 75 different drugs, drug combinations, or different growth conditions. (see Boshoff, H. I. M.; *J. Biol. Chem.* 2004, 279, 40174-40184) These studies have enabled the grouping of drugs according to mechanism of action and this transcriptional profiling is useful to highlight key metabolic responses. The experimental procedures for growth conditions, RNA isolation, hybridization, microarray preparation, data analysis and quantitative real-time PCR used for these studies was recently reported (see Boshoff, H. I. M.; *J. Biol. Chem.* 2004, 279, 40174-40184)

and can be used to evaluate selected inhibitors that demonstrate potent inhibition of *M. tuberculosis* H37Rv growth in the MIC assay described below. *M. tuberculosis* will be grown to logarithmic growth phase in GAST or GAST-Fe medium after which the cultures will be treated with the inhibitors (at 1, 10 and 100× the $MIC_{99}$ values) or with an equivalent amount of DMSO for 6 hours. RNA is isolated and microarray hybridizations are performed. Transcriptional profiles elicited by the mycobactin biosynthetic inhibitors will be compared to transcriptional profiles generated by other groups or classes of drugs by hierarchical cluster analysis and by use of a class prediction tool (see Tibshirani, R.; et al., *Proc. Natl. Acad. Sci. USA* 2002, 99, 6567-6572). It is anticipated that inhibition of mycobactin biosynthesis will lead to transcriptional profiles that share some overlap in gene expression profile with iron scavengers such as pyridoacridines, deferroxamine and dipyridyl although significant differences are expected due to the different mechanism of action of these compounds.

*M. tuberculosis* H37Rv MIC Assay. This assay uses *M. tuberculosis* H37Rv to determine MIC values. The use of a single strain for screening is justified since wild-type strains of *M. tuberculosis* tend to have uniform susceptibilities to inhibitors, unlike other mycobacteria such as the *M. avium* complex. *M. tuberculosis* H37Rv is cultured in GAST with no added iron for growth under iron limitation and in GAST supplemented with 200 μM $FeCl_3$ for iron-rich conditions. Minimum inhibitory concentrations (MICs) are determined in iron-deficient or iron-replete GAST according to the broth microdilution method (see Domenech, P; et al., *Infect Immun.* 2005, 73, 3492-3501) using drugs from DMSO stock solutions or with control wells treated with an equivalent amount of DMSO. Plates are incubated at 37° C. (100 μl/well) for 7-10 days and growth is recorded by measurement of optical density at 620 nm. $MIC_{50}$ values are calculated from the sigmoidal dose response curve. Representative compounds of the invention were found to inhibit *M. tuberculosis* H37Rv using this assay.

*M. tuberculosis* Drug-resistant Strains MIC Assay. Compounds can be tested against a panel of multidrug resistant strains for which to resistant-conferring mutation is known. These strains include ones that are resistant to combinations of some of the following drugs: isoniazid, rifampin, streptomycin, ethionamide, ethambutol, kanamycin, ofloxacin, and amikacin.

Macrophage Infection Assays. This assay has previously been reported (see De Voss, J. J.; et al., *Proc. Natl. Acad. Sci. USA* 2000, 97, 1252-1257). Briefly, J774 macrophages are infected with bacteria at a multiplicity of infection of 1:1 for 1 hr at 37° C., 5% $CO_2$. Bacteria used for J774 infections are from freshly grown logarithmic cultures. For inocula grown in various iron concentrations, bacteria are grown in GAST to midexponential phase ($OD_{620}$ 0.5), washed once with GAST-Fe, and used to inoculate GAST-Fe medium supplemented with 0, 0.5, 5, or 500 μM additional $FeCl_3$ to an $OD_{620}$ of 0.1. Two days later cultures are adjusted to $OD_{620}$ 0.2 with GAST-Fe and diluted to the appropriate cell density in DMEM/10% fetal calf serum. Infected monolayers then are washed four times with 1 mL of DMEM and fed 1 mL of DMEM/10% fetal calf serum. Cultures are incubated for 7 days before performing luciferase assays or cfu determinations. For this, the medium is removed by aspiration and 0.25 mL of 1% Triton X-100 added to lyse the J774 cells. After a 5-min incubation, 10-fold serial dilutions are made in 7H9 medium and 0.1 mL aliquots plated on 7H11 agar for CFU enumeration. Alternatively, 50 μL of lysate is mixed with 50 μL of LucLite substrate (Packard) in an opaque, 96-well plate (Dynex Technologies, Chantilly, Va.), incubated in the dark for 10 min, and assayed on a Top Count luminescent reader (Packard). Input relative light units are determined in quadruplicate directly from the diluted bacteria used for infection.

Latent TB Model Assay. The Wayne model (see Wayne, L. G.; Sohaskey, C. D.; *Ann. Rev. Microbiol.* 2001, 55, 139-163) for non-replicating persistence wherein growth is limited by oxygen depletion can be used in these assays. This model is based on the assumption that certain granulomas in the human lung become anoxic. In this model, cultures of *M. tuberculosis* are grown in Dubos medium in closed, sealed tubes with a head-space ratio of 0.5 with constant stirring. These cultures become anaerobic within 3 weeks and the ability of drugs to kill the anaerobically persisting cells is measured at 4 weeks. This is done in an anaerobic hood where cultures are dispensed in 24-well plates (1 mL per well)+/− drug or DMSO and incubated for one week. Metronidazole is used as positive control since *M. tuberculosis* becomes sensitive to this drug under anaerobic conditions whereas isoniazid is used as negative control where non-replicating *M. tuberculosis* becomes isoniazid-resistant. After 1 week, cultures are plated out on 7H11-based agar for CFU determination.

Pharmacokinetic Studies. To obtain dosage information for in-vivo studies in mice, PK studies can be performed using mice, which are dosed with several concentrations of inhibitor and bled at 15, 30, 60 and 120 minutes after drug administration. The serum concentration of drug can be determined by HPLC-based methods where drug is directly measured in the serum or by an indirect method where the serum is used to set up an MIC test using the broth microdilution method. In the latter assay, the presence of drug in the serum results in growth inhibition in the broth microdilution assay as long as the drug concentration exceeds a certain minimum concentration. The maximum amount of serum that can be used per well is 10% of the final volume, thus the serum concentration should typically be at least 10-fold higher than the MIC in order to obtain growth inhibition in the assay.

Mouse Model of TB. In brief, 6-8 week old female C57BL/6 mice are infected via the aerosol route with 100-200 CFU (colony forming units) per lung. On the day of infection, some mice are sacrificed for enumeration of lung CFU by homogenization of the lung in 2 mL 7H9-based media and plating of the homogenate on 7H11-based agar plates. To determine efficacy of the drug, mice will be treated with the drug after 10-14 days of infection when the CFU in the lung has reached 1000-10000. At this stage of infection the organism is still growing logarithmically in the lung since adaptive immunity has not yet fully set in. Treatment of mice at this stage of infection will thus enable us to determine efficacy of the drug against actively growing *M. tuberculosis* in vivo. Alternatively, mice can be treated with the drug after 4 weeks of infection after onset of acquired immunity. In C57BL/6 mice, the onset of acquired immunity results in restriction of bacterial growth in the lung so that bacterial numbers plateau at approximately $10^6$ CFU in the lung in a chronic phase that lasts for several months after which destruction of lung tissue contributes to organ failure, sudden increase in CFU and death of the animal. Mice can be treated for a duration of 4 weeks with daily drug administration by oral gavage with weekly plating of lungs and spleens of 4 mice per group for CFU enumeration.

The following Schemes 11-25 illustrate the synthesis of representative compounds of the invention. The invention also provides the synthetic methods and intermediates identified herein.

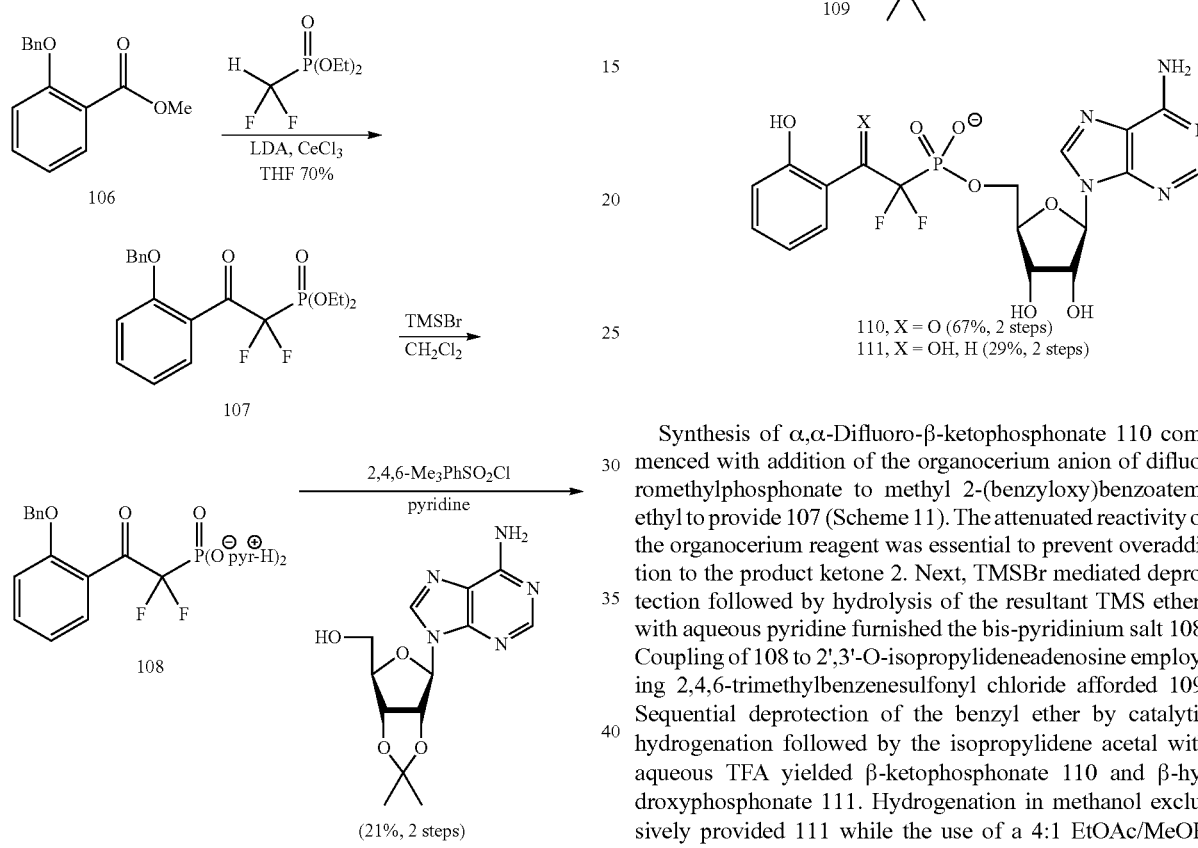

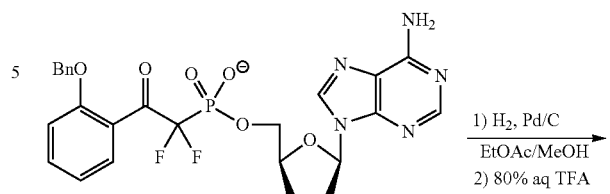

Synthesis of α,α-Difluoro-β-ketophosphonate 110 commenced with addition of the organocerium anion of difluoromethylphosphonate to methyl 2-(benzyloxy)benzoatemethyl to provide 107 (Scheme 11). The attenuated reactivity of the organocerium reagent was essential to prevent overaddition to the product ketone 2. Next, TMSBr mediated deprotection followed by hydrolysis of the resultant TMS ethers with aqueous pyridine furnished the bis-pyridinium salt 108. Coupling of 108 to 2',3'-O-isopropylideneadenosine employing 2,4,6-trimethylbenzenesulfonyl chloride afforded 109. Sequential deprotection of the benzyl ether by catalytic hydrogenation followed by the isopropylidene acetal with aqueous TFA yielded β-ketophosphonate 110 and β-hydroxyphosphonate 111. Hydrogenation in methanol exclusively provided 111 while the use of a 4:1 EtOAc/MeOH cosolvent afforded a selective route to 110.

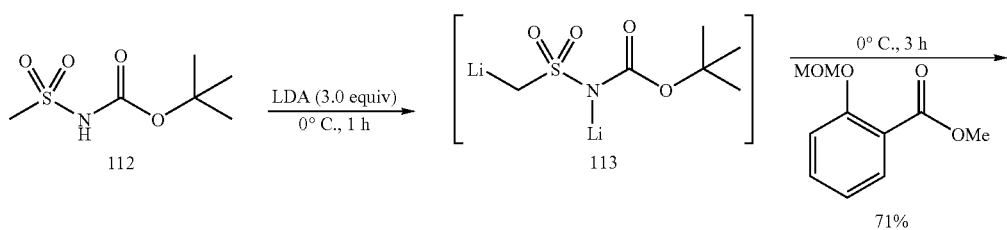

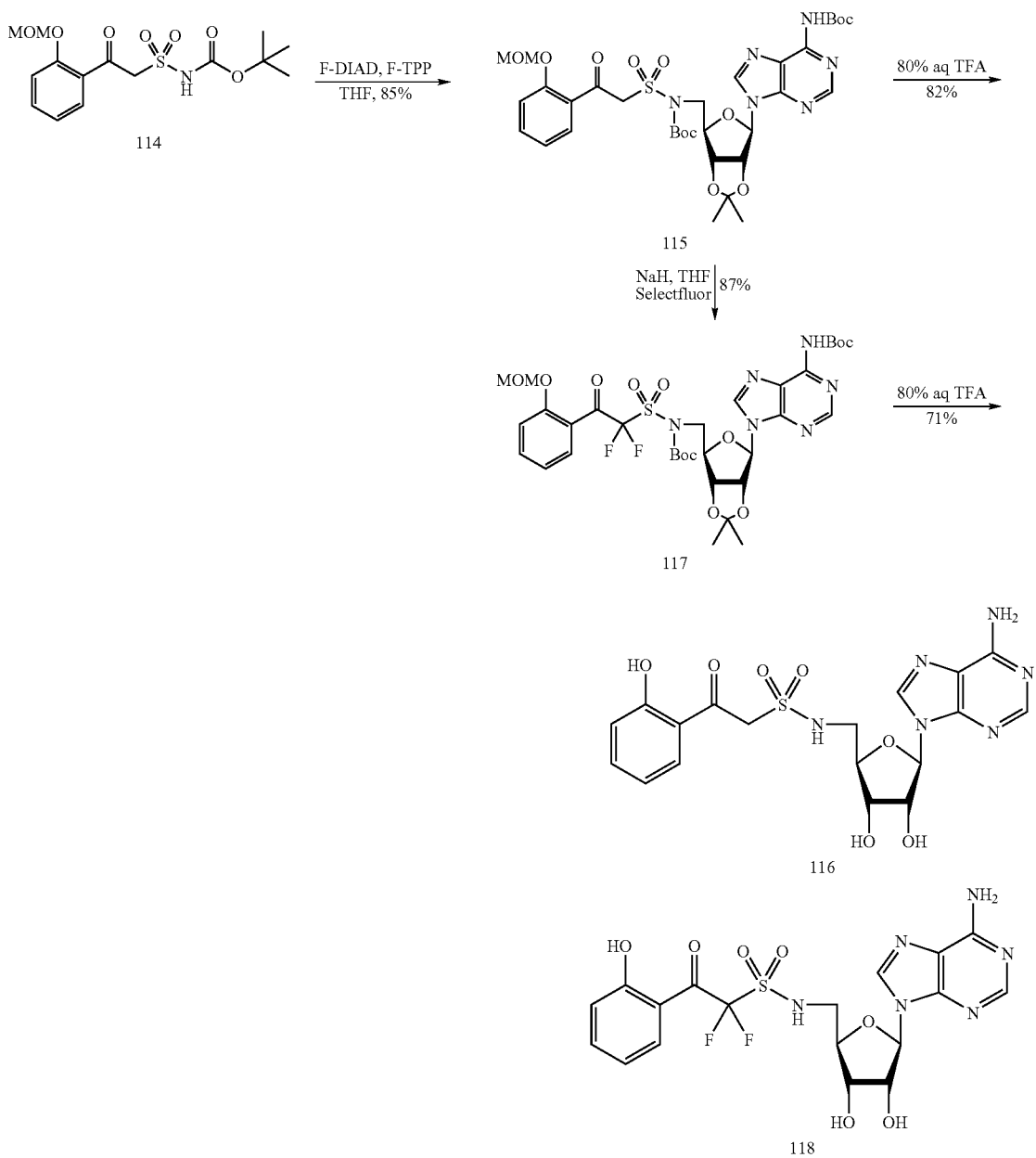

Addition of LDA to N-Boc-methylsulfonamide afforded dianion 113 (Scheme 12). Next a solution of methyl 2-(methoxymethoxy)benzoate was added to provide β-ketosulfonamide 114. Successful Mitsunobu coupling to afford 115 was achieved by addition of F-DIAD via syringe pump to a stirring solution of the β-ketosulfonamide 114, $N^6$-tert-butoxycarbonyl-2',3'-O-isopropylideneadenosine and F-TPP at 0° C. Optimization of these conditions revealed that the DIAD addition time was the most crucial parameter, thus the yield improved from 23% to 82% by increasing the addition time of F-DIAD from 5 to 30 minutes. Attempts to further improve the yield by increasing the total reaction time were unsuccessful, which we speculate is due to the condensation with dicarboalkoxyhydrazine (DCH) to afford an enamine adduct (not shown). The synthesis of β-ketosulfonamide 116 was completed by simultaneous deprotection of the MOM acetal, isopropylidene ketal, and Boc carbamates employing aqueous TFA. Fluorination of the active methylene of 115 with Selectfluor provided 117, which was deprotected to yield α,α-difluoro-β-ketosulfonamide 118.

Scheme 13

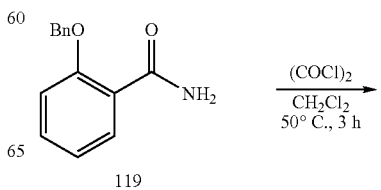

119

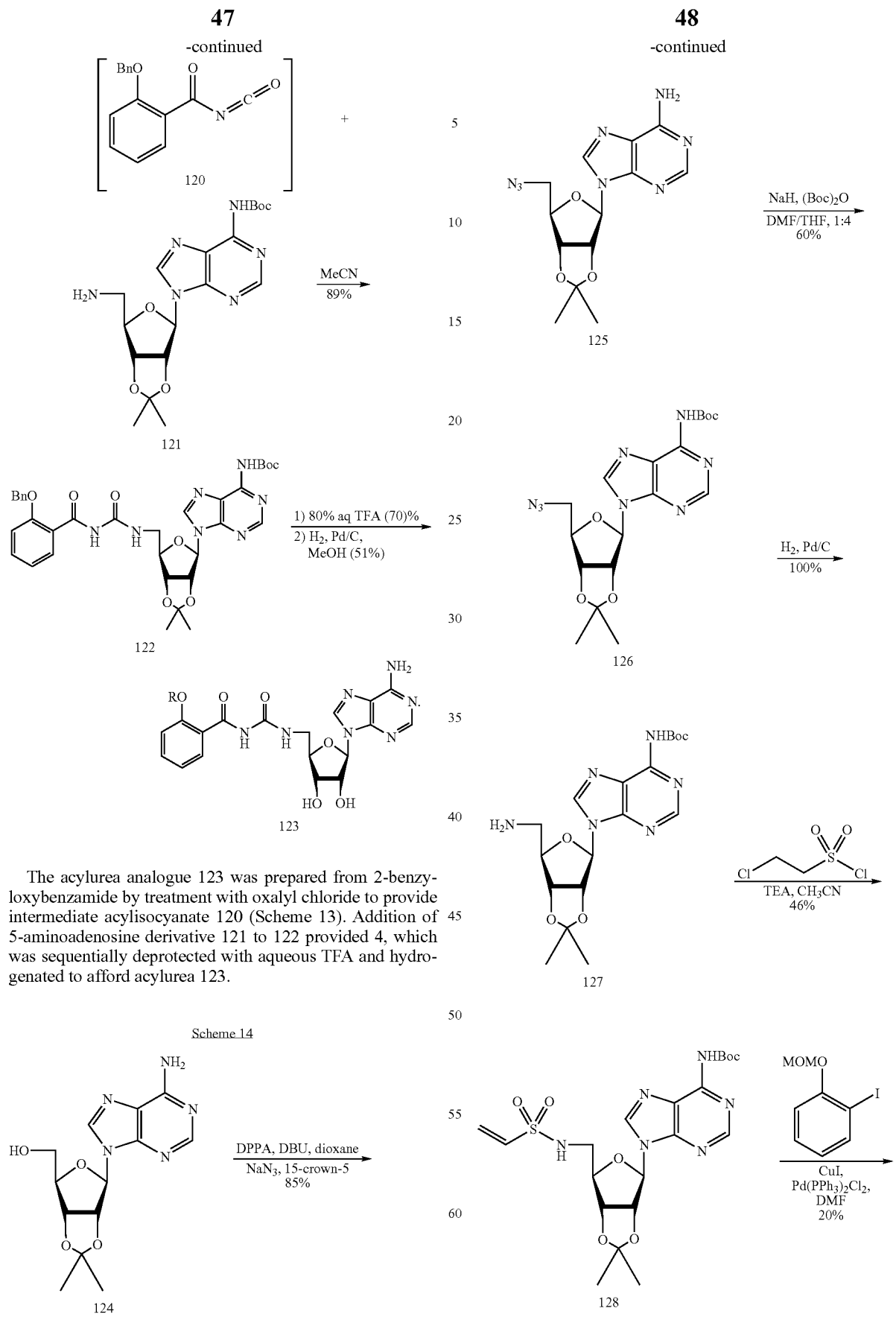
The acylurea analogue 123 was prepared from 2-benzyloxybenzamide by treatment with oxalyl chloride to provide intermediate acylisocyanate 120 (Scheme 13). Addition of 5-aminoadenosine derivative 121 to 122 provided 4, which was sequentially deprotected with aqueous TFA and hydrogenated to afford acylurea 123.

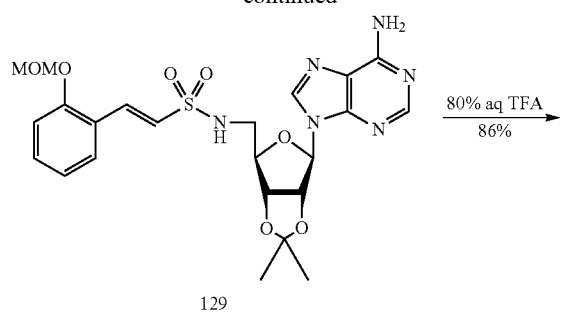

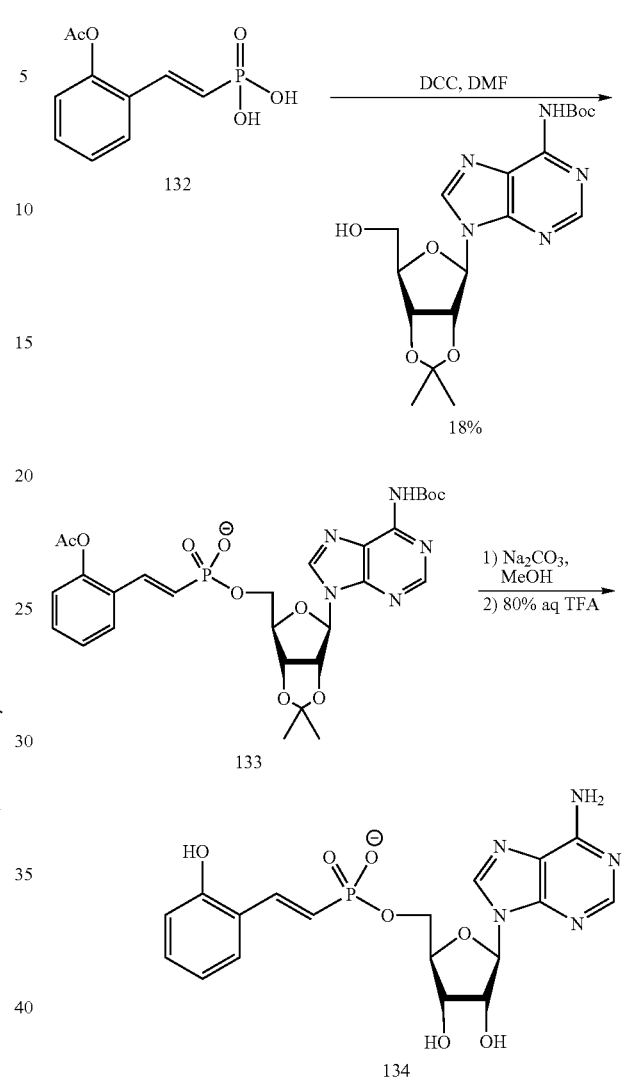

Synthesis of vinylsulfonamide inhibitor 130 was accomplished through conversion of 2′,3′-O-isopropylideneadenosine to the 5-azido derivative 125 employing the procedure of Liu and co-workers (see, Liu, F.; Austin, D. J. *J. Org. Chem.* 2001, 61, 8643-8645) (Scheme 14). Next, protection of the nucleoside as the N[6]-Boc was performed with NaH and Boc$_2$O to furnish 126 which was hydrogenated to provide 127. Treatment of 127 with 2-chloroethylsulfonyl chloride and one equivalent of Et$_3$N first provided a sulfonamide intermediate. Addition of a second equivalent of Et$_3$N then promoted β-elimination to vinylsulfonamide 128. Heck coupling with 1-iodo-2-methoxymethoxybenzene mediated by Pd(PPh$_3$)Cl$_2$ provided 129 that was treated with 80% aq TFA to yield 130.

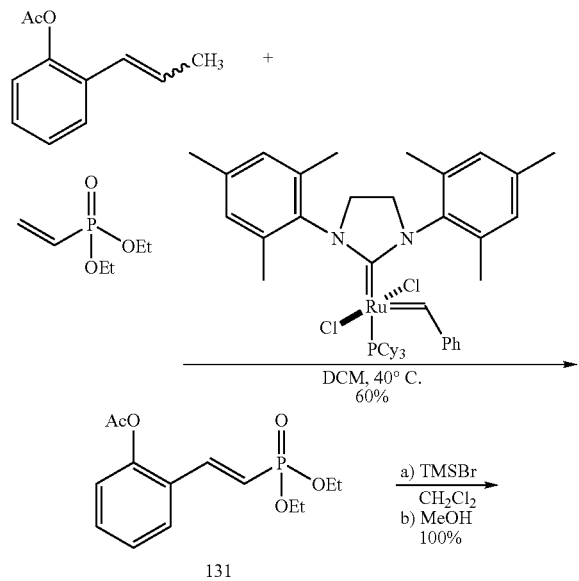

Cross-metathesis of (E/Z)2-[(2-acetoxy)phenyl]prop-2-ene with diethyl vinylphosphonate mediated by Grubb's second-generation imidazoylidene ruthenium carbene catalyst provided vinylphosphonate 131 in 60% yield along with a styrene derivative (31%) due to homocoupling of (E/Z)2-[(2-acetoxy)phenyl]prop-2-ene. Chemoselective deprotection of the phosphonate was achieved employing TMSBr to afford vinylphosphonic acid 132. DCC mediated coupling of 2 with N[6]-tert-butoxycarbonyl-2,3-O-isopropylideneadenosine furnished 133 in modest yield. Sequential deprotection of 133 with Na$_2$CO$_3$ and 80% aq TFA provided 134 (Scheme 15).

Scheme 16

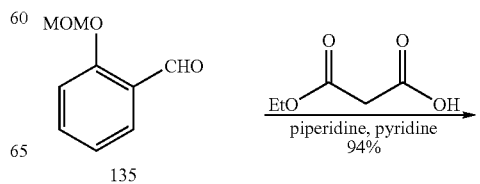

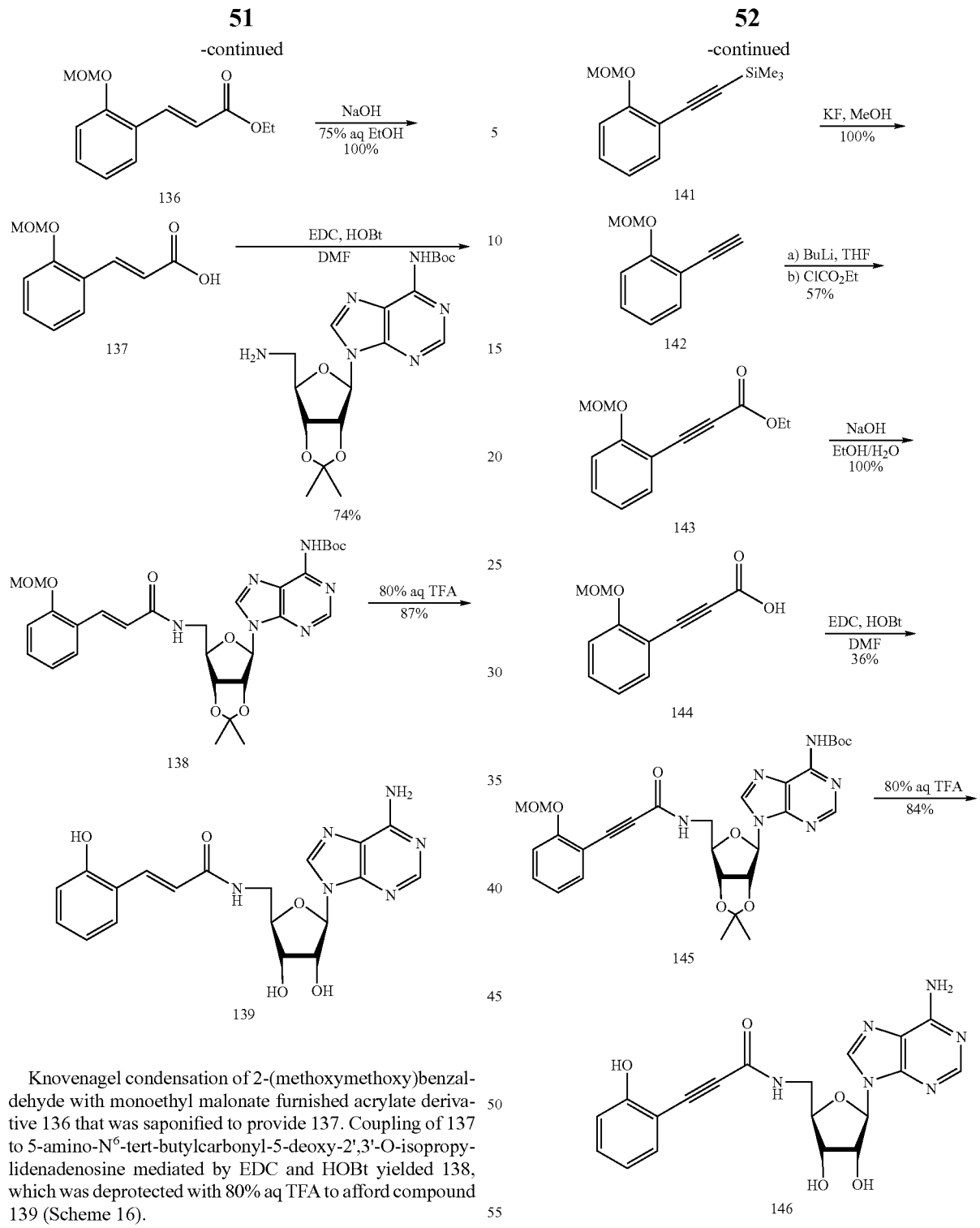

Knovenagel condensation of 2-(methoxymethoxy)benzaldehyde with monoethyl malonate furnished acrylate derivative 136 that was saponified to provide 137. Coupling of 137 to 5-amino-$N^6$-tert-butylcarbonyl-5-deoxy-2',3'-O-isopropylidenadenosine mediated by EDC and HOBt yielded 138, which was deprotected with 80% aq TFA to afford compound 139 (Scheme 16).

Scheme 17

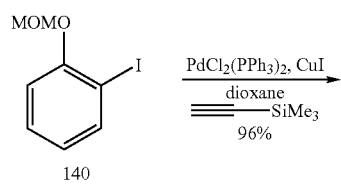

Sonogashira coupling of 2-iodo-2-methoxymethoxybenzene with (trimethylsilyl)acetylene provided 141 that was desilylated (KF, MeOH) to afford 142. Successive carbonylation of 142 with ethyl chloroformate to 143 and saponification yielded 144. Coupling of 144 with 5-amino-$N^6$-tert-butoxycarbonyl-5-deoxy-2',3'-O-isopropylideneadenosine mediated by EDC and HOBt furnished 145. Subsequent deprotection with 80% aqueous TFA afforded target inhibitor 146 (Scheme 17).

Scheme 18

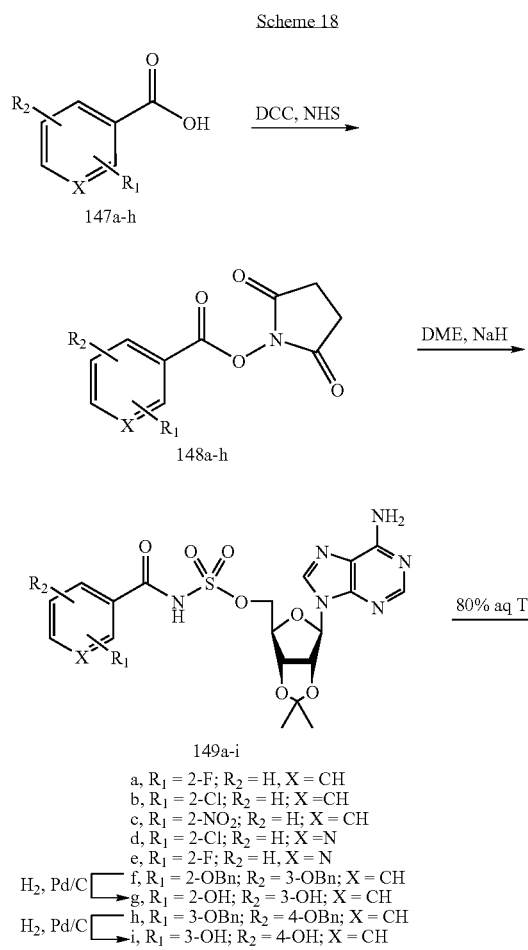

a, $R_1$ = 2-F; $R_2$ = H, X = CH
b, $R_1$ = 2-Cl; $R_2$ = H; X = CH
c, $R_1$ = 2-NO$_2$; $R_2$ = H; X = CH
d, $R_1$ = 2-Cl; $R_2$ = H; X = N
e, $R_1$ = 2-F; $R_2$ = H, X = N
$H_2$, Pd/C ⎡ f, $R_1$ = 2-OBn; $R_2$ = 3-OBn; X = CH
         ⎣→ g, $R_1$ = 2-OH; $R_2$ = 3-OH; X = CH
$H_2$, Pd/C ⎡ h, $R_1$ = 3-OBn; $R_2$ = 4-OBn; X = CH
         ⎣→ i, $R_1$ = 3-OH; $R_2$ = 4-OH; X = CH

150, $R_1$ = 2-F; $R_2$ = H, X = CH
151, $R_1$ = 2-Cl; $R_2$ = H; X = CH
152, $R_1$ = 2-NO$_2$; $R_2$ = H; X = CH
153, $R_1$ = 2-Cl; $R_2$ = H; X = N
154, $R_1$ = 2-F; $R_2$ = H, X = N
155, $R_1$ = 2-OH; $R_2$ = 3-OH; X = CH
156, $R_1$ = 3-OH; $R_2$ = 4-OH; X = CH

Scheme 19

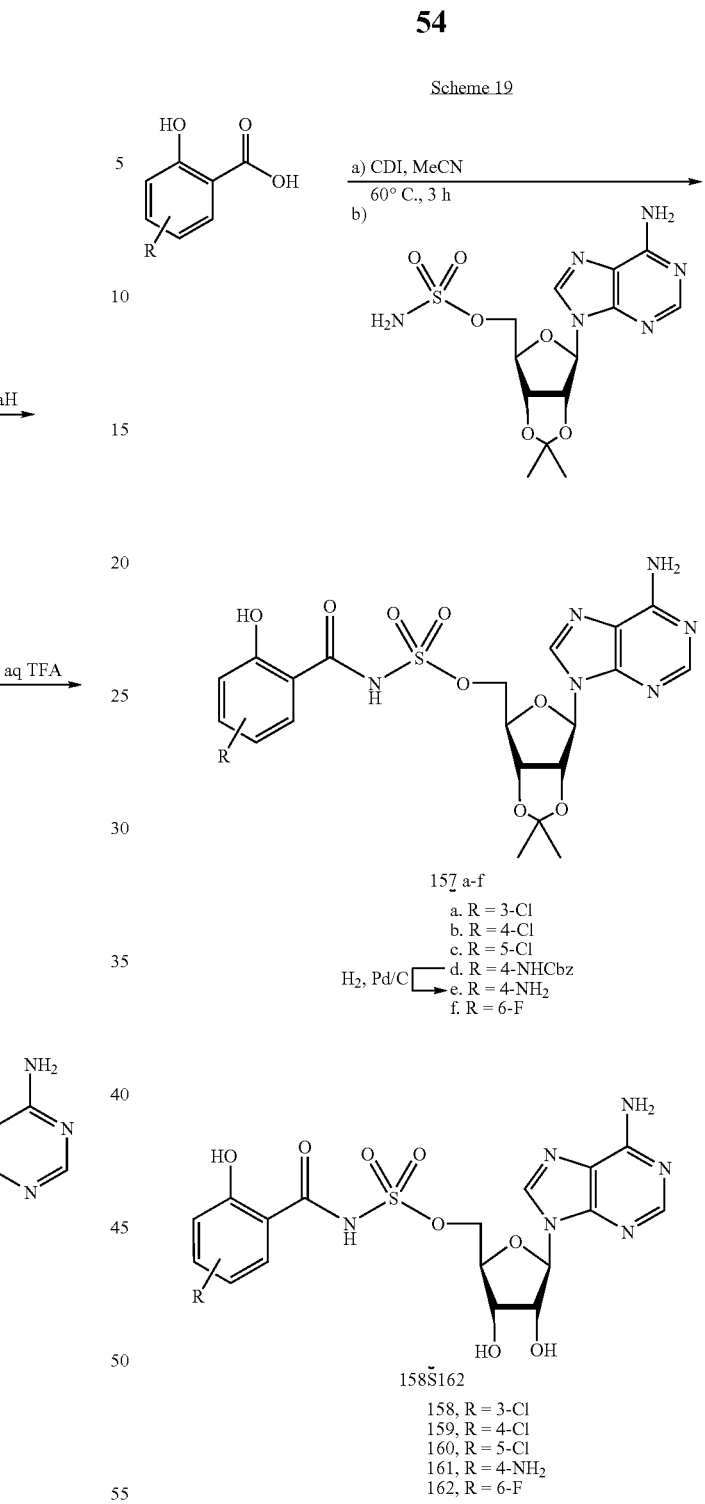

157 a-f
a. R = 3-Cl
b. R = 4-Cl
c. R = 5-Cl
$H_2$, Pd/C ⎡ d. R = 4-NHCbz
         ⎣→ e. R = 4-NH$_2$
f. R = 6-F

158–162
158, R = 3-Cl
159, R = 4-Cl
160, R = 5-Cl
161, R = 4-NH$_2$
162, R = 6-F

The preparation of aryl modified analogues was achieved through three different synthetic routes. For compounds 150-156, either commercial or protected aryl acids were reacted with N-hydroxysuccinimide (NHS) to provide the active NHS esters (148a-148h) using DCC as coupling reagent. Coupling to 2',3'-O-isopropylidene-5'-O-(sulfamoyl)adenosine mediated by DBU, afforded compounds 148a-148f, and 148h (Scheme 18). Hydrogenation of 148f and 148h afforded 148g and 148i respectively. Sequential deprotection of the isopropylidene acetal with aqueous TFA yielded 150-156.

An alternative route was employed for compounds 158-162 (Scheme 19). Direct activation of salicylic acid derivatives was accomplished with CDI in MeCN. These were coupled to 2',3'-O-isopropylidene-5'-O-sulfamoyladenosine employing DBU or Cs$_2$CO$_3$ as base to afford 157a-d, and 157f. Hydrogenation of 157d provided 157e. Deprotection with aqueous TFA furnished 158-162.

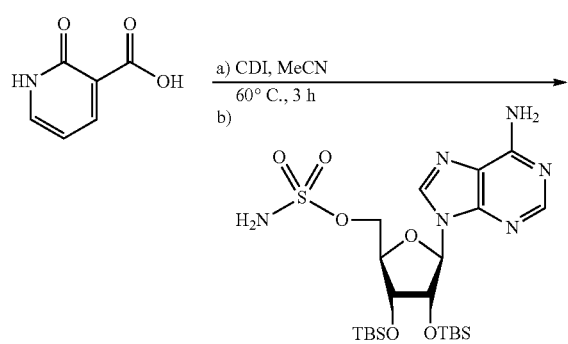

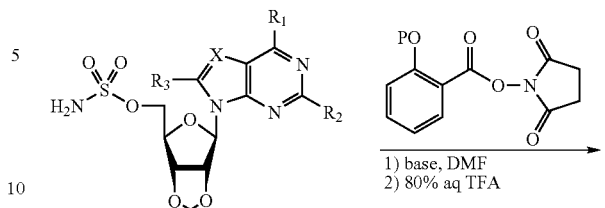

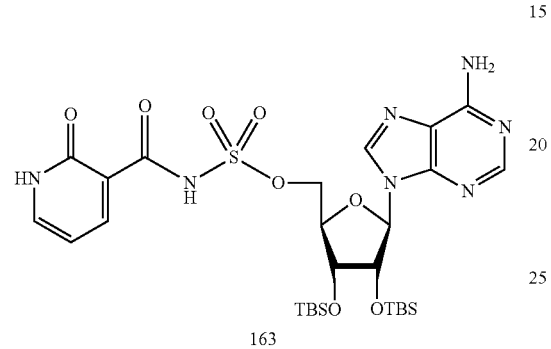

163

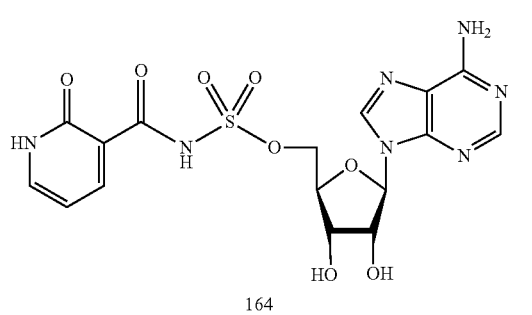

164

2-Pyridone derivative 164 was prepared analogously by CDI activation and coupled to 2',3'-O-bis(tert-butyldimethylsilyl)-5'-O-(sulfamoyl)adenosine to provide 163. Deprotection with TBAF yielded inhibitor 164 (Scheme 20).

166

167, $R^1 = O$; $R^2 = H$; $R^3 = H$; $X = N$
168, $R^1 = NMe_2$; $R^2 = H$; $R^3 = H$; $X = N$
169, $R^1 = NHCH_2CH(CH_2)_2$; $R^2 = H$; $R^3 = Br$; $X = N$
170, $R^1 = NH_2$; $R^2 = H$; $R^3 = Br$; $X = N$
171, $R^1 = NH_2$; $R^2 = H$; $R^3 = N_3$; $X = N$
172, $R^1 = NH_2$; $R^2 = H$; $R^3 = NH_2$; $X = N$
173, $R^1 = NH_2$; $R^2 = I$; $R^3 = H$; $X = N$
174, $R^1 = NH_2$; $R^2 = Ph$; $R^3 = H$; $X = N$
175, $R^1 = NH_2$; $R^2 = NHPh$; $R^3 = H$; $X = N$
176, $R^1 = NH_2$; $R^2 = CCPh$; $R^3 = H$; $X = N$
177, $R^1 = NH_2$; $R^2 = H$; $R^3 = H$; $X = CH$

Protection of the 2'- and 3'-hydroxyls of as the acetonides was accomplished with 2,2-dimethoxypropane and CSA in acetone, which were sulfamoylated to furnish compounds represented by 166. Coupling to N-hydroxysuccinimidyl (2-methoxymethoxy)benzoate or N-hydroxysuccinimidyl (2-benzyloxy)benzoate and deprotection with aqueous TFA afforded the target inhibitors 167-177 (Scheme 21).

Scheme 21

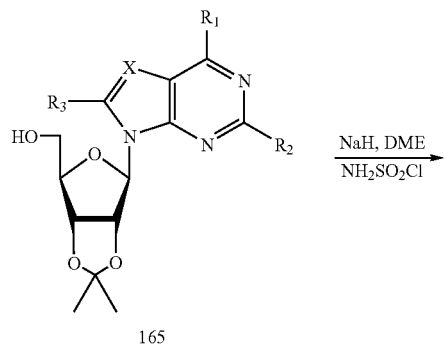

165

Scheme 22

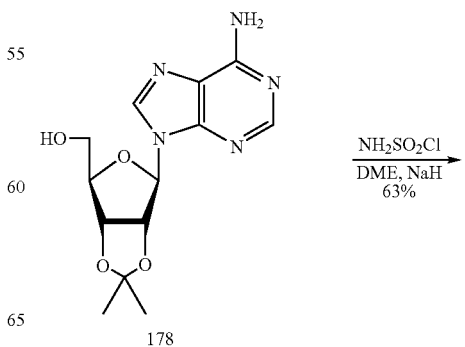

178

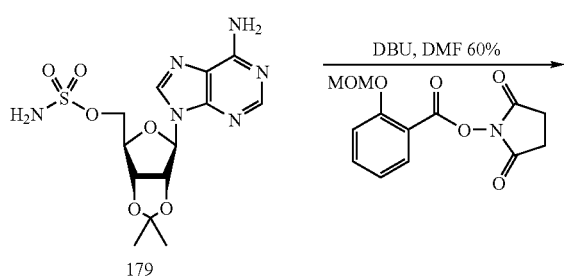

179

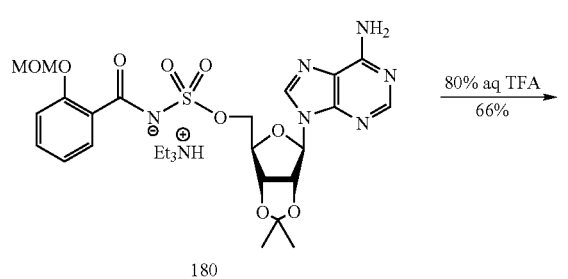

180

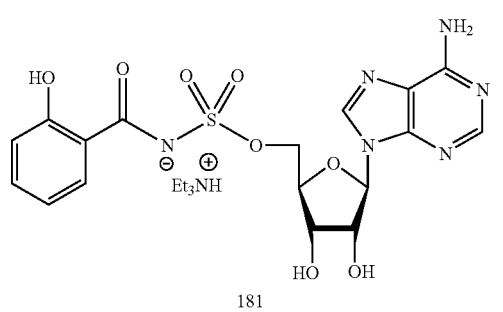

181

The synthesis of carbocyclic analog 181, wherein the ribofuranose ring oxygen is replaced by a $CH_2$ was most efficiently carried out from aristeromycin 178, a nucleoside antibiotic produced by *Streptomyces citricolor* (Scheme 22). Protection of 178 as the acetonide followed by sulfamoylation afforded 179. Salicylation with N-hydroxysuccinimidyl 2-(methoxymethoxy)benzoate in the presence of DBU provided 180, which was deprotected with 80% aqueous TFA to furnish 181.

Scheme 23

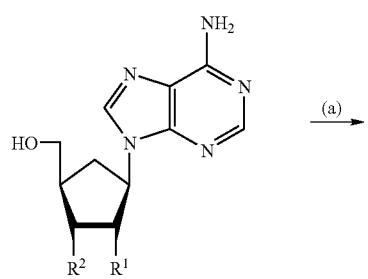

182, $R^1$ = H, $R^2$ = OH
183, $R^1$ = OH, $R^2$ = H

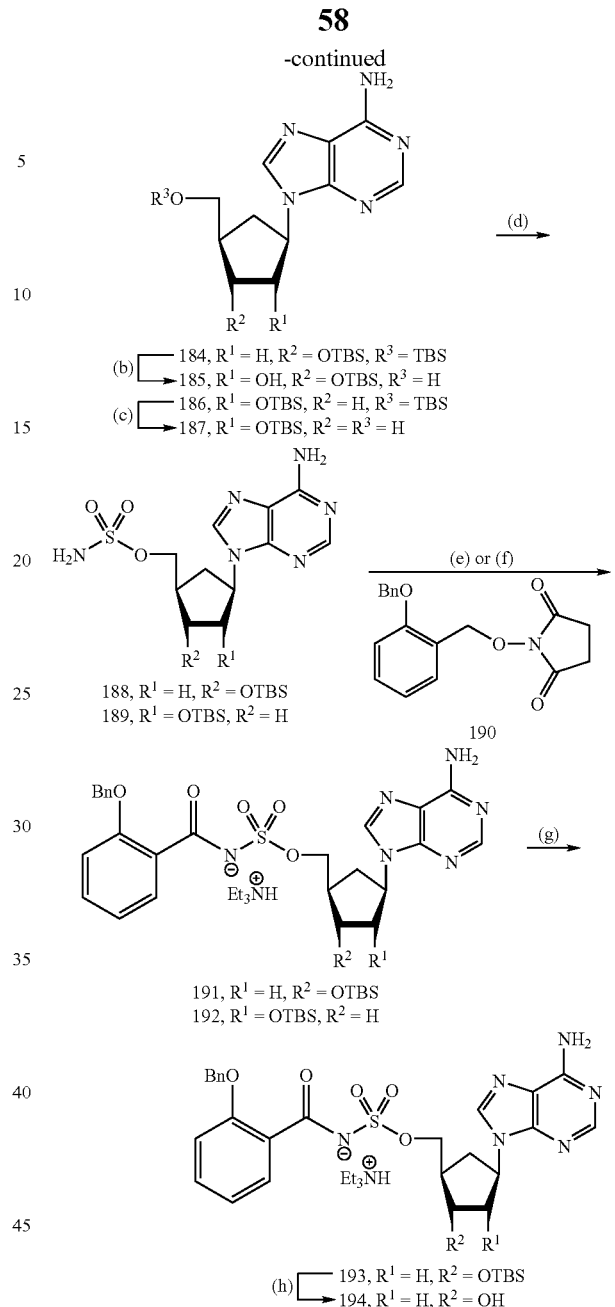

184, $R^1$ = H, $R^2$ = OTBS, $R^3$ = TBS
185, $R^1$ = OH, $R^2$ = OTBS, $R^3$ = H
186, $R^1$ = OTBS, $R^2$ = H, $R^3$ = TBS
187, $R^1$ = OTBS, $R^2$ = $R^3$ = H

188, $R^1$ = H, $R^2$ = OTBS
189, $R^1$ = OTBS, $R^2$ = H

190

191, $R^1$ = H, $R^2$ = OTBS
192, $R^1$ = OTBS, $R^2$ = H

193, $R^1$ = H, $R^2$ = OTBS
194, $R^1$ = H, $R^2$ = OH
195, $R^1$ = OTBS, $R^2$ = H
196, $R^1$ = OH, $R^2$ = H

<sup>a</sup>Reaction conditions: (a) TBSCl, imidazole, cat. DMAP, DMF, 84% (184); (b) 50% aq TFA, 60%; (c) p-TsOH, MeOH, 78% over 2 steps (187); (d) $NH_2SO_2Cl$, NaH, DME, 38% (188), 82% (189); (e) $Cs_2CO_3$, $DMF_3$; (f) DBU, DMF, 87% (192); (g) Pd/C, $H_2$, MeOH, 17% over 2 steps (193); (h) TBAF, THF, 50%; (i) 80% aq TFA, 53% over 2 steps.

Consistent with the greater instability of 2'-deoxy nucleosides, we found that 194 was unstable under acidic conditions (50% aq TFA, 3 h) previously employed for the synthesis of several analogues and for the conversion of 184 to 185 (vide infra). The choice of the benzyl ether to protect the salicyl group was guided by this consideration. The synthesis of analogue 194 began with bis-silylation of 182 to afford 184 followed by selective removal (50% aq TFA, 0° C., 3 h) of the 5'-O-TBS to provide 185 which was sulfamoylated to yield 188 (Scheme 23). Salicylation with 190 employing DBU as base afforded a recalcitrant DBU salt of 191, which was deprotected to afford the DBU salt of 194. The DBU could not be removed by ion-exchange or by chromatography (co-eluting with 1% Et₃N) that had previously been successful in cases where the DBU salt was obtained. We believe that the DBU salt forms a very tight complex as we observed the [M+DBU+H]⁺ ion by mass spectrometry. Additionally, we observed that the DBU salt of 194 was inactive in both the in vitro enzyme assay and against a whole-cell assay of *M. tuberculosis* (data not shown) while the triethylammonium salt of 194 displayed potent activity (vide infra). The lack of activity of the DBU salt also provides strong corroborating evidence that this forms a tight-complex with the inhibitor. Thus, coupling of 188 to NHS ester 190 was realized employing 3 equivalents of Cs₂CO₃ to provide 191. Sequential deprotection of the benzyl ether by catalytic hydrogenation to 193 and TBS ether with TBAF afforded 194. Synthesis of inhibitor 196 was initiated from the nucleoside antibiotic cordycepin 183 using an analogous series of reactions (Scheme 23). Protection as the di-O-TBS ether 186, followed by the selective cleavage of the 5'-O-TBS, optimally proceeded using p-TsOH in methanol to provide 187. Sulfamoylation of the 5'-OH afforded 189 that was coupled to 190 employing DBU to provide 192, which was isolated as the triethylammonium salt illustrating the capricious nature of this reaction. Sequential deprotection of the benzyl ether by catalytic hydrogenation to 195 and TBS ether with 80% aq TFA afforded 196.

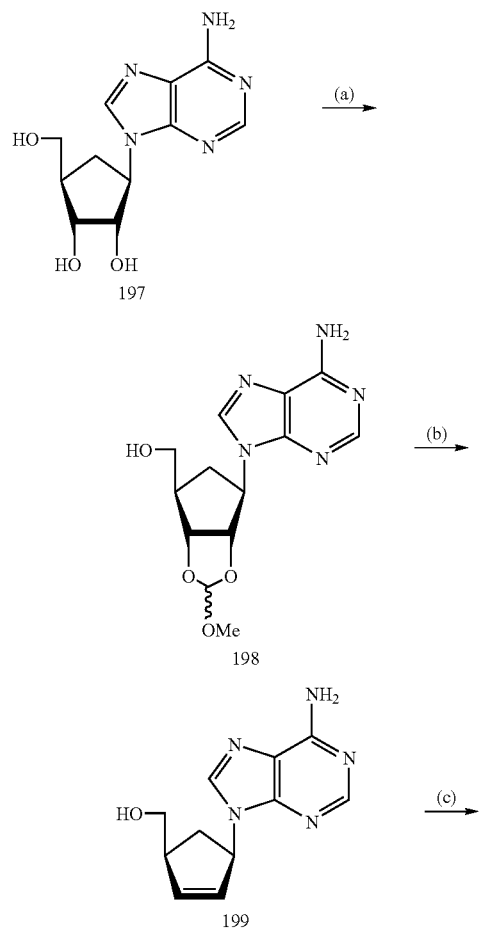

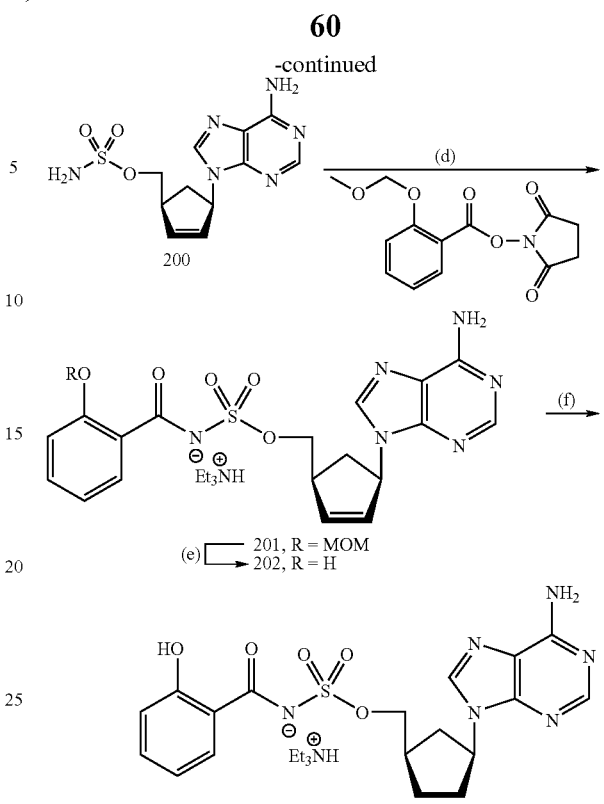

ᵃReaction conditions: (a) HC(OMe)₃, pTsOH; (b) i) Ac₂O, ii) 6N HCl, 48% from 197; (c) NH₂SO₂Cl, NaH, DME, 55%; (d) DBU, DMF, 81%; (e) 80% aq TFA, 80%; (f) Pd/C, H₂, MeOH, 36%.

Analogues 202 and 203 were also prepared (Scheme 24). For these analogues the carbocyclic sugar analogue was employed due to its greater stability. Aristeromycin 197 was transformed to a cyclic orthoester 198 using triethyl orthoformate and perchloric acid. Treatment of the resulting orthoester in refluxing Ac₂O followed by 4 N aq HCl afforded 199 with a overall yield of 48% from 197. Compound 199 was sulfamoylated to yield 200, which was coupled to N-hydroxysuccinimdyl 2-(methoxymethoxy)benzoate mediated by DBU to afford 201. Deprotection of 201 with 80% aqueous TFA provided analogue 202. Catalytic hydrogenation of 202 provided the fully reduced dideoxy analog 203.

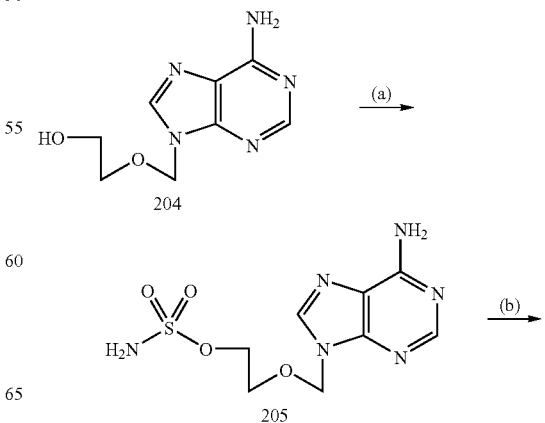

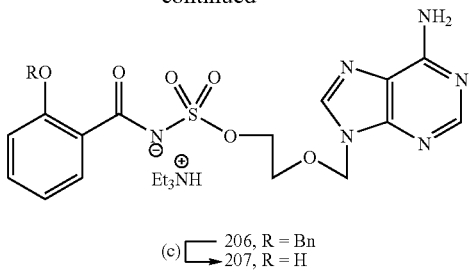

(c) ⎡ 206, R = Bn
    ⎣ 207, R = H

<sup>a</sup>Reaction conditions: (a) NH₂SO₂Cl, NaH, DME, 45%; (b) 190, DBU, DMF, 44%; (c) Pd/C, H₂, MeOH, 98%.

Additionally, the acyclo analogue 207 was prepared starting from the acyclo nucleoside 204, which was sulfamoylated to provide 205 (Scheme 25). Coupling of 205 with NHS ester 190 provided. Catalytic hydrogenation of 206 afforded the acyclo analog 207.

The invention will now be illustrated by the following non-limiting Examples.

Chemistry General Procedures. All commercial reagents (Sigma-Aldrich, Acros) were used as provided unless otherwise indicated. 2-Benzyloxybenzoic acid was purchased from Alfa Aesar. Sulfamoyl chloride was prepared by the method of Heacock except that this was used directly without recrystallization. An anhydrous solvent dispensing system using 2 packed columns of neutral alumina was used for drying THF, Et$_2$O, and CH$_2$Cl$_2$ while 2 packed columns of molecular sieves were used to dry DMF and the solvents were dispensed under argon. Anhydrous grade DME, MeOH, and MeCN were purchased from Aldrich. Pyridine was freshly distilled from KOH, Et$_3$N was distilled from CaH$_2$. Flash chromatography was performed with Silia P grade silica gel 60 (Silicycle) with the indicated solvent system. All reactions were performed under an inert atmosphere of dry Ar or N$_2$ in oven-dried (150° C.) glassware. $^1$H and $^{13}$C NMR spectra were recorded on a Varian 300 or 600 MHz spectrometer. Proton chemical shifts are reported in ppm from an internal standard of residual chloroform (7.26 ppm) or methanol (3.31 ppm), and carbon chemical shifts are reported using an internal standard of residual chloroform (77.3 ppm) or methanol (49.1 ppm). Proton chemical data are reported as follows: chemical shift, multiplicity (s=singlet, d=doublet, t=triplet, q=quartet, p=pentet, m=multiplet, br=broad), integration, coupling constant. Overlapping carbon signals were assigned by HMQC or HMBC analysis. High resolution mass spectra were obtained on Agilent TOF II TOF/MS instrument equipped with either an ESI or APCI interface. Analytical HPLC were obtained on a Agilent 1100 Series HPLC system with a PDA detector.

Unless otherwise stated, the following general procedures were used in the Examples below.

General procedure for acetonide protection. A mixture of nucleoside (4.0 mmol, 1.0 equiv), 2,2-dimethoxypropane (72 mmol, 18 equiv) and camphorsulfonic acid (4.0 mmol, 1.0 equiv) in acetone (50 mL) was stirred at 55° C. for 24 hours. Solid NaHCO$_3$ (400 mg) was added and the heterogenous mixture stirred 30 minutes. The reaction was filtered through Celite and the filtrate concentrated under reduced pressure. Purification by flash chromatography afforded the title compound.

General Procedure for NHS ester formation. To a solution of aryl acid (1.0 mmol, 1.0 equiv) in THF (10 mL) at 0° C. was added N-hydroxysuccinimide (1.0 mmol, 1.0 equiv) and DCC (1.0 mmol, 1.0 equiv). The resulting mixture was stirred for 30 minutes at 0° C. then 2 hours at room temperature. The reaction mixture was filtered to remove the DCU precipitate and the filtrate was concentrated under reduced pressure. Purification by flash chromatography afforded the desired N-hydroxysuccinimdyl aroyl ester.

General Procedure for CDI coupling. A solution of substituted salicylic acid (3.0 mmol, 3.0 equiv) and 1,1'-carbonyldiimidazole (3.6 mmol, 3.6 equiv) in DMF (10 mL) was stirred at 60° C. for 2 hours under Ar. The solution was cooled to room temperature. A mixture of 5'-O-sulfomyladenosine (1.0 mmol, 1.0 equiv) and DBU or Cs$_2$CO$_3$ (1.5 mmol, 1.5 equiv) was then added dropwise to the reaction mixture. The resulting solution was again stirred 2 hours at 60° C. The reaction mixture was concentrated in vacuo and the residue was applied to flash chromatography to afford the compound.

General Procedure for arylation of 2',3'-O-isopropylidene-5'-O-sulfamoyladenosine. To a solution of N-hydroxysuccinimdyl aroyl ester (1.0 mmol) in DMF (10 mL) at 0° C. was added 2',3'-O-isopropylidene-5'-O-(sulfamoyl)adenosine (1.5 mmol, 1.5 equiv) and DBU (Method A) or Cs$_2$CO$_3$ (Method B) (1.5 mmol, 1.5 equiv). The reaction mixture was warmed to room temperature and stirred for about 16 hours. The reaction was concentrated under reduced pressure and the residue taken up in EtOAc and filtered. The solids were washed with additional EtOAc (100 mL) and the combined filtrate was concentrated. Purification by flash chromatography (EtOAc/MeOH/Et$_3$N) afforded the compound.

General Procedure for TFA deprotection. To a solution of 5'-O—(N-aroylsulfamoyl)-2',3'-isopropylideneadenosine triethylammonium salt (0.2 mmol) was added 80% aq TFA (2.5 mL). The resulting solution was stirred for 30 minutes at 0° C. and was concentrated under reduced pressure. Purification by flash chromatography (EtOAc/MeOH/Et$_3$N) afforded the compound.

EXAMPLE 1

Preparation of 5'-O—(N-(2-Hydroxybenzoyl)sulfamoyl)-adenosine triethylammonium salt To N$^6$-tert-Butoxycarbonyl-5'-O—(N-(2-hydroxybenzoyl)sulfamoyl)-2',3'-isopropylideneadenosine triethylammonium salt (43 mg, 0.070 mmol, 1.0 equiv) was added 80% aq TFA (2 mL). After 2 h, the reaction mixture was concentrated under reduced pressure. Purification by flash chromatography (75:25:1 EtOAc/4eOH/Et$_3$N) afforded the title compound (30 mg, 74%). R$_f$=0.15 (2:3 MeOH/EtOAc); $^1$H NMR (300 MHz, CD$_3$OD) δ 1.24 (t, 9H, J=7.2 Hz), 3.10 (q, 6H, J=7.2 Hz), 4.28-4.38 (m, 1H), 4.38-4.48 (m, 3H), 4.72 (t, 1H, J=5.1 Hz), 6.08 (d, 1H, J=6.0 Hz), 6.72-6.84 (m, 2H), 7.28 (ddd, 1H, J=8.1, 7.2, 1.8 Hz), 7.92 (dd, 1H, J=7.8, 1.5 Hz), 8.16 (s, 1H), 8.51 (s, 1H); $^{13}$C NMR (CD$_3$OD, 75 MHz) δ 8.3, 46.7, 68.5, 71.3, 74.9, 83.4, 88.1, 116.7, 118.1, 118.9, 119.4, 130.1, 133.2, 139.9, 149.6, 150.9, 152.6, 160.8, 173.7; HRMS (ESI+) calcd. for C$_{17}$H$_{19}$N$_6$O$_8$S [M+H]$^+$ 467.0979, found 467.0986 (error 1.4 ppm).

The intermediate N$^6$-tert-Butoxycarbonyl-5'-O—(N-(2-hydroxybenzoyl)-sulfamoyl)-2',3'-isopropylideneadenosine triethylammonium salt was prepared as follows.

a. N-Hydroxysuccinimdyl 2-benzyloxybenzoate. To a solution of 2-benzyloxybenzoic acid (5.0 g, 21.9 mmol, 1.0 equiv) in THF (120 mL) at 0° C. was added N-hydroxysuccinimide (2.54 g, 21.9 mmol, 1.0 equiv) and DCC (4.53 g, 21.9 mmol, 1.0 equiv). The resulting mixture was stirred for 30 minutes at 0° C. then 2 hours at room temperature. The reaction mixture was filtered to remove the DCU precipitate and the filtrate was concentrated under reduced pressure. Purification by flash chromatography (4:1 EtOAc/hexane) afforded the title compound (5.91 g, 82%) as a white solid. $R_f$=0.85 (EtOAc); $^1$H NMR (300 MHz, CDCl$_3$) δ 2.87 (s, 4H), 5.22 (s, 2H), 6.98-7.12 (m, 2H), 7.22-7.42 (m, 3H), 7.44-7.60 (m, 3H), 8.20 (dd, 1H, J=7.8, 2.2 Hz); $^{13}$C NMR (CDCl$_3$, 75 MHz) δ 26.1, 70.8, 114.0, 114.8, 120.8, 127.0, 128.0, 128.8, 133.0, 136.1, 136.3, 159.7, 164.9, 169.9.

b. N$^6$-tert-Butoxycarbonyl-2',3' O-isopropylideneadenosine. To a solution of 2',3'-O-isopropylideneadenosine (10.0 g, 35.7 mmol, 1.0 equiv) in CH$_2$Cl$_2$ (250 mL) at 0° C. was added imidazole (3.64 g, 53.5 mmol, 1.5 equiv) and tert-butyldimethylsilyl chloride (16.3 g, 105 mmol, 3.5 equiv). After 16 h, the reaction mixture was filtered and the residue washed with acetone (100 mL). The combined filtrates were concentrated to afford 5'-O-tert-butyldimethylsilyl-2',3'-O-isopropylideneadenosine as a white solid that was directly carried onto the next step. An analytically pure sample was obtained by flash chromatography (3:1 hexane/EtOAc). $R_f$=0.85 (1:6 MeOH/EtOAc); $^1$H NMR (300 MHz, CDCl$_3$) δ −0.02 (s, 3H), −0.01 (s, 3H), 0.8 (s, 9H), 1.37 (s, 3H), 1.60 (s, 3H), 3.73 (dd, 1H, J=11.4, 4.2 Hz), 3.85 (dd, 1H, J=11.4, 4.2 Hz), 4.36-4.40 (m, 1H), 4.92 (dd, 1H, J=6.0, 2.1 Hz), 5.24 (dd, 1H, J=6.0, 2.1 Hz), 6.14 (d, 1H, J=2.4 Hz), 7.15-7.19 (m, 2H), 8.03 (s, 1H), 8.33 (s, 1H); $^{13}$C NMR (150 MHz, CDCl$_3$) δ −5.4 (2C), 19.2, 25.5, 26.3, 27.4, 64.8, 83.0, 85.9, 89.1, 92.4, 115.1, 120.5, 136.3, 141.4, 150.3, 153.9, 157.4; HRMS (ESI+) calcd. for C$_{19}$H$_{32}$N$_5$O$_4$Si [M+H]$^+$ 422.2220, found 422.2224 (error 0.9 ppm).

The crude product from sub-part b above was suspended in a mixture of THF (600 mL) and DMF (100 mL), then NaH (1.77 g, 44.3 mmol, 1.1 equiv, 60% dispersion in oil) was added portionwise with vigorous stirring at 0° C. After stirring the viscous mass for 15-20 minutes (Boc)$_2$O (8.8 g, 40.3 mmol, 1.0 equiv) was added. Another portion of (Boc)$_2$O (4.4 g. 20.2 mmol, 0.5 equiv) was added after 30 minutes. After 16 h, the reaction mixture was quenched with ice and concentrated under reduced pressure. The residue was partitioned between H$_2$O (100 mL) and EtOAc (100 mL) and the organic layer was dried (Na$_2$SO$_4$) and concentrated. Purification by flash chromatography (EtOAc/hexanes) afforded the desired N$^6$-Boc product (5.5 g, 30%) along with the N$^6$-bis-Boc side-product (1.90 g, 8%) and recovered starting material (8.0 g, 53%). Characterization data for N$^6$,N$^6$-bis(tert-butoxycarbonyl)-5'-O-tert-Butyldimethylsilyl-2',3'-O-isopropylideneadenosine: $R_f$=0.85 (3:1 hexanes/EtOAc); Characterization data for N$^6$-tert-butoxycarbonyl-5'-O-tert-butyldimethylsilyl-2',3'-O-isopropylideneadenosine: $R_f$=0.65 (3:1 hexanes/EtOAc); $^1$H NMR (300 MHz, CDCl$_3$) δ −0.03 (s, 3H), −0.02 (s, 3H), 0.8 (s, 9H), 1.38 (s, 3H), 1.53 (s, 9H), 1.61 (s, 3H), 3.74 (dd, 1H, J=11.2, 3.6 Hz), 3.87 (dd, 1H, J=11.2, 3.6 Hz), 4.40-4.50 (m, 1H), 4.92 (dd, 1H, J=6.0, 2.1 Hz), 5.24 (dd, 1H, J=5.7, 2.1 Hz), 6.19 (d, 1H, J=2.7 Hz), 8.18 (s, 1H), 8.77 (s, 1H); $^{13}$C NMR (75 MHz, CDCl$_3$) δ −5.2, −5.1, 18.7, 25.7, 26.2, 27.5, 28.5, 63.9, 81.8, 82.5, 85.4, 87.8, 92.2, 114.3, 122.2, 141.2, 149.8, 150.0, 150.4, 153.3; HRMS (ESI+) calcd. for C$_{24}$H$_{40}$N$_5$O$_6$Si [M+H]$^+$ 522.2742, found 522.2751 (error 1.7 ppm).

To a solution of the mono-N$^6$-Boc compound (1.40 g, 2.68 mmol, 1.0 equiv) in THF (100 mL) at room temperature was added TBAF (1.0 M solution in THF, 4.0 mL, 4.0 mmol, 1.5 equiv). After 4 h, the reaction mixture was concentrated under reduced pressure. Purification by flash chromatography (1-3% MeOH/EtOAc) afforded the title compound (1.1 g, 100%). $R_f$=0.30 (1:9 MeOH/EtOAc); $^1$HNMR (300 MHz, CDCl$_3$) δ 1.34 (s, 3H), 1.52 (s, 9H), 1.61 (s, 3H), 3.76 (br d, 1H, J=12.9 Hz), 3.94 (dd, 1H, J=12.9, 1.8 Hz), 4.46-4.56 (m, 1H), 5.07 (dd, 1H, J=6.0, 1.2 Hz), 5.17 (t, 1H, J=5.1 Hz), 5.88 (d, 1H, J=5.1 Hz), 8.0 (s, 1H), 8.47 (br s, 1H), 8.68 (s, 1H); $^{13}$C NMR (75 MHz, CDCl$_3$) δ 25.6, 27.9, 28.5, 63.5, 81.9, 82.8, 83.3, 86.4, 94.4, 114.3, 123.2, 142.2 (2C), 145.7, 150.8, 152.7; HRMS (APCI−) calcd. for C$_{18}$H$_{24}$N$_5$O$_6$ [M−H]$^−$ 406.1732, found 406.1764 (error 7.8 ppm).

c. N$^6$-tert-Butoxycarbonyl-2',3'-O-isopropylidene-5'-β-(sulfamoyl)adenosine. To a solution of N$^6$-tert-Butoxycarbonyl-2',3'-O-isopropylideneadenosine (0.5 g, 1.23 mmol, 1.0 equiv) in DME (50 mL) at 0° C. was added NaH (74 mg, 1.84 mmol, 1.5 equiv, 60% suspension in mineral oil) and the solution stirred 30 minutes at 0° C. Next, a solution of sulfamoyl chloride (213 mg, 1.84 mmol, 1.5 equiv) in DME (15 mL) was added dropwise over 5 minutes and the reaction stirred 16 hours at room temperature. The reaction mixture was quenched at 0° C. with MeOH (30 mL) and concentrated under reduced pressure. Purification by flash chromatography (19:1 EtOAc/MeOH) afforded the title compound (0.49 g, 82%). $R_f$=0.9 (19:1 EtOAc/MeOH); $^1$HNMR (300 MHz, CDCl$_3$) δ 1.35 (s, 3H), 1.50 (s, 9H), 1.58 (s, 3H), 4.30 (dd, 1H, J=10.8, 5.4 Hz), 4.37 (dd, 1H, J=10.8, 3.6 Hz), 4.52-4.56 (m, 1H), 5.05 (dd, 1H, J=6.0, 2.7 Hz), 5.36 (dd, 1H, J=6.3, 2.4 Hz), 6.03 (br s, 2H), 6.18 (d, 1H, J=2.4 Hz), 8.15 (s, 1H), 8.70 (s, 1H); $^{13}$C NMR (75 MHz, CDCl$_3$) δ 25.6, 27.4, 28.5, 69.6, 81.4, 82.7, 84.4, 84.8, 91.4, 115.0, 122.1, 142.0, 150.0, 150.2, 150.6, 153.0; HRMS (ESI−) calcd. for C$_{18}$H$_{25}$N$_6$O$_8$S [M−H]−485.1460, found 485.1497 (error 7.6 ppm).

d. N$^6$-tert-Butoxycarbonyl-5'-O—(N-(2-benzyloxybenzoyl)sulfamoyl)-2',3'-isopropylideneadenosine triethylammonium salt. To a solution of N$^6$-tert-Butoxycarbonyl-2',3'-O-isopropylidene-5'-O-(sulfamoyl)adenosine (0.37 g, 0.76 mmol, 1.0 equiv) in DMF (8.01 mL) at −20° C. was added N-Hydroxysuccinimdyl 2-benzyloxybenzoate (0.37 g, 1.14 mmol, 1.5 equiv) and Cs$_2$CO$_3$ (371 mg, 1.14 mmol, 1.5 equiv). The reaction mixture was warmed to room temperature and stirred 16 hours. The reaction was concentrated under reduced pressure and the residue taken up in EtOAc (50 mL) and filtered. The solids were washed with additional EtOAc (100 mL) and the combined filtrate was concentrated. Purification by flash chromatography (96:4:1 EtOAc/MeOH/Et$_3$N) afforded the title compound (0.48 g, 80%). $R_f$=0.55 (EtOAc); $^1$H NMR (300 MHz, CD$_3$OD) δ 1.22 (t, 9H, J=7.2 Hz), 1.34 (s, 3H), 1.58 (s, 9H), 1.59 (s, 3H), 3.11 (q, 6H, J=7.2 Hz), 4.10-4.20 (m, 2H), 4.32-4.40 (m, 1H), 5.02-5.10 (m, 3H), 5.32 (dd, 1H, J=6.3, 3.3 Hz), 6.25 (d, 1H, J=3.3 Hz), 6.92 (td, 1H, J=7.5, 0.9 Hz), 7.03 (d, 1H, J=8.4 Hz), 7.14-7.32 (m, 4H), 7.36-7.50 (m, 3H), 8.54 (s, 1H), 8.64 (s, 1H); $^{13}$C NMR (75 MHz, CDCl$_3$) δ 8.2, 24.5, 26.5, 27.4, 46.7, 60.4, 68.7, 70.4, 81.6, 82.2, 84.7, 91.0, 113.0, 113.9, 120.3, 121.9, 127.4, 127.6, 128.2, 128.6, 130.1, 130.3, 137.4, 142.5, 149.9, 151.0, 151.2, 152.0, 155.9, 175.5; HRMS calcd. for C$_{32}$H$_{37}$N$_6$O$_{10}$S [M+H]$^+$ 697.2292, found 697.2295 (error 0.4 ppm).

e. N$^6$-tert-Butoxycarbonyl-5'-O—(N-(2-hydroxybenzoyl)sulfamoyl)-2',3'-isopropylideneadenosine triethylammonium salt. To a solution of N$^6$-tert-Butoxycarbonyl-5'-O—(N-(2-benzyloxybenzoyl)sulfamoyl)-2',3'-isopropylideneadenosine triethylammonium salt (106 mg, 0.13 mmol) in abs. EtOH (20 mL) was added 10% Pd/C (40 mg) and the reaction placed under a H$_2$ atmosphere. After 3 h, the reaction mixture was filtered through a plug of Celite, which was further washed with MeOH (60 mL) and the combined filtrates were concentrated under reduced pressure. Purification by flash chromatography (100:10:1 EtOAc/MeOH/Et$_3$N) afforded the title compound (90 mg, 95%). $R_f$=0.25 (EtOAc); $^1$H NMR (300 MHz, CD$_3$OD) δ 1.24 (t, 9H, J=7.2 Hz), 1.34 (s, 3H), 1.56 (s, 3H), 1.57 (s, 9H), 3.14 (q, 6H, J=7.2 Hz), 4.32 (d, 2H, J=3.6 Hz), 4.56-4.62 (m, 1H), 5.12 (dd, 1H, J=5.7, 1.8 Hz), 5.41 (dd, 1H, J=6.0, 2.7 Hz), 6.27 (d, 1H, J=2.4 Hz), 6.70-6.80 (m, 2H), 7.26 (td, 1H, J=7.5, 0.6 Hz), 7.84 (dd, 1H, J=7.5, 0.6 Hz), 8.52 (s, 1H), 8.60 (s, 1H); $^{13}$C NMR (75 MHz, CD$_3$OD) δ 8.2, 24.4, 26.4, 27.5, 46.6, 68.8, 81.6, 82.2, 84.7, 85.0, 91.2, 114.0, 116.7, 118.1, 119.2, 121.8, 130.0, 133.2, 142.6, 150.0, 150.8, 151.1, 152.0, 160.7, 173.6; HRMS (ESI+) calcd. for C$_{25}$H$_{31}$N$_6$O$_{10}$S [M+H]$^+$ 607.1816, found 607.1819 (error 0.5 ppm).

EXAMPLE 2

Preparation of 5'-O—(N-(2-Aminobenzoyl)sulfamoyl)adenosine triethylammonium salt The title compound was prepared from 5'-O—(N-(2-aminobenzoyl)-sulfamoyl)-2',3'-isopropylideneadenosine triethylammonium salt (39 mg, 0.065 mmol) using a procedure similar to that described in Example 1. Purification by flash chromatography (75:25:1 EtOAc/MeOH/Et$_3$N) afforded the title compound (23 mg, 64%). R$_f$=0.4 (1:1 MeOH/EtOAc); $^1$H NMR (300 MHz, CD$_3$OD) δ 1.55 (t, 9H, J=7.2 Hz), 2.88 (q, 6H, J=7.2 Hz), 4.26-4.33 (m, 1H), 4.34-4.39 (m, 2H), 4.39-4.46 (m, 1H) 4.73 (t, 1H, J=5.7 Hz), 6.09 (d, 1H, J=6 Hz), 6.54 (ddd, 1H, J=8.1, 7.2, 1.2 Hz), 6.66 (dd, 1H, J=7.8, 0.9 Hz) 7.1 (ddd, 1, J=8.4, 7.2, 1.5 Hz), 7.9 (dd, 1H, J=8.1, 1.8 Hz), 8.16 (s, 1H), 8.55 (s, 1H); $^{13}$C NMR (150 MHz, CD$_3$OD) δ 9.3, 47.9, 69.1, 72.6, 76.2, 84.9, 89.0, 116.9, 118.0, 118.3, 120.6, 132.6, 132.9, 142.2, 151.0, 151.1, 153.9, 157.3; 175.9. HRMS (ESI+) calcd. for C$_{17}$H$_{20}$N$_7$O$_7$S [M+H]$^+$ 466.1139, found 466.1177 (error 8.1 ppm).

The intermediate 5'-O—(N-(2-aminobenzoyl)-sulfamoyl)-2',3'-isopropylideneadenosine triethylammonium salt was prepared as follows.

a. N-Hydroxysuccinimdyl 2-carbobenzyloxyamino benzoate. The title compound was prepared from 2-(2-benzyloxycarbonyl)amino benzoic acid (4.0 g, 14.8 mmol, 1.0 equiv; see Choo, H.-Y. P., et al., *Bioorg. Med. Chem.* 2002, 10, 517-523) using the procedure described in Example 1, sub-part a. The title compound was isolated as a white solid (4.6 g, 84%). R$_f$=0.85 (EtOAc); $^1$H NMR (600 MHz, CDCl$_3$) δ 2.88 (s, 4H), 5.19 (s, 2H), 7.09 (t, 1H, J=7.8 Hz), 7.28-7.42 (m, 6H), 7.65 (t, 1H, J=7.2 Hz), 8.17 (d, 1H, J=7.8 Hz), 9.73 (s, 1H); $^{13}$C NMR (75 MHz, CDCl$_3$) δ 25.9, 67.5, 109.9, 119.5, 122.3, 128.5, 128.6, 128.8, 131.4, 136.0, 137.1, 143.0, 153.2, 163.3, 169.3; MS (ESI+) calcd. for C$_{19}$H$_{16}$N$_2$NaO$_6$ [M+Na]$^+$ 391.1, found 391.2.

b. 5'-O—(N-(2-Carbobenzyloxyaminobenzoyl)sulfamoyl)-2',3'-O-isopropylideneadenosine. To a solution of 2',3'-O-isopropylidene-5'-O-(sulfamoyl)adenosine (0.25 g, 0.649 mmol, 1.0 equiv; see Heacock, D., et al., *Bioorg. Chem.* 1996, 24, 273-289) in DMF (7.5 ml) were added N-hydroxysuccinimdyl 2-carbobenzyloxyamino benzoate (0.21 g, 0.78 mmol, 1.20 equiv) and DBU (233 µl, 1.55 mmol, 2.4 equiv). After 12 h, the reaction mixture was concentrated under reduced pressure and the residue was purified by flash chromatography (1:10 MeOH/CHCl$_3$). Further purification by flash chromatography (1:9 MeOH/EtOAc) afforded the title compound (0.153 g, 36%) as an oil. R$_f$=0.35 (1:9 MeOH/EtOAc); $^1$H NMR (300 MHz, CD$_3$OD) δ 1.28 (s, 3H), 1.55 (s, 3H), 4.22-4.40 (m, 2H), 4.45-4.55 (m, 1H), 5.00-5.20 (m, 3H), 5.32 (dd, 1H, J=6.0, 3.0 Hz), 6.20 (d, 1H, J=3.0 Hz), 6.92 (t, 1H, J=7.8 Hz), 7.20-7.42 (m, 6H), 8.05 (dd, 1H, J=7.8, 1.2 Hz), 8.10 (s, 1H), 8.22 (d, 1H, J=7.8), 8.37 (s, 1H); $^{13}$C NMR (CDCl$_3$, 75 MHz) δ 24.3, 26.2, 66.3, 68.6, 82.1, 84.5, 84.6, 90.8, 114.1, 118.3, 119.0, 121.3, 122.9, 127.7, 127.8, 128.3, 128.4, 131.2, 136.8, 140.1, 140.2, 149.2, 152.7, 154.0, 156.0, 174.4; HRMS (ESI−) calcd. for C$_{28}$H$_{28}$N$_7$O$_9$S [M−H]$^-$ 638.1674, found 638.1626 (error 7.5 ppm).

c. 5'-O—(N-(2-Aminobenzoyl)sulfamoyl)-2',3'-isopropylideneadenosine triethylammonium salt. This title compound was prepared was prepared from 5'-O—(N-(2-carbobenzyloxyaminobenzoyl)sulfamoyl)-2',3'-O-isopropylideneadenosine (0.35 g, 0.55 mmol) using a procedure similar to that described in Example 1, sub-part e. Purification by flash chromatography (84:14:1 EtOAc/MeOH/Et$_3$N) afforded the title compound (135 mg, 41%). R$_f$=0.2 (1:6 MeOH/EtOAc); $^1$H NMR (300 MHz, CD$_3$OD) δ 1.25 (t, 9H, J=7.2 Hz), 1.35 (s, 3H), 1.59 (s, 3H), 3.12 (q, 6H, J=7.2 Hz), 4.28 (d, 2H, J=3.9 Hz), 4.50-4.60 (m, 1H), 5.14 (dd, 1H, J=6.3, 2.1 Hz), 5.38 (dd, 1H, J=6.3, 3.3 Hz), 6.23 (d, 1H, J=3.3 Hz), 6.53 (ddd, 1H, J=8.4, 7.2, 0.9 Hz), 6.67 (dd, 1H, J=8.1, 0.9 Hz), 7.10 (ddd, 1H, J=9.0, 7.5, 1.8 Hz), 7.89 (dd, 1H, J=8.1, 1.5 Hzj, 8.15 (s, 1H), 8.51 (s, 1H); $^{13}$C NMR (75 MHz, CDCl$_3$) δ 9.1, 25.5, 27.5, 47.7, 69.6, 83.2, 85.6, 85.7, 91.8, 115.1, 116.7, 117.8, 120.0, 120.1, 132.4, 133.0, 141.3, 150.2, 151.1, 153.7, 157.0, 176.9; HRMS (APCI−) calcd. for C$_{20}$H$_{22}$N$_7$O$_7$S [M−H]$^-$ 504.1306, found 504.1306 (error 0 ppm).

EXAMPLE 3

Preparation of 5'-O—(N-(Benzoyl)sulfamoyl)adenosine

The title compound was prepared from 5'-O—(N-(Benzoyl)sulfamoyl)-2',3'-isopropylideneadenosine (80 mg, 0.16 mmol) using a procedure similar to that described in Example 1. The title compound was isolated as a white solid (73 mg, 100%). R$_f$=0.18 (6:1 EtOAc/MeOH); $^1$HNMR (300 MHz, CD$_3$OD) δ 4.29-4.33 (m, 1H), 4.42 (t, 1H, J=5.1 Hz), 4.56 (t, 2H, J=3.6 Hz), 4.67 (t, 1H J=5.1 Hz), 6.03 (d, 1H, J=5.1 Hz), 6.80-7.43 (m, 3H), 7.84-7.88 (m, 2H), 8.18 (s, 1H), 8.41 (s, 1H); $^{13}$C NMR (150 MHz, CD$_3$OD) δ 68.1, 71.2, 74.9, 83.5, 88.1, 119.0, 127.6, 128.7, 130.9, 137.7, 140.0, 149.7, 152.7, 156.1, 174.2; HRMS (ESI+) calcd. for C$_{17}$H$_{19}$N$_6$O$_7$S [M+H]$^+$ 451.1036, found 451.1051 (error 3.3 ppm)

The intermediate 5'-O—(N-(Benzoyl)sulfamoyl)-2',3'-isopropylidene-adenosine was prepared as follows.

a. N-Hydroxysuccinimdyl benzoate. The title compound was prepared from benzoic acid (3.66 g, 30 mmol) using a procedure similar to that described in Example 1, sub-part a. Purification by flash chromatography (3:1 hexane/EtOAc) afforded the title compound (4.47 g, 68%) as a white solid. R$_f$=0.25 (3:1 hexane/EtOAc); $^1$H NMR (300 MHz, CDCl$_3$) δ 2.91 (s, 4H), 7.48-7.54 (m, 2H), 7.65-7.75 (m, 1H), 8.12-8.15 (m, 2H); $^{13}$C NMR (75 MHz, CDCl$_3$) δ 25.9, 125.3, 129.1, 130.8, 135.2, 162.1, 169.5; HRMS (APCI−) calcd. for C$_{11}$H$_8$NO$_4$ [M−H]$^-$ 218.0453, found 218.0457 (error 1.8 ppm).

b. 5'-O—(N-(Benzoyl)sulfamoyl)-2',3'-isopropylideneadenosine. The title compound was prepared from N-hydroxysuccinimdyl benzoate (263 mg, 1.2 mmol) using a procedure similar to that described in Example 2, sub-part b. Purification by flash chromatography (90:10:1 CHCl$_3$/MeOH/Et$_3$N) afforded the title compound (22 mg, 44%) as a white solid. R$_f$=0.25 (10:1 CHCl$_3$/MeOH); $^1$H NMR (300 MHz, CD$_3$OD) δ 1.34 (s, 3H), 1.58 (s, 3H), 4.30-4.33 (m, 2H), 4.52-4.56 (m, 1H), 5.15 (dd, 1H, J=6.0, 2.4 Hz), 5.35 (dd, 1H, J=6.0, 3.0 Hz), 6.21 (d, 1H, J=3.0 Hz), 7.30-7.40 (m, 3H), 7.90-8.10 (m, 2H), 8.14 (s, 1H), 8.44 (s, 1H); $^{13}$C NMR (150 MHz, CD$_3$OD) δ 24.3, 26.3, 68.6, 82.1, 84.5, 84.6, 90.7, 114.1, 119.0, 127.6, 128.8, 131.1, 137.4, 140.3, 149.2, 152.8, 156.1, 174.2; MS (ESI+) calcd. for C$_{20}$H$_{23}$N$_6$O$_7$S [M+H]$^+$ 491.13, found: 491.11.

EXAMPLE 4

Preparation of 5'-Deoxy-5'-N—(N-(2-hydroxybenzoyl)-sulfamoyl)aminoadenosine triethylammonium salt The title compound was prepared from $N^6$-tert-Butoxycarbonyl-5'-deoxy-5'-N—(N-(2-hydroxybenzoyl)sulfamoyl) amino-2',3'-O-isopropylideneadenosine triethylammonium salt (25 mg, 0.035 mmol) using a procedure similar to that described in Example 1. Purification by flash chromatography (60:40:1 EtOAc/MeOH/Et$_3$N) afforded the title compound (16.2 mg, 81%). $R_f$=0.15 (3:2 EtOAc/MeOH); $^1$H NMR (600 MHz, CD$_3$OD) δ 1.23 (t, 9H, J=7.2 Hz), 3.05 (q, 6H, J=7.2 Hz), 3.30-3.34 (m, 2H), 4.20-4.25 (m, 1H), 4.34 (dd, 1H, J=4.8, 2.4 Hz), 4.86 (t, 1H, J=6.6 Hz), 5.90 (d, 1H, J=6.6 Hz), 6.72-6.80 (m, 2H), 7.24 (t, 1H, J=7.2 Hz), 7.86 (d, 1H, J=7.8 Hz), 8.26 (s, 1H), 8.30 (s, 1H); $^{13}$C NMR (150 MHz, CD$_3$OD) δ 8.4, 45.3, 46.5, 71.9, 73.5, 84.8, 89.5, 116.6, 117.9, 119.7, 119.8, 129.7, 132.7, 140.8, 152.9, 156.1, 160.7, 171.9, 173.1; HRMS (ESI+) calcd. for $C_{17}H_{20}N_7O_7S$ [M+H]$^+$ 466.1139, found 466.1139 (error 0 ppm).

The intermediate $N^6$-tert-Butoxycarbonyl-5'-deoxy-5'-N—(N-(2-hydroxybenzoyl)sulfamoyl)amino-2',3'-O-isopropylideneadenosine triethylammonium salt was prepared as follows.

a. $N^6$-tert-Butoxycarbonyl-5'-azido-5'-deoxy-2',3'-O-isopropylidene-adenosine. To a solution of $N^6$-tert-Butoxycarbonyl-2',3'-O-isopropylidene-adenosine (2.15 g, 5.3 mmol, 1.0 equiv) in DMF (40 mL) at 0° C. was added PPh$_3$ (2.77 g, 10.6 mmol, 2.0 equiv), CBr$_4$ (3.5 g, 10.6 mmol, 2.0 equiv) and NaN$_3$ (6.8 g, 105.6 mmol, 20.0 equiv). The reaction was warmed to room temperature and stirred 16 hours then concentrated in-vacuo. The residue was taken up in EtOAc (50 mL) and filtered. The filtrate was concentrated and purified by flash chromatography (EtOAc/hexane) to afford the title compound (1.1 g, 48%). $R_f$=0.65 (EtOAc); $^1$H NMR (600 MHz, CDCl$_3$) δ 1.36 (s, 3H), 1.52 (s, 9H), 1.59 (s, 3H), 3.53 (d, 2H, J=5.4 Hz), 4.36 (ddd, 1H, J=9.0, 5.4, 3.6 Hz), 5.02 (dd, 1H, J=6.6, 3.6 Hz), 5.43 (dd, 1H, J=6.6, 2.4 Hz) 6.11 (d, 1H, J=2.4 Hz), 8.05 (br s, 1H), 8.22 (s, 1H), 8.74 (s, 1H); $^{13}$C NMR (150 MHz, CDCl$_3$) δ 25.5, 27.3, 28.3, 52.2, 82.1, 82.6, 84.2, 85.8, 90.9, 115.1, 122.5, 141.9, 149.8, 150.4, 150.5, 153.3; HRMS (ESI+) calcd. for $C_{18}H_{25}N_8O_5$ [M+H]$^+$ 433.1942, found 433.1939 (error 0.6 ppm).

b. $N^6$-tert-Butoxycarbonyl-5'-amino-5'-deoxy-2',3'-O-isopropylidene-adenosine. To a solution of $N^6$-tert-Butoxycarbonyl-5'-azido-5'-deoxy-2',3'-O-isopropylidene-adenosine (0.64 g, 1.48 mmol, 1.0 equiv) in MeOH (50 mL) was added 10% Pd/C (0.12 g) then the reaction was placed under a H$_2$ atm. After 16 h, the reaction mixture was filtered through a plug of Celite, washing with MeOH, and the combined filtrates were concentrated under reduced pressure. Purification by flash chromatography (4:1 EtOAc/MeOH) afforded the title compound (0.42 g, 70%). $R_f$=0.2 (4:1 EtOAc/MeOH); $^1$H NMR (600 MHz, CDCl$_3$) δ 1.37 (s, 3H), 1.57 (s, 9H), 1.59 (s, 3H), 2.84-2.92 (m, 2H), 4.20-4.26 (m, 1H), 5.02 (dd, 1H, J=5.8, 3.0 Hz), 5.49 (dd, 1H, J=5.8, 1.8 Hz), 6.20 (d, 1H, J=1.8 Hz), 8.44 (s, 1H), 8.57 (s, 1H); $^{13}$C NMR (150 MHz, CD$_3$OD) δ 25.6, 27.5, 28.5, 44.6, 82.8, 83.3, 85.0, 88.6, 91.8, 115.7, 123.7, 144.4, 151.6, 152.2, 152.4, 153.3; HRMS (APCI−) calcd. for $C_{18}H_{27}N_6O_5$ [M−H]$^-$ 405.1876, found 405.1891 (3.7 ppm).

c. $N^6$-tert-Butoxycarbonyl-5'-deoxy-2',3'-O-isopropylidene-5'-N-(sulfamoyl)aminoadenosine. To a solution of $N^6$-tert-Butoxycarbonyl-5'-amino-5'-deoxy-2',3'-O-isopropylidene-adenosine (0.2 g, 0.49 mmol, 1.0 equiv) in CH$_2$Cl$_2$ (5 mL) at 0° C. was added Et$_3$N (102 µL, 0.74 mmol, 1.5 equiv) followed by freshly prepared sulfamoyl chloride (85.2 mg, 0.74 mmol, 1.5 equiv). The reaction mixture was stirred for 24 hours then concentrated in-vacuo under reduced pressure. Purification by flash chromatography (1-2% MeOH/EtOAc) afforded the title compound (80 mg, 34%). $R_f$=0.9 (EtOAc); $^1$HNMR (600 MHz, CD$_3$OD) δ 1.35 (s, 3H), 1.56 (s, 9H), 1.58 (s, 3H), 3.32 (dd, 1H, J=13.2, 4.2 Hz); 3.36 (dd, 1H, J=13.2, 4.2 Hz), 4.44 (dd, 1H, J=6.6, 4.2 Hz), 5.10 (dd, 1H, J=6.6, 3.0 Hz), 5.36 (dd, 1H, J=6.6, 3.6 Hz), 6.11 (d, 1H, J=3.6 Hz), 8.39 (s, 1H), 8.61 (s, 1H); $^{13}$C NMR (150 MHz, CD$_3$OD) δ 24.4, 26.4, 27.3, 44.8, 81.7, 82.1, 83.3, 84.6, 91.8, 114.5, 122.7, 143.3, 150.5, 151.1, 152.2 (2C); HRMS (ESI+) calcd. for $C_{18}H_{28}N_7O_7S$ [M+H]$^+$ 486.1771, found 486.1755 (error 3.2 ppm).

d. $N^6$-tert-Butoxycarbonyl-5'-deoxy-5'-N—(N-(2-hydroxybenzoyl)-sulfamoyl)amino-2',3'-O-isopropylideneadenosine triethylammonium salt. Salicylic acid (43 mg, 0.31 mmol, 3.0 equiv) and CDI (61 mg, 0.37 mmol, 3.6 equiv) were suspended in CH$_3$CN (3.0 mL) and heated at 60° C. for 1 hours to afford a clear homogenous solution. The reaction mixture was cooled to room temperature then a solution of $N^6$-tert-Butoxycarbonyl-5'-deoxy-2',3'-O-isopropylidene-5'-N-(sulfamoyl)aminoadenosine (50 mg, 0.1 mmol, 1.0 equiv) and DBU (23 µL, 0.15 mol, 1.5 equiv) in CH$_3$CN (3.0 mL) were added to provide a yellow solution. The reaction mixture was heated at 60° C. for 1 hours during which time the yellow color faded. The reaction was quenched with MeOH and concentrated iii-vacuo under reduced pressure. Purification by flash chromatography (1-2% MeOH/EtOAc) led to recovery of unreacted starting 27 (16 mg, 33%). Further elution of the column (5-10% MeOH/EtOAc) afforded the title compound (25 mg, 40%), $R_f$=0.5 (1:9 MeOH/EtOAc); $^1$H NMR (600 MHz, CD$_3$OD) δ 1.26 (t, 9H, J=7.2 Hz), 1.32 (s, 3H), 1.55 (s, 3H), 1.57 (s, 9H), 3.15 (q, 6H, J=7.2 Hz), 3.27 (d, 2H, J=1.2 Hz), 4.38-4.44 (m, 1H), 5.10 (dd, 1H, J=6.6, 2.4 Hz), 5.38 (dd, 1H, J=6.0, 3.6 Hz), 6.14 (d, 1H, J=3.0 Hz), 6.70-6.80 (m, 2H), 7.23 (t, 1H, J=7.2 Hz), 7.77 (d, 1H, J=7.2 Hz), 8.42 (s, 1H), 8.57 (s, 1H); $^{13}$C NMR (150 MHz, CD$_3$OD) δ 8.1, 24.3, 26.3, 27.3, 45.5, 46.7, 81.6, 82.4, 83.8, 85.3, 91.1, 114.4, 116.6, 118.0, 119.5, 122.3, 129.7, 132.8, 143.0, 150.2, 150.7, 151.1, 152.3, 160.6, 173.1; HRMS (ESI+) calcd. for $C_{25}H_{32}N_7O_9S$ [M+H]$^+$ 606.1976, found 606.1951 (error 4.1 ppm).

EXAMPLE 5

Preparation of 5'-O—(N-(2-Hydroxybenzyl)sulfamoyl)adenosine

The title compound was prepared from 5'-O—(N-(2-hydroxybenzyl)-sulfamoyl)-2',3'-O-isopropylideneadenosine (30 mg, 0.060 mmol) using a procedure similar to that described in Example 1. Purification by flash chromatography (60:40:1 EtOAcMeOH:Et$_3$N) afforded the title compound (16.2 mg, 81%). $R_f$=0.23 (9:1 EtOAc/MeOH); $^1$H NMR (600 MHz, CD$_3$OD) δ 4.15-4.21 (m, 4H), 4.21-4.30 (m, 2H), 4.59 (t, 1H, J=4.8 Hz), 6.01 (d, 1H, J=4.8 Hz), 6.71 (t, 1H, J=7.2 Hz), 6.75 (d, 1H, J=8.4 Hz), 7.06 (t, 1H, J=7.8 Hz), 7.16 (d, 1H, J=7.8 Hz), 8.18 (s, 1H), 8.24 (s, 1H); $^{13}$C NMR (125 MHz, CD$_3$OD) δ 42.2, 68.6, 70.7, 74.3, 82.5, 88.6, 114.8, 119.3, 123.3, 128.9, 129.7, 139.7 (2C), 149.5, 152.8, 155.4, 156.1; HHRMS (APCI+) calcd. for $C_{17}H_{21}N_6O_7S$ [M+H]$^+$ 453.1197, found 453.1184 (error 2.8 ppm).

The intermediate 5'-O—(N-(2-Hydroxybenzyl)sulfamoyl)-2',3'-O-isopropylideneadenosine was prepared as follows.

a. 2-Benzyloxybenzaldehyde. To a solution of salicylaldehyde (5.0 g, 41.0 mmol, 1.0 equiv) in acetone (125 mL) was added $K_2CO_3$ (6.23 g, 45.1 mmol, 1.1 equiv) and benzyl bromide (4.87 mL, 41.0 mmol, 1.0 equiv). The reaction was heated at reflux for 5 hours then cooled to room temperature, filtered, and the filtrate was concentrated under reduced pressure. Purification by distillation (P=0.34 Torr) afforded the title compound (7.1 g, 95%) as a colorless oil. bp 140-145° C., 0.34 Torr; $^1$H NMR (600 MHz, $CDCl_3$) δ 5.18 (s, 2H), 7.0-7.07 (m, 2H), 7.32-7.46 (m, 5H), 7.52 (ddd, 1H, J=8.4, 7.2, 1.8 Hz), 7.86 (dd, 1H, J=7.8, 1.8 Hz), 10.57 (s, 1H); $^{13}$C NMR (150 MHz, $CD_3OD$) δ 70.7, 113.3, 121.3, 125.4, 127.5, 128.5, 128.7, 129.0, 136.2, 136.3, 161.3, 189.9.

b. 2-Benzyloxybenzyl alcohol. To a solution of 2-benzyloxybenzaldehyde (1.00 g, 4.71 mmol, 1.0 equiv) in MeOH (25 mL) at 0° C. was added $NaBH_4$ (0.40 g, 9.43 mmol, 2.0 equiv) portionwise over 10 minutes. After gas evolution ceased, the reaction mixture was warmed to room temperature and stirred for 30 minutes. The reaction was concentrated and the residue partitioned between $H_2O$ (50 mL) and EtOAc (50 mL). The organic phase was separated and the aqueous phase extracted with EtOAc (2×75 mL). The combined organic extracts were dried ($Na_2SO_4$) then concentrated to afford the title compound (0.98 g, 98%), which required no further purification. $^1$H NMR (600 MHz, $CDCl_3$) δ 2.22 (br s, 1H), 4.73 (s, 2H), 5.12 (s, 2H), 6.92-7.00 (m, 2H), 7.24-7.29 (m, 1H), 7.29-7.37 (m, 2H), 7.37-7.44 (m, 4H). $^{13}$C NMR (150 MHz, $CDCl_3$) δ62.4, 70.3, 111.9, 121.3, 127.6, 128.4, 129.0, 129.1, 129.2, 129.8, 137.0, 156.9.

c. 2-Benzyloxybenzyl bromide. To a solution of 2-benzyloxybenzyl alcohol (2.0 g, 9.3 mmol, 1.0 equiv) in $CH_2Cl_2$ (60 mL) at 0° C. was added $PPh_3$ (3.67 g, 14.0 mmol, 1.5 equiv) and $CBr_4$ (4.64 g, 14.0 mmol, 1.5 equiv). After 30 minutes the reaction was concentrated in-vacuo, then the residue was taken up in $Et_2O$ (50 mL) and placed at −20° C. for 30 minutes. The solution was filtered to remove solid $Ph_3PO$ and the filtrate was concentrated under reduced pressure. Purification by flash chromatography (hexanes/EtOAc) afforded the title compound (2.28 g, 88%). $R_f$=0.75 (9:1 Hexane/EtOAc); $^1$H NMR (600 MHz, $CDCl_3$) δ 4.62 (s, 2H), 5.16 (s, 2H), 6.80-7.10 (m, 2H), 7.20-7.55 (m, 7H); $^{13}$C NMR (150 MHz, $CDCl_3$) δ 29.4, 70.3, 112.5, 121.2, 126.8, 127.4, 128.1, 128.8, 130.4, 131.2, 137.1, 156.8.

d. 5'-O—(N-(2-Benzyloxybenzyl)sulfamoyl)-2',3'-O-isopropylidene-adenosine. To a solution of 2',3'-O-isopropylidene-5'-O-(sulfamoyl)adenosine (400 mg, 1.04 mmol, 1.0 equiv; see Heacock, D., et al., *Bioorg. Chem.* 1996, 24, 273-289) in a mixture of $CH_2Cl_2$ (25 mL) and DMF (3 mL) was added $Cs_2CO_3$ (675 mg, 2.1 mmol, 2.0 equiv) followed by a solution of 2-benzyloxybenzyl bromide (574 mg, 2.1 mmol, 2.0 equiv) in $CH_2Cl_2$ (5 mL) and the reaction stirred 16 hours at room temperature. The reaction was diluted with $H_2O$ (5 mL) and quenched by the addition of solid $KHSO_4$ with vigorous stirring until the pH of the aqueous layer was acidic (pH~3). The organic layer was separated and the aqueous layer extracted with $CHCl_3$ (2×30 mL). The combined organic layers were dried ($Na_2SO_4$) and concentrated under reduced pressure. Purification by flash chromatography (10:1 EtOAc/hexanes) afforded the title compound (289 mg, 48%) along with (150 mg, 20%) of the bis benzylated side-product. Characterization data for bis benzylated side-product: $R_f$=0.5 (EtOAc): $R_f$=0.41 (EtOAc); $^1$H NMR: (600 MHz, $CDCl_3$) δ 1.35 (s, 3H), 1.58 (s, 3H), 3.96-4.08 (m, 2H), 4.22 (d, 2H, J=5.4 Hz), 4.29 (dd, 1H, J=7.8, 4.8 Hz), 4.86 (dd, 1H, J=6.0, 3.0 Hz), 5.05 (s, 2H), 5.22 (dd, 1H, J=6.0, 2.4 Hz), 5.64 (t, 1H, J=6.0 Hz), 5.80 (br s, 2H), 6.02 (d, 1H, J=2.4 Hz), 6.84-6.92 (m, 2H), 7.18 (d, 1H, J=7.2 Hz), 7.22 (t, 1H, J=7.2 Hz), 7.26-7.32 (m, 1H), 7.32-7.38 (m, 4H), 7.77 (s, 1H), 8.24 (s, 1H); $^{13}$C NMR (150 MHz, $CD_3OD$) δ 25.0, 26.5, 44.4, 59.0, 71.0, 81.7, 86.5, 87.1, 93.5, 112.9, 115.0, 121.4, 121.8, 128.3, 128.7, 128.8, 129.2, 129.6, 130.4, 138.8, 140.5, 141.4, 150.2, 157.8, 158.8; HRMS (APCI−) calcd. for $C_{27}H_{29}N_6O_7S$ [M−H]$^-$ 581.1823, found 581.1822 (error 0.1 ppm).

e. 5'-O—(N-(2-Hydroxybenzyl)sulfamoyl)-2',3'-O-isopropylideneadenosine (33). The title compound was prepared from 5'-O—(N-(2-Benzyloxybenzyl)-sulfamoyl)-2',3'-O-isopropylidene-adenosine (50 mg, 0.090 mmol) using a procedure similar to that described in Example 1, sub-part e. Purification by flash chromatography (MeOH/EtOAc) afforded the title compound (35 mg, 83%). $R_f$=0.35 (EtOAc); $^1$H NMR (600 MHz, $CD_3OD$) δ 1.35 (s, 3H), 1.37 (s, 3H), 4.00-4.20 (m, 4H), 4.30-4.40 (m, 1H), 4.89 (dd, 1H, J=6.3, 2.4 Hz), 5.30 (dd, 1H, J=6.3, 1.5 Hz), 6.17 (d, 1H, J=1.5 Hz), 6.71 (t, 1H, J=7.2 Hz), 6.74 (d, 1H, J=8.4 Hz), 7.05 (t, 1H, J=7.8 Hz), 7.11 (d, 1H, J=7.2 Hz), 8.18 (s, 1H), 8.20 (s, 1H); $^{13}$C NMR (150 MHz, $CD_3OD$) δ 24.4, 26.2, 42.2, 68.7, 81.7, 84.3, 84.4, 90.7, 114.3, 114.8, 119.21, 119.23, 123.4, 129.0, 129.8, 140.2, 149.1, 152.9, 155.4, 156.2; HRMS (APCI−) calcd. for $C_{20}H_{23}N_6O_7S$ [M−H]$^-$ 491.1354, found 491.1370 (error 3.2 ppm).

EXAMPLE 6

Preparation of 5'-O-[(Hydroxy)(2-oxo-2-(2-hydroxyphenyl)-ethyl)phosphinyl]adenosine triethylammonium salt The title compound was prepared from 5'-O-[(hydroxy)(2-oxo-2-(2-hydroxyphenyl)ethyl)phosphinyl]-2',3'-O-isopropylideneadenosine triethylammonium salt (25 mg, 0.040 mmol) using a procedure similar to that described in Example 1. Purification by flash chromatography (66:33:1 EtOAc/MeOH/$Et_3N$) afforded the title compound (21 mg, 90%). $R_f$=0.15 (1:1 MeOH/EtOAc); $^1$H NMR (600 MHz, $CD_3OD$) δ 1.25 (t, 9H, J=7.2 Hz), 3.15 (q, 6H, J=7.2 Hz), 3.42-3.62 (m, 2H), 4.10-4.16 (m, 2H), 4.16-4.22 (m, 1H), 4.35 (dd, 1H, J=4.8, 3.6 Hz), 4.67 (t, 1H, J=5.4 Hz), 6.05 (d, 1H, J=6.0 Hz), 6.84-6.90 (m, 2H), 7.43 (t, 1H, J=9.0 Hz), 8.01 (d, 1H, J=7.8 Hz), 8.18 (s, 1H), 8.50 (s, 1H); $^{13}$C NMR (150 MHz, $CD_3OD$) δ 8.2, 46.5, 58.9, 64.5 (d, $^2J_{C,P}$=7.8 Hz), 71.1, 74.8, 84.6 (d, $^2J_{C,P}$=7.9 Hz), 87.8, 117.5, 118.8, 119.0, 120.1, 132.5, 136.2, 139.9, 149.7, 152.6, 156.0, 162.4, 201.9 (d, $^2J_{C,P}$=6.3 Hz), (—COCH$_2$PO$_3$— the underlined carbon [expected ~45 ppm] was not observed due to deuterium exchange, the resulting doublet of pentets due to coupling with deuterium and phosphorous nucleii precluded observation of this carbon signal. Acquisition of $^{13}$C spectra in aprotic solvents was hindered by limited substrate solubility); $^{31}$P NMR (195 MHz, $CD_3OD$) δ 13.6; HRMS (ESI+) calcd. for $C_{18}H_{21}N_5O_8P$ [M+H]$^+$ 466.1122, found 466.1162 (error 8.5 ppm).

The intermediate 5'-O-[(Hydroxy)(2-oxo-2-(2-hydroxyphenyl)-ethyl)phosphinyl]-2',3'-O-isopropylideneadenosine triethylammonium salt was prepared as follows.

a. Methyl 2-(benzyloxy)benzoate. To a solution of O-benzylsalycilic acid (5.0 g, 21.9 mmol, 1.0 equiv) in acetone (150 mL) was added solid $K_2CO_3$ (7.57 g, 54.8 mmol, 2.5 equiv) and MeI (2.05 mL, 32.9 mmol, 1.5 equiv) and the reaction heated at reflux for 4 hours. The reaction mixture cooled to room temperature, filtered, and the filtrate was concentrated under reduced pressure. Purification by flash chromatography (hexane/EtOAc) afforded the title compound (5.3 g, 100%) that was greater than 98% pure as judged by $^1$H NMR and was used without further purification. $^1$H NMR (600 MHz, $CDCl_3$) δ 3.90 (s, 3H), 5.18 (s, 2H), 6.80-7.04 (m, 2H), 7.35-7.48 (m, 4H), 7.50 (d, 2H, J=7.8 Hz), 7.83 (d, 1H, J=7.6 Hz); $^{13}$C NMR (150 MHz, CDCl$_3$) δ 52.2, 70.8, 114.1, 120.8, 121.1, 127.1, 128.0, 128.8, 132.0, 133.6, 137.0, 158.4, 167.0.

b. Dimethyl 2-(2-(benzyloxy)phenyl)-2-oxoethylphosphonate. To a solution of dimethyl methylphosphonate (0.537 g, 4.33 mmol, 2.1 equiv) in THF (6 mL) at −78° C. was added a solution of n-BuLi (2.5 M in hexanes, 1.8 mL, 4.33 mmol, 2.1 equiv) to afford a white heterogeneous mixture, which was stirred 15 minutes. Next, a solution of methyl 2-(benzyloxy) benzoate (500 mg, 2.06 mmol, 1.0 equiv) in THF (6 mL) was added slowly down the side of the flask to the lithium phosphonate solution at −78° C. to afford a clear solution. After stirring for 1 h, the cooling bath was removed and the solution was allowed to warm to 0° C. The reaction was partitioned between EtOAc (25 mL) and 1 M aq. HCl (10 mL) and sat'd aq. NaCl (10 mL). The organic layer was separated and the aq. layer was extracted with EtOAc (2×25 mL). The combined organic extracts were dried (Na$_2$SO$_4$), filtered, and concentrated under reduced pressure to a colorless oil. Purification by flash chromatography (4:1 EtOAc/hexane) afforded the title compound (610 mg, 88%) as a colorless oil. R$_f$=0.43 (EtOAc); $^1$H NMR (600 MHz, CDCl$_3$) δ 3.65 (d, 6H, $^3J_{H,P}$=11.4 Hz), 3.77 (d, 2H, $^2J_{H,P}$=21.6 Hz), 5.16 (s, 2H), 6.96-7.04 (m, 2H), 7.30-7.50 (m, 6H), 7.71 (dd, 1H, J=7.8, 1.8 Hz); $^{13}$C NMR (150 MHz, CDCl$_3$) δ 41.9 (d, $^1J_{C,P}$=131 Hz), 53.6 (d, $^2J_{C,P}$=6.0 Hz), 71.2, 113.2, 121.4, 127.9, 128.1, 128.7, 129.1, 131.3, 134.6, 136.1, 158.1, 193.5 (d, $^2J_{C,P}$=7.3 Hz); $^{31}$P NMR (195 MHz, CDCl$_3$) δ 25.1; HRMS (APCI−) calcd. for C$_{17}$H$_{18}$O$_5$P [M−H]$^−$ 333.0897, found 333.0928 (error 9.3 ppm).

c. 5'-O-[(Hydroxy)[(2-oxo-2(2-benzyloxyphenyl))ethyl]phosphinyl]-2',3'-O-isopropylideneadenosine triethylammonium salt. To a solution of dimethyl 2-(2-(benzyloxy)phenyl)-2-oxoethylphosphonate (2.0 g, 6.0 mmol, 1.0 equiv) in CH$_2$Cl$_2$ (30 mL) was added TMSBr (3.89 mL, 29.9 mmol, 5.0 equiv). The reaction was monitored by $^{31}$P NMR and found to be complete at 7 hours. The reaction was concentrated in-vacuo then treated with 5% aq pyridine. The reaction was concentrated under reduced pressure and the residue was azeotropically dried with anhydrous pyridine (3×30 mL) to provide crude material. To a solution of the crude material in anhydrous pyridine (30 mL) was added trisyl chloride (1.69 g, 7.8 mmol, 1.5 equiv). The reaction was slightly exothermic and stirred 15 minutes then 2',3'-O-isopropylideneadenosine (1.59 g, 5.7 mmol, 1.1 equiv) was added and the reaction was stirred 16 hours. The reaction was concentrated in-vacuo. Purification by flash chromatography (MeOH/EtOAc+1% Et$_3$N) afforded the title compound (184 mg, 6%). R$_f$=0.75 (1:2 MeOH/EtOAc); $^1$H NMR (300 MHz, CD$_3$OD) δ 1.22 (t, 9H, J=7.2 Hz), 1.35 (s, 3H), 1.58 (s, 3H), 3.08 (q, 6H, J=7.2 Hz), 3.50-3.70 (m, 2H), 3.81-3.92 (m, 2H), 4.28 (m, 1H), 4.95 (dd, 1H, J=6.0, 2.4 Hz), 5.15 (s, 2H), 5.24 (dd, 1H, J=6.0, 3.6 Hz), 6.14 (d, 1H, J=3.0 Hz), 6.92 (t, 1H, J=7.8 Hz), 7.06 (d, 1H, J=8.4 Hz), 7.22-7.28 (m, 1H), 7.32 (t, 2H, J=7.2 Hz), 7.35-7.41 (m, 1H), 7.41 (d, 2H, J=7.8 Hz), 7.56 (dd, 1H, J=7.8, 1.8 Hz), 8.12 (s, 1H), 8.40 (s, 1H); $^{13}$C NMR (150 MHz, CD$_3$CN) δ 8.0, 24.7, 26.6, 45.4 (d, $^1J_{C,P}$=130 Hz), 45.5, 64.6, 70.5, 81.9, 85.0, 86.0 (d, $^2J_{C,P}$=7.2 Hz), 90.4, 113.3, 113.5, 119.2, 120.7, 127.8, 128.1, 128.6, 130.3, 130.4, 132.8, 136.9, 140.0, 149.6, 152.9, 156.0, 157.0, 198.3; $^{31}$P NMR (195 MHz, CD$_3$CN) δ 14.9; HRMS (ESI+) calcd. for C$_{28}$H$_{31}$N$_5$O$_8$P [M+H]$^+$ 596.1904, found 596.1914 (error 1.6 ppm).

d. 5'-O-[(Hydroxy)(2-oxo-2-(2-hydroxyphenyl)ethyl)phosphinyl]-2',3'-O-isopropylideneadenosine triethylammonium salt. The title compound was prepared from 5'-O-(hydroxy) [(2-oxo-2(2-benzyloxyphenyl))ethyl)phosphinyl]-2',3'-O-isopropylideneadenosine triethylammonium salt (80 mg, 0.13 mmol) using a procedure similar to that described in Example 1, sub-part e. Purification by flash chromatography (60:40:1 EtOAc/MeOH/Et$_3$N) afforded the title compound (25 mg, 40%). R$_f$=0.16 (1:2 MeOH/EtOAc); $^1$H NMR (600 MHz, CD$_3$OD) δ 1.21 (t, 9H, J=7.2 Hz), 1.36 (s, 3H), 1.58 (s, 3H), 3.03 (q, 6H, J=7.2 Hz), 3.42-3.62 (m, 2H), 4.00-4.10 (m, 2H), 4.40-4.46 (m, 1H), 5.06 (dd, 1H, J=6.0, 1.8 Hz), 5.30 (dd, 1H, J=6.0, 3.0 Hz), 6.17 (d, 1H, J=3.0 Hz), 6.82-6.88 (m, 2H), 7.40-7.45 (m, 1H), 7.96 (dd, 1H, J=7.8 Hz), 8.20 (s, 1H), 8.41 (s, 1H); $^{13}$C NMR (150 MHz, CD$_3$OD) δ 8.4, 24.5, 26.5, 46.4, 64.8 (d, $^2J_{C,P}$=5.7 Hz), 82.1, 85.5 (d, $^2J_{C,P}$=12 Hz), 85.6, 90.6, 114.0, 117.5, 118.8, 119.0, 120.1, 132.5, 136.2, 140.1, 149.2, 152.7, 156.1, 162.4, 202.1, (—COCH$_2$PO$_3$— the underlined carbon [expected ~45 ppm] was not observed due to deuterium exchange, the resulting doublet of pentets due to coupling with deuterium and phosphorous nucleii precluded observation of this carbon signal. Acquisition of $^{13}$C spectra in aprotic solvents was hindered by limited substrate solubility); $^{31}$P NMR (195 MHz, CD$_3$OD) δ 13.8; HRMS (ESI+) calcd. for C$_{21}$H$_{25}$N$_5$O$_8$P [M+H]$^+$ 506.1435, found 506.1446 (error 2.1 ppm).

EXAMPLE 7

Preparation of 5'-Deoxy-5'-N-((4-(2-hydroxybenzoyl)-1H-1,2,3-triazol-1-yl)adenosine To a solution of N$^6$-tert-butoxycarbonyl-5'-N-(4-(2-benzyloxybenzoyl)-1H-1,2,3-triazol-1-yl)-5'-deoxy-2',3'-O-isopropylidene-adenosine (33 mg, 0.049 mmol) in MeOH (5 mL) was added 10% Pd/C (3.3 mg) and the reaction placed under an H$_2$ atm. After 16 h, the reaction was filtered through Celite and the filtrate concentrated under reduced pressure. The residue was treated with 80% aq TFA (2 mL) and stirred 30 minutes, then concentrated in-vacuo to afford the title compound (21.6 mg, 100%) as a white crystalline solid, which required no further purification. $^1$H NMR (600 MHz, CD$_3$OD) δ 4.40-4.44 (m, 1H), 4.50 (dd, 1H, J=7.2, 6.0 Hz), 4.65 (dd, 1H, J=4.8, 3.6 Hz), 4.88-4.95 (m, 2H), 4.95 (dd, 1H, J=4.8, 3.0 Hz), 6.02 (d, 1H, J=3.0 Hz), 6.93-6.98 (m, 1H), 7.54 (dd, 1H, J=7.8, 7.2 Hz), 8.31 (s, 1H), 8.20 (s, 1H), 8.38 (s, 1H), 8.65-8.68 (m, 2H); $^{13}$C NMR (150 MHz, CD$_3$OD) δ 50.6, 70.5, 73.4, 81.9, 90.3, 117.8, 119.1, 119.3, 119.7, 131.1, 133.0, 136.6, 142.7, 146.6, 146.8, 148.5, 152.4, 163.2, 189.1; HRMS (ESI+) calcd. for C$_{19}$H$_{19}$N$_8$O$_5$ [M+H]$^+$ 439.1478, found 439.1449 (error 6.6 ppm).

The intermediate N$^6$-tert-butoxycarbonyl-5'-N-(4-(2-benzyloxybenzoyl)-1H-1,2,3-triazol-1-yl)-5'-deoxy-2',3'-O-isopropylidene-adenosine was prepared as follows.

a. 2-(Benzyloxy)-N-methoxy-N-methylbenzamide. To a solution of 2-benzyloxybenzoic acid (1.14 g, 5.0 mmol, 1.0 equiv) in CH$_2$Cl$_2$ (50 mL) and a catalytic amount of DMF (2 drops) freshly distilled oxalyl chloride (472 µL, 6.0 mmol, 1.2 equiv) was slowly added via syringe at 0° C. The reaction was stirred for 2 hours then concentrated in-vacuo under reduced pressure. The crude acid chloride obtained was dissolved in ethanol-free anhydrous chloroform[24] (50 mL) and N,O-dimethylhydroxylamine-HCl (0.5 g, 6 mmol, 1.2 equiv) was added. The reaction mixture was cooled to 0° C. and Et$_3$N (20 mL) was added dropwise. The mixture was stirred at room temperature for 2.5 hours then concentrated in vacuo. The residue was partitioned between sat'd aq NaCl and 1:1 CH$_2$Cl$_2$/Et$_2$O. The organic layer was dried (Na$_2$SO$_4$) and concentrated to afford the title compound (1.19 g, 80%) as an oil that was greater than 98% pure based on $^1$H NMR. R$_f$=0.3 (3:1 hexanes/EtOAc); $^1$H NMR (600 MHz, CDCl$_3$) δ 3.23 (br s, 3H), 3.40 (br s, 3H), 5.09 (s, 2H), 6.55-6.95 (m, 2H), 7.29-7.40 (m, 7H); $^{13}$C NMR (150 MHz, CDCl$_3$) δ 33.3, 61.4, 70.6, 112.9, 121.1, 127.3, 128.1, 128.6, 128.7, 129.2, 130.8, 137.0, 155.1, 169.5; MS (ESI+) calcd. for C$_{16}$H$_{18}$NO$_3$ [M+H]$^+$ 272.12, found 272.13.

b. 1-(2-Benzyloxy)phenyl-3-(trimethylsilyl)prop-2-yn-1-one. To a solution of ethynyltrimethylsilane (424 µL, 3 mmol, 1.0 equiv) in THF (30 mL) was added n-BuLi (2.5 M in hexane, 1.2 mL, 3.4 mmol, 1.13 equiv) at 0° C. After stirring for 30 minutes, a solution of 2-(benzyloxy)-N-methoxy-N-methylbenzamide (814 mg, 3.0 mmol, 1.0 equiv) in THF (3 mL) was added dropwise via syringe. The reaction was allowed to slowly warm to 25° C. over 2 hours then diluted with Et$_2$O (30 mL) and poured onto sat'd aq NH$_4$Cl (30 mL). The organic phase was separated and the aqueous phase extracted with Et$_2$O (2×30 mL). The combined organic layers were dried (Na$_2$SO$_4$) and concentrated under reduced pressure. Purification by flash chromatography (15:1 hexanes/EtOAc) afforded the title compound (0.71 g, 76%) as a light yellow oil. R$_f$=0.27 (5:1 hexane/EtOAc); $^1$H NMR (600 MHz, CDCl$_3$) δ 0.00 (s, 9H), 5.01 (s, 2H), 6.78 (d, 1H, J=8.4 Hz), 6.80-6.82 (m, 1H), 7.08-7.10 (m, 1H), 7.15-7.18 (m, 2H), 7.24 (dd, 1H, J=7.8, 1.8 Hz), 7.29-7.32 (m, 2H), 7.76 (dd, 1H, J=7.8, 1.8 Hz); $^{13}$C NMR (150 MHz, CDCl$_3$) δ 0.00, 68.9, 71.1, 114.4, 121.3, 127.6, 128.5, 129.3, 129.5, 131.6, 133.4, 135.5, 137.2, 159.4, 177.4; HRMS (ESI+) calcd. for C$_{19}$H$_{21}$O$_2$Si [M+H]$^+$ 309.1311, found 309.1316 (error 1.6 ppm).

c. 1-(2-(Benzyloxy)phenyl)prop-2-yn-1-one. To a solution of 1-(2-benzyloxy)phenyl-3-(trimethylsilyl)prop-2-yn-1-one (450 mg, 1.46 mmol, 1.0 equiv) in THF (20 mL) at 0° C. was added TBAF (1.0 M solution in THF, 1.46 mL, 1.46 mmol, 1.0 equiv.). After 20 minutes, the reaction was diluted with Et$_2$O (40 mL) and was washed with sat'd aq NaCl (2×40 mL). The organic phase was dried (MgSO$_4$) and concentrated under reduced pressure. Purification by flash chromatography (20:1 hexane/EtOAc) afforded the title compound (272 mg, 79%) as colorless oil. R$_f$=0.24 (20:1 hexanes/EtOAc); $^1$H NMR (600 MHz, CDCl$_3$) δ 3.25 (s, 1H), 5.21 (s, 2H), 7.02 (d, 1H, J=8.4 Hz), 7.03-7.04 (m, 1H), 7.30-7.32 (m, 1H), 7.36-7.38 (m, 2H), 7.40-7.50 (m, 3H), 8.02 (dd, 1H, J=8.4, 1.8 Hz); $^{13}$C NMR (150 MHz, CDCl$_3$) δ 70.8, 79.8, 82.7, 113.9, 120.9, 126.6, 127.4, 128.2, 128.8, 133.0, 135.5, 136.4, 159.2, 176.2; MS (ESI+) calcd. for C$_{16}$H$_{13}$O$_2$ [M+H]$^+$ 237.09, found 237.00.

d. N$^6$-tert-Butoxycarbonyl-5'-N-(4-(2-benzyloxybenzoyl)-1H-1,2,3-triazol-1-yl)-5'-deoxy-2',3'-O-isopropylideneadenosine. To a suspension of 1-(2-(benzyloxy)phenyl)prop-2-yn-1-one (13 mg, 0.056 mmol, 1.0 equiv) and N$^6$-tert-butoxycarbonyl-5'-azido-5'-deoxy-2',3'-O-isopropylidene-adenosine (24 mg, 0.056 mmol, 1.0 equiv) in H$_2$O (600 µL) and tert-butyl alcohol (300 µL) was added sodium ascorbate (1.4 mg, 0.017 mmol, 0.30 equiv) followed by CuSO$_4$.(H$_2$O)$_5$ (1.4 mg, 0.0056 mmol, 0.1 equiv). The resulting heterogeneous mixture was stirred vigorously for 16 hours. The reaction mixture was concentrated in vacuo and the residue was subjected to flash chromatography (3:1 EtOAc/hexane) to afford the title compound (33.0 mg, 89%) as a white crystalline solid. R$_f$=0.26 (3:1 EtOAc/hexane); $^1$H NMR (600 MHz, CDCl$_3$) δ 1.37 (s, 3H), 1.56 (s, 9H), 1.59 (s, 3H), 4.57 (ddd, 1H, J=8.4, 4.2, 3.6 Hz), 4.70 (dd, 1H, J=14.4, 8.4 Hz), 4.82 (dd, 1H, J=14.4, 3.6 Hz), 5.03 (s, 2H), 5.19 (dd, 1H, J=6.0, 4.2 Hz), 5.38 (dd, 1H, J=6.0, 1.8 Hz), 6.06 (d, 1H, J=1.8 Hz), 7.01 (d, 1H, J=7.8), 7.03 (t, 1H, J=7.2 Hz), 7.16-7.25 (m, 5H), 7.43 (dt, 1H, J=7.8, 1.8 Hz), 7.54 (dd, 1H, J=7.2, 1.8 Hz), 7.86 (s, 1H), 7.99 (s, 1H), 8.73 (s, 1H); $^{13}$C NMR (150 MHz, CDCl$_3$) δ 25.5, 27.3, 28.3, 52.1, 70.7, 82.0, 83.0, 84.3, 85.6, 90.9, 113.5, 115.6, 121.1, 122.0, 127.2, 127.9, 128.1, 128.5, 128.8, 130.5, 133.1, 136.8, 142.2, 148.6, 149.8, 150.1, 150.4, 153.3, 157.4, 188.1; MS (ESI+) calcd. for C$_{34}$H$_{37}$N$_8$O$_7$ [M+H]$^+$ 669.28, found 669.28.

EXAMPLE 8

Preparation of 5'-O-{[1,1-Difluoro-2-(2-hydroxyphenyl)-2-oxo-ethyl][hydroxyl]phosphinyl}adenosine triethylammonium salt To a solution of 5'-{[2-(2-benzyloxyphenyl)-1,1-difluoro-2-oxo-ethyl][hydroxyl]phosphinyl}-2',3'-O-isopropylidene-adenosine triethylammonium salt (15 mg, 0.023 mmol, 1.0 equiv) in a mixture of EtOAc/MeOH (5:1, 20 mL) was added 10% Pd/C (5 mg) and the reaction was stirred under a H$_2$ atm for 4 hours. The reaction mixture was filtered through a plug of Celite and the residue was washed copiously with MeOH (4×10 mL). The combined filtrates were concentrated and the resulting crude oil was treated with 80% aq TFA (2.0 mL) for 2.5 hours. The reaction mixture was concentrated under reduced pressure. Purification by flash chromatography (30:70:1 MeOH/EtOAc/Et$_3$N) afforded the title compound (7.9 mg, 67%): R$_f$ 0.2 (1:1 MeOH/EtOAc); [α]$^{20}_D$ −28 (c 0.25, MeOH); $^1$H NMR (600 MHz, CD$_3$OD) δ 1.27 (t, J=7.2 Hz, 9H), 3.16 (q, J=7.2 Hz, 6H), 4.18-4.30 (m, 3H), 4.36 (dd, J=4.8, 3.0 Hz, 1H), 4.60 (t, J=5.4 Hz, 1H), 6.06 (d, J=6.6 Hz, 1H), 6.90 (t, J=7.8 Hz, 1H), 6.94 (d, J=8.4 Hz, 1H), 7.51 (t, J=3.0 Hz, 1H), 8.18 (s, 1H), 8.31 (d, J=8.4 Hz, 1H), 8.45 (s, 1H); $^{13}$C NMR (150 MHz, CD$_3$OD) δ 8.3, 47.9, 60.2, 67.5, 72.4, 76.2, 85.8 (d, $^2J_{C,P}$=6.7 Hz), 88.7, 118.1, 119.1, 120.1, 120.2, 134.6, 138.6, 141.1, 151.1, 154.0, 157.4, 164.7, 177.7; $^{31}$P δ 0.95 (t, $^2J_{F,P}$=205 Hz); HRMS (ESI+) calcd for C$_{18}$H$_{17}$F$_2$N$_5$O$_8$P [M+H]$^+$ 500.0783, found 500.0743 (error 7.9 ppm).

The intermediate 5'-O-{[2-(2-Benzyloxyphenyl)-1,1-difluoro-2-oxo-ethyl][hydroxyl]-phosphinyl}-2',3'-O-isopropylideneadenosine triethylammonium salt was prepared as follows.

a. Diethyl 2-(2-benzyloxyphenyl)-1,1-difluoro-2-oxo-ethylphosphonate. Butyllithium (2.95 mL of 1.4 M solution in hexanes, 4.13 mmol, 1.0 equiv) was added dropwise to a solution of diisopropylamine (0.58 ml, 4.13 mmol) in THF (7.0 ml) at −78° C. The solution was warmed to 0° C. for 10 minutes then freshly-dried CeCl$_3$ (1.0 g, 4.13 mmol, 1.0 equiv) was added in one portion and the mixture was re-cooled to −78° C. and stirred vigorously at that temperature for 15 minutes. Neat diethyl difluoromethylphosphonate (0.62 g, 4.13 mmol, 1.0 equiv) was added dropwise over 10 minutes and the mixture was stirred for 1 hour at −78° C. Next, methyl 2-benzyloxybenzoate (0.61 ml, 5.3 mmol, 1.28 equiv) was added slowly to the deep yellow orange suspension. The reaction was quenched after 1 hour with 3 M aq HCl (5 mL), then the stirred mixture was allowed to warm to room temperature over 20 minutes. The aqueous layer was extracted with CH$_2$Cl$_2$ (3×10 mL) and the combined organic extracts were washed with brine (10 mL), dried (Na$_2$SO$_4$) and concentrated under reduced pressure Purification by flash chromatography (1:1 EtOAc/hexanes) afforded the title compound (460 mg, 70%) as a colorless oil: R$_f$ 0.6 (1:1 EtOAc/hexanes); $^1$H NMR (600 MHz, CDCl$_3$) δ 1.33 (t, J=7.2 Hz, 6H), 4.2-4.40 (m, 4H), 5.16 (s, 2H), 6.80-7.10 (m, 2H), 7.20-7.50 (m, 6H), 7.64 (d, J=7.2 Hz, 1H); $^{13}$C NMR (150 MHz, CDCl$_3$) δ 16.5 (d, $^3J_{C,P}$=5.5 Hz), 63.4 (d, $^2J_{C,P}$=6.7 Hz), 70.8, 113.3, 120.8, 124.7, 127.3, 128.1, 128.7, 130.6 (d, $^3J_{C,P}$=2.8

Hz), 134.3, 136.5, 157.0, 192.0 (m); HRMS (ESI+) calcd for $C_{19}H_{21}F_2O_5P$ [M+H]$^+$ 399.1667, found 399.1666 (error 0.1 ppm).

b. 5'-O-{[2-(2-Benzyloxyphenyl)-1,1-difluoro-2-oxo-ethyl] [hydroxy]-phosphinyl}-2',3'-O-isopropylideneadenosine triethylammonium salt. To a solution of diethyl 2-(2-benzyloxyphenyl)-1,1-difluoro-2-oxo-ethylphosphonate. (0.20 g, 0.5 mmol, 1.0 equiv) in $CH_2Cl_2$ (5 mL) was added TMSBr (0.652 mL, 5.02 mmol, 10.0 equiv) at room temperature. The reaction was monitored by $^{31}P$ NMR and found to be complete after 16 hours. The reaction was concentrated in vacuo then treated with 5% aq pyridine. The reaction was concentrated under reduced pressure and the residue was azeotropically dried with anhydrous pyridine (3×20 mL) to provide crude 2-(2-benzyloxyphenyl)-1,1-difluoro-2-oxoethylphosphonic acid. To a solution of 2-(2-benzyloxyphenyl)-1,1-difluoro-2-oxoethylphosphonic acid (0.25 g, 0.5 mmol) in anhydrous pyridine (10 mL) was added 2,4,6-trimethylbenzenesulfonyl chloride (273 mg, 1.25 mmol, 2.5 equiv) at room temperature. The reaction was stirred for 15 minutes then 2',3'-O-isopropylideneadenosine (154 mg, 0.55 mmol, 1.1 equiv) was added and the reaction stirred for 24 hours at room temperature then concentrated in vacuo. Purification by flash chromatography (20:80:1 MeOH/EtOAc/Et$_3$N) afforded the title compound (66 mg, 21%): R$_f$ 0.4 (3:7 MeOH/EtOAc); [α]$^{20}_D$ −36.8 (c 0.89, MeOH); $^1$H NMR (600 MHz, CD$_3$OD) □ 1.15 (t, J=7.2 Hz, 9H), 1.35 (s, 3H), 1.60 (s, 3H), 2.96 (q, J=7.2 Hz, 4H), 4.18-4.30 (m, 2H), 4.48 (s, 1H), 5.06-5.14 (m, 3H), 5.14-5.20 (m, 1H), 6.26 (d, J=3.0 Hz, 1H), 6.64 (bs, 1H), 6.88-6.96 (m, 2H), 7.18-7.24 (m, 1H), 7.26-7.31 (t, J=7.2 Hz, 2H), 7.31-7.37 (m, 1H), 7.38-7.44 (m, 2H), 7.84 (d, J=7.2 Hz, 1H), 8.29 (s, 1H), 8.48 (s, 1H); $^{13}$C NMR (150 MHz, CD$_3$OD) □ 8.6, 25.6, 27.5, 45.9, 60.7, 67.2 (d, $^2J_{C,P}$=6.1 Hz), 70.8, 82.1, 85.4, 85.9 (d, $^2J_{C,P}$=6.2 Hz), 91.0, 113.2, 114.1, 119.6, 120.7, 126.1, 127.2, 128.0, 128.7, 131.0, 133.2, 136.9, 140.1, 150.0, 153.3, 155.8, 157.4, 195.8 (m); HRMS ESI(+) calcd for $C_{28}H_{29}N_5O_8F_2P$ [M+H]$^+$ 632.1716, found 632.1704 (error 1.9 ppm).

EXAMPLE 9

Preparation of (2R/2S)-5'-O-[1,1'-Difluoro-2-hydroxy-2-(2-hydroxyphenyl)ethyl][hydroxy] phosphinyl}adenosine triethylammonium salt To a solution of 5'-O-{[2-(2-benzyloxyphenyl)-1,1-difluoro-2-oxo-ethyl][hydroxy]phosphinyl}-2',3'-O-isopropylideneadenosine triethylammonium salt (48 mg, 0.076 mmol, 1.0 equiv) in MeOH (20 mL) was added 10% Pd/C (20 mg) and the reaction was stirred for 12 hours under an H$_2$ atm. The reaction mixture was filtered through a plug of Celite and the residue was washed with MeOH (4×10 mL). The combined filtrates were concentrated then treated with 80% aq TFA (2.0 mL) for 2.5 hours. The reaction mixture was concentrated under reduced pressure. Purification by flash chromatography (30:70:1 MeOH/EtOAc/Et$_3$N) afforded the title compound as a 1:1 mixture of diasteromers (10.7 mg, 29%): R$_f$ 0.3 (2:3 MeOH/EtOAc); $^1$H NMR (600 MHz, CD$_3$OD) δ 1.27 (t, J=7.2 Hz, 9H), 3.16 (q, J=7.2 Hz, 6H), 4.50-4.32 (m, 4H), 4.55 and 4.63 (t, J=5.4 Hz, 1H together), 5.44 and 5.47 (d, J=7.2 Hz, 1H together), 6.05 and 6.06 (d, J=6.6 Hz, 1H together), 6.76 (d, J=8.4 Hz, 1H), 6.70-6.87 (m, 1H), 7.05-7.15 (m, 1H), 7.37 (t, J=9.0 Hz, 1H), 8.17 (s, 1H), 8.47 and 8.50 (s, 1H together); $^{13}$C NMR (150 MHz, CD$_3$OD) δ 8.1, 46.6, 58.9, 66.8 and 66.9, 71.11 and 71.09, 75.1 and 75.0, 84.7 and 84.6, 87.6 and 87.5, 117.3 and 117.1, 120.1 and 120.0, 120.4 and 120.3, 124.4 and 124.1, 129.0 and 128.9, 129.7 and 129.6, 139.8, 149.8, 152.6, 157.1 and 156.9, 1.3 ppm).

EXAMPLE 10

Preparation of 5'-Amino-5'-deoxy-5'-N-{[2-(2-hydroxyphenyl)-2-oxo-ethyl]sulfonyl}adenosine To 5'-amino-5'-N,N$^6$-di-(tert-butoxycarbonyl)-5'-deoxy-2',3'-O-isopropylidene-5'-N-({2-[2-(methoxymethoxy)phenyl]-2-oxo-ethyl}sulfonyl)adenosine (70 mg, 0.09 mmol, 1.0 equiv) was added 80% aq TFA (3 mL). After 1 h, the reaction mixture was concentrated under reduced pressure. Purification by flash chromatography (5:95 MeOH/EtOAc) afforded the title compound (38 mg, 82%) as a white solid: mp 229-230° C.; R$_f$ 0.7 (10:90 MeOH/EtOAc); [α]$^{20}_D$ −36 (c 0.32, DMSO); $^1$H NMR (600 MHz, DMSO-d$_6$) δ 3.40-3.50 (obsc m, 2H, 5'-H: obscured by residual HDO: assigned by HMQC), 4.08 (s, 1H), 4.14 (s, 1H), 4.70 (br s, 1H), 4.90 (d, J=13.8 Hz, 1H), 5.02 (d, J=13.8 Hz, 1H), 5.30 (br s, 1H, D$_2$O exchangeable), 5.48 (br s, 1H, D$_2$O exchangeable), 5.84 (d, J=7.2 Hz, 1H), 6.94 (t, J=7.2 Hz, 1H), 6.98 (d, J=7.2 Hz, 1H), 7.41 (br s, 2H, D$_2$O exchangeable), 7.53 (t, J=7.2 Hz, 1H), 7.85 (d, J=7.2 Hz, 1H), 8.03 (s, 1H), 8.31 (s, 1H), 8.51-8.55 (m, 1H, D$_2$O exchangeable), 11.41 (s, 1H, D$_2$O exchangeable); $^{13}$C NMR (150 MHz, DMSO-d$_6$) δ 45.0, 60.0, 71.1, 72.3, 84.0, 88.3, 117.6, 119.2, 199.6, 121.2, 131.7, 136.5, 140.5, 148.6, 152.2, 156.2, 160.3, 193.7; HRMS (ESI+) calcd for $C_{18}H_{21}N_6O_7S$ [M+H]$^+$ 465.1197, found 465.1217 (error 6.5 ppm).

The intermediate 5'-Amino-5'-N,N$^6$-di-(tert-butoxycarbonyl)-5'-deoxy-2',3'-O-isopropylidene-5'-N-({2-[2-(methoxymethoxy)phenyl]-2-oxo-ethyl}sulfonyl)adenosine was prepared as follows.

a. N-tert-Butoxycarbonyl-2-[2-(methoxymethoxy)phenyl]-2-oxo ethylsulfonamide. n-BuLi (2.5 M in hexane, 19 mL, 47.7 mmol, 3.1 equiv) was added dropwise to freshly distilled (i-Pr)$_2$NEt (8.30 mL, 50.7 mmol, 3.30 equiv) in THF (50 mL) at 0° C. The mixture was stirred for 30 minutes, then N-Boc-methylsulfonamide (3.00 g, 15.3 mmol, 1 equiv) in THF (50 mL) was added and the reaction stirred for a further 1 hour at 0° C. Next, methyl 2-methoxymethoxybenzoate (3.00 g, 16.9 mmol, 1.1 equiv) in THF (10 mL) was added and the reaction was stirred for 3 hours at 0° C. The reaction mixture was quenched with saturated aq NaCl (50 mL) and 0.5 M aq NaH$_2$PO$_4$ (50 mL) and extracted with EtOAc (3×50 mL) and the combined organic extracts were dried (Na$_2$SO$_4$), and concentrated under reduced pressure. Purification by flash chromatography (30:70 EtOAc/hexane) afforded the title compound (3.93 g, 71%) as a white solid: mp 128-129° C.; R$_f$ 0.7 (70:30 EtOAc/hexane); $^1$H NMR (600 MHz, CDCl$_3$) δ 1.48 (s, 9H), 3.52 (s, 3H), 5.11 (s, 2H), 5.31 (s, 2H), 7.07 (t, J=7.2 Hz, 1H), 7.23 (d, J=8.4 Hz, 1H), 7.38 (br s, 1H), 7.50 (t, J=7.8 Hz, 1H), 7.78 (d, J=7.8 Hz, 1H); $^{13}$C NMR (150 MHz, CDCl$_3$) δ 28.0, 56.8, 61.6, 84.4, 94.8, 115.0, 122.0, 126.3, 130.9, 135.4, 149.6, 156.9, 188.9; HRMS (ESI+) calcd for $C_{15}H_{21}NNaO_7S$ [M+Na]$^+$ 382.0931, found 382.0908 (error 6.0 ppm).

b. 5'-Amino-5'-N,N$^6$-di-(tert-butoxycarbonyl)-5'-deoxy-2',3'-O-isopropylidene-5'-N-({2-[2-(methoxymethoxy)phenyl]-2-oxo-ethyl}sulfonyl)adenosine. Bis[1H, 1H, 2H, 2H, 3H, 3H-perfluoro]azodicarboxylate (804 mg, 0.96 mmol, 1.3 equiv) in THF (10 mL) was added dropwise over 30 minutes via syringe pump to a solution of N-tert-butoxycarbonyl-2-[2-(methoxymethoxy)phenyl]-2-oxo-ethylsulfonamide (300 mg, 0.74 mmol, 1.0 equiv), N$^6$-tert-butoxycarbonyl-2',3'-O-isopropylideneadenosine (264 mg, 0.74 mmol, 1.0 equiv) and bis[4-(1H, 1H, 2H, 2H-perfluoro-7-decyl)phenyl]phenylphospine (783 mg, 1.1 mmol, 1.5 equiv) in THF (50 mL) at 0° C. The reaction mixture was warmed to room temperature slowly overnight. After 12 hours the reaction was concentrated in vacuo and the crude reaction mixture (~2 g) was dissolved in THF (2.0 mL) and loaded on a Fluoroflash® SPE cartridge (Fluorous Technologies, Inc.) (10 g), which had been preconditioned with 70:30 MeOH:H$_2$O (20 mL) before loading the sample. Elution with 70:30 MeOH:H$_2$O (50 mL) afforded the title compound (469 mg, 85%) as a white solid: mp 97-98° C.; R$_f$ 0.5 (80:20 EtOAc/hexane); [α]$^{20}_D$ +29.3 (c 0.400, MeOH); $^1$H NMR (600 MHz, CDCl$_3$) δ 1.37 (s, 3H), 1.44 (s, 9H), 1.55 (s, 9H), 1.59 (s, 3H) 3.48 (s, 3H), 3.84 (dd, J=15.0, 7.2 Hz, 1H), 3.97 (dd, J=15.6, 6.0 Hz, 1H), 4.50-4.54 (m, 1H), 5.10 (ovlp d, J=15.6 Hz, 1H), 5.10-5.12 (ovlp m, 1H), 5.16 (d, J=15.6 Hz, 1H), 5.25 (s, 2H), 5.44 (d, J=6.6 Hz, 1H), 6.12 (s, 1H), 7.05 (t, J=7.8, 1H), 7.18 (d, J=7.8 Hz, 1H), 7.49 (t, J=7.8 Hz, 1H), 7.64 (d, J=7.8 Hz, 1H), 8.03 (s, 1H), 8.70 (s, 1H); $^{13}$C NMR (150 MHz, CDCl$_3$) δ 25.6, 27.3, 28.0, 28.3, 49.1, 56.9, 63.3, 82.4, 82.5, 84.4, 85.3, 85.9, 90.9, 95.1, 114.7, 115.2, 122.2, 126.7, 128.7, 131.0, 135.6, 142.1, 149.7, 150.0, 150.5, 151.4, 153.1, 157.0, 189.1; HRMS (ESI+) calcd for C$_{33}$H$_{45}$N$_6$O$_{12}$S [M+H]$^+$ 749.2811, found 749.2814 (error 0.4 ppm).

EXAMPLE 11

Preparation of 5'-Amino-5'-deoxy-5'-N-{[1,1-difluoro-2-(2-hydroxyphenyl)-2-oxo-ethyl]sulfonyl}adenosine To 5'-amino-5'-N,N$^6$-di-(tert-butoxycarbonyl)-5'-deoxy-2',3'-O-isopropylidene-5'-N-({1,1-difluoro-2-[2-(methoxymethoxy)phenyl]-2-oxo-ethyl}sulfonyl)adenosine (195 mg, 0.25 mmol, 1.0 equiv) was added 80% aq TFA (3 mL). After 1 h, the reaction mixture was concentrated under reduced pressure. Purification by flash chromatography (2:98 MeOH/EtOAc) afforded the title compound (132 mg, 71%) as a yellow solid: mp 218-220° C.; R$_f$ 0.7 (10:90 MeOH/EtOAc); [α]$^{20}_D$ −5.4 (c 0.34, MeOH); $^1$H NMR (600 MHz, DMSO-d$_6$) δ 3.45 (dd, J=13.8, 4.2 Hz, 1H), 3.53 (br d, J=13.8 Hz, 1H), 4.10 (br s, 1H), 4.14-4.17 (m, 1H), 4.69 (t, J=5.4 Hz, 1H), 5.42 (br s, 1H, D$_2$O exchangeable), 5.58 (br s, 1H, D$_2$O exchangeable), 5.89 (d, J=6.0 Hz, 1H), 6.97-7.00 (m, 1H), 7.03-7.05 (m, 1H), 7.54-7.60 (m, 2H, D$_2$O exchangeable), 7.69 (t, J=7.2 Hz, 1H), 8.06 (s, 1H), 8.36 (s, 1H), 10.07 (br s, 1H, D$_2$O exchangeable), 10.80 (s, 1H, D$_2$O exchangeable); $^{13}$C NMR (150 MHz, DMSO-d$_6$) δ 46.5, 71.7, 73.1, 84.5, 89.1, 115.9, 118.1, 119.8, 120.2, 131.3, 136.9, 141.4, 149.1, 152.2, 156.6, 159.9, 188.3 (t, $^2$J$_{C-F}$=26 Hz); HRMS (ESI−) calcd for C$_{18}$H$_{17}$F$_2$N$_6$O$_7$S [M−H]$^-$ 499.0853, found 499.0853 (error 0 ppm).

The intermediate 5'-Amino-5'-N,N$^6$-di-(tert-butoxycarbonyl)-5'-deoxy-2',3'-O-isopropylidene-5'-N-({1,1-difluoro-2-[2-(methoxymethoxy)phenyl]-2-oxo-ethyl}sulfonyl)adenosine was prepared as follows.

a. 5'-Amino-5'-N,N$^6$-di-(tert-butoxycarbonyl)-5'-deoxy-2',3'-O-isopropylidene-5'-N-({1,1-difluoro-2-[2-(methoxymethoxy)phenyl]-2-oxo-ethyl}sulfonyl)adenosine. To a solution of 5'-amino-5'-N,N$^6$-di-(tert-butoxycarbonyl)-5'-deoxy-2',3'-O-isopropylidene-5'-N-({2-[2-(methoxymethoxy)phenyl]-2-oxo-ethyl}sulfonyl)adenosine (300 mg, 0.41 mmol, 1.0 equiv) was added to a suspension of NaH (15.4 mg, 0.64 mmol, 1.6 equiv) in dry THF (5 mL) at 0° C. After 20 minutes the reaction mixture was cannulated into a solution of Selectfluor (284 mg, 0.80 mmol, 2.0 equiv) in CH$_3$CN (5 mL) at −10° C. and then the reaction was allowed to slowly warm to 0° C. over 2 hours. The reaction mixture was partitioned between EtOAc (50 mL) and H$_2$O (50 mL) and the aqueous layer extracted with EtOAc (2×25 mL). The combined organic extracts were dried (Na$_2$SO$_4$) and concentrated under reduced pressure. Purification by flash chromatography (40:60 EtOAc/hexane) afforded the title compound (275 mg, 87%) as a colorless oil: R$_f$ 0.7 (70:30 EtOAc/hexane); [α]$^{20}_D$ +16.8 (c 1.10, CHCl$_3$); $^1$H NMR (600 MHz, CDCl$_3$) δ 1.38 (s, 3H), 1.43 (s, 9H), 1.55 (s, 9H), 1.61 (s, 3H), 3.45 (s, 3H), 3.91 (dd, J=15.0, 7.8 Hz, 1H), 4.08 (dd, J=15.0, 5.4 Hz, 1H), 4.58-4.61 (m, 1H), 5.13 (dd, J=6.0, 3.0 Hz, 1H), 5.23 (AB system, J=7.2 Hz, Δν=2.4 Hz, 2H), 5.53 (d, J=6.0 Hz, 1H), 6.15 (s, 1H), 7.08 (t, J=7.2 Hz, 1H), 7.22 (d, J=9.0 Hz, 1H), 7.52 (t, J=8.4 Hz, 1H), 7.58 (d, J=7.2, 1H), 8.01 (s, 1H), 8.75 (s, 1H); $^{13}$C NMR (150 MHz, CDCl$_3$) δ 25.3, 27.0, 27.5, 28.1, 49.3, 56.5, 82.2, 82.5, 84.2, 85.8, 86.2, 91.1, 94.1, 114.4, 114.6, 121.8, 122.2, 123.2, 131.2, 135.7, 142.1, 149.5, 149.9, 150.1, 150.3, 152.9, 156.8, 186.2 (t, $^2$J$_{C-F}$=26 Hz); HRMS (ESI+) calcd for C$_{33}$H$_{43}$F$_2$N$_6$O$_{12}$S [M+H]$^+$ 785.2622, found 785.2597 (error 3.2 ppm).

EXAMPLE 12

Preparation of 5'-Amino-5'-deoxy-5'-N-{[(2-hydroxybenzoyl)amino]carbonyl}

To a solution of 5'-amino-5'-N-{[(2-benzyloxybenzoyl)amino]carbonyl}-5'-deoxyadenosine. (50 mg, 0.096 mmol) in MeOH (10 mL) was added 10% Pd/C (10 mg) and the flask placed under 1 atm H$_2$. After 2 h, the reaction was filtered through Celite and the filtrate concentrated under reduced pressure. Purification by flash chromatography (100:20 EtOAc/MeOH) afforded the title compound (21 mg, 51%): R$_f$ 0.12 (100:20 EtOAc/MeOH); $^1$H NMR (CD$_3$OD, 600 MHz) δ 3.66 (dd, J=14.4, 4.2 Hz, 1H), 3.80 (dd, J=14.4, 4.8 Hz, 1H), 4.20 (q, J=4.8 Hz, 1H), 4.42 (t, J=4.8 Hz, 1H), 4.74 (t, J=4.8 Hz, 1H), 6.00 (d, J=4.8 Hz, 1H), 6.90 (ovlp t, J=7.8 Hz, 1H), 6.91 (ovlp d, J=7.8 Hz, 1H), 7.40 (t, J=7.8 Hz, 1H), 7.91 (d, J=7.8 Hz, 1H), 8.16 (s, 1H), 8.32 (s, 1H); $^{13}$C NMR (CD$_3$OD, 150 MHz) δ 40.7, 71.2, 73.9, 83.3, 89.0, 116.7, 117.4, 119.3, 119.4, 130.9, 134.8, 140.4, 149.5, 152.7, 155.1, 156.1, 158.9, 167.5; HRMS (ESI−) calcd for C$_{18}$H$_{18}$N$_7$O$_6$ [M−H]$^-$ 428.1324, found 428.1327 (error 0.7 ppm).

The intermediate 5'-Amino-5'-N-{[(2-benzyloxybenzoyl)amino]carbonyl}-5'-deoxyadenosine was prepared as follows.

a. 2-Benzyloxybenzamide. To a solution of 2-hydroxybenzamide (2.74 g, 20 mmol, 1.0 equiv) and K$_2$CO$_3$ (3.30 g, 24 mmol, 1.2 equiv) in acetone (100 mL) was added benzyl bromide (2.80 mL, 24 mmol, 1.2 equiv) and the reaction heated at reflux for 16 hours. After cooling to room temperature, the solution was filtered and the filtrate was concentrated under reduced pressure. The crude solid was recrystallized from acetone to afford the title compound (2.89 g, 62%) as a white solid: $^1$H NMR (CDCl$_3$, 600 MHz) δ 5.19 (s, 2H), 5.92 (br s, 1H), 7.05-7.10 (m, 2H), 7.36-7.48 (m, 6H), 7.73 (br s, 1H), 8.23 (d, J=7.8 Hz, 1H); $^{13}$C NMR (CDCl$_3$, 150 MHz) δ 71.5, 112.9, 121.3, 121.8, 128.1, 129.0, 129.2, 132.9, 133.6, 135.8, 157.4, 167.2; HRMS (APCI+) calcd for C$_{14}$H$_{14}$NO$_2$ [M+H]$^+$ 228.1019, found 228.1042 (error 10.0 ppm).

b. 5'-Amino-5'-N-{[(2-benzyloxybenzoyl)amino]carbonyl}-N$^6$-tert-butoxycarbonyl-5'-deoxy-2',3'-O-isopropylideneadenosine. To a stirred solution of 2-benzyloxybenzamide (114 mg, 0.50 mmol, 1.0 equiv) in CH$_2$Cl$_2$ (20 mL) (COCl)$_2$ (129 μL, 1.5 mmol, 3 equiv) was added dropwise at room temperature. The solution was then heated at 50° C. for 3 hours. After cooling to room temperature, the reaction was concentrated in vacuo to afford a light yellow solid. Next, a solution of 5'-amino-N⁶-tert-butoxycarbonyl-5'-deoxy-2',3'-O-isopropylideneadenosine (244 mg, 0.6 mmol, 1.2 equiv) in CH$_3$CN (10 mL) was added and the resulting mixture was stirred 16 hours at room temperature. The crude reaction was concentrated in vacuo and the residue was partitioned between CH$_2$Cl$_2$ (25 mL) and H$_2$O (25 mL). The aqueous layer was extracted with CH$_2$Cl$_2$ (2×25 mL). The combined organic extracts were dried (Na$_2$SO$_4$) and concentration under reduced pressure. Purification by flash chromatography (7:3 EtOAc/hexanes) afforded the title compound (290 mg, 88%) as a white solid: R$_f$ 0.1 (60:40 EtOAc/hexane); $^1$H NMR (CDCl$_3$, 600 MHz) δ 1.35 (s, 3H), 1.54 (s, 9H), 1.59 (s, 3H), 3.64-3.71 (m, 2H), 4.41-4.44 (m, 1H), 4.99 (dd, J=6.0, 3.6 Hz, 1H), 5.28 (s, 2H), 5.37 (dd, J=6.0, 3.0 Hz, 1H), 6.12 (d, J=3.0 Hz, 1H), 7.05 (d, J=8.4 Hz, 1H), 7.10 (t, J=7.8 Hz, 1H), 7.35-7.37 (m, 1H), 7.40-7.43 (m, 4H), 7.48 (dt, J=8.4, 1.2 Hz, 1H), 8.05 (br s, 1H, NH), 8.12 (dd, J=7.8, 1.2 Hz, 1H), 8.18 (s, 1H), 8.74 (s, 1H), 8.85 (t, J=6.0 Hz, 1H, NH), 9.97 (s, 1H, NH); $^{13}$C NMR (CDCl$_3$, 150 MHz) δ 25.7, 27.5, 28.3, 41.5, 71.8, 81.9, 82.5, 84.2, 85.3, 90.4, 113.5, 115.2, 119.9, 122.1, 122.3, 127.7, 129.1, 129.2, 132.9, 134.9, 135.0, 141.7, 149.7, 150.2, 150.7, 153.4, 153.9, 157.2, 165.9; HRMS (ESI+) calcd for C$_{33}$H$_{38}$N$_7$O$_8$ [M+H]$^+$ 660.2776, found 660.2667 (error 16.5 ppm).

c. 5'-Amino-5'-N-{[(2-benzyloxybenzoyl)amino]carbonyl}-5'-deoxyadenosine. 5'-Amino-5'-N-{[(2-benzyloxybenzoyl)amino]carbonyl}-N⁶-tert-butoxycarbonyl-5'-deoxy-2',3'-O-isopropylideneadenosine (100 mg) was treated with 80% aq TFA (5 mL) for 1 hours at 0° C. then concentrated in vacuo. Purification by flash chromatography (500:3 EtOAc/MeOH) afforded the title compound (55 mg, 70%): R$_f$ 0.3 (500:3 EtOAc/MeOH); $^1$H NMR (CD$_3$OD, 600 MHz) δ 3.64 (dt, J=14.4, 4.8 Hz, 1H), 3.76 (dt, J=14.4, 6.0 Hz, 1H), 4.18 (q, J=4.8 Hz, 1H), 4.40 (t, J=5.4 Hz, 1H), 4.72 (t, J=5.4 Hz, 1H), 5.31 (s, 2H), 5.99 (d, J=5.4 Hz, 1H), 7.09 (t, J=7.8 Hz, 1H), 7.24 (d, J=8.4 Hz, 1H), 7.30 (t, J=7.2 Hz, 1H), 7.36 (t, J=7.8 Hz, 2H), 7.46 (d, J=7.8 Hz, 2H), 7.54 (t, J=7.2 Hz, 1H), 7.91 (d, J=7.8 Hz, 1H), 8.15 (s, 1H), 8.29 (s, 1H), 8.96 (br t, J=6.0 Hz, 1H, 5'-NH); $^{13}$C NMR (CD$_3$OD, 150 MHz) δ 40.7, 71.2, 71.4, 74.0, 83.2, 89.2, 113.8, 119.4, 120.5, 121.5, 127.6, 128.3, 128.7, 131.6, 134.6, 135.8, 140.7, 149.4, 151.8, 154.7, 155.5, 157.2, 166.6; HRMS (ESI−) calcd for C$_{25}$H$_{24}$N$_7$O$_6$ [M−H]$^−$ 518.1794, found 518.1795 (error 0.1 ppm).

EXAMPLE 13

Preparation of (E)-5'-Deoxy-5'-N-({[2-(2-hydroxyphenyl)ethenyl]sulfonyl}amino)adenosine To a solution of 5'-deoxy-5'-N-({2-(E)-[2-(methoxymethoxy)phenyl]ethenyl}sulfonyl)amino-2',3'-O-isopropylideneadenosine (8.3 mg, 0.015 mmol, 1.0 equiv) was added 80% aq TFA (2.0 mL). The solution was stirred 30 minutes at 0° C. then concentrated. Purification by flash chromatography (10:1 EtOAc/MeOH) afforded the title compound (6.6 mg, 86%) as white solid: R$_f$ 0.17 (10:1 EtOAc/MeOH); $^1$H NMR (600 MHz, CD$_3$OD) δ 3.33-3.36 (m, 2H), 4.25 (dd, J=3.6, 1.8 Hz, 1H), 4.35 (dd, J=5.4, 1.8 Hz, 1H), 4.85 (t, J=6.6 Hz, 1H), 5.87 (d, J=6.6 Hz, 1H), 6.81 (t, J=8.4 Hz, 1H), 7.05 (d, J=15.6 Hz, 1H), 7.20 (t, J=7.8 Hz, 1H), 7.38 (d, J=7.2 Hz, 1H), 7.61 (d, J=15.6 Hz, 1H), 8.20 (s, 1H), 8.23 (s, 1H); $^{13}$C NMR (150 MHz, CD$_3$OD) δ 44.6, 71.8, 73.1, 84.8, 90.2, 115.8, 119.6, 119.8, 119.9, 125.1, 129.8, 131.7, 137.4, 141.2, 148.7, 152.5, 156.4, 157.3; HRMS (ESI+) calcd for C$_{21}$H$_{25}$N$_6$O$_6$S [M+H]$^+$ 489.1556, found 489.1551 (error 1.0 ppm).

The intermediate (E)-5'-Deoxy-5'-N-({2-[2-(methoxymethoxy)phenyl]-ethenyl}sulfonyl)amino-2',3'-O-isopropylideneadenosine was prepared as follows.

a. 5'-Azido-5'-deoxy-2',3'-O-isopropylideneadenosine. To a suspension of 2',3'-O-isopropylideneadenosine (307 mg, 1.0 mmol, 1.0 equiv) in 1,4-dioxane (20 mL) at room temperature were added DBU (305 mg, 2.0 mmol, 2.0 equiv) and diphenylphosphoryl azide (DPPA) (826 mg, 3.0 mmol, 1.5 equiv). The reaction was stirred 16 hours at room temperature then NaN$_3$ (650 mg, 10 mmol, 10 equiv) and 15-crown-5 (22 mg, 0.1 mmol, 0.1 equiv) were added and the reaction was heated at reflux. After 48 hours the reaction was cooled to room temperature and concentrated in vacuo. Purification by flash chromatography (EtOAc) afforded the title compound (276 mg, 85%) as white solid: R$_f$ 0.50 (EtOAc); $^1$H NMR (600 MHz, CDCl$_3$) δ 1.38 (s, 3H), 1.61 (s, 3H), 3.57 (dd, J=3.6, 1.8 Hz, 2H), 4.38 (ddd, J=3.6, 3.0, 1.8 Hz, 1H), 5.03 (dd, J=6.6, 3.6 Hz, 1H), 5.42 (dd, J=6.6, 2.4 Hz, 1H), 6.01 (d, J=1.8 Hz, 1H), 6.07 (br s, 2H), 7.94 (s, 1H), 8.35 (s, 1H); $^{13}$C NMR (150 MHz, CDCl$_3$) δ 25.5, 27.3, 52.5, 82.1, 84.2, 85.8, 90.9, 115.0, 120.4, 140.4, 149.3, 152.2, 155.2; MS (APCI+) calcd for C$_{13}$H$_{17}$O$_3$N$_8$ [M+H]$^+$ 333.1, found 333.2.

b. 5'-Azido-N⁶-tert-butoxycarbonyl-5'-deoxy-2',3'-O-isopropylidene-adenosine. To a solution of 5'-azido-5'-deoxy-2',3'-O-isopropylideneadenosine (146 mg, 0.44 mmol, 1.0 equiv) in THF/DMF (4:1, 10 mL) was added sodium hydride (60% dispension in mineral oil, 20 mg, 0.5 mmol, 1.15 equiv) at room temperature. The resulting solution was stirred 30 minutes then solid di-tert-butyl dicarbonate (106 mg, 0.48 mmol, 1.1 equiv) was added in one portion. The reaction was monitored by TLC until complete consumption of the amine was observed (3 h). The solution was diluted with CH$_2$Cl$_2$ (20 mL) and washed with sat'd aq NaHCO$_3$ (20 mL). The aqueous phase was back extracted with CH$_2$Cl$_2$ (2×10 mL) and the combined organic phase was washed with H$_2$O (20 mL), saturated aq NaCl (30 mL), dried (Na$_2$SO$_4$) and concentrated. Purification by flash chromatography (40:60 hexane/EtOAc) afforded the title compound (114 mg, 60%): $^1$H NMR (600 MHz, CDCl$_3$) δ 1.35 (s, 3H), 1.53 (s, 9H), 1.58 (s, 3H), 3.54 (d, J=5.4 Hz, 2H), 4.36 (dd, J=3.6, 5.4 Hz, 1H), 5.01 (dd, J=6.6, 3.6 Hz, 1H), 5.42 (dd, J=6.6, 2.4 Hz, 1H), 6.13 (d, J=2.4 Hz, 1H), 8.09 (s, 1H), 8.74 (s, 1H); $^{13}$C NMR (150 MHz, CDCl$_3$) δ 25.5, 27.3, 28.3, 52.4, 82.0, 82.6, 84.2, 85.8, 90.9, 115.1, 122.3, 141.8, 149.8, 150.3, 150.4, 153.2; MS (APCI+) calcd for C$_{18}$H$_{25}$O$_5$N$_8$.[M+H]$^+$ 433.19, found 433.18.

c. 5'-Amino-N⁶-tert-butoxycarbonyl-5'-deoxy-2',3'-O-isopropylidene-adenosine. 5'-Azido-N⁶-tert-butoxycarbonyl-5'-deoxy-2',3'-O-isopropylideneadenosine was hydrogenated using Pd/C in MeOH at 2.5 atm H$_2$ for 3 hours to afford the title compound in quantitative yield that was directly used in the next reaction without purification.

d. 5'-Deoxy-5'-N-[(ethenyl)sulfonyl]amino-2',3'-O-isopropylidene-adenosine. To a solution of 2-chloroethanesulfonyl chloride (33 mg, 0.2 mmol, 1.0 equiv) in acetonitrile (3 mL) at 0° C. was added 5'-amino-N⁶-tert-butoxycarbonyl-5'-deoxy-2',3'-O-isopropylideneadenosine (81 mg, 0.2 mmol, 1.0 equiv) and TEA (16 mg, 0.2 mmol, 1.0 equiv). After the resulting mixture was stirred at 0° C. for 1 h, a second equivalent of TEA was added and the reaction was continued for another 1 hour. The solvent was evaporated and the residue was then diluted with CH$_2$Cl$_2$ (5 mL), and then poured onto a mixture of saturated NaHCO$_3$/ice, followed by addition more CH$_2$Cl$_2$ (3 mL). The organic phase was separated and the aqueous phase was extracted with CH$_2$Cl$_2$ (3×3 mL). The combined organic phase was washed successively with saturated NaHCO$_3$/ice-water, chilled 0.5 M HCl, saturated aq NaCl, dried ($Na_2SO_4$) and concentrated. Purification by flash chromatography (100:1 $CH_2Cl_2$/MeOH) afforded the title compound (51 mg, 46%) as a white crystalline solid: $R_f$ 0.27 (100:1 $CH_2Cl_2$/MeOH); $^1$H NMR (600 MHz, $CDCl_3$) δ 1.36 (s, 3H), 1.55 (s, 9H), 1.61 (s, 3H), 3.31 (dd, J=12.6, 2.4 Hz, 1H), 3.46 (ddd, J 2.4, 12.6, 4.2 Hz, 1H), 4.55 (dd, J=4.2, 1.8 Hz, 1H), 5.11 (dd, J=1.8, 6.6 Hz, 1H), 5.29 (dd, J=6.6, 4.8 Hz, 1H), 5.84 (d, J=4.8 Hz, 1H), 5.87 (d, J=10.2 Hz, 1H), 6.20 (d, J=16.8 Hz, 1H), 6.45 (dd, J=10.2, 16.8 Hz, 1H), 7.97 (s, 1H), 8.32 (d, J=13.0 Hz, 1H), 8.78 (s, 1H); $^{13}$C NMR (150 MHz, $CDCl_3$) δ 25.4, 27.6, 28.3, 45.1, 81.6, 82.7, 82.9, 83.4, 93.5, 115.2, 123.1, 126.6, 136.0, 142.1, 149.6, 149.7, 150.9, 153.1; MS (ESI+) calcd for $C_{20}H_{29}O_7N_6S$ $[M+H]^+$ 479.18, found 449.17.

e. (E)-5'-Deoxy-5'-N-({2-[2-(methoxymethoxy)phenyl]ethenyl}-sulfonyl)amino-2',3'-O-isopropylideneadenosine. A solution of 5'-deoxy-5'-N-[(ethenyl)sulfonyl]amino-2',3'-O-isopropylideneadenosine (55 mg, 0.12 mmol, 1.0 equiv), 1-iodo-2-methoxymethoxybenzene (32 mg, 0.13 mmol, 1.1 equiv), TEA (36 mg, 0.36 mmol, 3.0 equiv), and $PdCl_2$ $(PPh_3)_2$ (4 mg, 5% mmol) in DMF (5 mL) was degassed by freeze-pump-thaw (3×). The reaction mixture was heated at 80° C. for 2 d then concentrated in vacuo. Purification by flash chromatography (10:1 EtOAc/hexane) afforded the title compound (13 mg, 20%) as a white solid: $R_f$ 0.2 (10:1 EtOAc/hexane); $^1$H NMR (600 MHz, $CD_3OD$) δ 1.32 (s, 3H), 1.56 (s, 3H), 3.32-3.34 (m, 2H), 3.40 (s, 3H), 4.38-4.40 (m, 1H), 5.07 (dd, J=6.0, 3.0 Hz, 1H), 5.23 (dd, J=9.6, 6.6 Hz, 2H), 5.33 (dd, J=6.0, 3.6 Hz, 1H), 6.11 (d, J=3.6 Hz, 1H), 6.97-7.00 (m, 1H), 7.14 (d, J=8.4 Hz, 1H), 7.31-7.37 (m, 2H), 7.46-7.49 (m, 1H), 7.63 (d, J=15.6 Hz, 1H), 8.27 (s, 2H); $^{13}$C NMR (150 MHz, $CD_3OD$) δ 24.3, 26.3, 44.5, 55.4, 81.9, 83.5, 84.8, 91.4, 94.6, 114.6, 114.8, 121.9, 122.2, 126.3, 128.0, 128.9, 128.9, 131.8, 135.9, 141.4, 148.5, 150.7, 156.1; HRMS (ESI+) calcd for $C_{23}H_{28}N_6O_7S$ $[M+H]^+$ 533.1818, found 533.1809 (error 1.7 ppm).

EXAMPLE 14

Preparation of (E)-5'-O-{[Hydroxy][2-(2-hydroxyphenyl)ethenyl]-phosphinyl}adenosine To a solution of (E)-5'-O-{[2-(2-acetoxyphenyl)ethenyl]-[hydroxy]phosphinyl}-2',3'-O-isopropylideneadenosine (15 mg, 0.025 mmol) in MeOH (3 mL) was added granular $Na_2CO_3$ (10 mg). The solution was stirred for 2 hours at room temperature, then filtered. The filtrate was concentrated and the residue was dissolved in 80% aqueous TFA (2 mL) at 0° C. and the solution was stirred 30 minutes. After removing the solvent, the residue was purified by HPLC (C18 reverse-phase 41×250 mm, flow rate: 40 mL/min, A: 40 mM TEAB, B: 70% $CH_3CN$; 40% β isocratic, retention time 20 minutes) to afford the title compound as a white solid: $^1$H NMR (600, $D_2O$) δ 4.23-4.26 (m, 2H), 4.44 (br s, 1H), 4.65 (t, J=5.4 Hz, 1H), 4.93 (t, J=5.4 Hz, 1H), 6.12 (d, J=4.2 Hz, 1H), 6.17 (t, J=18 Hz, 1H), 6.81-6.84 (m, 2H), 7.14 (dd, J=22.2, 18.0 Hz, 1H), 7.17 (d, J=7.8 Hz, 1H), 7.23 (t, J=7.8 Hz, 1H), 8.24 (s, 1H), 8.47 (s, 1H); $^{13}$C NMR (150 MHz, $D_2O$) δ 64.3, 70.5, 73.9, 84.6, 89.0, 113.6, 115.6, 117.5, 118.7, 120.7, 127.3, 131.1, 143.2, 144.3, 148.2, 149.4, 154.1, 163.1; $^{31}$P NMR (195 MHz, $D_2O$) δ 18.2; HRMS (ESI−) calcd for $C_{18}H_{19}N_5O_7P$ $[M-H]^-$ 448.1022 found 448.1031 (error 2.0 ppm).

The intermediate (E)-5'-O-{[2-(2-acetoxyphenyl)ethenyl]-[hydroxy]-phosphinyl}-2',3'-O-isopropylideneadenosine was prepared as follows.

a. (E)-Diethyl[2-(2-acetoxyphenyl)ethenyl]phosphonate. To a solution of (E/Z-1-(2-acetoxyphenyl)prop-1-ene (0.88 g, 5.0 mmol) and diethyl vinylphosphonate (0.82 g, 0.77 mL, 5.0 mmol) in degassed $CH_2Cl_2$ (10 mL) was added benzylidene[1,3-bis(2,4,6-trimethylphenyl)-2-imidazolidinylidene]dichloro-(tricyclohexylphosphine)ruthenium (42 mg, 0.50 mmol, 0.10 equiv). The solution was refluxed for 48 hours then concentrated in vacuo. Purification by flash chromatography (9:1 to 5:1 to 3:1, hexane/EtOAc) afforded the title compound (0.90 g, 60%) as a dark green liquid: $^1$H NMR (600 MHz, $CDCl_3$) δ 1.24 (t, J=7.2 Hz, 6H), 2.24 (s, 3H), 4.02 (q, J=7.2 Hz, 4H), 6.17 (t, J=17.4 Hz, 1H), 7.00 (d, J=8.4 Hz, 1H), 7.15 (t, J=7.2 Hz, 1H), 7.29 (t, J=8.4 Hz, 1H), 7.42-7.51 (m, 2H); $^{13}$C NMR (150 MHz, $CDCl_3$) δ 16.5, 20.2, 62.0, 116.2, 123.2, 126.4, 127.3, 127.7, 131.1, 142.0, 149.1, 169.1; $^{31}$P NMR (195 MHz, $CDCl_3$) δ 19.3; HRMS (APCI+) calcd for $C_{14}H_{20}O_5P$ $[M+H]^+$ 299.1048, found 299.1048 (error 0 ppm).

b. (E)-bis(Trimethylsilyl) [2-(2-acetoxyphenyl)ethenyl]phosphonate. To a solution of (E)-diethyl[2-(2-acetoxyphenyl)ethenyl]phosphonate (150 mg, 0.5 mmol) in $CH_2Cl_2$ (5 mL) was added bromotrimethylsilane (0.3 g, 0.27 mL, 2.0 mmol, 4 equiv). The resulting solution was stirred for 12 hours at room temperature then concentrated in vacuo to afford the title compound as a dark green liquid (193 mg, 100%): $^1$H NMR (600 MHz, $CDCl_3$) δ 0.25 (s, 18H), 2.26 (s, 3H), 6.28 (t, J=16.2 Hz, 1H), 7.03 (d, J=8.4 Hz, 1H), 7.16 (t, 1H), 7.28-7.41 (m, 2H), 7.50 (d, J=4.8 Hz, 1H); $^{13}$C NMR (150 MHz, $CDCl_3$) δ 0.0, 19.9, 118.5, 122.0, 125.2, 126.2, 126.8, 129.6, 138.0, 147.3, 168.0; $^{31}$P NMR (195 MHz, $CDCl_3$) δ 13.0; HRMS (ESI+) calcd for $C_{10}H_{12}O_5P$ $[M-2(Me_3Si)+3H]^+$ 243.0417, found 243.0422 (error 2.0 ppm).

c. [2-(2-Acetoxyphenyl)ethenyl]phosphonic acid. A solution of (E)-bis(trimethylsilyl) [2-(2-acetoxyphenyl)ethenyl]phosphonate (193 mg, 0.5 mmol) in methanol (5.0 mL) was stirred for 30 minutes then concentrated in vacuo to afford the title compound (120 mg, 100%) as dark green liquid: $^1$H NMR (600 MHz, $CD_3OD$) δ 2.32 (s, 3H), 6.48 (t, J=18.0 Hz, 1H), 7.09 (d, J=7.8 Hz, 1H), 7.26 (t, J=7.8 Hz, 1H), 7.37-7.46 (m, 2H), 7.68 (d, J=7.8 Hz, 1H); $^{13}$C NMR (150 MHz, $CD_3OD$) δ 19.5, 119.3, 123.1, 126.3, 126.9, 128.2, 130.6, 130.8, 138.6, 145.4, 149.3, 169.7; $^{31}$P NMR (195 MHz, $CD_3OD$) δ 16.9; HRMS (ESI+) calcd for $C_{10}H_{12}O_5P$ $[M+H]^+$ 243.0417, found 243.0422 (error 2.0 ppm).

d. (E)-5'-O-{[2-(2-Acetoxyphenyl)ethenyl][hydroxy]phosphinyl}-2',3'-O-isopropylideneadenosine. To a solution of [2-(2-acetoxyphenyl)ethenyl]-phosphonic acid (32 mg, 0.13 mmol) and DCC (82 mg, 0.4 mmol, 3 equiv) in DMF (3 mL) was added $N^6$-tert-butoxycarbonyl-2',3'-O-isopropylideneadenosine (72 mg, 1.05 equiv). The reaction mixture was stirred for 4 hours at room temperature then concentrated in vacuo. Purification by HPLC afforded the title compound (15 mg, 18%) as white solid: $^1$H NMR (600 MHz, $CD_3OD$) δ 2.27 (s, 3H), 3.94-3.96 (m, 1H), 4.01-4.04 (m, 1H), 4.51 (s, 1H), 5.10 (d, J=6.0 Hz, 1H), 5.36 (dd, J=3.0, 6.0 Hz, 1H), 6.22-6.28 (m, 2H), 7.00 (d, J=7.8 Hz, 1H), 7.15-7.22 (m, 2H), 7.28 (t, J=7.8 Hz, 1H), 7.45 (d, J=7.8 Hz, 1H), 8.51 (s, 1H), 8.60 (s, 1H); HRMS (ESI−) calcd for $C_{28}H_{33}N_5O_{10}P$ $[M-H]^+$ 630.1960, found 630.1964 (error 0.6 ppm).

EXAMPLE 15

Preparation of (E)-5'-Amino-5'-deoxy-5'-N-{[3-(2-methoxymethoxy)phenyl]prop-2-ene-1-oyl}adenosine A solution of (E)-5'-amino-$N^6$-tert-butoxycarbonyl-5'-deoxy-5'-N-{[3-(2-methoxymethoxy)phenyl]prop-2-ene-1- oyl}-2',3'-O-isopropylideneadenosine (45 mg, 0.07 mmol) in 80% aq TFA (3 mL) was stirred for 30 minutes at 0° C. The reaction mixture was concentrated. Purification by flash column chromatography (10:1 EtOAc/MeOH) afforded the title compound (27 mg, 87%) as a white solid: $R_f$ 0.2 (10:1 EtOAc/MeOH); $^1$H NMR (600 MHz, CD$_3$OD) δ 3.47 (dd, J=14.0, 3.0 Hz, 1H), 3.96 (dd, J=14.0, 4.2 Hz, 1H), 4.24 (ddd, J=5.4, 4.2, 3.0 Hz, 1H), 4.80 (t, J=5.4 Hz, 1H), 5.90 (d, J=6.0 Hz, 1H), 6.81 (t, J=7.8 Hz, 1H), 6.90 (d, J=16.2 Hz, 1H), 7.15 (dt, J=6.0, 1.8 Hz, 1H), 7.37 (d, J=7.8 Hz, 1H), 7.77 (d, J=16.2 Hz, 1H), 8.22 (s, 1H), 8.31 (s, 1H); $^{13}$C NMR (150 MHz, CD$_3$OD) δ 41.1, 71.7, 73.2, 84.6, 89.8, 115.8, 119.5, 120.0, 120.4, 121.8, 129.6, 130.6, 137.7, 141.2, 149.1, 152.6, 156.3, 157.0, 168.7; HRMS (ESI+) calcd for $C_{19}H_{20}N_6O_5$ [M+H]$^+$ 413.1573, found 413.1541 (error 7.2 ppm).

The intermediate (E)-5'-amino-N$^6$-tert-butoxycarbonyl-5'-deoxy-5'-N-{[3-(2-methoxymethoxy)phenyl]prop-2-ene-1-oyl}-2',3'-O-isopropylideneadenosine was prepared as follows.

a. (E)-Ethyl[3-(2-methoxymethoxy)phenyl]prop-2ene-1-oate. To a solution of 2-(methoxymethoxy)benzaldehyde (0.75 g, 4.4 mmol, 1.0 equiv), monoethyl malonate (0.67 g, 4.8 mmol, 1.1 equiv) in pyridine (50 mL) was added piperidine (75 mg, 0.88 mmol, 0.2 equiv). The reaction mixture was heated at reflux for 5 hours. After cooling, the solution was concentrated. The residue was diluted with CH$_2$Cl$_2$ (40 mL) and the resulting solution was washed with 1.0 N HCl (20 mL) and saturated aqueous NaHCO$_3$ (10 mL). The organic phase was dried (Na$_2$SO$_4$) and concentrated. Purification by flash chromatography (10:1 hexanes/EtOAc) afforded title compound (0.95 g, 94%) as a colorless viscous oil: $R_f$ 0.23 (10:1 hexanes/EtOAc); $^1$H NMR (600 MHz, CDCl$_3$) δ 1.31 (t, J=7.2 Hz, 3H), 3.46 (s, 3H), 4.23 (q, J=7.2 Hz, 2H), 5.22 (s, 2H), 6.47 (d, J=16.2 Hz, 1H), 6.97 (t, J=7.8 Hz, 1H), 7.13 (d, J=8.6 Hz, 1H), 7.27 (dd, J=8.6, 1.8 Hz, 1H), 7.50 (dd, J=7.8, 1.8 Hz, 1H), 8.0 (d, J=16.2 Hz, 1H); $^{13}$C NMR (150 MHz, CDCl$_3$) δ 14.5, 56.4, 60.5, 94.7, 115.0, 119.0, 122.1, 124.3, 128.5, 131.6, 139.9, 156.1, 167.5; MS (APCI-) calcd for $C_{13}H_{17}O_4$ [M-H]$^-$ 237.1, found 237.0.

b. (E)-[3-(2-Methoxymethoxy)phenyl]prop-2-ene-1-oic acid. To a solution of (E)-ethyl[3-(2-methoxymethoxy)phenyl]prop-2-ene-1-oate (0.5 g, 2.1 mmol, 1.0 equiv) in 80% aq EtOH was added NaOH (500 mg, 12.5 mmol, 6.0 equiv). The reaction mixture was stirred at room temperature for 3 hours. The solution was adjusted to pH 3.0 by adding 1 N aqueous HCl and then extracted with EtOAc (2×50 mL). The organic phase was dried (Na$_2$SO$_4$) and concentrated to afford the title compound (0.43 g, 100%) as a white solid: $^1$H NMR (600 MHz, CD$_3$OD) δ 3.47 (s, 3H), 5.27 (s, 2H), 6.50 (d, J=16.2 Hz, 1H), 7.01 (t, J=7.8 Hz, 1H), 7.16 (d, J=7.8 Hz, 1H), 7.33 (dt, J=8.4, 1.8 Hz, 1H), 7.60 (dd, J=8.4, 1.8 Hz, 1H), 8.00 (d, J=16.2 Hz, 1H); $^{13}$C NMR (150 MHz, CD$_3$OD) δ5.3, 94.5, 114.8, 118.5, 121.8, 124.0, 128.1, 131.4, 140.1, 156.1, 169.5; MS (APCI-) calcd for $C_{11}H_{11}O_4$ [M-H]$^-$ 207.06, found 207.07.

c. (E)-5'-Amino-N$^6$-tert-butoxycarbonyl-5'-deoxy-5'-N-{[3-(2-methoxylmethoxy)phenyl]prop-2-ene-1-oyl}-2',3'-O-isopropylideneadenosine. To a mixture of (E)-[3-(2-methoxymethoxy)phenyl]prop-2-ene-1-oic acid (55 mg, 0.25 mmol, 1.0 equiv) and 5'-amino-N$^6$-tert-butoxycarbonyl-5'-deoxy-2',3'-O-isopropylideneadenosine (100 mg, 0.25 mmol, 1.0 equiv) in DMF (5 mL) was added EDC (76 mg, 0.4 mmol, 1.6 equiv) and HOBt (61 mg, 0.4 mmol, 1.6 equiv) and the reaction stirred 16 hours. The reaction was concentrated in vacuo and partitioned between EtOAc (20 mL) and H$_2$O (10 mL). The organic layer was separated and washed successively with 1 N HCl (5 mL), H$_2$O (5 mL), saturated aqueous Na$_2$CO$_3$ (5 mL) and H$_2$O (5 mL). The organic phase was dried (Na$_2$SO$_4$) and concentrated. Purification by flash chromatography (3:1 EtOAc/hexanes) afforded title compound (83 mg, 74%) as white solid: $R_f$ 0.19 (3:1 EtOAc/hexanes); $^1$H NMR (600 MHz, CDCl$_3$) δ 1.30 (s, 3H), 1.53 (s, 9H), 1.59 (s, 3H), 3.38 (d, J=14.4 Hz, 1H), 3.43 (s, 3H), 4.25 (m, 1H), 4.53 (br s, 1H), 4.86 (dd, J=6.0, 1.8 Hz, 1H), 5.20 (s, 2H), 5.28 (t, J=4.8 Hz, 1H), 5.85 (d, J=4.8 Hz, 1H), 6.61 (d, J=16.0 Hz, 1H), 6.99 (t, J=7.2 Hz, 1H), 7.11 (d, J=7.8 Hz, 1H), 7.28 (dd, J=7.8, 1.8 Hz, 1H), 7.50 (d, J=7.8 Hz, 1H), 7.98 (d, J=7.8 Hz, 1H), 8.02 (s, 1H), 8.07 (d, J=16.0 Hz, 1H), 8.83 (s, 1H); $^{13}$C NMR (150 MHz, CDCl$_3$) δ 25.5, 27.7, 28.3, 31.1, 41.3, 56.4, 81.7, 82.4, 82.8, 84.0, 92.8, 94.8, 115.0, 115.1, 120.7, 122.3, 124.6, 127.8, 131.2, 137.0, 142.6, 149.6, 150.1, 150.8, 152.9, 156.0, 167.1; HRMS (ESI+) calcd for $C_{29}H_{37}N_6O_8$ [M+H]$^+$ 597.2673, found 597.2673 (error 0 ppm).

EXAMPLE 16

Preparation of 5'-Amino-5'-deoxy-5'-N-[3-(2-hydroxyphenyl)-prop-2-yn-1-oyl]adenosine A solution of 5-amino-N$^6$-tert-butoxycarbonyl-5'-deoxy-5'-N-{[3-(2-methoxymethoxy)phenyl]prop-2-yn-1-oyl}-2',3'-O-isopropylideneadenosine (15 mg, 0.025 mmol) in 80% aq TFA (2 mL) was stirred for 30 minutes at 0° C. The reaction mixture was concentrated in vacuo. Purification by flash column chromatography (100:3 EtOAc/MeOH) afforded the title compound (8.4 mg, 84%) as white solid: $R_f$ 0.12 (100:3 EtOAc/MeOH); $^1$H NMR (600 MHz, CD$_3$OD) δ 3.20-3.30 (m, 2H), 3.45 (d, J=14.4 Hz, 1H), 3.94 (d, J=15.6 Hz, 1H), 4.24 (br s, 2H), 5.92 (d, J=5.4 Hz, 1H), 6.83 (t, J=7.8 Hz, 1H), 6.85 (d, J=8.4 Hz, 1H), 7.27 (t, J=7.8 Hz, 1H), 7.34 (d, J=7.8 Hz, 1H), 8.26 (s, 1H), 8.38 (s, 1H); $^{13}$C NMR (150 MHz, CD$_3$OD) δ 41.3, 71.6, 73.3, 83.2, 84.4, 86.3, 90.1, 107.1, 115.5, 119.5, 120.0, 131.9, 133.7, 141.5, 148.9, 151.6, 155.3, 159.8, 161.7; HRMS (ESI+) calcd for $C_{19}H_{19}N_6O_5$ [M+H]$^+$ 411.1417, found 411.1420 (error 1.0 ppm).

The intermediate 5-amino-N$^6$-tert-butoxycarbonyl-5'-deoxy-5'-N-{[3-(2-methoxymethoxy)phenyl]prop-2-yn-1-oyl}-2',3'-O-isopropylideneadenosine was prepared as follows.

a. 2-[2-(Methoxymethoxy)phenyl]ethynyltrimethylsilane. To a stirred solution of 1-iodo-2-(methoxymethoxy)benzene (0.40 g, 1.5 mmol, 1 equiv) and Et$_3$N (1.5 g, 15 mmol, 10 equiv) in dioxane (5 mL) were added (trimethylsilyl)acetylene (162 mg, 1.65 mmol, 1.1 equiv), PdCl$_2$(PPh$_3$)$_2$ (53 mg, 0.075 mmol, 0.05 equiv), and CuI (15 mg, 0.075 mmol, 0.05 equiv) and the reaction mixture was stirred at room temperature for 5 hours. The reaction was partitioned between Et$_2$O (10 mL) and 0.1 N HCl (5 mL) and the organic layer was separated and washed successively with saturated aqueous NaHCO$_3$, H$_2$O, then dried (Na$_2$SO$_4$), and concentrated under reduced pressure. Purification by flash chromatography (40:1 hexanes/EtOAc) afforded the title compound (0.34 g, 96% yield): $R_f$ 0.38 (20:1 hexanes/EtOAc); $^1$H NMR (600 MHz, CDCl$_3$) δ 0.06 (s, 9H), 3.34 (s, 3H), 5.05 (s, 2H), 6.76 (t, J=7.8 Hz, 1H), 6.87 (d, J=7.8 Hz, 1H), 7.05 (dt, J=7.2, 1.2 Hz, 1H), 7.25 (dd, J=7.2, 1.2 Hz, 1H); $^{13}$C NMR (150 MHz, CDCl$_3$) δ 0.2, 56.5, 95.4, 98.6, 101.4, 114.2, 115.8, 122.1, 130.0, 134.1, 158.3.

b. 2-Ethynyl-1-(methoxymethoxy)benzene. To a stirred solution of 2-[2-(methoxymethoxy)phenyl]ethynyltrimethylsilane (230 mg, 1.0 mmol, 1.0 equiv) in MeOH (5 mL) was added KF (280 mg, 3.0 mmol, 3 equiv). The reaction mixture was stirred for 3 hours at room temperature. The reaction mixture was diluted by CH$_2$Cl$_2$ and H$_2$O. The organic phase was dried (Na$_2$SO$_4$) and concentrated. Purification by flash chromatography afforded the title compound (160 mg, 100%) as a light yellow oil: $^1$H NMR (600 MHz, CDCl$_3$) δ 3.28 (s, 1H), 3.49 (s, 3H), 5.24 (s, 2H), 6.95 (t, J=7.8 Hz, 1H), 7.11 (d, J=8.4 Hz, 1H), 7.27 (dt, J=8.4, 1.2 Hz, 1H), 7.45 (dd, J=7.8, 1.2 Hz, 1H); $^{13}$C NMR (150 MHz, CDCl$_3$) δ 56.4, 80.2, 81.3, 95.0, 112.6, 115.1, 121.9, 130.4, 134.3, 158.5.

c. Ethyl 3-(2-methoxymethoxy)phenylpropiolate. To a solution of 2-ethynyl-1-(methoxymethoxy)benzene (162 mg, 1.0 mmol, 1.0 equiv) in THF (3 mL) was slowly added n-BuLi (440 μL 2.5 M solution in hexane, 1.1 mmol, 1.1 equiv) at −35° C. After stirring for 20 minutes, a solution of ethyl chloroformate (114 mg, 1.05 mmol, 1.05 equiv) in THF (1.0 mL) was added dropwise and the reaction mixture was stirred for an additional 30 minutes then allowed to warm to room temperature, and poured into a saturated aqueous NH$_4$Cl solution (5.0 mL). The aqueous phase was extracted with Et$_2$O (3×5 mL), the combined organic phases were dried (Na$_2$SO$_4$) and concentrated. Purification by flash chromatography (10:1 hexanes/EtOAc) afforded the title compound (130 mg, 57%) as colorless oil: R$_f$ 0.2 (10:1 hexanes/EtOAc); $^1$H NMR (600 MHz, CDCl$_3$) δ 1.32 (t, J=7.2 Hz, 3H), 4.26 (q, J=7.2 Hz, 2H), 3.49 (s, 3H), 5.23 (s, 2H), 6.97 (t, J=7.2 Hz, 1H), 7.12 (d, J=8.4 Hz, 1H), 7.35 (dt, J=8.4, 1.8 Hz, 1H), 7.50 (dd, J=7.2, 1.8 Hz, 1H); $^{13}$C NMR (150 MHz, CDCl$_3$) δ 14.3, 56.6, 62.1, 83.2, 84.6, 95.1, 110.4, 115.2, 122.0, 132.3, 134.9, 154.4, 159.5; MS (APCI−) calcd for C$_{13}$H$_{13}$O$_4$ [M−H]$^−$ 233.1, found 233.1.

d. 3-(2-Methoxymethoxy)phenylpropiolic acid. To a solution of ethyl 3-(2-methoxymethoxy)phenylpropiolate (64 mg, 0.26 mmol, 1.0 equiv) in 80% aqueous EtOH (2 mL) was added NaOH (100 mg, 2.5 mmol, 10 equiv). The mixture was stirred for 2 hours at room temperature and neutralized by adding 1 N HCl to pH 2.0. The reaction was extracted by EtOAc (3×5 mL), and the combined organic phase was dried (Na$_2$SO$_4$) and concentrated to afford the title compound (50 mg, 100%) as white solid: $^1$H NMR (600 MHz, CD$_3$OD) δ 3.48 (s, 3H), 5.27 (s, 2H), 7.01 (t, J=7.2 Hz, 1H), 7.19 (d, J=7.2 Hz, 1H), 7.41 (t, J=7.8 Hz, 1H), 7.49 (d, J=7.8 Hz, 1H); $^{13}$C NMR (150 MHz, CD$_3$OD) δ 55.4, 82.4, 84.5, 94.8, 110.2, 115.0, 121.7, 132.1, 134.4, 155.7, 159.4; MS (APCI−) calcd for C$_{11}$H$_9$O$_4$ [M−H]$^−$ 205.1, found 205.1.

e. 5-Amino-N$^6$-tert-butoxycarbonyl-5'-deoxy-5'-N-{[3-(2-methoxymethoxy)phenyl]prop-2-yn-1-oyl}-2',3'-O-isopropylideneadenosine. To a mixture of 3-(2-methoxymethoxy)phenylpropiolic acid (28 mg, 0.14 mmol, 1.0 equiv) and 5'-amino-N$^6$-tert-butoxycarbonyl-5'-deoxy-2',3'-O-isopropylideneadenosine (65 mg, 0.15 mmol, 1.05 equiv) in DMF (3 mL) was added EDC (42 mg, 0.22 mmol, 1.6 equiv) and HOBt (34 mg, 0.22 mmol, 1.6 equiv). After stirring 2.5 hours at room temperature, the reaction was concentrated in vacuo. The resulting residue was dissolved in EtOAc (10 mL). The EtOAc layer was washed successively with H$_2$O (50 mL), 1 N HCl (3 mL), H$_2$O (3 mL), saturated aqueous Na$_2$CO$_3$ (5 mL) and H$_2$O (3 mL). The organic phase was dried (Na$_2$SO$_4$) and concentrated. Purification by flash chromatography (4:1 EtOAc/hexanes) afforded title compound (30 mg, 36%) as white solid: R$_f$ 0.24 (4:1 EtOAc/hexanes); $^1$H NMR (600 MHz, CD$_3$OD) δ 1.34 (s, 3H), 1.52 (s, 9H), 1.61 (s, 3H), 2.14 (s, 3H), 3.37 (d, J=14.4 Hz, 1H), 3.45 (s, 3H), 4.23 (ddd, J=14.4, 6.0, 1.8 Hz, 1H), 4.53 (d, J=1.8 Hz, 1H), 4.90 (dd, J=6.0, 1.8 Hz, 1H), 5.25 (s, 2H), 5.32 (t, J=4.8 Hz, 1H), 5.86 (d, J=4.8 Hz, 1H), 6.95 (t, J=7.2 Hz, 1H), 7.13 (d, J=7.8 Hz, 1H), 7.31 (t, J=7.8 Hz, 1H), 7.48 (d, J=7.8 Hz, 1H), 8.00 (s, 1H), 8.88 (d, J=7.8 Hz, 1H), 8.94 (s, 1H); $^{13}$C NMR (150 MHz, CD$_3$OD) δ 25.5, 27.7, 28.3, 41.7, 56.5, 81.6, 82.6, 82.7, 83.0, 83.7, 87.1, 92.9, 95.0, 110.5, 115.0, 115.2, 122.0, 123.2, 131.8, 134.7, 142.3, 149.6, 150.1, 150.7, 153.5, 14.6, 159.0; HRMS (ESI+) calcd for C$_{29}$H$_{35}$N$_6$O$_8$ [M+H]$^+$ 595.2516, found 595.2516 (error 0 ppm).

EXAMPLE 17

Preparation of 5'-O—[N-(2-Fluorobenzoyl)sulfamoyl]adenosine triethylammonium salt This was prepared form 5'-O—[N-(2-fluorobenzoyl)-sulfamoyl]-2',3'-O-isopropylideneadenosine triethylammonium salt using general procedure for TFA deprotection. Purification by flash chromatography (100:15:2 EtOAc/MeOH/TEA) afforded the title compound (83%): R$_f$=0.16 (100:15:2 EtOAc/MeOH/TEA); [α]$_D^{25}$=−76° (c 0.47, MeOH); $^1$H NMR (600 MHz, CD$_3$OD) δ 1.23 (t, J=7.2 Hz, 9H), 3.06 (q, J=7.2 Hz, 6H), 4.30-4.32 (m, 1H), 4.35-4.43 (m, 3H), 4.73 (t, J=5.4 Hz, 1H), 6.08 (d, J=2.4 Hz, 1H), 7.05 (t, J=9.6 Hz, 1H), 7.12 (t, J=7.8 Hz, 1H), 7.34-7.36 (m, 1H), 7.71 (t, J=7.2 Hz, 1H), 8.17 (s, 1H), 8.51 (s, 1H); $^{13}$C NMR (150 MHz, CD$_3$OD) δ 8.3, 46.5, 68.3, 71.3, 74.8, 83.5, 87.9, 115.9 (d, J=22.8 Hz), 118.9, 123.5 (d, J=3.9 Hz), 127.5 (d, J=12.3 Hz), 130.6 (d, J=2.3 Hz), 131.4 (d, J=8.3 Hz), 139.9, 149.7, 152.7, 156.1, 160.1 (d, J=25.5 Hz), 172.3 (d, J=1.7 Hz); HRMS (APCI+) calcd for C$_{17}$H$_{18}$FN$_6$O$_7$S [M+H]$^+$ 469.0942, found 469.0950 (error 1.7 ppm).

The intermediate 5'-O—[N-(2-fluorobenzoyl)-sulfamoyl]-2',3'-O-isopropylideneadenosine triethylammonium salt was prepared as follows.

a. N-Hydroxysuccinimdyl 2-fluorobenzoate. This was prepared from 2-fluorobenzoic acid using the general procedure for NHS ester coupling. Flash chromatography (1:1 Hex/EtOAc) afforded the title compound (73%): R$_f$ 0.5 (1:1 Hex/EtOAc); $^1$H NMR (600 MHz, CDCl$_3$) δ 2.89 (s, 4H), 7.21 (dd, J=11.4, 7.2 Hz, 1H), 7.27 (dd, J=7.5, 7.2 Hz, 1H), 7.65 (dd, J=11.4, 7.2 Hz, 1H), 8.07 (dd, J=7.5, 7.2 Hz, 1H); $^{13}$C NMR (150 MHz, CDCl$_3$) δ 25.9, 113.9 (d, J=10.05 Hz), 117.6 (d, J=21.8 Hz), 124.6 (d, J=3.9 Hz), 132.8, 136.9 (d, J=9.5 Hz), 159.5 (d, J=4.5 Hz), 162.0 (d, J=263 Hz), 169.3; MS (ESI+) calcd for C$_{11}$H$_9$FNO$_4$ [M+H]$^+$ 237.0, found 237.1.

b. 5'-O—[N-(2-Fluorobenzoyl)sulfamoyl]-2',3'-O-isopropylideneadenosine triethylammonium salt. This was prepared from N-hydroxysuccinimdyl 2-fluorobenzoate using the general procedure for arylation of 2',3'-O-isopropylidene-5'-O-(sulfamoyl)adenosine. Purification by flash chromatography (100:10:1 EtOAc/MeOH/TEA) afforded the title compound (17%): R$_f$ 0.16 (100:10:1 EtOAc/MeOH/TEA); [α]$_D^{25}$=+9.60 (c 1.94, CH$_3$OH); $^1$H NMR (600 MHz, CD$_3$OD) δ 1.24 (t, J=7.2 Hz, 9H), 1.35 (s, 3H), 1.59 (s, 3H), 3.10 (q, J=7.2 Hz, 6H), 4.32 (d, J=3.6 Hz, 2H), 4.55-4.59 (m, 1H), 5.17 (dd, J=6.0, 1.8 Hz, 1H), 5.38 (dd, J=5.4, 3.0 Hz, 1H), 6.23 (d, J=3.0 Hz, 1H), 7.02-7.13 (m, 3H), 7.68 (t, J=6.0 Hz, 1H), 8.16 (s, 1H), 8.46 (s, 1H); $^{13}$C NMR (150 MHz, CD$_3$OD) δ 8.2, 24.3, 26.3, 46.5, 68.7, 82.2, 84.5 (d, J=3.3 Hz), 85.5 (d, J=30.2 Hz), 90.7, 114.1, 115.9 (d, J=22.2 Hz), 123.6 (d, J=4.8 Hz), 130.3 (d, J=3.3 Hz), 130.6 (d, J=2.7 Hz), 131.5 (d, J=8.4 Hz), 140.2, 149.3, 152.8, 156.1, 160.3 (d, J=250.5 Hz), 162.5, 172.3 (d, J=2.3 Hz); HRMS (APCI+) calcd for C$_{20}$H$_{22}$FN$_6$O$_7$S [M+H]$^+$ 509.1255, found 509.1233 (error 4.3 ppm).

EXAMPLE 18

Preparation of 5'-O—[N-(2-Chlorobenzoyl)sulfamoyl]adenosine. 5'-O—[N-(2-Chlorobenzoyl)sulfamoyl]adenosine This was prepared form 5'-O—[N-(2-chlorobenzoyl)sulfamoyl]-2',3'-O-isopropylideneadenosine using the general procedure for TFA deprotection. Purification by flash chromatography (100:15:2 MeOH/EtOAc/TEA) afforded the title compound as a white solid (93%): $R_f$ 0.18 (100:15:2 MeOH/EtOAc/TEA); $[\alpha]_D^{25}$=−18.7° (c 0.83, MeOH); $^1$H NMR (600 MHz, CD$_3$OD) δ 4.37 (br s, 1H), 4.49 (t, J=4.8 Hz, 1H), 4.62-4.70 (m, 3H), 6.11 (dd, J=4.8 Hz, 1H), 7.34-7.37 (m, 1H), 7.44-7.47 (m, 3H), 8.36 (s, 1H), 8.51 (s, 1H); $^{13}$C NMR (150 MHz, CD$_3$OD) δ 70.3, 71.5, 74.5, 82.4, 89.3, 119.3, 127.1, 128.9, 130.2, 130.9, 132.4, 133.5, 142.7, 144.3, 148.9, 150.8, 165.7; HRMS (ESI+) calcd for $C_{17}H_{18}ClN_6O_7S$ [M+H]$^+$ 485.0646, found 485.0649 (error 0.6 ppm).

The intermediate 5'-O—[N-(2-chlorobenzoyl)sulfamoyl]-2',3'-O-isopropylideneadenosine was prepared as follows.

a. N-Hydroxysuccinimdyl 2-chlorobenzoate. This was prepared from 2-chlorobenzoic acid using the general procedure for NHS ester synthesis. Purification by flash chromatography (1:1 hexanes/EtOAc) afforded the title compound (70%): $R_f$ 0.5 (1:1 hexanes/EtOAc); $^1$H NMR (600 MHz, CDCl$_3$) δ 2.91 (s, 4H), 7.39 (dt, J=5.4, 1.8 Hz, 1H), 7.53-7.57 (m, 2H), 8.10 (dd, J=7.2, 1.2 Hz, 1H); $^{13}$C NMR (150 MHz, CDCl$_3$) δ 25.9, 124.8, 127.1, 131.8, 132.6, 134.8, 135.8, 160.4, 169.2; MS (ESI+) calcd for $C_{11}H_9ClNO_4$ [M+H]$^+$ 253.0, found 252.9.

b. 5'-O—[N-(2-Chlorobenzoyl)sulfamoyl]-2',3'-O-isopropylideneadenosine. This was prepared from N-hydroxysuccinimdyl 2-chlorobenzoate using the general procedure for arylation of 2',3'-O-isopropylidene-5'-O-(sulfamoyl)adenosine. Purification by flash chromatography (100:10:1 EtOAc/MeOH/TEA) afforded the title compound (22%): $R_f$ 0.2 (100:10:1 EtOAc/MeOH/TEA); $[\alpha]_D^{25}$=−102° (c 2.79, MeOH); $^1$H NMR (600 MHz, CD$_3$OD) δ 1.36 (s, 3H), 1.59 (s, 3H), 4.35 (d, J=1.8 Hz, 2H), 4.58 (d, J=1.8 Hz, 1H), 5.20 (dd, J=6.0 Hz, 1H), 5.37 (dd, J=6.0, 3.0 Hz, 1H), 6.24 (d, J=3.0 Hz, 1H), 7.24 (t, J=7.2 Hz, 1H), 7.28 (t, J=7.2 Hz, 1H), 7.33 (d, J=7.8 Hz, 1H), 7.46 (d, J=7.8 Hz, 1H), 8.18 (s, 1H), 8.46 (s, 1H); $^{13}$C NMR (150 MHz, CD$_3$OD) δ 24.4, 26.3, 68.9, 82.1, 84.5, 84.6, 90.7, 114.1, 118.9, 126.4, 128.9, 129.6, 129.8, 130.7, 139.5, 140.3, 149.3, 152.8, 156.1, 174.7; HRMS (APCI+) calcd for $C_{20}H_{21}ClN_6O_7S$ [M+H]$^+$ 525.0954, found 525.0953 (error 0.2 ppm).

EXAMPLE 19

Preparation of 5'-O—[N-(2-Nitrobenzoyl)sulfamoyl]adenosine triethylammonium salt This was prepared form 2',3'-O-isopropylidene-5'-O—[N-(2-nitrobenzoyl)sulfamoyl]adenosine triethylammonium salt using general procedure for TFA deprotection. Purification by flash chromatography (100:25:2.5 EtOAc/MeOH/TEA) afforded the title compound (22%): $R_f$ 0.15 (100:25:2.5 EtOAc/MeOH/TEA); $[\alpha]_D^{25}$=−99.7° (c 0.29, MeOH); $^1$H NMR (600 MHz, CD$_3$OD) δ 1.24 (t, J=7.8 Hz, 9H), 3.14 (q, J=7.8 Hz, 6H), 4.31-4.34 (m, 1H), 4.40 (t, J=3.6 Hz, 2H), 4.45 (dd, J=7.8, 3.6 Hz, 1H), 4.72 (t, J=6.0 Hz, 1H), 6.09 (d, J=6.0 Hz, 1H), 7.52 (t, J=8.4, 1H), 7.61 (t, J=7.2 Hz, 1H), 7.68 (d, J=7.2 Hz, 1H), 7.83 (d, J=8.4 Hz, 1H), 8.18 (s, 1H), 8.49 (s, 1H); $^{13}$C NMR (150 MHz, CD$_3$OD) δ 8.0, 46.7, 68.5, 71.3, 74.9, 83.5, 87.9, 118.9, 123.4, 129.3, 129.5, 132.7, 135.7, 139.8, 147.9, 149.7, 152.7, 156.1, 172.7; HRMS (APCI+) calcd for $C_{17}H_{18}N_7O_9S$ [M+H]$^+$ 496.0887, found 496.0904 (error 3.4 ppm).

The intermediate 2',3'-O-isopropylidene-5'-O—[N-(2-nitrobenzoyl)sulfamoyl]adenosine triethylammonium salt was prepared as follows.

a. N-Hydroxysuccinimdyl 2-nitrobenzoate. This was prepared from 2-nitrobenzoic acid using the general procedure for NHS ester synthesis. Purification by flash chromatography (60:40 hexanes/EtOAc) afforded the title compound (85%): $R_f$ 0.2 (60:40 hexanes/EtOAc); $^1$H NMR (600 MHz, CDCl$_3$) δ 2.89 (s, 4H), 7.76-7.79 (m, 2H), 7.92-7.95 (m, 1H), 8.06-8.08 (m, 1H); $^{13}$C NMR (150 MHz, CDCl$_3$) δ 25.9, 123.2, 124.8, 130.9, 133.6, 133.7, 147.9, 161.2, 168.7; MS (ESI+) calcd for $C_{11}H_9N_2O_6$ [M+H]$^+$ 265.0, found 264.9.

b. 2',3'-O-Isopropylidene-5'-O—[N-(2-nitrobenzoyl)sulfamoyl]adenosine triethylammonium salt. This was prepared from N-hydroxysuccinimdyl 2-nitrobenzoate using the general procedure for arylation of 2',3'-O-isopropylidene-5'-O-(sulfamoyl)adenosine. Purification by flash chromatography (100:10:1 EtOAc/MeOH/TEA) afforded the title compound (28%): $R_f$ 0.17 (100:10:1 EtOAc/MeOH/TEA); $[\alpha]_D^{25}$=−142° (c 2.38, MeOH); $^1$H NMR (600 MHz, CD$_3$OD) δ 1.23 (t, J=7.2 Hz, 9H), 1.36 (s, 3H), 1.59 (s, 3H), 3.13 (q, J=7.2 Hz, 6H), 4.32-4.35 (m, 2H), 4.58 (br s, 1H), 5.18 (d, J=6.0, 1H), 5.37-5.39 (m, 1H), 6.23 (d, J=2.4, 1H), 7.52 (t, J=7.8 Hz, 1H), 7.62 (t, J=8.4 Hz, 1H), 7.66 (d, J=7.2 Hz, 1H), 7.82 (d, J=8.4 Hz, 1H), 8.18 (s, 1H), 8.45 (s, 1H); $^{13}$C NMR (150 MHz, CD$_3$OD) δ 8.0, 24.4, 26.3, 46.7, 68.8, 82.2, 84.5, 84.6, 90.7, 114.1, 118.9, 123.4, 129.3, 129.7, 132.6, 135.5, 140.2, 148.1, 149.3, 152.8, 156.1, 172.6; HRMS (ESI+) calcd for $C_{20}H_{21}N_7O_9S$ [M+H]$^+$ 536.1194, found 536.1201 (error 1.3 ppm).

EXAMPLE 20

Preparation of 5'-O—[N-(2-Chloronicotinoyl)sulfamoyl]adenosine triethylammonium salt This was prepared form 5'-O—[N-(2-chloronicotinoyl)sulfamoyl]-2',3'-O-isopropylideneadenosine triethylammonium salt using general procedure for TFA deprotection. Purification by flash chromatography (100:20:1 EtOAc/MeOH/TEA) afforded the title compound (53%): $R_f$ 0.10 (100:20:1 EtOAc/MeOH/TEA); $[\alpha]_D^{25}$=−65° (c 0.34, MeOH) $^1$H NMR (600 MHz, CD$_3$OD) δ 1.26 (t, J=7.8 Hz, 9H), 3.15 (q, J=7.8 Hz, 6H), 4.33 (dd, J=6.6, 3.0 Hz, 1H), 4.39-4.46 (m, 3H), 4.73 (t, J=6.0 Hz, 1H), 6.09 (d, J=4.8 Hz, 1H), 7.35 (dd, J=7.2, 4.2 Hz, 1H), 7.94 (dd, J=7.2, 1.8 Hz, 1H), 8.19 (s, 1H), 8.31 (dd, J=4.2, 1.8 Hz, 1H), 8.49 (s, 1H); $^{13}$C NMR (150 MHz, CD$_3$OD) δ 8.1, 46.7, 68.5, 71.2, 74.8, 83.4, 88.1, 119.0, 122.6, 136.2, 138.3, 139.9, 147.3, 148.9, 149.7, 152.7, 156.1, 172.4; HRMS (ESI+) calcd for $C_{16}H_{17}ClN_7O_7S$ [M+H]$^+$ 486.0599, found 486.0598 (error 0.2 ppm).

The intermediate 5'-O—[N-(2-chloronicotinoyl)sulfamoyl]-2',3'-O-isopropylideneadenosine triethylammonium salt was prepared as follows.

a. N-Hydroxysuccinimdyl 2-chloronicotinate. This was prepared from 2-chloronicotinic acid using the general procedure for NHS ester coupling. Purification by flash chromatography (1:1 hexanes/EtOAc) afforded the title compound (52% yield): $R_f$ 0.21 (1:1 hexanes/EtOAc); $^1$H NMR (600 MHz, CDCl$_3$) δ 2.92 (s, 4H), 7.41 (dd, J=7.8, 3.6 Hz, 1H), 8.42 (dd, J=7.2, 1.8 Hz, 1H), 8.63 (dd, J=9.6, 1.8 Hz, 1H); $^{13}$C NMR (150 MHz, CDCl$_3$) δ 25.9, 122.1, 122.4, 141.4, 151.7, 153.9, 159.6, 168.9; HRMS (ESI+) calcd for $C_{10}H_7N_2O_4Cl$ [M+H]$^+$ 255.0167, found 255.0163 (error 0.2 ppm).

b. 5'-O—[N-(2-Chloronicotinoyl)sulfamoyl]-2',3'-O-isopropylideneadenosine triethylammonium salt. This was prepared from N-hydroxysuccinimdyl 2-chloronicotinate using the general procedure for arylation of 2',3-O-isopropylidene-5'-O-(sulfamoyl)adenosine. Purification by flash chromatography (100:10:1 EtOAc/MeOH/TEA) afforded, the title compound (82%): $R_f$ 0.15 (100:10:1 EtOAc/MeOH/TEA); $[\alpha]_D^{25}$=−94° (c 0.34, MeOH); $^1$H NMR (600 MHz, CD$_3$OD)

δ 1.27 (t, J=7.8 Hz, 9H), 1.36 (s, 3H), 1.59 (s, 3H), 3.16 (q, J=7.8 Hz, 6H), 4.35 (ddd, J=6.0, 5.4, 3.6 Hz, 2H), 4.57 (dd, J=6.0, 5.4 Hz, 1H), 5.20 (dd, J=6.0, 2.4 Hz, 1H), 5.39 (dd, J=5.4, 2.4 Hz, 1H), 6.24 (d, J=3.0 Hz, 1H), 7.35 (dd, J=7.8, 4.8 Hz, 1H), 7.90 (dd, J=7.8, 1.8 Hz, 1H), 8.19 (s, 1H), 8.32 (dd, J=4.8, 1.8 Hz, 1H), 8.45 (s, 1H); $^{13}$C NMR (150 MHz, CD$_3$OD) δ 8.0, 24.4, 26.3, 46.7, 68.9, 82.1, 84.5, 84.6, 90.7, 114.2, 119.0, 122.7, 136.1, 138.3, 140.2, 147.3, 149.0, 149.3, 152.8, 156.1, 172.3; HRMS (ESI+) calcd for C$_{19}$H$_{21}$ClN$_7$O$_7$S [M+H]$^+$ 526.0906, found 526.0909 (error 0.6 ppm).

EXAMPLE 21

Preparation of 5'-O—[N-(2-Fluoronicotinoyl)sulfamoyl]adenosine triethylammonium salt This was prepared form 5'-O—[N-(2-fluoronicotinoyl]-2',3'-O-isopropylideneadenosine using general procedure for TFA deprotection. Purification by flash chromatography (100:20:1.5 EtOAc/MeOH/TEA) afforded the title compound as a white solid (50%): R$_f$ 0.17 (100.20:1.5 EtOAc/MeOH/TEA); [α]$_D^{25}$=−69.6° (c 2.55, MeOH); $^1$H NMR (600 MHz, CD$_3$OD) δ 1.24 (t, J=1.36 Hz, 9H), 3.13 (q, J=1.36 Hz, 6H), 4.31-4.32 (m, 1H), 4.32-4.43 (m, 3H), 4.70 (t, J=4.8 Hz, 1H), 6.08 (d, J=5.4 Hz, 1H), 7.27-7.29 (m, 1H), 8.16 (s, 1H), 8.18 (d, J=4.2 Hz, 1H), 8.24-8.27 (m, 1H), 8.50 (s, 1H); $^{13}$C NMR (150 MHz, CD$_3$OD) δ 8.1, 46.5, 68.4, 71.2, 74.8, 83.4, 87.9, 118.9, 121.5 (d, J=4.5 Hz), 122.1 (d, J=25.65 Hz), 139.9, 142.2 (d, J=2.7 Hz), 148.3 (d, J=13.95 Hz), 149.6, 152.7, 156.1, 160.6 (d, J=243.3 Hz), 170.1 (d, J=6.15 Hz); HRMS (ESI−) calcd for C$_{16}$H$_{15}$FN$_7$O$_7$S [M−H]$^-$ 468.0742, found 468.0740 (error 0.4 ppm).

The intermediate 5'-O—[N-(2-fluoronicotinoyl]-2',3-O-isopropylideneadenosine was prepared as follows.

a. N-Hydroxysuccinimdyl 2-fluoronicotinate. This was prepared from 2-fluoronicotinic acid using the general procedure for NHS ester coupling. Purification by flash chromatography (1:1 hexanes/EtOAc) afforded the title compound (50%): R$_f$ 0.18 (1:1 hexanes/EtOAc); $^1$H NMR (600 MHz, CDCl$_3$) δ 2.91 (s, 4H), 7.38 (t, J=6.0 Hz, 1H), 8.51 (t, J=6.0 Hz, 2H); $^{13}$C NMR (150 MHz, CDCl$_3$) δ 23.3, 107.0 (d, J=25.1 Hz), 119.4 (d, J=4.95 Hz), 141.4, 151.4 (d, J=15.6 Hz), 155.9 (d, J=15.6 Hz), 159.0 (d, J=251.1 Hz), 166.4; HRMS (ESI+) calcd for C$_{10}$H$_8$FN$_2$O$_4$ [M+H]$^+$ 239.0463, found 239.0469 (error 2.5 ppm).

b. 5'-O—[N-(2-Fluoronicotinoyl]-2',3'-O-isopropylideneadenosine. This was prepared from N-hydroxysuccinimdyl 2-fluoronicotinate using the general procedure for arylation of 2',3'-O-isopropylidene-5'-O-(sulfamoyl)adenosine. Purification by flash chromatography (100:15 EtOAc/MeOH) afforded the title compound as a white solid (27%): R$_f$ 0.17 (100:15 EtOAc/MeOH); [α]$_D^{25}$=−63.00 (c 2.5, MeOH); $^1$H NMR (600 MHz, CD$_3$OD) δ 1.36 (s, 3H), 1.59 (s, 3H), 4.32 (d, J=3.6 Hz, 2H), 4.56-4.58 (m, 1H), 5.15 (dd, J=6.0, 2.4 Hz, 1H), 5.37 (dd, J=6.0, 3.0 Hz, 1H), 6.22 (d, J=3.0 Hz, 1H), 7.26-7.30 (m, 1H), 8.16 (s, 1H), 8.17-8.19 (m, 1H), 8.20-8.23 (m, 1H), 8.45 (s, 1H); $^{13}$C NMR (150 MHz, CD$_3$OD) δ 24.3, 26.3, 46.3, 68.7, 82.1, 84.5, 84.6, 90.7, 114.1, 118.9, 121.4 (d, J=3.3 Hz), 140.2, 142.2, 148.2, 148.3, 149.3, 152.7, 156.1, 170.1 (d, J=251.7 Hz), 173.7; HRMS (ESI−) calcd for C$_{19}$H$_{19}$FN$_7$O$_7$S [M−H]$^-$ 508.1056, found 508.1059 (error 0.6 ppm).

EXAMPLE 22

Preparation of 5'-O—[N-(2,3-Dihydroxybenzoyl)sulfamoyl]-adenosine triethylammonium salt 5'-O—[N-(2,3-Dibenzyloxybenzoyl)sulfamoyl]-2',3'-O-isopropylideneadenosine triethylammonium salt (0.45 g, 0.56 mmol) was hydrogenated with 10% Pd/C (90 mg) under H$_2$ (1 atm) in MeOH (20 mL) at room temperature. After completion, the reaction mixture was filtered, washed with MeOH, and concentrated. Crude 5'-O—[N-(2,3-dihydroxybenzoyl)sulfamoyl]-2',3'-O-isopropylideneadenosine (150 mg, 0.24 mmol) was treated with 80% aq TFA (2.0 mL) using the general procedure for TFA deprotection. Purification by flash chromatography (25:75:1 MeOH/EtOAc/Et$_3$N) afforded the title compound (122 mg, 88%) as a white solid: R$_f$ 0.2 (1:1 MeOH/EtOAc); mp 138-140° C.; [α]$^2$D−23.5 (c 0.48, MeOH); $^1$H NMR (600 MHz, CD$_3$OD) δ 1.24 (t, J=7.8 Hz, 9H), 3.12 (q, J=7.8 Hz, 6H), 4.26-4.50 (m, 4H), 4.71 (t, J=4.8 Hz, 1H), 6.08 (d, J=5.4 Hz, 1H), 6.61 (t, J=7.2 Hz, 1H), 6.84 (d, J=8.4 Hz, 1H), 7.43 (d, J=7.8 Hz, 1H), 8.16 (s, 1H), 8.50 (s, 1H); $^{13}$C NMR (150 MHz, CD$_3$OD) δ 9.3, 47.8, 69.6, 72.4, 76.0, 84.6, 89.2, 118.6, 119.3, 120.2, 120.9, 121.9, 141.1, 146.1, 146.8, 150.9, 153.9, 157.3, 175.0; HRMS (ESI+) calcd for C$_{17}$H$_{19}$N$_6$O$_9$S [M+H]$^+$ 483.0934, found 483.0917 (error 4.3 ppm).

The intermediate 5'-O—[N-(2,3-Dibenzyloxybenzoyl)sulfamoyl]-2',3'-O-isopropylideneadenosine triethylammonium salt was prepared as follows.

a. N-Hydroxysuccinimdyl 2,3-dibenzyloxybenzoate. This was prepared from 2,3-dibenzyloxybenzoic acid using the general procedure for NHS ester coupling. Purification by flash chromatography (4:1 EtOAc/hexanes) afforded the title compound (0.80 g, 62%) as a viscous brown oil: R$_f$ 0.85 (EtOAc); $^1$H NMR (600 MHz, CDCl$_3$) δ 4.49 (br s, 4H), 5.13 (s, 4H), 7.12 (t, J=8.4 Hz, 1H), 7.20-7.30 (m, 4H), 7.32-7.39 (m, 4H), 7.39-7.44 (m, 3H), 7.85 (dd, J=8.4, 1.2, Hz, 1H); $^{13}$C NMR (150 MHz, CDCl$_3$) δ 25.9, 71.6, 76.1, 120.4, 121.3, 123.9, 124.4, 127.8, 128.2, 128.4, 128.5, 128.8, 128.9, 136.5, 137.2, 150.1, 153.2, 160.9, 169.4.

b. 5'-O—[N-(2,3-Dibenzyloxybenzoyl)sulfamoyl]-2',3'-O-isopropylideneadenosine triethylammonium salt. This was prepared from N-hydroxysuccinimdyl 2,3-dibenzyloxybenzoate using the general procedure for arylation of 2',3'-O-isopropylidene-5'-O-(sulfamoyl)adenosine. Purification by flash column chromatography (15:85:1 MeOH/EtOAc/Et$_3$N) afforded the title compound (0.49 g, 43%) as a viscous oil: R$_f$ 0.30 (1:5 MeOH/EtOAc); [α]$^{25}_D$ −43.5 (c 0.54, MeOH); $^1$H NMR (600 MHz, CD$_3$OD) δ 1.08 (t, J=7.2 Hz, 9H), 1.32 (s, 3H), 1.57 (s, 3H), 2.77 (q, J=7.2 Hz, 6H), 4.24 (d, J=3.6 Hz, 2H), 4.40-4.48 (m, 1H), 5.04-5.12 (m, 5H), 5.29 (dd, J=5.4, 3.0 Hz, 1H), 6.19 (d, J=3.0 Hz, 1H), 7.00-7.06 (m, 2H), 7.06-7.10 (m, 1H), 7.14-7.22 (m, 3H), 7.26-7.36 (m, 3H), 7.38-7.46 (m, 4H), 8.17 (s, 1H), 8.44 (s, 1H); $^{13}$C NMR (150 MHz, CD$_3$OD) δ 10.2, 25.6, 27.5, 47.3, 69.8, 72.0, 76.6, 83.2, 85.6, 85.7, 91.8, 115.2, 116.1, 120.2, 121.8, 125.1, 128.6, 128.9, 129.0, 129.1, 129.5, 129.6, 137.7, 138.5, 139.4, 141.4, 146.8, 150.5, 153.5, 153.9, 157.3, 176.4; HRMS (ESI+) calcd for C$_{34}$H$_{33}$N$_6$O$_9$S [M+H]$^+$ 701.2035, found 701.2082 (error 6.7 ppm).

EXAMPLE 23

Preparation of 5'-O—[N-(3,4-Dihydroxybenzoyl)sulfamoyl]adenosine

5'-O—[N-(3,4-Dibenzyloxybenzoyl)sulfamoyl]-2',3'-O-isopropylideneadenosine (0.45 g, 0.56 mmol) was treated with 10% Pd/C (90 mg) under H$_2$ (1 atm) in MeOH (20 mL) at room temperature. After completion, the reaction mixture was filtered, washed with MeOH, and concentrated. Crude 5'-O—[N-(3,4-dihydroxybenzoyl)sulfamoyl]-2',3'-O-isopropylideneadenosine (150 mg, 0.24 mmol) was treated with 80% aq TFA (2.0 mL) using the general procedure for TFA deprotection. Purification by flash chromatography (40:60:1 MeOH/EtOAc/Et$_3$N) afforded the title compound (120 mg, 72%) as a white solid: mp>190° C. (decomposed); R$_f$ 0.1 (2:3 MeOH:EtOAc); [α]$^{20}$$_D$ −101 (c 0.49, MeOH); $^1$H NMR (600 MHz, CD$_3$OD) δ 4.28-4.40 (m, 3H), 4.42 (t, J=3.6 Hz, 1H), 4.71 (t, J=5.4 Hz, 1H), 6.08 (d, J=6.0 Hz, 1H), 6.71 (d, J=7.8 Hz, 1H), 7.44 (d, J=7.8 Hz, 1H), 7.50 (s, 1H), 8.15 (s, 1H), 8.51 (s, 1H); $^{13}$C NMR (150 MHz, CDCl$_3$) δ 69.3, 72.5, 76.3, 84.8, 89.4, 115.5, 117.4, 120.3, 122.9, 130.5, 141.3, 145.6, 150.3, 150.9, 153.9, 157.3, 175.7; HRMS (ESI−) calcd for C$_{17}$H$_{17}$N$_6$O$_9$S [M−H]$^−$ 481.0783, found 481.0784 (error 0.2 ppm).

The intermediate 5'-O—[N-(3,4-Dibenzyloxybenzoyl)sulfamoyl]-2',3'-O-isopropylideneadenosine was prepared as follows.

a. N-Hydroxysuccinimidyl 3,4-dibenzyloxybenzoate. This was prepared from 3,4-dibenzyloxybenzoate using the general procedure for NHS ester coupling. Purification by flash chromatography (4:1 EtOAc/hexane) afforded the title compound (1.19 g, 92%) as a white solid: mp 134-136° C.; R$_f$ 0.80 (3:7 EtOAc/hexanes); $^1$H NMR (600 MHz, CDCl$_3$) δ 2.86 (br s, 4H), 5.17 (s, 2H), 5.24 (s, 2H), 7.96 (d, J=9.0 Hz, 1H), 7.28-7.34 (m, 2H), 7.34-7.40 (m, 4H), 7.40-7.48 (m, 4H), 7.67 (br s, 1H), 7.75 (dd, J=8.4, 1.8 Hz, 1H); $^{13}$C NMR (CDCl$_3$, 75 MHz) δ 25.9, 71.1, 71.6, 113.5, 116.1, 117.6, 125.9, 127.4, 129.7, 128.3, 128.4, 128.8, 128.9, 136.3, 136.7, 148.9, 154.8, 161.7, 169.7.

b. 5'-O—[N-(3,4-Dibenzyloxybenzoyl)sulfamoyl]-2',3'-O-isopropylideneadenosine. This was prepared from N-hydroxysuccinimidyl 3,4-dibenzyloxybenzoate using the general procedure for arylation of 2',3'-O-isopropylidene-5'-O-(sulfamoyl)adenosine. Purification by silica gel flash column chromatography (80:20:1 EtOAc/MeOH/Et$_3$N) afforded the title compound (0.45 g, 92%) as a thick oil: R$_f$ 0.2 (9:1 MeOH/EtOAc); [α]$^{20}$$_D$ −66 (c 0.65, MeOH); $^1$H NMR (600 MHz, CD$_3$OD) δ 1.31 (s, 3H), 1.56 (s, 3H), 4.26-4.36 (m, 2H), 4.52-4.58 (m, 1H), 5.07 (s, 2H), 5.10-5.16 (m, 3H), 5.32 (dd, J=6.0, 3.6 Hz, 1H), 6.20 (d, J=3.0 Hz, 1H), 6.94 (d, J=8.4 Hz, 1H), 7.20-7.36 (m, 6H), 7.38-7.44 (m, 4H), 7.63 (d, J=8.4 Hz, 1H), 7.76 (s, 1H), 8.13 (s, 1H), 8.45 (s, 1H); $^{13}$C NMR (150 MHz, CD$_3$OD) δ 25.6, 27.6, 69.9, 72.1, 72.4, 83.4, 85.8, 85.9, 92.1, 114.5, 115.4, 116.7, 116.8, 120.3, 124.5, 128.7, 128.8, 128.9, 129.0, 129.5, 129.6, 138.6, 138.8, 141.6, 149.9, 150.7, 153.2, 154.1, 157.4, 174.9; HRMS (ESI−) calcd for C$_{34}$H$_{33}$N$_6$O$_9$S [M−H]$^−$ 701.2035, found 701.2027 (error 1.1 ppm).

EXAMPLE 24

Preparation of 5'-O—[N-(3-Chloro-2-hydroxybenzoyl)sulfamoyl]-adenosine triethylammonium salt This was prepared form 5'-O—[N-(3-chloro-2-hydroxybenzoyl)sulfamoyl]-2',3'-O-isopropylideneadenosine using general procedure for TFA deprotection. Purification by flash chromatography (100:15:1 EtOAc/MeOH/TEA) afforded the title compound (65%): R$_f$ 0.17 (100:15:1 EtOAc/MeOH/TEA); [α]$_D$$^{25}$=−32.8° (c 0.57, MeOH); $^1$H NMR (600 MHz, CD$_3$OD) δ 1.28 (t, J=7.2 Hz, 9H), 3.18 (q, J=7.2 Hz, 6H), 4.34-4.35 (m, 1H), 4.39-4.46 (m, 3H), 4.74 (t, J=5.4 Hz, 1H), 6.11 (d, J=6.0 Hz, 1H), 6.76 (t, J=7.8 Hz, 1H), 7.40 (dd, J=7.8, 1.2 Hz, 1H), 7.91 (dd, J=7.8, 1.2 Hz, 1H), 8.20 (s, 1H), 8.53 (s, 1H); $^{13}$C NMR (150 MHz, CD$_3$OD) δ 12.1, 50.6, 72.5, 75.1, 78.8, 87.3, 91.9, 121.9, 122.9, 124.9, 125.3, 132.7, 137.1, 143.8, 153.6, 156.6, 160.0, 160.7, 176.6; HRMS (ESI+) calcd for C$_{17}$H$_{18}$ClN$_6$O$_8$S [M+H]$^+$ 501.0590, found 501.0585 (error 1.0 ppm).

The intermediate 5'-O—[N-(3-chloro-2-hydroxybenzoyl)sulfamoyl]-2',3'-O-isopropylideneadenosine was prepared as follows.

a. 5'-O—[N-(3-Chloro-2-hydroxybenzoyl)sulfamoyl]-2',3'-O-isopropylideneadenosine. This was prepared from 3-chlorosalicylic acid using the general procedure for CDI coupling. Purification by flash chromatography (100:5:1 EtOAc/MeOH/TEA) afforded the title compound (15%): R$_f$ 0.15 (100:5:1 EtOAc/MeOH/TEA); [α]$_D$$^{25}$=−32.3° (c 2.0, MeOH); $^1$H NMR (600 MHz, CD$_3$OD) δ 1.31 (s, 3H), 1.55 (s, 3H), 4.32-4.34 (m, 2H), 4.54 (br, 1H), 5.09-5.11 (m, 1H), 5.34 (dd, J=6.0, 3.0 Hz, 1H), 6.20 (d, J=3.0 Hz, 1H), 6.71 (t, J=7.8 Hz, 1H), 7.35 (d, J=8.4 Hz, 1H), 7.83 (d, J=7.8 Hz, 1H), 8.14 (s, 1H), 8.39 (s, 1H); $^{13}$C NMR (150 MHz, CD$_3$OD) δ 24.3, 26.2, 68.9, 82.1, 84.5, 84.6, 90.8, 114.1, 118.0, 119.0, 120.8, 121.3, 128.7, 133.3, 140.2, 149.2, 152.7, 156.1, 156.8, 172.9; HRMS (ESI+) calcd for C$_{20}$H$_{20}$ClN$_6$O$_8$S [M+H]$^+$ 541.0903, found 541.0903 (error 0 ppm).

EXAMPLE 25

Preparation of 5'-O—[N-(4-Chloro-2-hydroxybenzoyl)sulfamoyl]-adenosine triethylammonium salt This was prepared form 5'-O—[N-(4-chloro-2-hydroxybenzoyl)sulfamoyl]-2',3'-O-isopropylideneadenosine triethylammonium salt using general procedure for TFA deprotection. Purification by flash chromatography (100:15:1 EtOAc/MeOH/TEA) afforded the title compound (60% yield): R$_f$ 0.14 (100:15:1 EtOAc/MeOH/TEA); [α]$_D$$^{25}$=−23.3° (c 1.81, MeOH); $^1$H NMR (600 MHz, CD$_3$OD) δ 1.24 (t, J=7.8 Hz, 9H), 3.13 (q, J=7.8 Hz, 6H), 4.30 (dd, J=6.6, 3.0 Hz, 1H), 4.34-4.42 (m, 3H), 4.70 (t, J=5.4 Hz, 1H), 6.07 (d, J=5.4 Hz, 1H), 6.74 (dd, J=8.4, 1.2 Hz, 1H), 6.79 (d, J=1.2 Hz, 1H), 7.88 (d, J=2.4 Hz, 1H), 8.16 (s, 1H), 8.47 (s, 1H); $^{13}$C NMR (150 MHz, CD$_3$OD) δ 8.1, 46.7, 60.3 68.5, 71.2, 74.8, 83.3, 88.1, 116.6, 118.3, 119.0, 131.5, 138.3, 139.9, 149.7, 152.7, 156.1, 161.7, 172.6; HRMS (ESI+) calcd for C$_{17}$H$_{18}$ClN$_6$O$_8$S [M+H]$^+$ 501.0590, found 501.0592 (error 0.4 ppm).

The intermediate 5'-O—[N-(4-chloro-2-hydroxybenzoyl)sulfamoyl]-2',3'-O-isopropylideneadenosine triethylammonium salt was prepared as follows.

a. 5'-O—[N-(4-Chloro-2-hydroxybenzoyl)sulfamoyl]-2',3'-O-isopropylideneadenosine triethylammonium salt. This was prepared from 4-chlorosalicylic acid using the general procedure for CDI coupling. Purification by flash chromatography (100:10:1 EtOAc/MeOH/TEA) afforded the title compound (70%): R$_f$ 0.15 (100:10:1 EtOAc/MeOH/TEA); [α]$_D$$^{25}$=−88.4° (c 1.86, MeOH); $^1$H NMR (600 MHz, CD$_3$OD) δ 1.24 (t, J=7.8 Hz, 9H), 1.34 (s, 3H), 1.58 (s, 3H), 3.09 (q, J=7.8 Hz, 6H), 4.29 (dd, J=10.8, 4.2 Hz, 1H), 4.32 (dd, J=10.8, 3.6 Hz, 1H), 4.54 (ddd, J=4.2, 3.4, 1.8 Hz, 1H), 5.11 (dd, J=6.0, 1.8 Hz, 1H), 5.37 (dd, J=6.0, 3.0 Hz, 1H), 6.21 (d, J=2.4 Hz, 1H), 6.72-6.80 (m, 2H), 7.83 (d, J=9.0 Hz, 1H), 8.14 (s, 1H), 8.41 (s, 1H); $^{13}$C NMR (150 MHz, CD$_3$OD) δ 8.3, 24.2, 26.2, 46.6, 68.8, 82.2, 84.5, 84.5, 90.8, 114.1, 115.9, 116.6, 118.3, 118.4, 131.6, 138.3, 140.2, 149.2, 152.8, 156.1, 161.7, 172.6; MS (ESI+) calcd for C$_{20}$H$_{21}$ClN$_6$O$_8$S [M+H]$^+$ 541.1, found 541.1.

EXAMPLE 26

Preparation of 5'-O—[N-(5-Chloro-2-hydroxybenzoyl)sulfamoyl]-adenosine triethylammonium salt This was prepared form 5'-O—[N-(5-chloro-2-hydroxybenzoyl)sulfamoyl]-2',3'-O-isopropylideneadenosine using general procedure for TFA deprotection. Purification by flash chromatography (100:20:1.5 EtOAc/MeOH/TEA) afforded the title compound (59% yield): $R_f$ 0.15 (100:20:1.5 EtOAc/MeOH/TEA); $[\alpha]_D^{25}=-23.3°$ (c 1.72, MeOH); $^1$H NMR (600 MHz, CD$_3$OD) δ 1.17 (t, J=7.2 Hz, 9H), 2.90 (q, J=7.2 Hz, 6H), 4.31-4.42 (m, 4H), 4.68 (t, J=5.4 Hz, 1H), 6.06 (d, J=5.4 Hz, 1H), 6.76 (d, J=8.4 Hz, 1H), 7.22 (d, J=8.4 Hz, 1H), 7.87 (s, 1H), 8.15 (s, 1H), 8.44 (s, 1H); $^{13}$C NMR (150 MHz, CD$_3$OD) δ 8.8, 46.3, 68.5, 71.1, 74.8, 83.2, 88.3, 116.8, 118.0, 118.4, 120.6, 122.7, 129.4, 132.8, 139.9, 152.7, 156.1, 159.5, 172.4; HRMS (ESI+) calcd for C$_{17}$H$_{18}$ClN$_6$O$_8$S [M+H]$^+$ 501.0590, found 501.0594 (error 0.8 ppm).

The intermediate 5'-O—[N-(5-chloro-2-hydroxybenzoyl)sulfamoyl]-2',3'-O-isopropylideneadenosine was prepared as follows.

a. 5'-O—[N-(5-Chloro-2-hydroxybenzoyl)sulfamoyl]-2',3'-O-isopropylideneadenosine. This was prepared from 5-chlorosalicylic acid using the general procedure for CDI coupling. Purification by flash chromatography (100:5:1.5 EtOAc/MeOH/TEA) afforded the title compound (12% yield): $R_f$ 0.18 (100:5:1.5 EtOAc/MeOH/TEA); $[\alpha]_D^{25}=-96.0°$ (c 1.26, MeOH); $^1$H NMR (600 MHz, CD$_3$OD) δ 1.33 (s, 3H), 1.56 (s, 3H), 4.30-4.33 (m, 2H), 4.53 (br s, 1H), 5.10 (d, J=6.0 Hz, 1H), 5.35 (dd, J=5.4, 2.4 Hz, 1H), 6.19 (d, J=2.4 Hz, 1H), 6.75 (d, J=8.4 Hz, 1H), 7.22 (dd, J=8.4, 2.4 Hz, 1H), 7.84 (d, J=2.4 Hz, 1H), 8.13 (s, 1H), 8.39 (s, 1H); $^{13}$C NMR (150 MHz, CD$_3$OD) δ 24.2, 26.2, 68.9, 82.1, 84.5, 84.6, 90.8, 104.7, 114.1, 118.5, 119.0, 120.5, 122.7, 129.3, 132.8, 140.2, 152.7, 156.0, 159.5, 172.4; HRMS (ESI+) calcd for C$_{20}$H$_{21}$ClN$_6$O$_8$S [M+H]$^+$ 541.0903, found 541.0914 (error 2.0 ppm).

EXAMPLE 27

Preparation of 5'-O—[N-(4-Amino-2-hydroxybenzoyl)sulfamoyl]-adenosine triethylammonium salt This was prepared form 5'-O—[N-(4-amino-2-hydroxybenzoyl)sulfamoyl]-2',3'-O-isopropylideneadenosine triethylammonium salt using general procedure for TFA deprotection. Purification by flash chromatography (100:30:3 MeOH/EtOAc/TEA), $R_f$=0.10) afforded the title compound as a white solid (35%): $R_f$ 0.10 (100:30:3 MeOH/EtOAc/TEA); $[\alpha]_D^{21}=-55.1°$ (c 3.75, MeOH); $^1$H NMR (600 MHz, CD$_3$OD) δ 1.18 (t, J=7.2 Hz, 9H), 3.17 (q, J=7.2 Hz, 6H), 4.29-4.40 (m, 4H), 4.72 (t, J=6.0 Hz, 1H), 6.02 (br s, 1H), 6.08 (d, J=6.0 Hz, 1H), 6.10 (d, J=9.0 Hz, 1H), 7.66 (d, J=9.0 Hz, 1H), 8.16 (s, 1H), 8.50 (s, 1H); $^{13}$C NMR (150 MHz, CD$_3$OD) δ 8.0, 46.4, 68.2, 71.3, 74.9, 83.5, 88.0, 100.3, 106.2, 109.0, 118.9, 131.7, 139.9, 149.7, 152.7, 153.8, 156.1, 162.7, 177.8; HRMS (ESI−) calcd for C$_{17}$H$_{18}$N$_7$O$_8$S [M−H]$^−$ 480.0943, found 480.0941 (error 0.4 ppm).

The intermediate 5'-O—[N-(4-amino-2-hydroxybenzoyl)sulfamoyl]-2',3'-O-isopropylideneadenosine triethylammonium salt was prepared as follows.

a. 4-(Benzyloxycarbonyl)amino-2-hydroxybenzoic acid. To a solution of 4-aminosalicylic acid (2.0 g, 13.1 mmol) in THF (40 mL) was added saturated NaHCO$_3$ solution (40 mL) followed by benzyl chloroformate (2.04 mL, 14.4 mmol, 1.1 equiv). The reaction was stirred for 16 hours at room temperature then concentrated in vacuo to remove THF. The remaining aqueous layer was extracted with EtOAc (2×100 μL) and these organic extracts were discarded. The aqueous layer was acidified with aqueous 20% HCl to pH 3-4, then extracted with CHCl$_3$ (2×100 mL). The CHCl$_3$ extracts were dried (Na$_2$SO$_4$) and concentrated to afford the title compound as a light brown solid (2.30 g, 61%): $^1$H NMR (600 MHz, CD$_3$OD) δ 5.17 (s, 2H), 6.91 (dd, J=9.0, 1.8 Hz, 1H), 7.14 (s, 1H), 7.29-7.39 (m, 4H), 7.72 (d, J=9.0 Hz, 1H), 9.57 (s, 1H); $^{13}$C NMR (150 MHz, CD$_3$OD) δ 66.6, 105.2, 107.2, 109.3, 127.9, 128.0, 128.3, 131.1, 136.6, 145.9, 154.0, 163.1, 172.0; HRMS (ESI−) calcd for C$_{15}$H$_{12}$NO$_5$ [M−H]$^−$ 286.0721, found 286.0727 (error 2.1 ppm)

b. 5'-O-{N-[4-(Benzyloxycarbonyl)amino-2-hydroxybenzoyl]sulfamoyl}-2',3'-O-isopropylideneadenosine. This was prepared from 4-(benzyloxycarbonyl)amino-2-hydroxybenzoic acid using the general procedure for CDI coupling. Purification by flash chromatography (100:7 MeOH/EtOAc) afforded the title compound as a white solid (38% yield): $R_f$ 0.20 (100:7 MeOH/EtOAc); $^1$H NMR (600 MHz, CD$_3$OD) δ 1.32 (s, 3H), 1.56 (s, 3H), 4.30 (t, J=4.2 Hz, 2H), 4.53-4.54 (br s, 1H), 5.10 (dd, J=7.8, 1.8 Hz, 1H), 5.15 (s, 2H), 5.35 (dd, J=7.2, 4.8 Hz, 1H), 6.20 (d, J=3.0 Hz, 1H), 6.81 (d, J=8.4 Hz, 1H), 7.28 (d, J=7.2 Hz, 1H), 7.34 (t, J=7.2 Hz, 3H), 7.38 (d, J=7.2 Hz, 2H), 7.80 (d, J=8.4 Hz, 1H), 8.13 (s, 1H), 8.40 (s, 1H); $^{13}$C NMR (150 MHz, CD$_3$OD) δ 24.2, 26.2, 66.4, 68.7, 82.2, 84.5, 90.8, 105.6, 108.8, 114.1, 119.0, 121.4, 127.8, 127.9, 128.3, 130.9, 135.1, 136.8, 140.2, 143.9, 149.2, 152.7, 154.2, 156.1, 161.8, 173.9; HRMS (ESI+) calcd for C$_{28}$H$_{30}$N$_7$O$_{10}$S [M+H]$^+$ 656.1775, found 656.1707 (error 10 ppm).

c. 5'-O—[N-(4-Amino-2-hydroxybenzoyl)sulfamoyl]-2',3'-O-isopropylideneadenosine triethylammonium salt. 5'-O-{N-[4-(benzyloxycarbonyl)amino-2-hydroxybenzoyl]sulfamoyl}-2',3'-O-isopropylideneadenosine (120 mg, 0.18 mmol) was hydrogenated with 10% Pd/C (12 mg, 10% by wt) in MeOH (5 mL) under H$_2$ (1 atm) at room temperature for 12 hours. The reaction mixture was filtered through a plug of Celite and washed with MeOH (3×10 mL). Purification by flash chromatography (100:10:1 MeOH/EtOAc/TEA) afforded the title compound as a white solid (89%): $R_f$ 0.10 (100:10:1 MeOH/EtOAc/TEA); $[\alpha]_D^{25}=-153°$ (c 1.88, MeOH); $^1$H NMR (600 MHz, CD$_3$OD) δ 1.18 (t, J=7.2 Hz, 9H), 2.97 (q, J=7.2 Hz, 4H), 4.27 (d, J=3.6 Hz, 2H), 4.55 (br s, 1H), 5.11 (d, J=6.0 Hz, 1H), 5.37 (dd, J=6.0, 3.6 Hz, 1H), 6.02 (d, J=1.8 Hz, 1H), 6.11 (dd, J=8.4, 1.8 Hz, 1H), 6.20 (d, J=−2.4 Hz, 1H), 7.64 (d, J=8.4 Hz, 1H), 8.15 (s, 1H), 8.48 (s, 1H); $^{13}$C NMR (150 MHz, CD$_3$OD) δ 8.6, 24.2, 26.2, 46.4, 68.6, 82.3, 84.4, 84.5, 90.8, 100.3, 106.2, 108.9, 114.1, 118.9, 131.5, 131.7, 140.2, 149.3, 152.8, 153.8, 156.1, 162.7; HRMS (ESI+) calcd for C$_{20}$H$_{24}$N$_7$O$_8$S [M+H]$^+$ 522.1407, found 522.1385 (error 4.2 ppm).

EXAMPLE 28

Preparation of 5'-O—[N-(6-Fluoro-2-hydroxybenzoyl)sulfamoyl}-adenosine triethylammonium salt This was prepared form 5'-O—[N-(6-fluoro-2-hydroxybenzoyl)sulfamoyl]-2',3'-O-isopropylideneadenosine triethylammonium salt using general procedure for TFA deprotection. Purification by flash chromatography (100:16:3 EtOAc/MeOH/TEA) afforded the title compound (76% yield): $R_f$ 0.09 (100:16:3 EtOAc/MeOH/TEA); $[\alpha]_D^{21}=-47.0°$ (c 0.34, MeOH); $^1$H NMR (600 MHz, CD$_3$OD) δ 1.14 (t, J=7.2 Hz, 9H), 2.85 (q, J=7.2 Hz, 6H), 4.33 (d, J=6.6, 3.0 Hz, 1H), 4.38-4.45 (m, 3H), 4.69 (t, J=5.4 Hz, 1H), 6.08 (d, J=5.4 Hz, 1H), 6.47 (dd, J=11.4, 8.4 Hz, 1H), 6.60 (d, J=8.4 Hz, 1H), 7.18 (dd, J=8.4, 6.6 Hz, 1H), 8.15 (s, 1H), 8.41 (s, 1H); $^{13}$C NMR (150 MHz, CD$_3$OD) δ 8.9, 46.2, 68.6, 71.1, 74.8, 83.2, 88.3, 106.1 (d, J=24 Hz), 109.8 (d, J=9.0 Hz), 112.7 (d, J=3.3 Hz), 119.1, 132.4 (d, J=12.3 Hz), 139.9, 149.5, 152.7, 156.1, 162.0 (d, J=125 Hz), 164.1, 171.1 (d, J=3.3 Hz); HRMS (ESI+) calcd for $C_{17}H_{18}FN_6O_8S$ [M+H]$^+$ 485.0885, found 485.0906 (error 4.3 ppm).

The intermediate 5'-O—[N-(6-fluoro-2-hydroxybenzoyl) sulfamoyl]-2',3'-O-isopropylideneadenosine triethylammonium salt was prepared as follows.

a. 5'-O—[N-(6-Fluoro-2-hydroxybenzoyl)sulfamoyl]-2',3'-O-isopropylideneadenosine triethylammonium salt. This was prepared from 6-fluorosalicylic acid using the general procedure for CDI coupling. Purification by flash chromatography (100:7.5:1 EtOAc/MeOH/TEA) afforded the title compound (60% yield): $R_f$ 0.15 (100:7.5:1 EtOAc/MeOH/TEA); $[\alpha]_D^{25}=-53°$ (c 0.42, MeOH); $^1$H NMR (600 MHz, CD$_3$OD) δ 1.23 (t, J=7.2 Hz, 9H), 1.35 (s, 3H), 1.58 (s, 3H), 3.08 (q, J=7.2 Hz, 6H), 4.31 (dd, J=10.8, 4.2 Hz, 1H), 4.35 (dd, J=10.8, 4.2 Hz, 1H), 4.54 (dd, J=4.2, 1.8 Hz, 1H), 5.14 (dd, J=3.0, 1.8 Hz, 1H), 5.37 (dd, J=6.0, 3.0 Hz, 1H), 6.22 (d, J=6.0 Hz, 1H), 6.44-6.62 (m, 2H), 7.17-7.22 (m, 1H), 8.15 (s, 1H), 8.42 (s, 1H); $^{13}$C NMR (150 MHz, CD$_3$OD) δ 8.2, 24.3, 26.3, 46.6, 68.9, 82.2, 84.5 (d, J=3.1 Hz), 90.8, 105.4 (d, J=24 Hz), 109.9, 112.6, 114.1, 119.0, 131.8 (d, J=11.7 Hz), 132.3 (d, J=12.2 Hz), 140.2, 149.3, 152.8, 156.1, 161.5, 162.4, 170.8; HRMS (ESI+) calcd for $C_{20}H_{22}FN_6O_8S$ [M+H]$^+$ 525.1198, found 525.1215 (error 3.2 ppm).

EXAMPLE 29

Preparation of 5'-O—[N-(2-Pyridon-1-yl)sulfamoyl] adenosine triethylammonium salt To a solution of 2',3'-O-bis(tert-Butyldimethylsilyl)-5'-O—[N-(2-pyridon-1-yl)sulfamoyl]adenosine triethylammonium salt (35 mg, 0.05 mmol, 1.0 equiv) in THF (2 mL) was added TBAF (126 μL, 1.0 M solution in THF, 0.125 mmol, 2.5 equiv), and the resulting mixture was stirred 30 minutes at 0° C. The reaction was concentrated in vacuo. Purification by flash chromatography (90:5:7 MeOH/EtOAc/TEA) afforded the title compound as a white solid (6.1 mg, 87% yield): $R_f$ 0.03 (90:5:7 MeOH/EtOAc/TEA); $[\alpha]_D^{25}=-105°$ (c 0.76, MeOH); $^1$H NMR (600 MHz, DMSO) δ 1.15 (t, J=6.6 Hz, 9H), 2.95 (q, J=6.6 Hz, 6H), 4.11-4.14 (m, 1H), 4.14-4.17 (m, 1H), 4.19 (dd, J=7.8, 4.2 Hz, 1H), 4.24 (dd, J=10.8, 4.2 Hz, 1H), 4.60 (dd, J=10.8, 6.0 Hz, 1H), 5.38 (d, J=4.2 Hz, 1H), 5.53 (d, J=6.0 Hz, 1H), 5.92 (d, J=6.0 Hz, 1H), 6.82 (br s, 1H), 8.11 (s, 1H), 8.15 (br s, 2H), 8.39 (s, 1H); $^{13}$C NMR (150 MHz, CD$_3$OD) δ 9.3, 45.7, 68.3, 70.7, 73.5, 82.4, 86.9, 115.3, 118.9, 139.1 (br), 139.3, 149.6, 151.4 (br), 152.7, 156.1; HRMS (ESI–) calcd for $C_{16}H_{16}N_7O_8S$ [M–H]$^-$ 466.0787, found 466.0767 (error 4.3 ppm).

The intermediate 2',3'-O-bis(tert-Butyldimethylsilyl)-5'-O—[N-(2-pyridon-1-yl)sulfamoyl]adenosine triethylammonium salt was prepared as follows.

a. 2',3'-O-bis(tert-Butyldimethylsilyl)-5'-O—[N-(2-pyridon-1-yl)sulfamoyl]adenosine triethylammonium salt. This was prepared from 2-pyridone using the general procedure for CDI coupling. Purification by flash chromatography (100:10:2 MeOH/EtOAc/TEA) afforded the title compound as a white solid (15%): $R_f$ 0.27 100:10:2 MeOH/EtOAc/TEA); $[\alpha]_D^{25}=-148°$ (c 4.2, MeOH); $^1$H NMR (600 MHz, CD$_3$OD) δ –0.39 (s, 3H), –0.07 (s, 3H), 0.13 (s, 3H), 0.15 (s, 3H), 0.69 (s, 9H), 0.95 (s, 9H), 1.27 (t, J=7.2 Hz, 9H), 3.18 (q, J=7.2 Hz, 6H), 4.31 (br s, 1H), 4.44-4.47 (m, 3H), 4.87 (dd, J=7.2, 4.8 Hz, 2H), 6.10 (d, J=7.2 Hz, 1H), 6.76 (br s, 1H), 7.98 (br s, 1H), 8.18 (s, 1H), 8.34 (d, J=6.0 Hz, 1H), 8.57 (s, 1H); $^{13}$C NMR (150 MHz, CD$_3$OD) δ –5.1, –4.2, –4.2, –4.1, 9.4, 14.8, 18.7, 19.0, 22.7, 26.3, 26.4, 26.5, 35.4, 47.8, 69.7, 74.8, 77.5, 86.1, 88.6, 105.9, 114.1 (br), 120.3, 141.6 (br), 142.9, 148.0 (br), 151.1, 154.0, 157.5, 166.0 (br), 172.6; HRMS (ESI–) calcd for $C_{28}H_{45}N_7O_8SSi_2$ [M–H]$^-$ 694.2516, found 694.2548 (error 4.6 ppm).

EXAMPLE 30

Preparation of 5'-O—[N-(2-Hydroxybenzoyl)sulfamoyl]inosine triethylammonium salt 2',3'-O-Isopropylidene-5'-O-(sulfamoyl)inosine was converted to the title compound using the general procedure for salicylation and TFA deprotection. Purification by flash chromatography (85:15 EtOAc/MeOH/) afforded the title compound (48 mg, 87%) as a white solid: $R_f$ 0.2 (7:3 EtOAc/MeOH); $[\alpha]_D^{20}$ –11.7 (c 1.40, MeOH); $^1$H NMR (600 MHz, CD$_3$OD) δ 1.27 (t, J=7.2 Hz, 9H), 3.17 (q, J=7.2 Hz, 6H), 4.31-4.32 (m, 1H), 4.35-4.38 (m, 1H), 4.41-4.42 (m, 2H), 4.76 (t, J=6.0 Hz, 1H), 6.07 (d, J=6.0 Hz, 1H), 6.76-6.79 (m, 2H), 7.29 (t, J=7.8 Hz, 1H), 7.92 (d, J=8.4 Hz, 1H), 8.00 (s, 1H), 8.44 (s, 1H); $^{13}$C NMR (150 MHz, CDCl$_3$) δ 9.4, 47.9, 69.7, 72.6, 76.1, 84.8, 89.9, 118.0, 119.4, 120.8, 125.7, 131.4, 134.5, 140.9, 146.9, 150.3, 159.1, 162.1, 174.9; MS (APCI–) calcd for $C_{17}H_{16}N_5O_9S$ [M–H] 466.1 found 466.1

The intermediate 2',3'-O-Isopropylidene-5'-O-(sulfamoyl) inosine was prepared as follows.

a. 2',3'-O-Isopropylideneinosine. Inosine was converted to the title compound using the general procedure for acetonide protection. Purification by flash chromatography (95:5 EtOAc/MeOH) afforded the title compound (876 mg, 76%) as a white solid: $R_f$ 0.5 (1:9 MeOH/EtOAc); $[\alpha]_D^{20}$ –35 (c 0.50, DMSO); $^1$H NMR (600 MHz, CD$_3$OD) δ 1.41 (s, 3H), 1.3 (s, 3H), 3.75 (dd, J=11.4, 3.6 Hz, 1H), 3.80 (dd, J=12.0, 3.6 Hz, 1H), 4.38 (d, J=2.4 Hz, 1H), 5.04 (d, J=2.4 Hz, 1H), 5.29 (q, J=3.0 Hz, 1H), 6.22 (d, J=2.4 Hz, 1H), 8.09 (s, 1H), 8.35 (s, 1H); $^{13}$C NMR (150 MHz, CD$_3$OD) δ 25.6, 27.6, 63.4, 83.0, 86.0, 88.6, 92.5, 115.4, 126.0, 141.1, 146.9, 149.6, 158.9; MS (APCI–) calcd for $C_{13}H_{15}N_4O_5$ [M]$^-$ 307.1047, found 307.1072 (error 8.1).

b. 2',3'-O-Isopropylidene-5'-O-(sulfamoyl)inosine. 2',3'-O-Isopropylideneinosine was converted to the title compound using the general procedure for sulfamoylation. Purification by flash chromatography (95:5 EtOAc/MeOH) afforded the title compound (288 mg, 92%) as a white solid: $R_f$ 0.4 (8:2 EtOAc/MeOH); $[\alpha]_D^{20}$ –14 (c 0.75, DMSO); $^1$H NMR (600 MHz, CD$_3$OD) δ 1.35 (s, 3H), 1.56 (s, 3H), 4.23-4.31 (m, 2H), 4.50 (br s, 1H), 5.08 (br s, 1H), 5.36 (d, J=3.6 Hz, 1H), 6.21 (s, 1H), 8.07 (s, 1H), 8.20 (s, 1H); $^{13}$C NMR (150 MHz, CD$_3$OD) δ 24.3, 26.2, 68.6, 81.6, 84.5, 84.7, 90.9, 114.4, 124.6, 139.7, 145.9, 148.3, 157.7; HRMS (APCI–) calcd for $C_{13}H_{16}N_5O_7S$ [M–H]$^-$ 386.0775, found 386.0798 (error 5.9).

EXAMPLE 31

Preparation of $N^6,N^6$-Dimethyl-5'-O—[N-(2-hydroxybenzoyl)-sulfamoyl]-2',3'-O-isopropylideneadenosine triethylammonium salt $N^6,N^6$-Dimethyl-2',3'-O-isopropylidene-5'-O-(sulfamoyl) adenosine was converted to the title compound using the general procedure for salicylation and TFA deprotection. Purification by flash chromatography (10:90 MeOH/EtOAc) afforded the title compound (69 mg, 81%) as a white solid: $R_f$ 0.4 (15:85 MeOH/EtOAc); $[\alpha]_D^{20}$ –32 (c 0.5, MeOH); $^1$H NMR (600 MHz, CD$_3$OD) δ 1.24 (t, J=7.2 Hz, 9H), 3.05 (q, J=7.2 Hz, 6H), 3.47 (br s, 6H), 4.34 (q, J=3.6 Hz, 1H), 4.39-4.48 (m, 3H), 4.68 (t, J=5.4 Hz, 1H), 6.08 (d, J=5.4 Hz, 1H), 6.79 (q, J=8.4 Hz, 2H), 7.29 (t, J=7.2 Hz, 1H), 7.95 (dd, J=8:4, 1.8 Hz, 1H), 8.17 (s, 1H), 8.30 (s, 1H); $^{13}$C NMR (150 MHz, CD$_3$OD) δ 9.8, 47.7, 70.0, 72.3, 75.9, 84.2, 89.6, 117.3, 118.1, 119.2, 119.4, 120.3, 121.3, 131.7, 134.8, 139.1, 151.5, 153.2, 156.1, 175.5.

The intermediate N$^6$,N$^6$-Dimethyl-2',3'-O-isopropylidene-5'-O-(sulfamoyl)adenosine was prepared as follows.

a. 6-Chloro-9-(2',3'-O-isopropylidene-β-D-ribofuranosyl)purine. 6-Chloro-9-(β-D-ribofuranosyl)purine was converted to the title compound using the general procedure for acetonide protection. Purification by flash chromatography (60:40 EtOAc/hexane) afforded the title compound (890 mg, 75%) as colorless oil: R$_f$ 0.7 (EtOAc); [α]$^{20}$$_D$ −28.4 (c 0.820, MeOH); $^1$H NMR (600 MHz, CDCl$_3$) δ 1.38 (s, 3H), 1.65 (s, 3H), 3.84 (t, J=10.8 Hz, 1H), 3.98 (dd, J=12.6, 1.2 Hz, 1H), 4.55 (br s, 1H), 4.98 (d, J=9.6 Hz, 1H), 5.11 (d, J=6.0 Hz, 1H), 5.20 (t, J=5.4 Hz, 1H), 6.01 (d, J=3.6 Hz, 1H), 8.29 (d, J=1.2 Hz, 1H), 8.76 (d, J=1.2 Hz, 1H); $^{13}$C NMR (150 MHz, CDCl$_3$) δ 25.4, 27.7, 63.3, 81.7, 83.5, 86.6, 94.1, 114.6, 133.3, 144.9, 150.6, 151.9, 152.4; MS (APCI+) calcd for C$_{13}$H$_{16}$$^{35}$ClN$_4$O$_4$ [M+H]$^+$ calculated 327.0854, found 327.0857 (error 0.9 ppm).

b. N$^6$,N$^6$-dimethyl-2',3'-O-isopropylideneadenosine. To a stirred solution of 6-chloro-9-(2',3'-O-isopropylidene-β-D-ribofuranosyl)purine in tert-BuOH (20 mL) in sealed tube was added N,N-dimethylamine (1 mL) and the reaction heated at 85° C. for 3 hours. The solvent was removed under vacuum. Purification by flash chromatography (1:1 EtOAc/hexane) afforded the title compound (198 mg, 96%) as white solid: R$_f$ 0.4 (EtOAc); [α]$^{20}$$_D$ −62.4 (c 0.5, MeOH); $^1$H NMR (600 MHz, CD$_3$OD) δ 1.51 (s, 3H), 1.77 (s, 3H), 3.65 (br s, 6H), 3.89 (dd, J=12.6, 3.6 Hz, 1H), 4.00 (dd, J=12, 3 Hz, 1H), 4.56 (d, J=2.4 Hz, 1H), 5.18 (dd, J=6.6, 1.8 Hz, 1H), 5.34 (t, J=6 Hz, 1H), 6.21 (d, J=4.2 Hz, 1H), 8.27 (s, 1H), 8.34 (s, 1H); $^1$H NMR (600 MHz, CDCl$_3$) δ 1.37 (s, 3H), 1.64 (s, 3H), 3.49 (br s, 6H), 3.79 (d, J=13.2 Hz, 1H), 3.98 (d, J=12.6 Hz, 1H), 4.53 (s, 1H), 5.12 (d, J=5.4 Hz, 1H), 5.24 (t, J=5.4 Hz, 1H), 5.82 (d, J=4.8 Hz, 1H), 7.36 (s, 1H), 8.26 (s, 1H); $^{13}$C NMR (150 MHz, CDCl$_3$) δ 25.4, 27.9, 63.7, 81.9, 82.8, 86.2, 94.6, 105.0, 105.0, 114.0, 121.8, 138.2, 148.9, 151.9, 155.3; MS (APCI+) calcd for C$_{15}$H$_{22}$N$_5$O$_4$ [M+H]$^+$ 336.1, found 336.1 c. N$^6$,N$^6$-Dimethyl-2',3'-O-isopropylidene-5'-O-(sulfamoyl)adenosine. N$^6$,N$^6$-dimethyl-2',3'-O-isopropylideneadenosine was converted to the title compound using the general procedure for sulfamoylation. Purification by flash chromatography (EtOAc/hexane 60:40) afforded the title compound (190 mg, 88%) as a white solid: R$_f$ 0.5 (EtOAc); [α]$^{20}$$_D$ −27.6 (c 1.30, MeOH); $^1$H NMR (600 MHz, CD$_3$OD) δ 1.42 (s, 3H), 1.65 (s, 3H), 3.51 (br s, 6H), 4.32 (q, J=4.8 Hz, 1H), 4.38 (dd, J=10.8, 4.2 Hz, 1H), 4.55 (q, J=4.8 Hz, 1H), 5.16 (dd, J=6.0, 3.0 Hz, 1H), 5.42 (dd, J=6.0, 2.4 Hz, 1H), 6.26 (d, J=2.4 Hz, 1H), 8.19 (s, 1H), 8.24 (s, 1H); $^{13}$C NMR (150 MHz, CD$_3$OD) δ 14.6, 25.6, 27.5, 39.2, 70.1, 83.0, 85.6, 85.6, 91.7, 115.7, 121.3, 139.5, 151.1, 153.5, 156.2; MS (APCI+) calcd for C$_{15}$H$_{23}$N$_6$O$_6$ [M+H]$^+$ 415.1, found 415.1

EXAMPLE 32

Preparation of Compound N$^6$-Cyclopropyl-5'-O—[N-(2-hydroxybenzoyl)sulfamoyl]adenosine triethylammonium salt N$^6$-Cyclopropyl-2',3'-O-isopropylidene-5'-O-(sulfamoyl)adenosine was converted to the title compound using the general procedure for salicylation and TFA deprotection. Purification by flash chromatography (8:92 MeOH/EtOAc) afforded the title compound (84 mg, 76%) as a white solid: R$_f$ 0.3 (10:90 MeOH/EtOAc); [α]$^{20}$$_D$ −46.4 (c 0.50, MeOH); $^1$H NMR (600 MHz, CD$_3$OD) δ 0.65-0.66 (m, 2H), 0.88-0.92 (m, 2H), 1.09 (t, J=1.2 Hz, 9H), 2.65 (q, J=7.2 Hz, 6H), 2.96 (br s, 1H), 4.34 (t, J=2.4 Hz, 1H), 4.39 (dd, J=10.8, 3 Hz, 1H), 4.25-4.44 (m, 2H), 4.72 (t, J=10.8 Hz, 1H), 6.11 (d, J=6.0 Hz, 1H), 6.80 (q, J=18.0, 9.0 Hz, 2H), 7.28-7.30 (m, 1H), 7.95 (d, J=7.8 Hz, 1H), 8.28 (br s, 1H), 8.48 (br s, 1H); $^{13}$C NMR (150 MHz, CD$_3$OD) δ 7.7, 10.9, 19.4, 47.7, 69.6, 72.5, 76.2, 84.7, 89.4, 118.0, 119.3, 120.7, 120.8, 131.5, 134.4, 140.9, 153.9, 157.2, 162.2, 175.2; MS (APCI+) calcd for C$_{20}$H$_{23}$N$_6$O$_8$S [M+H] 507.1, found 507.1.

The intermediate N$^6$-Cyclopropyl-2',3'-O-isopropylidene-5'-O-(sulfamoyl)adenosine was prepared as follows.

a. N$^6$-Cyclopropyl-2',3'-O-isopropylideneadenosine. To a stirred solution of 6-chloro-9-(2',3'-O-isopropylidene-β-D-ribofuranosyl)purine in $^t$BuOH (20 mL) in sealed tube was added cyclopropyl amine (1 mL) and heated at 85° C. for 3 hours. The solvent was removed under vacuum and purification of the crude residue by flash chromatography (EtOAc/hexane 50:50) afforded the title compound (200 mg, 94%) as a white solid: R$_f$ 0.4 (EtOAc); [α]$^{20}$$_D$ −230 (c 1.0, MeOH); $^1$H NMR (600 MHz, CDCl$_3$) δ 0.67 (br s, 2H), 0.95 (q, J=6.0 Hz, 2H), 1.37 (s, 3H), 1.63 (s, 3H), 3.78 (d, J=12.6 Hz, 1H), 3.96 (d, J=13.2 Hz, 1H), 4.53 (s, 1H), 5.11 (d, J=6.0 Hz, 1H), 5.19 (t, J=5.4 Hz, 1H), 5.86 (d, J=4.2 Hz, 1H), 7.81 (s, 1H), 8.40 (s, 1H); $^{13}$C NMR (150 MHz, CDCl$_3$) δ 7.6, 23.9, 25.4, 27.8, 63.5, 81.9, 83.2, 86.3, 94.5, 114.2, 121.5, 140.0 (3 Aromatic carbons are missing For this I have given more no. of scans and increased relaxation time also); MS (APCI+) calcd for C$_{16}$H$_{20}$N$_5$O$_4$ [M+H]$^+$ 346.1520, found 346.1551 (error 8.9).

b. N$^6$-Cyclopropyl-2',3'-O-isopropylidene-5'-O-(sulfamoyl)adenosine. N$^6$-Cyclopropyl-2',3'-O-isopropylideneadenosine was converted to the title compound using the general procedure for sulfamoylation. Purification by flash chromatography (EtOAc/hexane 45:55) afforded the title compound (190 mg, 76%) as a white solid: R$_f$ 0.5 (EtOAc); [α]$^{20}$$_D$ −58 (c 1.8, MeOH); $^1$H NMR (600 MHz, CD$_3$OD) δ 0.66-0.68 (m, 2H), 0.89-0.93 (m, 2H), 1.41 (s, 1H), 1.63 (1H), 2.97 (br s, 1H), 4.30 (dd, J=10.8, 5.4 Hz, 1H), 4.36 (dd, J=10.8, 4.8 Hz, 1H), 4.55 (q, J=5.4 Hz, 1H), 5.16 (q, J=2.4 Hz, 1H), 5.45 (dd, J=6.6, 2.4 Hz, 1H), 6.27 (d, J=2.4 Hz, 1H), 8.24 (s, 1H), 8.33 (s, 1H); $^{13}$C NMR (150 MHz, CD$_3$OD) δ 7.7, 24.6, 25.6, 27.5, 70.0, 83.0, 85.6, 85.8, 91.9, 115.7, 121.0, 149.9, 141.2, 154.1, 157.2; HRMS (APCI−) calcd for C$_{16}$H$_{21}$N$_6$O$_6$S [M−H] 425.1248, found 425.1281 (error 7.7).

EXAMPLE 33

Preparation of 8-Bromo-5'-O—[N-(2-hydroxybenzoyl)sulfamoyl]-adenosine triethylammonium salt 8-Bromo-2',3'-O-isopropylidene-5'-O-(sulfamoyl)adenosine was converted to the title compound using the general procedure for salicylation and TFA deprotection. Purification by flash chromatography (9:1 EtOAc/MeOH) afforded the title compound (86 mg, 66%) as a white solid: R$_f$ 0.2 (8:2 EtOAc/MeOH); [α]$^{20}$$_D$ −5.7 (c 1.0, MeOH); $^1$H NMR (600 MHz, CD$_3$OD) δ 1.28 (t, J=7.2 Hz, 9H), 3.17 (q, J=7.2 Hz, 6H), 4.27-4.32 (m, 2H), 453 (q, J=6.0 Hz, 1H), 4.60 (t, J=3.6 Hz, 1H), 5.39 (t, J=6.0 Hz, 1H), 6.03 (d, J=5.4 Hz, 1H), 6.76 (q, J=7.8 Hz, 2H), 7.28 (t, J=7.8 Hz, 1H), 7.90 (d, J=7.8 Hz, 1H), 8.03 (s, 1H); $^{13}$C NMR (150 MHz, CD$_3$OD) δ 9.2, 47.9, 69.6, 72.3, 72.4, 84.2, 92.2, 117.8, 119.2, 120.7, 121.1, 129.1, 131.2, 134.2, 152.0, 153.8, 156.1, 161.9, 174.7.

The intermediate 8-Bromo-2',3'-O-isopropylidene-5'-O-(sulfamoyl)adenosine was prepared as follows.

a. 8-Bromo-2',3'-O-isopropylideneadenosine. 8-Bromoadenosine was converted to the title compound using the general procedure for acetonide protection. Purification by flash chromatography (8:2 EtOAc/hexane) afforded the title compound (1.09 g, 65%) as a white solid: $R_f$ 0.3 (EtOAc); $[\alpha]^{20}_D$ −16.2 (c 1.25, DMSO); $^1$H NMR (600 MHz, CDCl$_3$) δ 1.36 (s, 3H), 1.66 (s, 3H), 3.78 (d, J=12.6 Hz, 1H), 3.95 (d, J=13.2 Hz, 1H), 4.51 (s, 1H), 5.06 (d, J=5.4 Hz, 1H), 5.26 (d, J=5.4 Hz, 1H), 5.94 (s, 2H, NH$_2$), 6.094 (d, J=4.8 Hz, 1H), 7.24 (s, 1H), 8.25 (s, 1H); $^{13}$C NMR (150 MHz, CDCl$_3$) δ 25.7, 28.0, 63.5, 81.8, 82.7, 86.0, 94.0, 114.3, 120.9, 127.4, 150.1, 152.7, 154.8; HRMS (APCI+) calcd for $C_{13}H_{17}{}^{79}BrN_5O_4$ [M+H]$^+$ 386.0, found 386.1.

b. 8-Bromo-2',3'-O-isopropylidene-5'-O-(sulfamoyl)adenosine. 8-Bromo-2',3'-O-isopropylideneadenosine was converted to the title compound using the general procedure for sulfamoylation. Purification by flash chromatography (7:3 EtOAc/hexane) afforded the title compound (510 mg, 85%) as a colorless oil: $R_f$ 0.6 (EtOAc); $[\alpha]^{20}_D$ +1.0 (c 2.5, MeOH); $^1$H NMR (600 MHz, CD$_3$OD) δ 1.37 (s, 3H), 1.57 (s, 3H), 4.14 (dd, J=10.2, 7.2 Hz, 1H), 4.28 (dd, J=10.2, 6.0 Hz, 1H), 4.41-4.43 (m, 1H), 5.24 (dd, J=6.0, 3.0 Hz, 1H), 5.73 (d, J=6.6 Hz, 1H), 6.21 (s, 1H), 8.17 (s, 1H); $^{13}$C NMR (150 MHz, CD$_3$OD) δ 25.5, 27.5, 69.7, 83.5, 84.7, 86.9, 93.0, 115.6, 121.0, 128.6, 151.4, 154.2, 156.4; MS (APCI+) calcd for $C_{13}H_{18}{}^{79}BrN_6O_6S$ [M+H]$^+$ 465.0, found 465.2.

EXAMPLE 34

Preparation of 8-Azido-5'-O—[N-(2-hydroxybenzoyl)sulfamoyl]-adenosine triethylammonium salt 8-Azido-2',3'-O-isopropylidene-5'-O-(sulfamoyl)adenosine was converted to the title compound using the general procedure for salicylation and TFA deprotection. Purification by flash chromatography (5:95 MeOH/EtOAc) afforded the title compound (350 mg, 89%) as a white solid: $R_f$ 0.2 (10:90 MeOH/EtOAc); $[\alpha]^{20}$-21.6 (c 1.0, MeOH); $^1$H NMR (600 MHz, CD$_3$OD) δ 1.28 (t, J=2.4 Hz, 9H), 3.18 (q, J=7.2 Hz, 6H), 4.27 (q, J=4.8 Hz, 1H), 4.38 (q, J=6.6 Hz, 1H), 4.50 (q, J=5.4 Hz, 1H), 4.58 (t, J=4.8 Hz, 1H), 5.10 (t, J=5.4 Hz, 1H), 5.90 (d, J=5.4 Hz, 1H), 6.80 (q, J=8.4 Hz, 2H), 7.28-7.31 (m, 1H), 7.92 (d, J=7.8 Hz, 1H), 8.04 (s, 1H); $^{13}$C NMR (150 MHz, CD$_3$OD) δ 9.3, 48.0, 70.0, 72.3, 72.9, 83.9, 89.3, 118.0, 118.6, 119.3, 120.7, 131.3, 134.4, 147.0, 151.4, 152.9, 155.5, 162.0, 174.8.

The intermediate 8-Azido-2',3'-O-isopropylidene-5'-O-(sulfamoyl)-adenosine was prepared as follows.

a. 8-Azido-2',3'-O-isopropylideneadenosine. 8-Bromo-2',3'-O-isopropylideneadenosine (550 mg, 1.42 mmol, 1.0 equiv) and NaN$_3$ (370 mg, 5.69 mmol, 4 equiv) were heated in DMF (10 mL) at 70° C. for 12 hours. The reaction mixture was concentrated in vacuo and the residue was purified by flash chromatography (50:50 EtOAc/hexane) to afford the title compound (410 mg, 83%) as a white solid: $R_f$ 0.4 (EtOAc); $[\alpha]^{20}_D$ −28 (c 1.2, MeOH); $^1$H NMR (600 MHz, CDCl$_3$) δ 1.35 (s, 3H), 1.63 (s, 3H), 3.75 (d, J=12.6 Hz, 1H), 3.92 (d, J=12.6 Hz, 1H), 4.63 (s, 1H, OH), 5.05 (d, J=6.0 Hz, 1H), 5.19 (t, J=5.4 Hz, 1H), 5.71 (d, J=6.6 Hz, 1H), 5.82 (d, J=5.4 Hz, 1H), 8.19 (s, 1H); $^{13}$C NMR (150 MHz, CDCl$_3$) δ 25.5, 27.8, 63.5, 81.7, 82.7, 85.9, 91.4, 114.1, 118.5, 145.4, 149.2, 151.7, 154.0; HRMS (APCI+) calcd for $C_{13}H_{17}N_8O_4$ [M+H]$^+$ calculated 349.1367, found 349.1308 (error 16.8 ppm).

b. 8-Azido-2',3'-O-isopropylidene-5'-O-(sulfamoyl)adenosine. 8-Azido-2',3'-O-isopropylideneadenosine was converted to the title compound using the general procedure for sulfamoylation. Purification by flash chromatography (80:20 EtOAc/hexane) afforded the title compound (230 mg, 48%) as a white solid: $R_f$ 0.5 (EtOAc); $[\alpha]^{20}_D$ −0.29 (c 2.0, MeOH); $^1$H NMR (600 MHz, CD$_3$OD) δ 1.36 (s, 3H), 1.56 (s, 3H), 4.17 (dd, J=10.2, 6.6 Hz, 1H), 4.30 (dd, J=10.2, 5.4 Hz, 1H), 4.38 (dd, J=9.6, 6.0, Hz, 1H), 5.16 (dd, J=6.0, 3.6 Hz, 1H), 5.54 (d, J=6.0 Hz, 1H), 6.03 (s, 1H), 8.10 (s, 1H); $^{13}$C NMR (150 MHz, CD$_3$OD) δ 25.6, 27.5, 69.7, 83.1, 84.7, 86.4, 90.0, 115.6, 118.7, 146.6, 150.8, 153.2, 155.7; MS (APCI+) calcd for $C_{13}H_{18}N_9O_6S$ [M+H]$^+$ 428.1, found 428.1.

EXAMPLE 35

Preparation of 8-Amino-5'-O—[N-(2-hydroxybenzoyl)-sulfamoyl]adenosine triethylammonium salt 8-Azido-5'-O—[N-(2-hydroxybenzoyl)sulfamoyl]adenosine triethylammonium salt (100 mg) was treated with Pd/C (5 mg) in MeOH (10 mL) under a H$_2$ (1 atm) for 2 hours. The reaction was filtered thru Celite then concentrated in vacuo. Purification by flash chromatography (10:90 MeOH/EtOAc) afforded the title compound (69 mg, 73%) as a white solid: $R_f$ 0.3 (20:80 MeOH/EtOAc); $[\alpha]^{20}_D$ −18.9 (c 1.0, MeOH); $^1$H NMR (600 MHz, CD$_3$OD) δ 1.28 (t, J=6.6 Hz, 9H), 3.18 (q, J=7.2 Hz, 6H), 4.30 (d, J=2.4 Hz, 1H), 4.38-4.60 (m, 3H), 4.87-4.90 (ovlp m, 1H), 6.04 (d, J=7.2 Hz, 1H), 6.83 (q, J=9.0 Hz, 2H), 7.33 (q, J=7.2 Hz, 1H), 7.97 (d, J=7.8 Hz, 1H), 7.98 (s, 1H); $^{13}$C NMR (150 MHz, CD$_3$OD) δ 9.35, 48.0, 69.7, 71.9, 72.0, 84.6, 88.6, 117.8, 118.0, 119.4, 120.6, 131.5, 134.6, 150.4, 151.1, 153.5, 153.8, 162.1, 175.2; HRMS (ESI+) calcd for $C_{17}H_{20}N_7O_5S$ [M+H]$^+$ 482.1088, found 482.1079 (error 1.8)

EXAMPLE 36

Preparation of 5'-O—[N-(2-Hydroxybenzoyl)sulfamoyl]-2-iodoadenosine triethylammonium salt 2-Iodo-2',3'-O-isopropylidene-5'-O-(sulfamoyl)adenosine was converted to the title compound using the general procedure for salicylation (Cs$_2$CO$_3$ method) and TFA deprotection. Purification by flash chromatography (10:90:1 MeOH/EtOAc/Et$_3$N) afforded the title compound (77 mg, 85%) as a white solid: $R_f$ 0.4 (10:90 MeOH/EtOAc); $[\alpha]^{20}_D$ −4.5 (c 0.32, MeOH); $^1$H NMR (600 MHz, CD$_3$OD) δ 1.27 (t, J=7.2 Hz, 9H), 3.18 (t, J=7.2 Hz, 6H), 4.27-4.30 (m, 1H), 4.30-4.34 (m, 1H), 4.36-4.46 (m, 3H), 4.65 (t, J=4.8 Hz, 1H), 6.01 (d, J=5.4 Hz, 1H), 6.74-6.82 (m, 2H), 7.28 (dt, J=1.8, 8.4 Hz, 1H), 7.93 (dd, J=1.8, 7.8 Hz, 1H), 8.36 (s, 1H); $^{13}$C NMR (150 MHz, CD$_3$OD) δ 9.2, 47.9, 69.8, 72.4, 76.1, 84.5, 89.5, 118.0, 119.4, 120.1, 120.7, 120.9, 131.4, 134.5, 140.8, 151.3, 157.1, 162.1, 174.9; HRMS (ESI−) calcd for $C_{17}H_{16}IN_6O_8S$ [M−H]$^-$ 590.9800, found 590.9784 (error 2.7 ppm).

The intermediate 2-Iodo-2',3'-O-isopropylidene-5'-O-(sulfamoyl)adenosine was prepared as follows.

a. 2-Iodo-2',3'-O-isopropylidene-5'-O-(sulfamoyl)adenosine. 2-Iodo-2',3'-O-isopropylideneadenosine (150 mg, 0.35 mmol, 1.0 equiv) was treated with sulfamoyl chloride (100 mg, 0.85 mmol, 2.5 equiv) and NaH (27.0 mg, 0.45 mmol, 2.0 equiv) using the general procedure for sulfamoylation. Purification by flash column chromatography (4:1 EtOAc/hexanes) afforded the title compound (160 mg, 90%) as a viscous transparent syrup: $R_f$ 0.55 (3:1, EtOAc/hexanes); $[\alpha]^{20}_D$ −0.92 (c 1.3, CH$_3$OH); $^1$H NMR (600 MHz, CD$_3$OD) δ 1.37 (s, 3H), 1.58 (s, 3H), 4.27 (dd, J=11.1, 5.4 Hz, 1H), 4.32 (dd, J=11.1, 5.4 Hz, 1H), 4.4-4.52 (m, 1H), 5.06-5.09 (m, 1H), 5.32 (d, J=6.0 Hz, 1H), 6.18 (s, 1H), 8.12 (s, 1H); $^{13}$C NMR (150 MHz, CD$_3$OD) δ 24.3, 26.2, 68.8, 81.7, 84.4, 84.9, 90.3, 114.4, 119.0, 119.6, 139.9, 149.4, 155.9; HRMS (ESI+) calcd for C$_{13}$H$_{18}$IN$_6$O$_6$S [M+H]$^+$ 513.0048, found 513.0056 (error 0.2 ppm).

EXAMPLE 37

Preparation of 5'-O—[N-(2-Hydroxybenzoyl)sulfamoyl]-2-phenyladenosine triethylammonium salt 2',3'-O-isopropylidene-2-phenyl-5'-O-(sulfamoyl)adenosine was converted to the title compound using the general procedure for salicylation (Cs$_2$CO$_3$ method) and TFA deprotection. Purification by flash chromatography (5:95 MeOH/EtOAc) afforded the title compound (16.6 mg, 83%) as a thick oil: R$_f$ 0.2 (3:7 MeOH/EtOAc); [α]$^{20}_D$ +7.4 (c 0.56, MeOH); $^1$H NMR (600 MHz, CD$_3$OD) δ 1.25 (t, J=7.2 Hz, 9H), 3.14 (q, J=7.2 Hz, 6H), 4.32-4.37 (m, 1H), 4.39 (dd, J=11.4, 3.6 Hz, 1H), 4.45 (dd, J=11.4, 3.6 Hz, 1H), 4.49 (t, J=4.2 Hz, 1H), 4.82-4.86 (m, 1H), 6.22 (d, J=5.4 Hz, 1H), 6.74-6.84 (m, 2H), 7.28 (dt, J=8.4, 1.8 Hz, 1H), 7.38-7.46 (m, 3H), 7.94 (dd, J=7.8, 1.8 Hz, 1H), 8.36 (dd, J=8.4, 1.8 Hz, 2H), 8.47 (s, 1H); $^{13}$C NMR (150 MHz, CD$_3$OD) δ 9.3, 48.0, 69.8, 72.6, 75.9, 84.5, 89.3, 117.9, 119.1, 119.4, 120.7, 129.3, 129.4, 130.9, 131.4, 134.4, 139.8, 141.5, 152.3, 157.2, 161.1, 162.1, 175.1; HRMS (ESI+) calcd for C$_{17}$H$_{16}$IN$_6$O$_8$S [M+H]$^+$ 543.1293, found 543.1291 (error 0.3 ppm).

The intermediate 2',3'-O-isopropylidene-2-phenyl-5'-O-(sulfamoyl)adenosine was prepared as follows.
a. 2',3'-O-Isopropylidene-2-phenyladenosine. In an oven-dried, screw-cap vial equipped with a stirring bar were placed Pd(OAc)$_2$ (5.2 mg, 23 μmol, 0.1 equiv) and 2-(dicyclohexylphosphino)biphenyl (12.1 mg, 35 μmol, 0.15 equiv). Freshly distilled 1,4-dioxane (1.5 mL) was added, the vial was flushed with nitrogen, sealed, and the mixture was stirred at room temperature for 3 minutes. Next, phenylboronic acid (43 mg, 0.35, 1.5 equiv), 2-iodo-2',3'-O-isopropylideneadenosine (100 mg, 0.23 mmol, 1.0 equiv) and K$_3$PO$_4$ (98 mg, 0.46 mmol, 2.0 equiv) were added to the vial, the vial was again flushed with nitrogen, sealed with a cap, and placed in a sand bath that was maintained at 100-102° C. The reaction was monitored by TLC, and upon completion (18 h), the reaction mixture was filtered through Celite, the residue was washed with CH$_2$Cl$_2$, and the filtrate was evaporated to dryness. Purification by flash column chromatography (1:49 MeOH/EtOAc) afforded the title compound (82 mg, 92%) as an off-white sticky solid: R$_f$ (0.5 EtOAc); HRMS ESI(+) calcd for C$_{19}$H$_{22}$N$_5$O$_4$ [M+H]$^+$ 384.1666, found 384.1667 (error 0.1 ppm).
b. 2',3'-O-Isopropylidene-2-phenyl-5'-O-(sulfamoyl)adenosine. 2',3'-O-Isopropylidene-2-phenyladenosine (40 mg, 0.10 mmol, 1.0 equiv) was treated with sulfamoyl chloride (24 mg, 0.21 mmol, 2.0 equiv) and NaH (6.2 mg, 0.16 mmol, 1.5 equiv) using the general procedure. Purification by flash column chromatography (9:1 EtOAc/hexanes) provided the title compound as a thick oil (35 mg, 66%): R$_f$ 0.4 (EtOAc); [α]$^{20}_D$ +40 (c 0.78, MeOH); $^1$H NMR (600 MHz, CD$_3$OD) δ 1.40 (s, 3H), 1.63 (s, 3H), 4.27 (dd, J=10.8, 4.8 Hz, 1H), 3.34 (dd, J=10.8, 4.8 Hz, 1H), 5.18 (dd, J=5.4, 2.4 Hz, 1H), 5.5 (dd, J=6.0, 1.8 Hz, 1H), 6.27 (d, J=2.4 Hz, 1H), 7.40-7.50 (m, 3H), 8.12 (s, 1H), 8.20-8.35 (m, 2H); $^{13}$C NMR (150 MHz, CD$_3$OD) δ 24.7, 26.6, 68.5, 81.3, 84.0, 84.2, 90.2, 114.4, 117.8, 127.8, 128.1, 129.8, 137.7, 139.9, 149.9, 155.4, 159.7; HRMS ESI(+) calcd for C$_{19}$H$_{23}$N$_6$O$_6$S [M+H]$^+$ 463.1394, found 463.1397 (error 0.6 ppm).

EXAMPLE 38

Preparation of 5'-O—[N-(2-Hydroxybenzoyl)sulfamoyl]-2-(phenyl)aminoadenosine triethylammonium salt 2',3'-O-Isopropylidene-5'-O-{N-[2-(methoxymethoxy)benzoyl]sulfamoyl}-2-[(phenyl)amino]adenosine (25 mg, 38.9 μmol) was converted to the title compound using the general procedure for TFA deprotection. Purification by flash chromatography (25:75:1 MeOH/EtOAc/Et$_3$N) afforded the title compound (13.7 mg, 63%): R$_f$ 0.7 (1:3 MeOH/EtOAc); [α]$^{20}_D$ +6.5 (c 0.20, MeOH); $^1$H NMR (600 MHz, CD$_3$OD) δ 1.25 (t, J=7.2 Hz, 9H), 3.14 (q, J=7.2 Hz, 6H), 4.28-4.32 (m, 1H), 4.35 (dd J=11.4, 3.6 Hz, 1H), 4.41 (dd J=4.8, 3.0 Hz, 1H), 4.43 (dd, J=11.4, 3.6 Hz, 1H), 4.78 (t, J=5.4 Hz, 1H), 6.10 (d, J=6.0 Hz, 1H), 6.74-6.84 (m, 2H), 6.92 (t, J=7.2 Hz, 1H), 7.24-7.32 (m, 3H), 7.68 (d, J=7.8 Hz, 2H), 7.94 (dd, J=7.8, 1.8 Hz, 1H), 8.18 (s, 1H); $^{13}$C NMR (150 MHz, CD$_3$OD) δ 9.3, 48.0, 68.9, 72.6, 75.6, 84.4, 89.5, 115.2, 117.9, 119.4, 120.3, 120.8, 122.5, 129.7, 131.5, 134.4, 138.9, 142.4, 152.9, 157.4, 158.5, 162.2, 175.5; HRMS (ESI–) calcd for C$_{23}$H$_{22}$N$_7$O$_8$S [M–H]$^-$ 556.1256, found 556.1252 (error 0.7 ppm).

The intermediate 2',3'-O-Isopropylidene-5'-O-{N-[2-(methoxymethoxy)-benzoyl]sulfamoyl}-2-[(phenyl)amino]adenosine was prepared as follows.
a. 2',3'-O-Isopropylidene-2-(phenyl)aminoadenosine. In an oven-dried, two necked flask equipped with a stirring bar were placed Pd$_2$(dba)$_3$.CHCl$_3$ (71.4 mg, 0.069 mmol, 0.1 equiv), K$_3$PO$_4$ (220 mg, 1.06 mmol, 1.5 equiv) and 2-(dicyclohexylphosphino)biphenyl (73.0 mg, 0.2 mmol. 0.3 equiv). Next, a solution of 2-Iodo-2',3'-O-isopropylideneadenosine (300 mg, 0.69 mmol, 1.0 equiv) in 1,2-DME (7.2 mL) was added, and the flask heated at 80-82° C. for 16 hours. The reaction was cooled to room temperature, diluted with CHCl$_3$ and filtered through a plug of Celite, and the filtrate concentrated. Purification by flash chromatography (1:19 MeOH/EtOAc) afforded the title compound (180 mg, 65%) as a thick yellow oil: R$_f$ 0.3 (1:19 MeOH/EtOAc); [α]$^{20}_D$ –27.6 (c 0.31, CH$_3$OH); HRMS (ESI+) calcd for C$_{19}$H$_{23}$N$_6$O$_4$ [M–H]$^-$ 399.1775, found 399.1762 (error 3.2 ppm).
b. 2',3'-O-Isopropylidene-2-(phenyl)amino-5'-O-(sulfamoyl)adenosine. 2',3'-O-Isopropylidene-2-(phenyl)aminoadenosine (90 mg, 0.23 mmol, 1.0 equiv) was treated with sulfamoyl chloride (53 mg, 0.45 mmol, 2.0 equiv) and NaH (18.0 mg, 0.45 mmol, 1.5 equiv) using the general procedure for sulfamoylation. Purification by flash column chromatography (1:19 MeOH/EtOAc) afforded the title compound (40 mg, 37%) as thick oil: R$_f$ 0.55 (1:19, MeOH/EtOAc); [α]$^{20}_D$ +36 (c 0.47, CH$_3$OH); HRMS (ESI+) calcd for C$_{19}$H$_{24}$N$_7$O$_6$S [M+H]$^+$ 478.1503, found 478.1497 (error 1.2 ppm).
c. 2',3'-O-Isopropylidene-5'-O-{N-[2-(methoxymethoxy)benzoyl]-sulfamoyl}-2-[(phenyl)amino]adenosine. To a solution of 2',3'-O-isopropylidene-2-(phenyl)amino-5'-O-(sulfamoyl)adenosine (40 mg, 0.08 mmol, 1.0 equiv) in DMF (3.0 mL) at 0° C. was added NHS ester (82.0 mg, 0.25 mmol, 3.0 equiv) followed by Cs$_2$CO$_3$ (71.0 mg, 0.25 mmol, 3.0 equiv) and the reaction was stirred 16 hours at room temperature. The reaction mixture was filtered to remove solids and washed with DMF (2×1.5 mL). Concentration under reduced pressure gave a pale brown mass. Purification by flash chromatography (90:10:1 EtOAc/MeOH/Et$_3$N) afforded the title compound (38 mg, 71%): R$_f$ 0.45 (3:17 MeOH/EtOAc);

$[\alpha]^{20}_D$ +11.4 (c 0.11, CH$_3$OH); HRMS (ESI+) calcd for C$_{28}$H$_{32}$N$_7$O$_9$S [M+H]$^+$ 642.1982, found 642.1981 (0.1 ppm).

EXAMPLE 39

Preparation of 5'-O—[N-(2-Hydroxybenzoyl)sulfamoyl]-2-[(phenyl)ethynyl]adenosine triethylammonium salt 2',3'-O-Isopropylidene-2-(phenyl)ethynyl-5'-O-(sulfamoyl)adenosine was converted to the title compound using the general procedure for salicylation (Cs$_2$CO$_3$ method) and TFA deprotection. Purification by flash chromatography (5:95 MeOH/EtOAc) afforded the title compound (8 mg, 63%): R$_f$ 0.35 (1:9 MeOH/EtOAc); $[\alpha]^{20}_D$ +10.9 (c 0.11, MeOH); $^1$H NMR (600 MHz, CD$_3$OD) δ 1.25 (t, J=7.2 Hz, 9H), 3:14 (q, J=7.2 Hz, 6H), 4.32-4.36 (m, 1H), 4.38-4.49 (m, 3H), 4.66 (t, J=4.8 Hz, 1H), 6.12 (d, J=5.4 Hz, 1H), 6.70-6.82 (m, 2H), 7.28 (t, J=7.2 Hz, 1H), 7.38-7.46 (m, 3H), 7.62 (d, J=8.4 Hz, 2H), 7.94 (d, J=7.2 Hz, 1H), 7.59 (br s, 1H); $^{13}$C NMR (150 MHz, CD$_3$OD) δ 9.3, 48.0, 61.6, 69.6, 72.3, 76.5, 84.7, 86.2, 89.4, 117.9, 119.3, 120.8, 123.2, 129.8, 130.7, 131.5, 133.3, 134.4, 142.0, 147.8, 151.2, 155.6, 157.2, 162.2, 175.2; HRMS (ESI−) calcd for C$_{25}$H$_{21}$N$_6$O$_8$S [M+H]$^−$ 565.1147, found 565.1140 (error 1.2 ppm).

The intermediate 2',3'-O-Isopropylidene-2-(phenyl)ethynyl-5'-O-(sulfamoyl)adenosine was prepared as follows.

a. 2',3'-O-isopropylidene-2-[(phenyl)ethynyl]adenosine. In an oven-dried, screw-cap vial equipped with a stirring bar were placed 2-iodo-2',3'-O-isopropylideneadenosine (100 mg, 0.23 mmol, 1.0 equiv), PdCl$_2$(PPh$_3$)$_2$ (16.2 mg, 23.1 μmol, 0.1 equiv), CuI (8.8 mg, 46.2 μmmol, 0.2 equiv) followed by DMF (0.4 mL) and Et$_3$N (68 μL, 0.48 mmol, 2.1 equiv). The vial was evacuated and back-flushed with nitrogen (5×) then placed in a sand bath that was maintained at 80-82° C. for 16 hours. The reaction was cooled to room temperature, diluted with CHCl$_3$, filtered through a plug of Celite, and the filtrated concentrated. Purification by flash chromatography (19:1 MeOH/EtOAc) afforded the title compound (53 mg, 57%): R$_f$ 0.3 (EtOAc); HRMS (ESI+) calcd for C$_{21}$H$_{22}$N$_5$O$_4$S [M+H]$^+$ 408.1666, found 408.1635 (error 7.5 ppm).

b. 2',3'-O-Isopropylidene-2-(phenyl)ethynyl-5'-O-(sulfamoyl)adenosine. 2',3'-O-isopropylidene-2-[(phenyl)ethynyl]adenosine (50 mg, 0.12 mmol, 1.0 equiv) was treated with sulfamoyl chloride (29.0 mg, 0.24 mmol, 2.0 equiv) and NaH (10.0 mg, 0.24 mmol, 2.0 equiv) using the general procedure for sulfamoylation. Purification by flash chromatography (1:49 MeOH/EtOAc) provided the title compound (39 mg, 66%): R$_f$ 0.5 (1:19 MeOH/EtOAc); $[\alpha]^{20}_D$ −15.0 (c 0.16, MeOH); HRMS (ESI+) calcd for C$_{21}$H$_{23}$N$_6$O$_6$S [M+H]$^+$ 487.1394, found 487.1395 (error 0.1 ppm).

EXAMPLE 40

Preparation of 7-deaza-5'-O—[N-(2-hydroxybenzoyl)sulfamoyl]-adenosine triethylammonium salt 7-Deaza-2',3'-O-isopropylidene-5'-O-(sulfamoyl)adenosine was converted to the title compound using the general procedure for salicylation and TFA deprotection. Purification by flash chromatography (9:1 EtOAC/MeOH) afforded the title compound (28 mg, 75%) as a white solid: R$_f$ 0.3 (8:2 EtOAc/MeOH); $[\alpha]^{20}_D$ −7.71 (c 1.27, MeOH); $^1$H NMR (600 MHz, CD$_3$OD) δ 1.24 (t, J=7.2 Hz, 9H), 3.09 (q, J=7.2 Hz, 6H), 4.23-4.26 (m, 1H), 4.32-4.36 (m, 3H), 4.52 (t, J=6.0 Hz, 1H), 6.23 (d, J=6.6 Hz, 1H), 6.58 (d, J=3.6 Hz, 1H), 6.76-6.82 (m, 2H), 7.29 (t, J=7.2 Hz, 1H), 7.50 (d, J=3.6 Hz, 1H), 7.93 (d, J=7.2 Hz, 1H), 8.05 (s, 1H); MS (ESI+) 465.0949, found.

The intermediate 7-Deaza-2',3'-O-isopropylidene-5'-O-(sulfamoyl)adenosine was prepared as follows.

a. 7-Deaza-2',3'-O-isopropylideneadenosine. 7-Deazaadenosine (Tubericidin) was converted to the title compound using the general procedure for acetonide protection. Purification by flash chromatography (197:3 EtOAc/MeOH) afforded the title compound (304 mg, 88%) as a colorless oil: R$_f$ 0.6 (17:3 EtOAc/MeOH); $[\alpha]^{20}_D$ −220 (c 0.230, MeOH); $^1$H NMR (600 MHz, CD$_3$OD) δ 1.33 (s, 3H), 1.58 (s, 3H), 3.68 (dd, J=12.0, 4.2 Hz, 1H), 3.76 (dd, J=12.0, 3.0 Hz, 1H), 4.25 (q, J=3.0 Hz, 1H), 4.96 (dd, J=6.0, 2.4 Hz, 1H), 5.12 (dd, J=6.0, 4.2 Hz, 1H), 6.12 (d, J=4.2 Hz, 1H), 6.57 (d, J=3.6 Hz, 1H), 7.26 (d, J=3.6 Hz, 1H), 8.06 (s, 1H); $^{13}$C NMR (150 MHz, CD$_3$OD) δ 24.4, 26.5, 62.4, 81.4, 83.9, 85.6, 91.5, 99.8, 104.0, 114.1, 123.3, 149.3, 151.0, 157.9; MS (APCI+) calcd for C$_{14}$H$_{19}$N$_4$O$_4$ [M+H]$^+$ 307.1, found 307.1.

b. 7-Deaza-2',3'-O-isopropylidene-5'-O-(sulfamoyl)adenosine. 7-Deaza-2',3'-O-isopropylideneadenosine was converted to the title compound using the general procedure for sulfamoylation. Purification by flash chromatography (199:1 EtOAc/MeOH) afforded the title compound (220 mg, 70%) as a white solid: R$_f$ 0.7 (85:15 EtOAc/MeOH); $[\alpha]^{20}_D$ −8.0 (c 1.2, MeOH); $^1$H NMR (600 MHz, CD$_3$OD) δ 1.40 (s, 3H), 1.63 (s, 3H), 4.28 (dd, J=12, 4.8 Hz, 1H), 4.32 (dd, J=10.2, 4.6 Hz, 1H), 4.46 (q, J=3.6 Hz, 1H), 5.08 (dd, J=6.0, 2.4 Hz, 1H), 5.23 (dd, J=6.0, 3.0 Hz, 1H), 6.32 (d, J=3.0 Hz, 1H), 6.66 (d, J=3.6 Hz, 1H), 7.32 (d, J=3.6 Hz, 1H), 8.13 (s, 1H); $^{13}$C NMR (150 MHz, CD$_3$OD) δ 25.7, 2.6, 70.1, 82.7, 84.3, 85.6, 91.2, 101.7, 104.9, 115.8, 123.8, 151.2, 152.7, 159.1; MS (APCI+) calcd for C$_{14}$H$_{20}$N$_5$O$_6$S [M+H]$^+$ 386.1, found 386.1

EXAMPLE 41

Preparation of 5'-O—[N-(2-Hydroxybenzoyl)sulfamoyl]-aristeromycin triethylammonium salt 5'-O—[N-(2-Hydroxybenzoyl)-sulfamoyl]aristeromycin triethylammonium salt. This was prepared from 2',3-O-isopropylidene-5'-O-(sulfamoyl)aristeromycin (90 mg, 0.23 mmol, 1.0 equiv) and N-hydroxysuccinimidyl 2-(methoxymethoxy)benzoate (196 mg, 0.70 mmol) using the general salicylation procedure A. Purification by flash chromatography (85:15:1 EtOAc/MeOH/Et$_3$N) provided the salicylated adduct as a DBU salt (40 mg, 25%), further elution afforded the salicylated adduct (120 mg, 60%) as the desired triethylammonium salt.

The triethylammonium salt (70 mg, 0.11 mmol) was treated with 80% aq TFA (1.0 mL) at room temperature for 4 hours. The reaction was thoroughly concentrated in vacuo to remove all residual TFA. Purification of the residue by flash chromatography (70:30:1 EtOAc/MeOH/Et$_3$N) afforded the title compound (40 mg, 66%): R$_f$ 0.20 (7:3 EtOAc/MeOH); $[\alpha]^{20}_D$ −49 (c 0.78, CH$_3$OH); $^1$H NMR (600 MHz, CD$_3$OD) δ 1.23 (t, J=7.2 Hz, 9H), 1.95-2.05 (m, 1H), 2.40-2.55 (m, 2H), 3.07 (q, J=7.2 Hz, 6H), 4.12 (dd, J=5.4, 3.0 Hz, 1H), 4.27 (d, J=5.0 Hz, 2H), 4.50 (dd, J=9.0, 5.4 Hz, 1H), 4.80-4.95 (m, 1H), 6.70-6.85 (m, 2H), 7.27 (t, J=7.2 Hz, 1H), 7.91 (d, J=7.8 Hz, 1H), 8.13 (s, 1H), 8.31 (s, 1H); $^{13}$C NMR (150 MHz, CDCl$_3$) δ 9.5, 30.2, 44.3, 47.7, 61.0, 71.5, 73.6, 76.8, 117.9, 119.3, 120.4, 120.7, 131.3, 134.3, 141.6, 151.2, 153.4, 157.2, 162.0, 174.8; HRMS (ESI+) calcd for C$_{18}$H$_{21}$N$_6$O$_7$S [M+H]$^+$ 465.1187, found 465.1204 (error 3.7 ppm).

The intermediate 2',3-O-isopropylidene-5'-O-(sulfamoyl) aristeromycin was prepared as follows.

a. 2',3-O-Isopropylidene-5'-O-(sulfamoyl)aristeromycin. This was prepared from 2',3'-O-isopropylidenearisteromycin (290 mg, 0.95 mmol, 1.0 equiv) using the general procedure for sulfamoylation. Purification by flash chromatography (4:1 EtOAc/MeOH) afforded the title compound as a thick oil (230 mg, 63%): $R_f$ 0.70 (3:1 EtOAc/MeOH); $[\alpha]^{20}_D$ −6.6 (c 1.8, $CH_3OH$); $^1H$ NMR (600 MHz, $CD_3OD$) δ 1.29 (s, 3H), 1.54 (s, 3H), 2.37 (q, J=12.0 Hz, 1H), 2.46-2.54 (m, 1H), 2.54-2.64 (m, 1H), 4.24 (dd, J=16.2, 6.6 Hz, 1H), 4.28 (dd, J=16.2, 6.6 Hz, 1H), 4.70 (t, J=6.0 Hz, 1H), 4.88-4.96 (m, 1H), 5.09 (t, J=6.6 Hz, 1H), 8.19 (s, 1H), 8.21 (s, 1H); $^{13}C$ NMR (150 MHz, $CDCl_3$) δ 25.4, 27.7, 34.9, 44.5, 62.6, 71.1, 82.2, 84.8, 115.3, 120.6, 141.6, 150.7, 153.6, 157.4.

b. N-Hydroxysuccinimidyl 2-(methoxymethoxy)benzoate. A solution of LiOH (660 mg, 27.5 mmol, 3.0 equiv) in MeOH (18 mL) and water (2 mL) was added to methyl 2-(methoxymethoxy)benzoate (1.81 g, 9.17 mmol, 1.0 equiv) and the reaction mixture was refluxed for 4 hours. The reaction mixture was concentrated and the residue was dissolved in $H_2O$ (20 mL) and the pH was adjusted to 3 then extracted with EtOAc (3×50 mL). The combined organic extracts were concentrated to afford 2-(methoxymethoxy)benzoic acid (1.56 g, 93%) which was directly carried onto the next step: $^1H$ NMR (600 MHz, $CDCl_3$) δ 3.54 (s, 3H), 5.34 (s, 2H), 7.15 (t, J=7.8 Hz, 1H), 7.26 (d, J=8.4 Hz, 1H), 7.51 (t, J=9.0 Hz, 1H), 8.14 (d, J=7.8 Hz, 1H); $^{13}C$ NMR (150 MHz, $CDCl_3$) δ 57.0, 95.8, 115.1, 118.4, 122.9, 133.5, 134.9, 156.2, 166.0.

To a solution of the crude product (1.56 g, 8.56 mmol, 1.0 equiv) from above in THF (80 mL) at 0° C. was added N-hydroxysuccinimide (0.988 g, 8.56 mmol, 1.0 equiv) and DCC (1.76 g, 8.56 mmol, 1.0 equiv). The resulting mixture was stirred for 30 minutes at 0° C. then 2 hours at room temperature. The reaction mixture was filtered to remove the DCU precipitate and the filtrate was concentrated under reduced pressure. Purification by flash chromatography (4:1 EtOAc/hexanes) afforded the title compound (2.02 g, 85%): $R_f$ 0.85 (EtOAc); $^1H$ NMR (600 MHz, $CDCl_3$) δ 2.86 (br s, 4H), 3.50 (s, 3H), 5.26 (s, 2H), 7.08 (t, J=7.8 Hz, 1H), 7.23 (d, J=8.4 Hz, 1H), 7.55 (t, J=8.4 Hz, 1H), 8.02 (d, J=7.8 Hz, 1H); $^{13}C$ NMR (150 MHz, $CDCl_3$) δ 25.7, 56.5, 94.8, 115.3, 121.5, 132.4, 135.7, 158.1, 160.3, 169.4.

EXAMPLE 42

Preparation of 2'-Deoxy-5'-O—[N-(2-hydroxybenzoyl)sulfamoyl]-adenosine triethylammonium salt To a solution of 3'-O-tert-butyldimethylsilyl-2'-deoxy-5'-O—[N-(2-hydroxybenzoyl)sulfamoyl]-adenosine (10.5 mg, 0.018 mmol, 1.0 equiv) in THF (2.0 mL) was added TBAF (1.0 M solution in THF, 0.1 mL, 6.0 equiv) and the solution stirred 3 hours at room temperature. The reaction mixture was concentrated and purification of the residue by flash chromatography (65:35:1 EtOAc/MeOH/$Et_3N$) afforded the title compound (5.1 mg, 50%): $R_f$ 0.15 (3:1 EtOAc/MeOH); $[\alpha]^{20}_D$ −99 (c 0.25, $CH_3OH$) $^1H$ NMR (600 MHz, $CD_3OD$) δ 1.29 (t, J=7.2 Hz, 9H), 2.44 (ddd, J=13.8, 5.4, 2.4 Hz, 1H), 2.70-2.90 (m, 1H), 3.18 (q, J=7.2 Hz, 6H), 4.24 (s, 1H), 4.32 (dd, J=11.4, 3.6 Hz, 1H), 4.35 (dd, J=10.8, 3.6 Hz, 1H), 4.62-4.70 (m, 1H), 6.50 (t, J=6.6 Hz, 1H), 6.75-6.84 (m, 2H), 7.29 (t, J=7.8 Hz, 1H), 7.93 (d, J=7.8 Hz, 1H), 8.16 (s, 1H), 8.50 (s, 1H); $^{13}C$ NMR (150 MHz, $CD_3OD$) δ 9.4, 41.6, 48.1, 70.0, 73.5, 85.9, 87.0, 118.0, 119.4, 120.3, 120.8, 131.5, 134.5, 141.3, 150.6, 153.9, 157.4, 162.2, 175.1; HRMS (ESI+) calcd for $C_{17}H_{19}N_6O_7S$ $[M+H]^+$ 451.1030, found 451.1014 (error 3.5 ppm).

The intermediate 3'-O-tert-butyldimethylsilyl-2'-deoxy-5'-O—[N-(2-hydroxybenzoyl)sulfamoyl]adenosine was prepared as follows.

a. 3',5'-O-bis(tert-Butyldimethylsilyl)-2-deoxyadenosine. To a solution of 2-deoxyadenosine (3.00 g, 11.1 mmol, 1.0 equiv) in DMF (16 mL) at 0° C. were added imidazole (4.54 g, 66.8 mmol, 6.0 equiv) and DMAP (200 mg, 1.6 mmol, 0.15 equiv). Next, a solution of TBSCl (4.20 g, 27.9 mmol, 2.5 equiv) in DMF (8.0 mL) was added dropwise at 0° C. and the reaction stirred 30 minutes. The reaction mixture was diluted with saturated aqueous $NaHCO_3$ (100 mL) and extracted with EtOAc (3×100 mL). The combined organic extracts were dried ($Na_2SO_4$), filtered and concentrated under reduced pressure. Purification by flash chromatography (6:1 EtOAc/hexanes) afforded the title compound (4.5 g, 84%) as a white solid: mp 123-125° C.; $R_f$ 0.7 (1:3 EtOAc/hexanes); $[\alpha]^{20}_D$ −2.7 (c 0.96, $CHCl_3$); $^1H$ NMR (600 MHz, $CDCl_3$) δ 0.00 (s, 6H), 0.01 (s, 6H), 0.82 (s, 18H), 2.34 (ddd, J=13.2, 6.0, 4.2 Hz, 1H), 2.50-2.58 (m, 1H), 3.68 (dd, J=10.8, 3.0 Hz, 1H), 3.78 (dd, J=11.4, 4.2 Hz, 1H), 3.92 (dd, J=6.6, 3.0 Hz, 1H), 4.52 (dd, J=9.0, 3.6 Hz, 1H), 5.70 (br s, 2H), 6.36 (t, J=6.6 Hz, 1H), 8.05 (s, 1H), 8.26 (s, 1H); $^{13}C$ NMR (150 MHz, $CDCl_3$) δ −5.5, −5.4, −4.1, −4.7, 18.0, 18.4, 25.8, 26.0, 41.3, 62.8, 71.9, 84.3, 87.9, 120.0, 139.1, 149.6, 152.8, 155.3; HRMS (ESI+) calcd for $C_{22}H_{40}N_5O_3Si_2$ $[M-H]^+$ 478.2664, found 478.2656 (error 1.7 ppm).

b. 3'-O-tert-Butyldimethylsilyl-2-deoxyadenosine. To a solution of 3',5'-O-bis(tert-butyldimethylsilyl)-2-deoxyadenosine (1.0 g, 2.08 mmol, 1.0 equiv) in THF (25 mL) was added 50% aq TFA (12 mL). After 3 h, the reaction mixture was quenched with 10 M aqueous $NH_4OH$ until the pH was basic (~10). The reaction mixture was concentrated under reduced pressure and the solid obtained was dried, dissolved in ethyl acetate and washed with saturated aqueous NaCl. The aqueous layer was extracted with EtOAc (3×50 m/L). The combined EtOAc extracts were dried ($Na_2SO_4$), filtered and concentrated. Purification by flash chromatography (EtOAc) afforded the title compound (0.45 g, 60%) as a white solid: mp 178-182° C.; $R_f$ 0.2 (EtOAc); $[\alpha]^{20}_D$ −4.8 (c 0.89, $CH_3OH$); $^1H$ NMR (600 MHz, $CDCl_3$) δ 0.14 (s, 6H), 0.94 (s, 9H), 2.37 (ddd, J=13.2, 6.0, 2.4 Hz, 1H), 2.80 (ddd, J=13.2, 7.8, 5.4 Hz, 1H), 3.70 (dd, J=12.0, 3.0 Hz, 1H), 3.81 (dd, J=12.0, 3.0 Hz, 1H), 4.03 (d, J=2.4 Hz, 1H), 4.68 (t, J=3.0 Hz, 1H), 6.42 (t, J=6.6 Hz, 1H), 8.17 (s, 1H), 8.31 (s, 1H); $^{13}C$ NMR (150 MHz, $CDCl_3$) δ −4.6 (2C), 18.7, 26.3, 42.1, 63.4, 74.4, 87.1, 90.4, 120.8, 141.6, 150.0, 153.4, 157.4; HRMS (ESI+) calcd for $C_{16}H_{28}N_5O_3Si$ $[M+H]^+$ 366.1956, found 366.1984 (error 7.7 ppm).

c. 3'-O-tert-Butyldimethylsilyl-2'-deoxy-5'-O-(sulfamoyl) adenosine. This was prepared from 3'-O-tert-butyldimethylsilyl-2-deoxyadenosine (1.81 g, 4.92 mmol, 1.0 equiv) using the general procedure for sulfamoylation. Purification by flash chromatography (19:1 EtOAc/MeOH) afforded the title compound (0.80 g, 38%) as a viscous colorless oil: $R_f$ 0.55 (9:1 EtOAc/MeOH); $[\alpha]^{20}_D$ −41.7 (c 0.690, $CH_3OH$); $^1H$ NMR (600 MHz, $CDCl_3$) δ 0.69 (s, 6H), 0.98 (s, 9H), 2.43 (ddd, J=13.2, 6.0, 3.6 Hz, 1H), 2.60-2.75 (m, 1H), 4.18 (dd, J=9.0, 3.0 Hz, 1H), 4.25 (dd, J=10.8, 4.2 Hz, 1H), 4.20 (dd, J=10.8, 3.0 Hz, 1H), 4.60-4.70 (m, 1H), 6.43 (t, J=6.6 Hz, 1H), 8.16 (s, 1H), 8.20 (s, 1H); $^{13}C$ NMR (150 MHz, $CDCl_3$) δ −5.6, −5.5, 17.4, 25.1, 40.4, 68.1, 72.0, 84.1, 84.8, 118.8, 138.8, 148.7, 152.3, 155.3.

d. 3'-O-tert-Butyldimethylsilyl-2'-deoxy-5'-O—[N-(2-hydroxybenzoyl)-sulfamoyl]adenosine. 3'-O-tert-Butyldimethylsilyl-2'-deoxy-5'-O-(sulfamoyl)adenosine (100 mg, 0.22 mmol, 1.0 equiv) was coupled to N-hydroxysuccinimidyl 2-(benzyloxy)benzoate (215 mg, 0.66 mmol, 3.0 equiv) using the general salicylation procedure. The reaction mixture was filtered then concentrated in vacuo. Purification by flash chromatography afforded the salicylated adduct as the triethylammonium salt.

The compound prepared above was treated with Pd/C (15 mg), H$_2$ (1 atm) in MeOH (15 mL) for 6 hours at room temperature. The reaction mixture was filtered, washed with MeOH and the filtrate concentrated. Purification by flash chromatography (80:20:1 EtOAc/MeOH/Et$_3$N) afforded the title compound (21 mg, 17% over two steps) as a thick oil: R$_f$ 0.5 (4:1 EtOAc/MeOH); [α]$^{20}_D$ −93 (c 0.88, CH$_3$OH); $^1$H NMR (600 MHz, CD$_3$OD) δ 0.08 (s, 3H), 0.10 (s, 3H), 0.90 (s, 9H), 2.39 (ddd, J=13.2, 6.0 Hz, 1H), 2.80-2.90 (m, 1H), 4.16-4.24 (m, 1H), 4.32 (dd, J=10.8, 3.6 Hz, 1H), 4.36 (dd, J=10.8, 3.6 Hz, 1H), 4.70-4.80 (m, 1H), 6.48 (t, J=6.6 Hz, 1H), 6.70-6.84 (m, 2H), 7.29 (t, J=8.4 Hz, 1H), 7.95 (d, J=7.8 Hz, 1H), 8.17 (s, 1H), 8.47 (s, 1H); $^{13}$C NMR (150 MHz, CD$_3$OD) δ −4.6, −4.5, 18.9, 26.4, 42.2, 69.9, 74.9, 85.9, 87.5, 118.1, 119.4, 120.3, 120.6, 131.6, 134.6, 141.3, 150.5, 153.9, 157.4, 162.3, 175.4; HRMS (ESI+) calcd for C$_{23}$H$_{33}$N$_6$O$_7$SSi [M+H]$^+$ 565.1895, found 565.1817 (error 13.8 ppm).

EXAMPLE 43

Preparation of 3'-Deoxy-5'-O—[N-(2-hydroxybenzoyl)sulfamoyl]-adenosine triethylammonium salt To a solution of 5'-O—[N-(2-benzyloxybenzoyl)sulfamoyl]-2'-O-tert-butyldimethylsilyl-3'-deoxyadenosine triethylammonium salt (70 mg, 0.092 mmol, 1.0 equiv) in MeOH (10 mL) was added 10% Pd/C (20 mg) and the reaction was stirred under H$_2$ (1 atm) for 8 hours at room temperature. The reaction mixture was filtered through a plug of Celite and the residue was washed with MeOH (4×10 mL). The combined filtrates were concentrated and the crude obtained was treated with 80% aq TFA (2.0 mL) for 8 hours. The reaction was concentrated in vacuo. Purification by flash chromatography (10:90:1 MeOH/EtOAc/Et$_3$N) afforded the title compound (27 mg, 53%) as a viscous oil: R$_f$ 0.3 (1:4 MeOH/EtOAc); [α]$^{20}_D$ −10 (c 0.28, MeOH); $^1$H NMR (600 MHz, CD$_3$OD) δ 1.26 (t, J=7.2 Hz, 9H), 2.05-2.20 (m, 1H), 2.40-2.55 (m, 1H), 3.15 (q, J=7.2 Hz, 6H), 4.32 (dd, J=11.4, 4.2 Hz, 1H), 4.46 (d, J=11.4 Hz, 1H), 4.60-4.80 (m, 2H), 6.00 (s, 1H), 6.70-6.85 (m, 2H), 7.27 (t, J=7.2 Hz, 1H), 7.91 (d, J=7.8 Hz, 1H), 8.12 (s, 1H), 8.47 (s, 1H); $^{13}$C NMR (150 MHz, CD$_3$OD) δ 9.3, 34.9, 47.9, 70.7, 76.9, 79.9, 92.9, 117.9, 119.3, 120.3, 120.7, 131.3, 134.3, 140.7, 150.2, 153.7, 157.3, 162.0, 174.9; HRMS (ESI+) calcd for C$_{17}$H$_{19}$N$_6$O$_7$S [M+H]$^+$ 451.1030, found 451.1053 (error 5.1 ppm).

The intermediate 5'-O—[N-(2-benzyloxybenzoyl)sulfamoyl]-2'-O-tert-butyldimethylsilyl-3'-deoxyadenosine triethylammonium salt was prepared as follows.

a. 2'-O-tert-Butyldimethylsilyl-3-deoxyadenosine. 3-Deoxyadenosine (100 mg, 0.37 mmol, 1.0 equiv) was treated with TBSCl (140 mg, 0.93 mmol, 2.5 equiv) to afford 2',5'-O-bis(tert-butyldimethylsilyl)-3-deoxyadenosine using the procedure described for the preparation of 3',5'-O-bis(tert-butyldimethylsilyl)-2-deoxyadenosine. The di-TBS product obtained was used directly for the next step.

To a solution of crude 2',5'-O-bis(tert-butyldimethylsilyl)-3-deoxyadenosine prepared above (170 mg, 0.37 mmol, 1.0 equiv) in MeOH/EtOAc (1:1, 10 mL) at 0° C. was added pTsOH.H$_2$O (0.35 g, 1.83 mmol, 2.8 equiv). After 5 hours the reaction was complete and the reaction mixture was quenched using an excess of solid K$_2$CO$_3$ (500 mg), and stirred for 1 h, filtered and concentrated under reduced pressure. Purification by flash chromatography (1:20 MeOH/EtOAc) afforded the title compound (106 mg, 78% over two steps) as a white solid: mp 154-156° C.; R$_f$ 0.2 (EtOAc); [α]$^{20}_D$ −49.4 (c 0.890, CH$_3$OH); $^1$H NMR (600 MHz, CDCl$_3$) δ 0.00 (s, 3H), 0.14 (s, 3H), 1.06 (s, 9H), 2.44-2.56 (m, 1H), 2.83 (ddd, J=10.8, 7.2, 2.4 Hz, 1H), 3.82 (d, J=12.6 Hz, 1H), 4.26 (d, J=12.6 Hz, 1H), 4.77 (d, J=9.0 Hz, 1H), 5.33 (q, J=7.2 Hz, 1H), 5.87 (d, J=6.0 Hz, 1H), 6.11 (br s, 2H, NH$_2$), 6.49 (br s, 1H, OH), 8.10 (s, 1H), 8.62 (s, 1H); $^{13}$C NMR (150 MHz, CDCl$_3$) δ −5.4, −5.2, 17.8, 25.5, 34.8, 69.4, 73.9, 80.4, 93.6, 121.1, 140.5, 148.6, 152.5, 155.9; HRMS (ESI+) calcd for C$_{16}$H$_{28}$N$_5$O$_3$Si [M+H]$^+$ 366.1956, found 366.1976 (error 5.5 ppm).

b. 2'-O-tert-Butyldimethylsilyl-3'-deoxy-5'-O-(sulfamoyl)adenosine. This was prepared from 2'-O-tert-butyldimethylsilyl-3-deoxyadenosine (90 mg, 0.246 mmol, 1.0 equiv) using the general procedure for sulfamoylation. Purification by flash chromatography (30:1 EtOAc/MeOH) afforded the title compound (90 mg, 82%): mp 238-240° C. melted with charring; R$_f$ 0.40 (97:3 EtOAc/MeOH); [α]$^{20}_D$+13.7 (c 0.980, CH$_3$OH); $^1$H NMR (600 MHz, CD$_3$OD) δ 0.03 (s, 3H), 0.06 (s, 3H), 0.87 (s, 9H), 2.11 (ddd, J=13.2, 6.0, 3.0 Hz, 1H), 2.35 (ddd, J=13.2, 8.4, 6.0 Hz, 1H), 4.29 (dd, J=10.8, 3.6 Hz, 1H), 4.43 (dd, J=10.8, 2.4 Hz, 1H), 4.65-4.75 (m, 1H), 4.75-4.85 (m, 1H), 5.98 (d, J=2.4 Hz, 1H), 8.19 (s, 1H), 8.30 (s, 1H); $^{13}$C NMR (150 MHz, CD$_3$OD) δ −4.9, −4.8, 18.8, 26.1, 35.8, 70.9, 77.7, 79.2, 92.8, 120.3, 140.4, 150.5, 152.9, 157.3; MS (ESI+) calcd for C$_{16}$H$_{26}$N$_5$O$_2$Si [M—SO$_2$NH$_2$]$^+$ 348.2, found 348.1.

c. 5'-O—[N-(2-Benzyloxybenzoyl)sulfamoyl]-2'-O-tert-butyldimethylsilyl-3'-deoxyadenosine triethylammonium salt. This was prepared from 2'-O-tert-butyldimethylsilyl-3'-deoxy-5'-O-(sulfamoyl)adenosine (70 mg, 0.157 mmol, 1.0 equiv) and N-hydroxysuccinimidyl 2-(benzyloxy)benzoate (154 mg, 0.47 mmol. 3.0 equiv) using the general salicylation procedure A. Purification by flash chromatography (90:10:1 EtOAc/MeOH/Et$_3$N) afforded the title compound (90 mg, 87%) as a thick oil: R$_f$ 0.55 (1:9 MeOH/EtOAc); [α]$^{20}_D$+19 (c 0.70, CH$_3$OH); $^1$H NMR (600 MHz, CD$_3$OD) δ 0.01 (s, 3H), 0.05 (s, 3H), 0.86 (s, 9H), 1.20 (t, J=7.2 Hz, 9H), 1.85-1.95 (m, 1H), 2.20-2.40 (m, 1H), 3.07 (q, J=7.2 Hz, 6H), 4.15 (d, J=11.4 Hz, 1H), 4.30 (d, J=10.8 Hz, 1H), 4.40-4.50 (m, 1H), 4.73 (d, J=2.4 Hz, 1H), 5.10 (s, 2H), 5.93 (s, 1H), 6.93 (t, J=7.2 Hz, 1H), 7.06 (d, J=9.0 Hz, 1H), 7.20-7.40 (m, 4H), 7.35 (d, J=7.8 Hz, 1H), 7.48 (d, J=7.8 Hz, 2H), 8.18 (s, 1H), 8.47 (s, 1H); $^{13}$C NMR (150 MHz, CD$_3$OD) δ −4.8, −4.7, 9.2, 18.8, 26.1, 35.7, 47.7, 70.6, 71.6, 78.1, 79.6, 92.5, 114.3, 120.2, 121.5, 128.8, 128.9, 129.4, 129.7, 131.2, 131.9, 138.7, 140.8, 150.5, 153.8, 157.1, 157.2, 176.7; HRMS (ESI+) calcd for C$_{30}$H$_{39}$N$_6$O$_7$SSi [M+H]$^+$ 655.2365, found 655.2389 (error 3.7 ppm).

EXAMPLE 44

Preparation of (1'R, 4'S)-9-{4-[([N-(2-Hydroxybenzoyl)-sulfamoyl]oxy)methyl]cyclopent-2-en-1-yl}adenine triethylammonium salt (1'R, 4'S)-9{[4-[({N-[2-(Methoxymethoxy)benzoyl]sulfamoyl}oxy)-methyl]cyclopent-2-en-1-yl}adenine triethylammonium salt (50 mg, 0.086 mmol, 1.0 equiv) was stirred in 80% aq TFA (2.0 mL) for 3 hours then concentrated in vacuo. Purification by flash chromatography (25:75:1 MeOH/EtOAc/Et$_3$N) afforded the title compound (36 mg, 80%) as a viscous oil: R$_f$ 0.4 (4:1 EtOAc/MeOH); [α]$^{20}_D$+22 (c 0.21, CH$_3$OH); $^1$H NMR (600 MHz, CD$_3$OD) δ 1.28 (t, J=7.2 Hz, 9H), 1.80-1.95 (m, 1H), 2.80-2.95 (m, 1H), 3.18 (q, J=7.2 Hz, 6H), 3.23 (br s, 1H), 4.15-4.30 (m, 2H), 5.69 (t, J=6.0 Hz, 1H), 5.90-6.00 (m, 1H), 6.21 (d, J=5.4 Hz, 1H), 6.70-6.80 (m, 2H), 7.26 (t, J=7.8 Hz, 1H), 7.84 (d, J=7.8 Hz, 1H), 8.17 (s, 1H), 8.18 (s, 1H); $^{13}$C NMR (150 MHz, CD$_3$OD) δ 8.0, 34.3, 46.7, 59.9, 71.2, 116.7, 118.1, 119.0, 119.5, 129.9, 130.0, 133.1, 137.6, 139.9, 149.1, 151.8, 155.7, 160.7, 161.9, 173.3; HRMS (ESI+) calcd for C$_{18}$H$_{19}$N$_6$O$_5$S [M+H]$^+$ 431.1132, found 431.1102 (error 7.0 ppm).

The intermediate (1'R, 4'S)-9{[4-[({N-[2-(Methoxymethoxy)benzoyl]-sulfamoyl}oxy)-methyl]cyclopent-2-en-1-yl} adenine triethylammonium salt was prepared as follows.

a. (1'R, 4'S)-9-[4-(Hydroxymethyl)cyclopent-2-en-1-yl]adenine. To a solution of aristeromycin (0.7 g, 2.63 mmol, 1.0 equiv) and trimethyl orthoformate (7.0 mL, 64 mmol, 24.3 equiv) in DMF (2.1 mL) was added pTsOH.H$_2$O (720 mg, 3.81 mmol, 1.45 equiv). After 36 hours at room temperature, anhydrous K$_2$CO$_3$ (1.05 g, 7.27 mmol) was added and the mixture stirred for 2 hours. The reaction mixture was filtered and the solids were washed with a minimum amount of trimethyl orthoformate (2.0 mL). The combined filtrates and washings were concentrated under reduced pressure to provide a gummy residue, which was azeotropically dried with toluene (20 mL) on a rotary evaporator.

The crude product from above was refluxed 16 hours in Ac$_2$O (10 mL). The reaction was cooled to room temperature, filtered through a plug of silica gel, and concentrated under reduced pressure to afford a dark yellow solid, which was treated with 6 N aq HCl (6 mL) at room temperature for 12 hours. The reaction was concentrated in vacuo. Purification by flash chromatography (3:7 MeOH/EtOAc) afforded the title compound (150 mg, 48%): R$_f$ 0.3 (3:7 MeOH/EtOAc); [c]$^{20}_D$ −6.2 (c 0.59, MeOH); $^1$H NMR (600 MHz, CD$_3$OD) δ 1.73 (dt, J=13.8, 6.0 Hz, 1H), 2.82 (ddd, J=13.8, 8.4, 5.4 Hz, 1H), 3.02 (br s, 1H), 3.58 (dd, J=10.4, 4.8 Hz, 1H), 3.65 (dd, J=10.4, 5.4 Hz, 1H), 5.68 (t, J=6.0 Hz, 1H), 5.95 (d, J=6.0, 1H), 6.21 (d, J=6.0 Hz, 1H), 8.12 (s, 1H), 8.19 (s, 1H); $^{13}$C NMR (150 MHz, CD$_3$OD) δ 35.6, 49.2, 61.3, 65.4, 120.3, 130.5, 140.1, 140.9, 150.3, 153.5, 157.3; HRMS (ESI+) calcd for C$_{11}$H$_{14}$N$_5$O [M+H]$^+$ 232.1193, found 232.1197 (1.7 ppm).

b. (1'R, 4'S)-9-(4-{[(Sulfamoyl)oxy]methyl}cyclopent-2-en-1-yl)adenine. This was prepared from (1'R, 4'S)-9-[4-(Hydroxymethyl)cyclopent-2-en-1-yl]adenine (150 mg, 0.648 mmol, 1.0 equiv) using the general procedure for sulfamoylation. Purification by flash chromatography (30:1 EtOAc/MeOH) afforded the title compound (110 mg, 55%) as an oil: R$_f$ 0.50 (7:3 EtOAc/MeOH); [α]$^{20}_D$ +70.8 (c 0.290, CH$_3$OH); $^1$H NMR (600 MHz, CD$_3$OD) δ 1.77 (dt, J=14.4, 6.0 Hz, 1H), 2.91 (ddd, J=13.8, 9.0, 5.4 Hz, 1H), 3.27 (br s, 1H), 4.16 (dd, J=9.6, 4.8 Hz, 1H), 4.22 (dd, J=9.6, 4.8 Hz, 1H), 5.73 (t, J=6.0 Hz, 1H), 6.01 (d, J=6.0 Hz, 1H), 6.21 (d, J=5.4 Hz, 1H), 8.09 (s, 1H), 8.20 (s, 1H); $^{13}$C N (150 MHz, CDCl$_3$) δ 35.5, 46.1, 61.0, 72.3, 120.2, 131.5, 138.3, 140.8, 150.4, 153.6, 157.3; MS (ESI+) calcd for C$_{11}$H$_{12}$N$_5$ [M-SO$_2$NH$_2$]$^+$ 214.1, found 214.1.

c. (1'R, 4'S)-9{[4-[({N-[2-(Methoxymethoxy)benzoyl]sulfamoyl}-oxy)methyl]cyclopent-2-en-1-yl}adenine triethylammonium salt. This was prepared from (1'R, 4'S)-9-(4-{[(Sulfamoyl)oxy]methyl}cyclopent-2-en-1-yl)adenine (100 mg, 0.32 mmol) and N-hydroxysuccinimidyl 2-(methoxymethoxy)benzoate (270 mg, 0.96 mmol, 3.0 equiv) using the general salicylation procedure A. Purification by flash chromatography (80:20:1 EtOAc/MeOH/Et$_3$N) afforded the title compound (150 mg, 81%) as a viscous oil: R$_f$ 0.65 (7:3 EtOAc/MeOH); [α]$^{20}_D$ +42.8 (c 0.980, CH$_3$OH); $^1$H NMR (600 MHz, CD$_3$OD) δ 1.25 (t, J=7.2 Hz, 9H), 1.85-1.95 (m, 1H), 2.85-2.95 (m, 1H), 3.14 (q, J=7.2 Hz, 6H), 3.27 (br s, 1H), 3.43 (s, 3H), 4.20-4.32 (m, 2H), 5.25 (s, 2H), 5.73 (t, J=6.0 Hz, 1H), 5.97 (d, J=5.4 Hz, 1H), 6.24 (d, J=6.0 Hz, 1H), 6.95 (t, J=7.2 Hz, 1H), 7.10 (d, J=8.4 Hz, 1H), 7.25 (t, J=8.4 Hz, 1H), 7.38 (d, J=7.2 Hz, 1H), 8.19 (s, 1H), 8.23 (s, 1H); $^{13}$C NMR (150 MHz, CD$_3$OD) δ 8.0, 34.5, 45.2, 55.5, 59.9, 71.1, 95.3, 115.9, 119.0, 121.3, 121.4, 128.6, 129.9, 130.0, 131.3, 137.6, 139.9, 149.2, 152.4, 154.5, 156.1, 175.2; HRMS (ESI+) calcd for C$_{20}$H$_{23}$N$_6$O$_6$S [M+H]$^+$ 475.1394, found 475.1391 (error 0.6 ppm).

EXAMPLE 45

Preparation of (1'R, 3'S)-9-[3-({[N-(2-Hydroxybenzoyl)sulfamoyl]-oxy}methyl)cyclopent-1-yl]adenine triethylammonium salt To (1'R, 4'S)-9-{4-[([N-(2-Hydroxybenzoyl)sulfamoyl]oxy)methyl]cyclopent-2-en-1-yl}adenine triethylammonium salt (25 mg, 0.047 mmol, 1.0 equiv) in MeOH (5 mL) was added 10% Pd/C (20 mg) and the reaction stirred for 6 hours under H$_2$ (1 atm) at room temperature. The reaction mixture was filtered thru a plug of Celite and the solids washed with MeOH (4×10 mL). The filtrate was concentrated under reduced pressure. Purification by flash chromatography (30:70:1 MeOH/EtOAc/Et$_3$N) afforded the title compound (9.0 mg, 36%) as a viscous oil: R$_f$ 0.4 (4:1 EtOAc/MeOH); [α]$^{20}_D$ +1.0 (c 0.44, CH$_3$OH); $^1$H NMR (600 MHz, CD$_3$OD) δ 1.28 (t, J=7.2 Hz, 9H), 1.82-1.92 (m, 1H), 1.94-2.04 (m, 2H), 2.06-2.16 (m, 1H), 2.22-2.32 (m, 1H), 2.44-2.50 (m, 1H), 2.50-2.60 (m, 1H), 3.18 (q, J=7.2 Hz, 6H), 4.17 (dd, J=10.2, 6.6 Hz, 1H), 4.21 (dd, J=10.2, 6.6 Hz, 1H), 4.86-4.96 (m, 1H), 6.72-6.82 (m, 2H), 7.27 (t, J=7.8 Hz, 1H), 7.91 (d, J=7.8 Hz, 1H), 8.16 (s, 1H), 8.27 (s, 1H); $^{13}$C NMR (150 MHz, CD$_3$OD) δ 9.2, 27.6, 32.7, 36.4, 38.5, 47.9, 57.1, 73.6, 117.9, 119.2, 120.3, 120.8, 131.3, 134.3, 140.9, 150.7, 153.4, 157.2, 161.9, 174.6; HRMS (ESI+) calcd for C$_{18}$H$_{21}$N$_6$O$_5$S [M+H]$^+$ 433.1289, found 433.1327 (error 8.8 ppm).

EXAMPLE 46

Preparation of 9-[({[N-(2-Hydroxybenzoyl)sulfamoyl]oxy}ethoxy)-methyl]adenine triethylammonium salt This was prepared from 9-[{(hydroxy)ethoxy]methyl}adenine (100 mg, 0.346 mmol, 1.0 equiv) and N-hydroxysuccinimidyl 2-(benzyloxy)benzoate (338 mg, 1.04 mmol, 3.0 equiv) using the general salicylation procedure A. Purification by flash chromatography (85:15:1 EtOAc/MeOH/Et3N) afforded 9-{[({N-[2-(benzyloxy)benzoyl]sulfamoyl}-oxy)ethoxy]methyl}adenine (80 mg, 44%). 9-{[({N-[2-(Benzyloxy)-benzoyl]sulfamoyl}oxy)ethoxy]methyl}adenine prepared above was dissolved in MeOH (15.0 mL) and stirred under H$_2$ (1 atm) in presence of 10% Pd/C (20 mg) at room temperature. After 4 hours the reaction mixture was filtered through a plug of Celite. Purification by flash chromatography afforded the title compound as a white solid (65 mg, 98%): mp 93-95° C.; R$_f$ 0.35 (3:1 EtOAc/MeOH); $^1$H NMR (600 MHz, CD$_3$OD) δ 1.28 (t, J=7.2 Hz, 9H), 3.17 (q, J=7.2 Hz, 6H), 3.82 (t, J=4.2 Hz, 2H), 4.25 (t, J=4.2 Hz, 2H), 5.67 (s, 2H), 6.72-6.84 (m, 2H), 7.22 (t, J=7.8 Hz, 1H), 7.89 (d, J=7.2 Hz, 1H), 8.19 (s, 1H), 8.24 (s, 1H); $^{13}$C NMR (150 MHz, CD$_3$OD) δ 8.0, 46.7, 67.5, 68.3, 72.9, 116.6, 118.0, 118.8, 119.5, 130.1, 133.1, 141.9, 149.7, 152.9, 156.2, 160.8, 173.6; HRMS (ESI+) calcd for C$_{15}$H$_{17}$N$_6$O$_6$S [M+H]+ 409.0925, found 409.0904 (error 5.1 ppm).

EXAMPLE 47

The following illustrate representative pharmaceutical dosage forms, containing a compound of formula I ('Compound X'), for therapeutic or prophylactic use in humans.

| (i) Tablet 1 | mg/tablet |
|---|---|
| Compound X | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s |
| Water for injection | q.s. ad 1 mL |

| (v) Injection 2 (10 mg/ml) | mg/ml |
|---|---|
| Compound X (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

$R_1$-L-$R_2$—B    (I)

wherein:

$R_1$ is a ring selected from phenyl, furyl, thienyl, pyridyl, pyrrolyl, cyclohexyl, cyclopentyl, pyranyl, 1,2-dihydro-2-oxo-1H-pyrid-3-yl, and 2-oxopyranyl; which ring is optionally substituted with one or more $R_a$; or $R_1$-L- together are a group of the following formula:

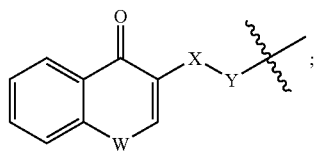

L is selected from —C(═O)—NH—S(═O)$_2$—O—, —C(═O)—NH—S(═O)$_2$—NH—, —C(═O)—C(R$_b$)$_2$—S(═O)$_2$—NH—, —C(R$_b$)$_2$—NH—S(═O)$_2$—O—, —C(═O)—C(R$_b$)$_2$—P(═O)(OH)O—, —C(═O)—C(R$_b$)$_2$—C(═O)—NH—, —CH═CH—S(═O)$_2$—NH—, —C(═O)—C(═N$_2$)—S(═O)$_2$—NH—, —S(═O)$_2$—C(R$_b$)$_2$—S(═O)$_2$—NH—, —S(═O)(═NH)—C(R$_b$)$_2$—S(═O)$_2$—NH—, —C(═O)—C(═O)—C(R$_b$)$_2$—NH—, —C(═O)—C(═O)—C(═O)—NH—, —C(═O)—C(R$_b$)$_2$—S(═O)$_2$—NH—, —CH(OH)—C(R$_b$)$_2$—P(═O)(OH)O—, —C(═O)—NH—C(═O)—NH—, —CH═CH—P(═O)(OH)O—, —CH═CH—C(═O)—NH—, —C(═O)—NH—, —C(═O)—NH—S(═O)$_2$—CH$_2$—, —S(═O)$_2$—NH—C(═O)—NH—, —C(═O)—NH—NH—C(═O)—CH$_2$—, —C(═O)—NH—O—C(═O)—CH$_2$—, —S(═O)$_2$—NH—S(═O)$_2$—NH—, —C(═O)—CH═CH—C(═O)—NH—,

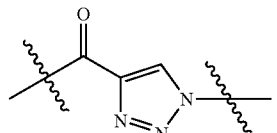

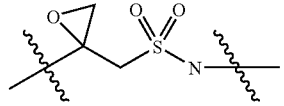

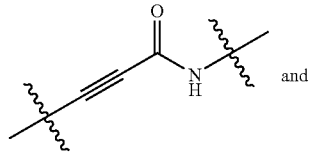

and

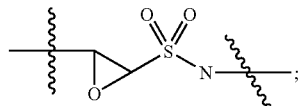

$R_2$ has the following formula:

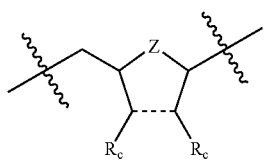

wherein the bond represented by ------ is a single bond and each $R_c$ is independently hydrogen, hydroxy, fluoro, azido, $(C_1-C_{12})$alkoxy, $(C_1-C_{12})$alkanoyloxy, or amino; or the bond represented by ------ is a double bond and each $R_c$ is absent;
B is:

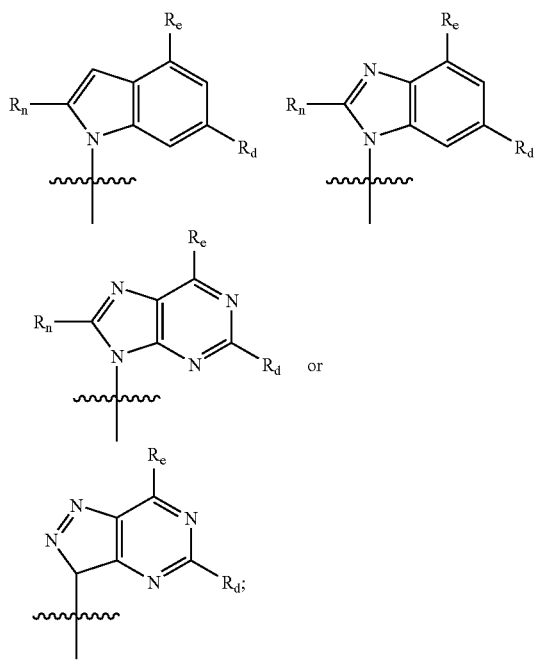

W is O or NH;
X is —C(=O)— or —S(=O)$_2$—;
Y is —NH— or —O—;
Z is O, —NH—, —CH$_2$—CH$_2$—, or CH$_2$;
each $R_a$ is independently hydroxy, amino, halo, $(C_1-C_6)$alkanoyloxy, nitro, $(C_1-C_6)$alkyl, $(C_2-C_6)$alkenyl, $(C_2-C_6)$alkynyl, or $(C_1-C_6)$alkanoylthio;
each $R_b$ is independently hydrogen, fluoro, or chloro;
each $R_d$ is independently azido, hydrogen, halo, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkylthio, $(C_2-C_6)$alkenyloxy, $(C_1-C_6)$alkenylthio, $(C_2-C_6)$alkynyloxy, $(C_1-C_6)$alkynylthio, aryl, aryl$(C_1-C_6)$alkyl, aryl$(C_2-C_6)$alkenyl, aryl$(C_2-C_6)$alkynyl, carboxy$(C_1-C_6)$alkyl, carboxy$(C_1-C_6)$alkenyl, or $NR_fR_g$; wherein each $R_f$ and $R_g$ is independently hydrogen, aryl, aryloxy, or $(C_1-C_6)$alkyl;
each $R_e$ is independently hydrogen, hydroxy, $(C_1-C_6)$alkylthio, or $NR_kR_m$; wherein each $R_k$ and $R_m$ is independently hydrogen, $(C_3-C_6)$cycloalkyl aryl, or $(C_1-C_6)$alkyl; and
each $R_n$ is independently hydrogen, halo, azido, or amino; or a salt thereof;
excluding the compound 5'-O—(N-(2-Hydroxybenzoyl)sulfamoyl)-adenosine.

2. The compound of claim 1 which is a compound of formula I:

$$R_1\text{-L-}R_2\text{—B} \quad (I)$$

wherein:
$R_1$ is a ring selected from phenyl, furyl, thienyl, pyridyl, pyrrolyl, cyclohexyl, cyclopentyl, pyranyl, 1,2-dihydro-2-oxo-1H-pyrid-3-yl, and 2-oxopyranyl; which ring is optionally substituted with one or more $R_a$; or $R_1$-L-together are a group of the following formula:

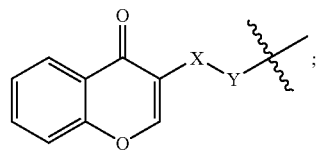

L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, —C(=O)—C(R$_b$)$_2$—C(=O)—NH—, —CH=CH—S(=O)$_2$—NH—, —C(=O)—C(=N$_2$)—S(=O)$_2$—NH—, —S(=O)$_2$—C(R$_b$)$_2$—S(=O)$_2$—NH—, —S(=O)(=NH)—C(R$_b$)$_2$—S(=O)$_2$—NH—, —C(=O)—C(=O)—C(R$_b$)$_2$—NH—, —C(=O)—C(=O)—C(=O)—NH—, —C(=O)—C(R$_b$)$_2$—S(=O)$_2$—NH—, —CH(OH)—C(R$_b$)$_2$—P(=O)(OH)O—, —C(=O)—NH—C(=O)—NH—, —CH=CH—P(=O)(OH)O—, —CH=CH—C(=O)—NH—, —C(=O)—NH—,

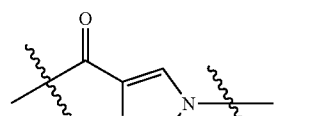

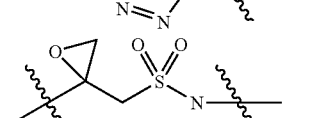

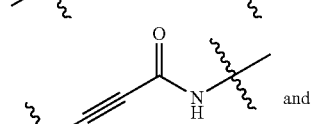

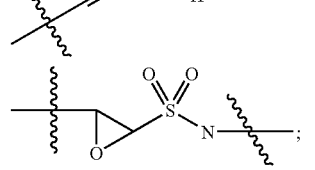

$R_2$ has the following formula:

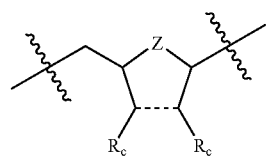

wherein the bond represented by ------ is a single bond and each $R_c$ is independently hydrogen, hydroxy, fluoro, azido, $(C_1$-$C_{12})$alkanoyloxy, or amino; or the bond represented by ------ is a double bond and each $R_c$ is absent;

B is:

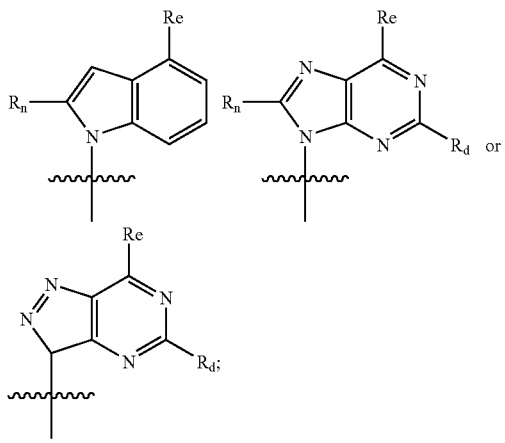

X is —C(=O)— or —S(=O)$_2$—;
Y is —NH— or —O—;
Z is O, or CH$_2$;
each $R_a$ is independently hydroxy, amino, halo, $(C_1$-$C_6)$ alkanoyloxy nitro, or $(C_1$-$C_6)$alkanoylthio;
each $R_b$ is independently hydrogen, fluoro, or chloro;
each $R_d$ is independently hydrogen, halo, $(C_1$-$C_6)$alkyl, $(C_2$-$C_6)$alkenyl, $(C_2$-$C_6)$alkynyl, $(C_1$-$C_6)$alkoxy, $(C_1$-$C_6)$alkylthio, $(C_2$-$C_6)$alkenyloxy, $(C_1$-$C_6)$alkenylthio, $(C_2$-$C_6)$alkynyloxy, $(C_1$-$C_6)$alkynylthio, phenyl, phenyl$(C_1$-$C_6)$alkyl, phenyl$(C_2$-$C_6)$alkenyl, phenyl$(C_2$-$C_6)$alkynyl, or $NR_fR_g$; wherein each $R_f$ and $R_g$ is independently hydrogen, phenyl, or $(C_1$-$C_6)$alkyl;
each $R_e$ is independently hydroxy or $NR_kR_m$; wherein each $R_k$ and $R_m$ is independently hydrogen, $(C_3$-$C_6)$cycloalkyl or $(C_1$-$C_6)$alkyl;
each $R_n$ is independently hydrogen, halo, azido, or amino;
or a salt thereof;
excluding the compound 5'-O—(N-(2-Hydroxybenzoyl) sulfamoyl)-adenosine.

3. The compound of claim 1 which is a compound of formula I:

$$R_1\text{-L-}R_2\text{—B} \quad (I)$$

wherein:
$R_1$ is a ring selected from phenyl, furyl, thienyl, pyridyl, pyrrolyl, cyclohexyl, cyclopentyl, pyranyl, and 2-oxopyranyl; which ring is optionally substituted with one or more $R_a$; or $R_1$-L- together are a group of the following formula:

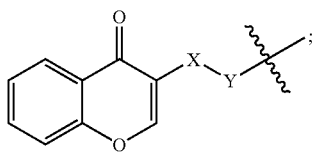

L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, —C(=O)—C(R$_b$)$_2$—C(=O)—NH—, —CH=CH—S(=O)$_2$—NH—, —C(=O)—C(=N$_2$)—S(=O)$_2$—NH—, —S(=O)$_2$—C(R$_b$)$_2$—S(=O)$_2$—NH—, —S(=O)(=NH)—C(R$_b$)$_2$—S(=O)$_2$—NH—, —C(=O)—C(=O)—C(R$_b$)$_2$—NH—, —C(=O)—C(=O)—C(=O)—NH—, —C(=O)—C(R$_b$)$_2$—S(=O)$_2$—NH—,

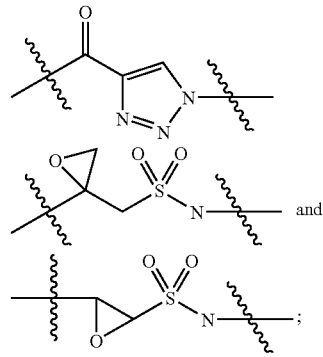

and

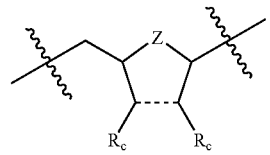

$R_2$ has the following formula:

wherein the bond represented by ------ is a single bond and each $R_c$ is independently hydrogen, hydroxy, fluoro, azido, $(C_1$-$C_{12})$alkanoyloxy, or amino; or the bond represented by ------ is a double bond and each $R_c$ is absent;

B is:

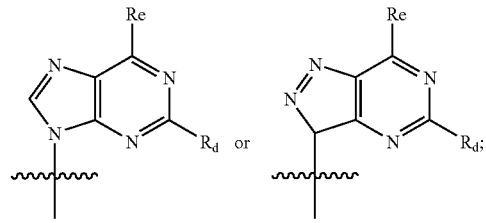

X is —C(=O)— or —S(=O)$_2$—;
Y is —NH— or —O—;
Z is O, or CH$_2$;
each $R_a$ is independently hydroxy, amino, halo, $(C_1$-$C_6)$ alkanoyloxy or $(C_1$-$C_6)$alkanoylthio;
each $R_b$ is independently hydrogen, fluoro, or chloro;
each $R_d$ is independently hydrogen, halo, $(C_1$-$C_6)$alkyl, $(C_2$-$C_6)$alkenyl, $(C_2$-$C_6)$alkynyl, $(C_1$-$C_6)$alkoxy, $(C_1$-$C_6)$alkylthio, $(C_2$-$C_6)$alkenyloxy, $(C_1$-$C_6)$alkenylthio, $(C_2$-$C_6)$alkynyloxy, $(C_1$-$C_6)$alkynylthio, or $NR_fR_g$; wherein each $R_f$ and $R_g$ is independently hydrogen or $(C_1$-$C_6)$alkyl; and
each $R_e$ is independently hydroxy or amino;
or a pharmaceutically acceptable salt thereof;

excluding the compound 5'-O—(N-(2-Hydroxybenzoyl)sulfamoyl)adenosine.

4. The compound of claim 1 wherein $R_1$ is a ring selected from phenyl, furyl, thienyl, pyridyl, and pyrrolyl, which ring is optionally substituted with one or more $R_a$.

5. The compound of claim 1 wherein $R_1$ is a ring of the following formula:

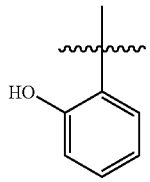

wherein the ring is optionally substituted with one or more $R_a$.

6. The compound of claim 1 wherein $R_1$ is 2-hydroxyphenyl, 2-aminophenyl, phenyl, 2,3-dihydroxyphenyl, 4 amino-2-hydroxyphenyl, 2-fluorophenyl, 2-chlorophenyl, 2-hydroxy-3-pyridyl, 2-hydroxy-4-pyridyl, 4-hydroxy-3-pyridyl, 3-hydroxy-2-pyridyl, 2-oxo-3-pyranyl, 2-acetoxyphenyl, 2-propanoyloxyphenyl, 2-acetylthiophenyl, 2-propanoylthiophenyl, cyclopentyl, cyclohexyl, 2-hydroxycyclopentyl, 2-hydroxycyclohexyl, or 2,6-dihydroxyphenyl.

7. The compound of claim 1 wherein L is selected from —C(=O)—NH—S(=O)$_2$—O—, —C(=O)—NH—S(=O)$_2$—NH—, —C(=O)—C(R$_b$)$_2$—S(=O)$_2$—NH—, —C(R$_b$)$_2$—NH—S(=O)$_2$—O—, —C(=O)—C(R$_b$)$_2$—P(=O)(OH)O—, and —C(=O)—C(R$_b$)$_2$—C(=O)—NH—, and

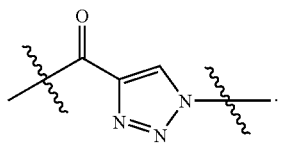

8. The compound of claim 1 wherein L is selected from —CH=CH—S(=O)$_2$—NH—, —C(=O)—C(R$_b$)$_2$—S(=O)$_2$—NH—, —C(=O)—C(=N$_2$)—S(=O)$_2$—NH—,

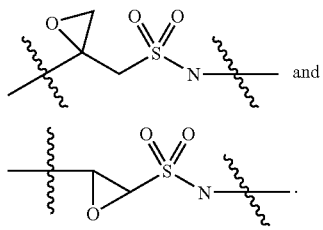
and

9. The compound of claim 1 wherein L is —C(=O)—NH—S(=O)$_2$—NH—.

10. The compound of claim 1 wherein $R_1$-L- together are a group of the following formula:

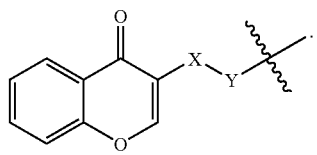

11. The compound of claim 1 wherein $R_2$ is selected from

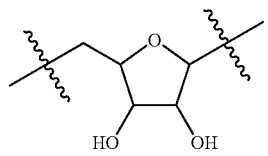
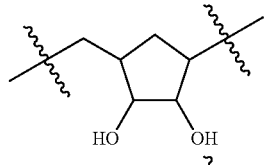
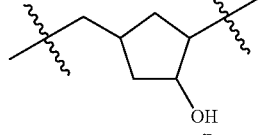
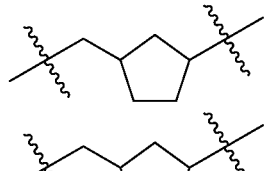
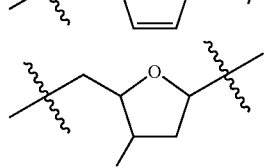
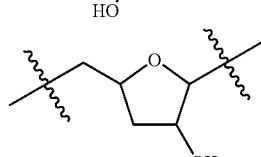
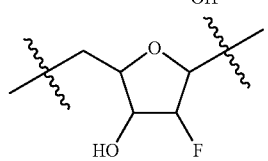
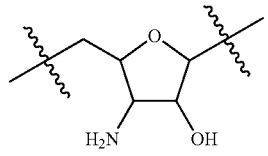
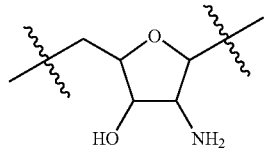

-continued

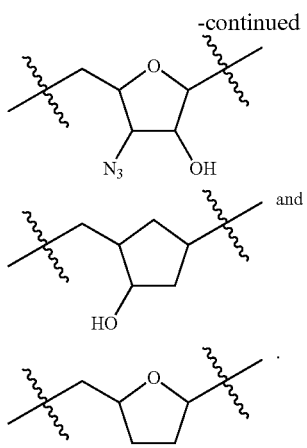

12. The compound of claim 1 wherein B is:

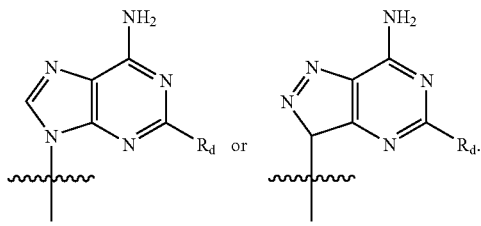

13. A salt of a compound of formula I:

R₁-L-R₂—B    (I)

wherein:
R₁ is a ring selected from phenyl, furyl, thienyl, pyridyl, pyrrolyl, cyclohexyl, cyclopentyl, pyranyl, 1,2-dihydro-2-oxo-1H-pyrid-3-yl, and 2-oxopyranyl; which ring is optionally substituted with one or more $R_a$; or R₁-L- together are a group of the following formula:

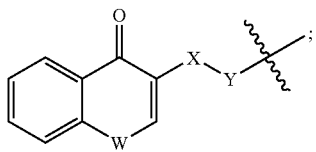

L is selected from —C(=O)—NH—S(=O)₂—O—, —C(=O)—NH—S(=O)₂—NH—, —C(=O)—C($R_b$)₂—S(=O)₂—NH—, —C($R_b$)₂—NH—S(=O)₂—O—, —C(=O)—C($R_b$)₂—P(=O)(OH)O—, —C(=O)—C($R_b$)₂—C(=O)—NH—, —CH=CH—S(=O)₂—NH—, —C(=O)—C(=N₂)—S(=O)₂—NH—, —S(=O)₂—C($R_b$)₂—S(=O)₂—NH—, —S(=O)(=NH)—C($R_b$)₂—S(=O)₂—NH—, —C(=O)—C(=O)—C($R_b$)₂—NH—, —C(=O)—C(=O)—C(=O)—NH—, —C(=O)—C($R_b$)₂—S(=O)₂—NH—, —CH(OH)—C($R_b$)₂—P(=O)(OH)O—, —C(=O)—NH—C(=O)—NH—, —CH=CH—P(=O)(OH)O—, —CH=CH—C(=O)—NH—, —C(=O)—NH—, —C(=O)—NH—S(=O)₂—CH₂—, —S(=O)₂—NH—C(=O)—NH—, —C(=O)—NH—NH—C(=O)—CH₂—, —C(=O)—NH—O—C(=O)—CH₂—, —S(=O)₂—NH—S(=O)₂—NH—, —C(=O)—CH=CH—C(=O)—NH—,

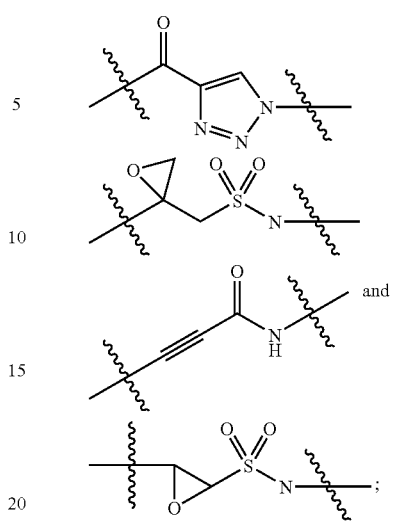

R₂ has the following formula:

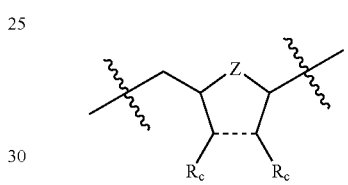

wherein the bond represented by ------ is a single bond and each $R_c$ is independently hydrogen, hydroxy, fluoro, azido, (C₁-C₁₂)alkoxy, (C₁-C₁₂)alkanoyloxy, or amino; or the bond represented by ------ is a double bond and each $R_c$ is absent;
B is:

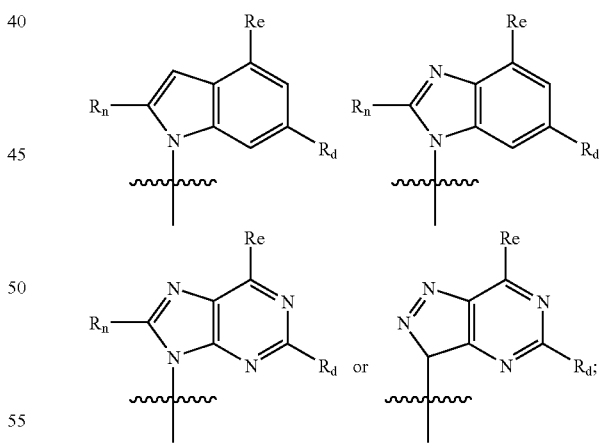

W is O or NH;
X is —C(=O)— or —S(=O)₂—;
Y is —NH— or —O—;
Z is O, —NH—, —CH₂—CH₂—, or CH₂;
each $R_a$ is independently hydroxy, amino, halo, (C₁-C₆)alkanoyloxy, nitro, (C₁-C₆)alkyl, (C₂-C₆)alkenyl, (C₂-C₆)alkynyl, or (C₁-C₆)alkanoylthio;
each $R_b$ is independently hydrogen, fluoro, or chloro;
each $R_d$ is independently azido, hydrogen, halo, (C₁-C₆) alkyl, (C₃-C₆)cycloalkyl, (C₂-C₆)alkenyl, (C₂-C₆)alkynyl, $(C_1$-$C_6)$alkoxy, $(C_1$-$C_6)$alkylthio, $(C_2$-$C_6)$alkenyloxy, $(C_1$-$C_6)$alkenylthio, $(C_2$-$C_6)$alkynyloxy, $(C_1$-$C_6)$alkynylthio, aryl, aryl$(C_1$-$C_6)$alkyl, aryl$(C_2$-$C_6)$alkenyl, aryl$(C_2$-$C_6)$alkynyl, carboxy$(C_1$-$C_6)$alkyl, carboxy$(C_1$-$C_6)$alkenyl, or $NR_fR_g$; wherein each $R_f$ and $R_g$ is independently hydrogen, aryl, aryloxy, or $(C_1$-$C_6)$alkyl;

each $R_e$ is independently hydrogen, hydroxy, $(C_1$-$C_6)$alkylthio, or $NR_kR_m$; wherein each $R_k$ and $R_m$ is independently hydrogen, $(C_3$-$C_6)$cycloalkyl aryl, or $(C_1$-$C_6)$alkyl; and each $R_n$ is independently hydrogen, halo, azido, or amino.

14. The salt of claim 13 which is a pharmaceutically acceptable salt.

15. The salt of claim 13 which is in solid form.

16. A pharmaceutical composition comprising a compound I as described in claim 1 or a pharmaceutically acceptable salt thereof; and a pharmaceutically acceptable diluent or carrier.

17. A pharmaceutical composition comprising a pharmaceutically acceptable salt as described in claim 14; and a pharmaceutically acceptable diluent or carrier.

18. A method for treating a bacterial infection in an animal comprising administering an effective amount of a compound, prodrug, or pharmaceutically acceptable salt as described in claim 1 to the animal.

19. A method for treating a bacterial infection in an animal comprising administering an effective amount of a pharmaceutically acceptable salt as described in claim 14 to the animal.

20. A method for inhibiting an adenylating enzyme comprising contacting the enzyme with an effective inhibitory amount of a compound, prodrug, or salt as described in claim 1.

* * * * *